United States Patent
No et al.

(10) Patent No.: US 11,527,723 B2
(45) Date of Patent: Dec. 13, 2022

(54) HETEROCYCLIC COMPOUND AND ORGANIC LIGHT EMITTING ELEMENT COMPRISING SAME

(71) Applicant: LT MATERIALS CO., LTD., Yongin (KR)

(72) Inventors: Young Seok No, Osan-si (KR); Ju Hyon Cha, Osan-si (KR); Dongjun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 434 days.

(21) Appl. No.: 16/496,878

(22) PCT Filed: Mar. 26, 2018

(86) PCT No.: PCT/KR2018/003532
§ 371 (c)(1),
(2) Date: Sep. 23, 2019

(87) PCT Pub. No.: WO2018/174678
PCT Pub. Date: Sep. 27, 2018

(65) Prior Publication Data
US 2020/0123133 A1    Apr. 23, 2020

(30) Foreign Application Priority Data
Mar. 24, 2017  (KR) .......... 10-2017-0037979
Feb. 14, 2018  (KR) .......... 10-2018-0018782

(51) Int. Cl.
*C07D 209/86*    (2006.01)
*H01L 51/00*    (2006.01)
(Continued)

(52) U.S. Cl.
CPC ........ *H01L 51/0072* (2013.01); *C07D 209/86* (2013.01); *C07D 403/14* (2013.01);
(Continued)

(58) Field of Classification Search
None
See application file for complete search history.

(56) References Cited

U.S. PATENT DOCUMENTS 4,356,429 A    10/1982   Tang
9,406,892 B2    8/2016   Zeng et al.
(Continued)

FOREIGN PATENT DOCUMENTS

JP    3139321 B2    2/2001
JP    2012-49518 A    3/2012
(Continued)

OTHER PUBLICATIONS

International Search Report for PCT/KR2018/003532 (PCT/ISA/210) dated Jul. 20, 2018, with English translation.
(Continued)

*Primary Examiner* — Robert S Loewe
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

9 Claims, 2 Drawing Sheets

(51) Int. Cl.

| | | |
|---|---|---|
| C07D 405/14 | (2006.01) | |
| C07D 487/04 | (2006.01) | |
| C07D 491/048 | (2006.01) | |
| C07D 495/04 | (2006.01) | |
| C09K 11/06 | (2006.01) | |
| C07D 403/14 | (2006.01) | |
| H01L 51/50 | (2006.01) | |

(52) U.S. Cl.
CPC ......... *C07D 405/14* (2013.01); *C07D 487/04* (2013.01); *C07D 491/048* (2013.01); *C07D 495/04* (2013.01); *C09K 11/06* (2013.01); *H01L 51/001* (2013.01); *H01L 51/0054* (2013.01); *H01L 51/0058* (2013.01); *H01L 51/0067* (2013.01); *H01L 51/0071* (2013.01); *H01L 51/0073* (2013.01); *H01L 51/0074* (2013.01); *C09K 2211/1018* (2013.01); *H01L 51/5012* (2013.01); *H01L 51/5016* (2013.01); *H01L 51/5072* (2013.01); *H01L 51/5092* (2013.01); *H01L 51/5096* (2013.01); *H01L 2251/5384* (2013.01)

(56) References Cited

U.S. PATENT DOCUMENTS

| | | |
|---|---|---|
| 9,865,822 B2 | 1/2018 | Song et al. |
| 9,911,925 B2 | 3/2018 | Lee et al. |
| 10,217,946 B2 | 2/2019 | Wolleb et al. |
| 10,381,577 B2 | 8/2019 | Park et al. |
| 2015/0008423 A1 | 1/2015 | Inoue et al. |
| 2016/0149139 A1 | 5/2016 | Xia et al. |
| 2016/0268516 A1 | 9/2016 | Tanaka et al. |
| 2017/0186965 A1 | 6/2017 | Parham et al. |
| 2017/0207399 A1 | 7/2017 | Parham et al. |
| 2018/0037546 A1 | 2/2018 | Sugino et al. |
| 2018/0037547 A1 | 2/2018 | Cha et al. |
| 2019/0047991 A1* | 2/2019 | Jung .................. C07D 405/04 |
| 2019/0372012 A1* | 12/2019 | Cho .................. H01L 51/0067 |
| 2020/0303655 A1* | 9/2020 | Huh .................. C07D 239/26 |

FOREIGN PATENT DOCUMENTS

| | | |
|---|---|---|
| JP | 2016-128432 A | 7/2016 |
| JP | 2016-149473 A | 8/2016 |
| JP | 2016-149520 A | 8/2016 |
| JP | 2016-149558 A | 8/2016 |
| KR | 10-2011-0112098 A | 10/2011 |
| KR | 10-2014-0065863 A | 5/2014 |
| KR | 10-2015-0094398 A | 8/2015 |
| KR | 10-2016-0028524 A | 3/2016 |
| KR | 10-2016-0030402 A | 3/2016 |
| KR | 10-2017-0013153 A | 2/2017 |
| KR | 10-2017-0032170 A | 3/2017 |
| KR | 10-2018-0045798 A | 5/2018 |
| WO | WO 2015/140073 A1 | 9/2015 |
| WO | WO 2016/015810 A1 | 2/2016 |

OTHER PUBLICATIONS

Kuwabara et al., "Thermally Stable Mulitlayered Organic Electroluminescent Devices Using Novel Starburst Molecules, 4,4',4''-Tri(N-carbazolyl)triphenylamine (TCTA) and 4,4',4''-Tris(3-methylphenylphenyl-amino)triphenylamine (m-MTDATA), as Hole-Transport Materials", Advanced Materials. vol. 6, No. 9, 1994, pp. 677-679.

Lee et al., "The Effect of the Substitution Position of Dibenzofuran on the Photophysical and Charge-Transport Properties of Host Materials for Phosphorescent Organic Light-Emitting Diodes", Chemistry A European Journal, vol. 19, 2013, pp. 1194-1198.

European Office Action dated Oct. 1, 2021 for Application No. 18 772 275.6.

U.S. Office Action for U.S. Appl. No. 16/496,712, dated Feb. 3, 2022.

* cited by examiner

【FIG. 1】
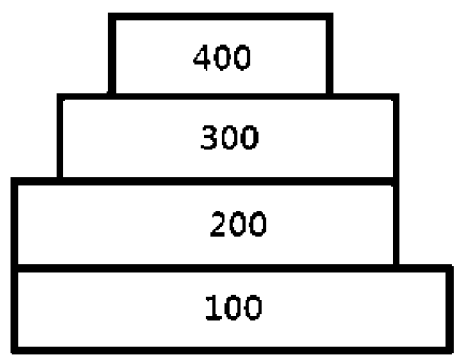
【FIG. 2】
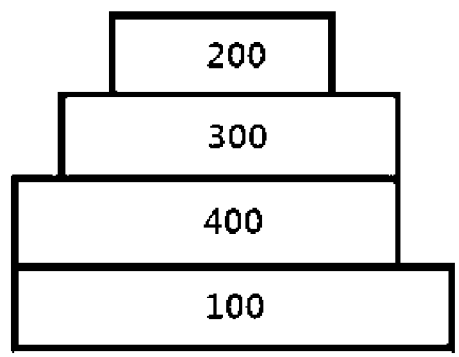

[FIG. 3]
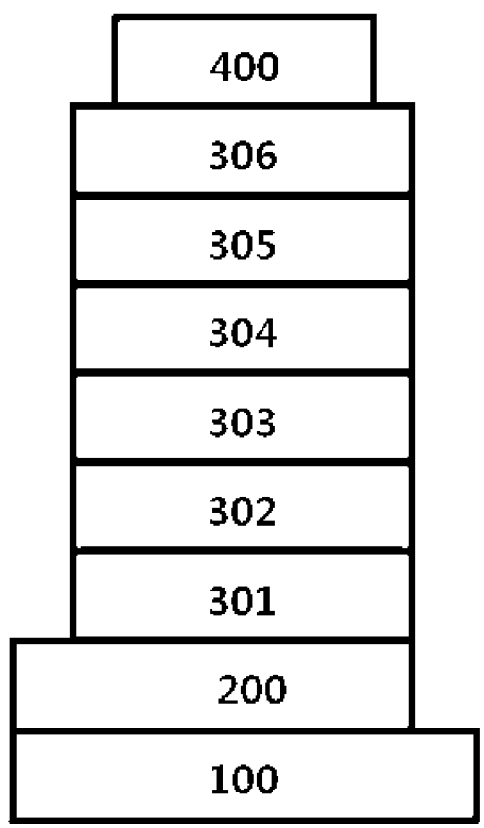

HETEROCYCLIC COMPOUND AND ORGANIC LIGHT EMITTING ELEMENT COMPRISING SAME

TECHNICAL FIELD

This application claims priority to and the benefits of Korean Patent Application No. 10-2017-0037979, filed with the Korean Intellectual Property Office on Mar. 24, 2017, and Korean Patent Application No. 10-2018-0018782, filed with the Korean Intellectual Property Office on Feb. 14, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves may be used alone, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

Researches for an organic light emitting device comprising a compound capable of satisfying conditions required for materials usable in an organic light emitting device, for example, a proper energy level, electrochemical stability, thermal stability and the like, and having a chemical structure that may perform various roles required in an organic light emitting device depending on substituents have been required.

Technical Solution

One embodiment of the present application provides a heterocyclic compound represented by the following Chemical Formula 1.

[Chemical Formula 1]

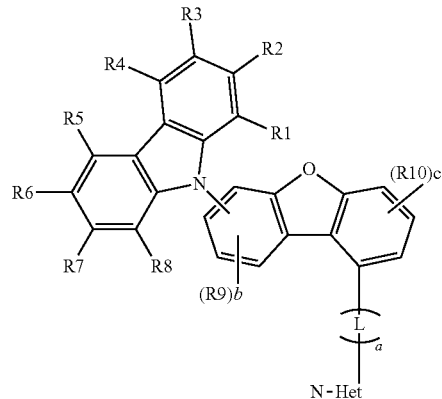

In Chemical Formula 1,

N-Het is a monocyclic or multicyclic heterocyclic group substituted or unsubstituted, and comprising one or more Ns, L is a direct bond; a substituted or unsubstituted arylene group; or a substituted or unsubstituted heteroarylene group, a is an integer of 1 to 3, and when a is 2 or greater, Ls are the same as or different from each other, R1 to R10 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, b and c are each an integer of 1 to 3, and when b is 2 or greater, R9s are the same as or different from each other and when c is 2 or greater, R10s are the same as or different from each other.

Another embodiment of the present application provides an organic light emitting device comprising a first electrode; a second electrode provided opposite to the first electrode; and one or more organic material layers provided between the first electrode and the second electrode, wherein one or muse layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in an organic light emitting device. Particularly, the compound can be used as a light emitting layer material of an organic light emitting device. For example, the compound can be used as a light emitting material alone, or as a host material of a light emitting layer.

Particularly, Chemical Formula 1 has a structure with more electron stability by having an N-containing ring substituting a position of number 1 carbon in a dibenzofuran structure, and having a carbazole structure substituting benzene that is not substituted with the N-containing ring in the dibenzofuran structure, and a device lifetime can be enhanced therefrom.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

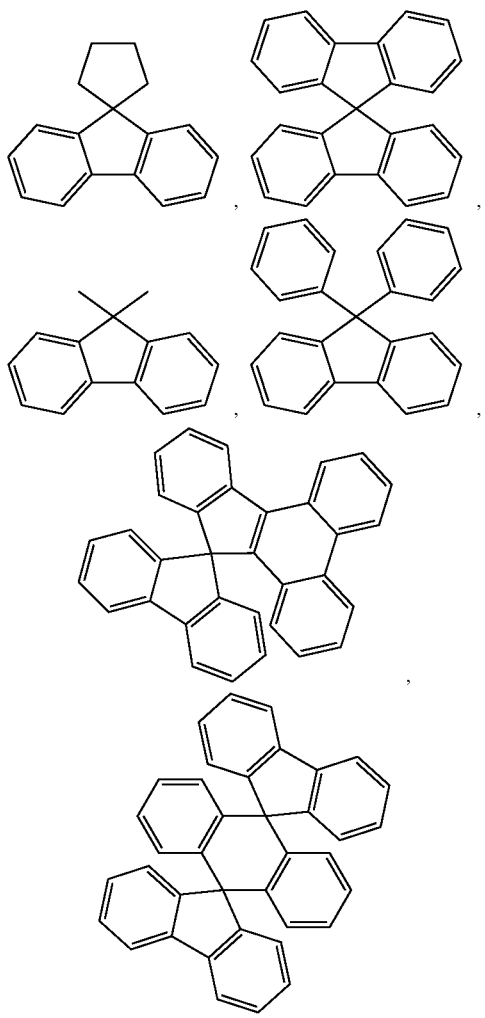

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinazolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, the phosphine oxide group may specifically be substituted with an aryl group, and the examples described above may be used as the aryl group. Examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups adjacent to each other.

Structures illustrated as the cycloalkyl group, the cycloheteroalkyl group, the aryl group and the heteroaryl group described above may be used as the aliphatic or aromatic hydrocarbon ring or heteroring that adjacent groups may form except for those that are not monovalent.

One embodiment of the present application provides a compound represented by Chemical Formula 1.

In one embodiment of the present application, Chemical Formula 1 may be represented by one of the following Chemical Formulae 2 to 5.

[Chemical Formula 2]

[Chemical Formula 3]

[Chemical Formula 4]

[Chemical Formula 5]

In Chemical Formulae 2 to 5, substituents have the same definitions as in Chemical Formula 1.

In one embodiment of the present application, N-Het is a monocyclic or multicyclic heteroring substituted or unsubstituted, and comprising one or more Ns.

In another embodiment, N-Het is a monocyclic or multicyclic heteroring unsubstituted or substituted with one or more substituents selected from the group consisting of an aryl group and a heteroaryl group, and comprising one or more Ns.

In another embodiment, N-Het is a monocyclic or multicyclic heteroring unsubstituted or substituted with one or more substituents selected from the group consisting of a phenyl group, a biphenyl group, a naphthyl group, a dimethylfluorene group, a dibenzofuran group and a dibenzothiophene group, and comprising one or more Ns.

In another embodiment, N-Het is a monocyclic or multicyclic heteroring unsubstituted or substituted with one or more substituents selected from the group consisting of a phenyl group, a biphenyl group, a naphthyl group, a dimethylfluorene group, a dibenzofuran group and a dibenzothiophene group, and comprising one or more and three or less Ns.

In one embodiment of the present application, N-Het is a monocyclic heteroring substituted or unsubstituted, and comprising one or more Ns.

In one embodiment of the present application, N-Het is a dicyclic or higher heteroring substituted or unsubstituted, and comprising one or more Ns.

In one embodiment of the present application, N-Het is a monocyclic or multicyclic heteroring substituted or unsubstituted, and comprising two or more Ns.

In one embodiment of the present application, N-Het is a dicyclic or higher multicyclic heteroring comprising two or more Ns.

In one embodiment of the present application, Chemical Formula 1 is represented by one of the following Chemical Formulae 6 to 8.

[Chemical Formula 6]

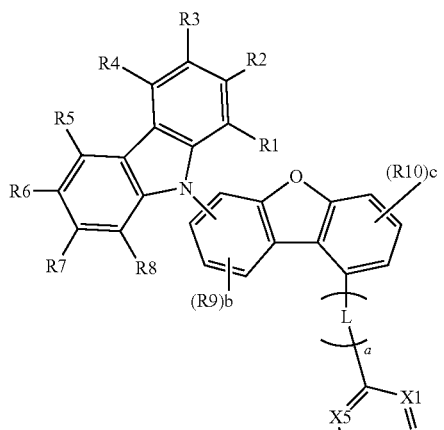

[Chemical Formula 7]

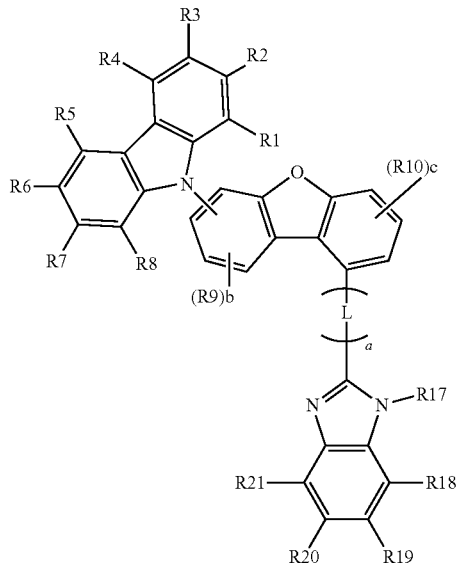

[Chemical Formula 8]

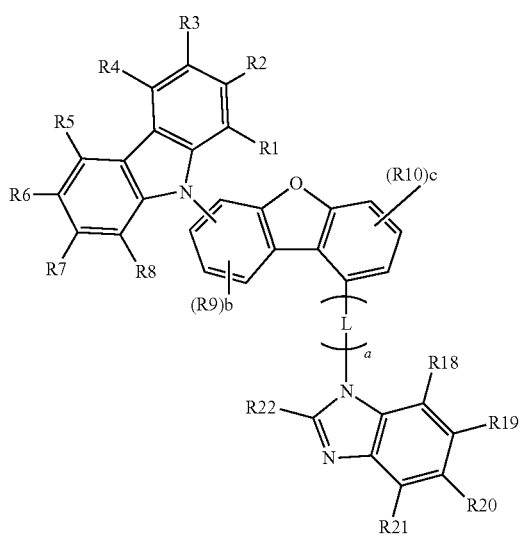

In Chemical Formulae 6 to 8, R1 to R10, L, a, b and c have the same definitions as in Chemical Formula 1, X1 is CR11 or N, X2 is CR12 or N, X3 is CR13 or N, X4 is CR14 or N, and X5 is CR15 or N, R11 to R15 and R17 to R22 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

In one embodiment of the present application,

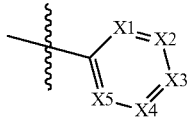

may be represented by one of the following Chemical Formulae 9 to 12. Herein,

is a site linked to L.

[Chemical Formula 9]

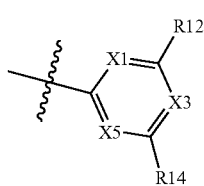

[Chemical Formula 10]

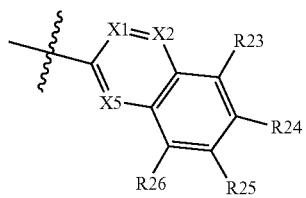

[Chemical Formula 11]

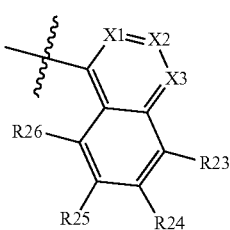

-continued

[Chemical Formula 12]

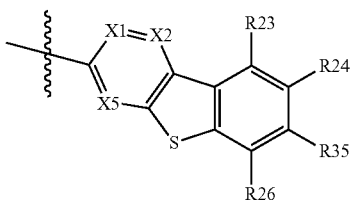

In Chemical Formula 9, one or more of X1, X3 and X5 are N, and the rest have the same definitions as in Chemical Formula 6, in Chemical Formula 10, one or more of X1, X2 and X5 are N, and the rest have the same definitions as in Chemical Formula 6, in Chemical Formula 11, one or more of X1 to X3 are N, and the rest have the same definitions as in Chemical Formula 6, in Chemical Formula 12, one or more of X1, X2 and X5 are N, and the rest have the same definitions as in Chemical Formula 6, and R12, R14 and R23 to R26 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

In one embodiment of the present application, Chemical Formula 9 may be selected from among the following structural formulae.

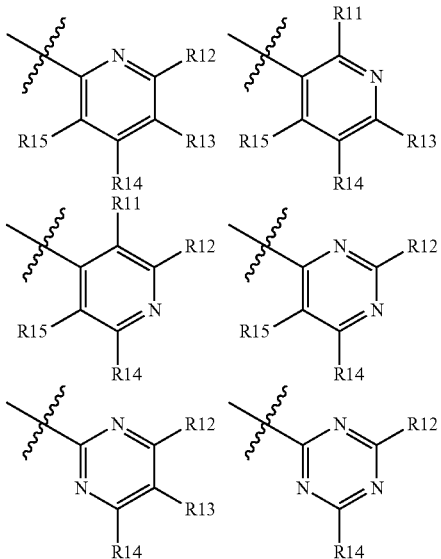

In one embodiment of the present application, Chemical Formula 10 may be represented by the following Chemical Formula 13.

[Chemical Formula 13]

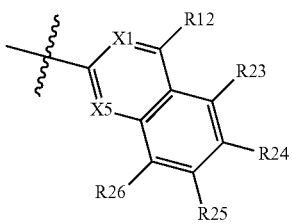

Substituents of Chemical Formula 13 have the same definitions as in Chemical Formula 10.

In one embodiment of the present application, Chemical Formula 11 may be represented by the following Chemical Formula 14.

[Chemical Formula 14]

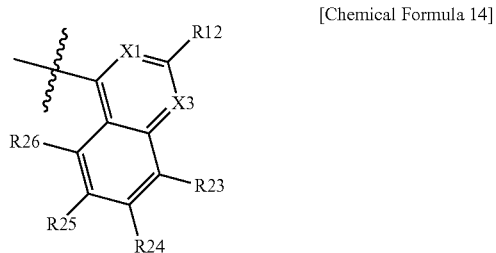

Substituents of Chemical Formula 14 have the same definitions as in Chemical Formula 11.

In one embodiment of the present application, Chemical Formula 10 may be represented by the following Chemical Formula 15.

[Chemical Formula 15]

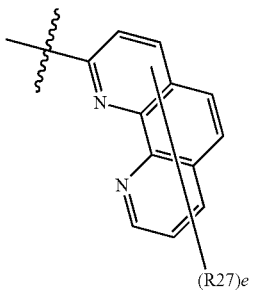

In Chemical Formula 15, R27s are the same as or different from each other, and selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, e is an integer of 0 to 7, and when e is 2 or greater, R27s are the same as or different from each other.

In one embodiment of the present application, Chemical Formula 12 may be represented by the following Chemical Formula 16.

[Chemical Formula 16]

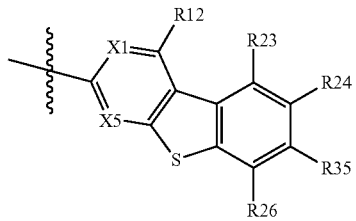

Substituents of Chemical Formula 16 have the same definitions as in Chemical Formula 12.

In another embodiment, L is a direct bond or an arylene group.

In another embodiment, L is a direct bond or a phenylene group.

In another embodiment, R9 and R10 are hydrogen; or deuterium.

In another embodiment, R9 and R10 are hydrogen.

In another embodiment, R1 to R8 are hydrogen; deuterium; an aryl group unsubstituted or substituted with an alkyl group, an aryl group or a heteroaryl group; or a heteroaryl group unsubstituted or substituted with an aryl group or a heteroaryl group.

In another embodiment, R1 to R8 are hydrogen; deuterium; an aryl group; a heteroaryl group; or a heteroaryl group substituted with an aryl group.

In another embodiment, R1 to R8 are hydrogen; deuterium; a phenyl group; a dibenzofuran group; a dibenzothiophene group; a carbazole group; or a carbazole group substituted with phenyl.

In another embodiment, R1 to R8 are hydrogen; deuterium; a phenyl group; a dibenzofuran group; or a carbazole group substituted with phenyl.

In another embodiment, adjacent two substituents among R1 to R8 bond to each other to form a substituted or unsubstituted ring.

In another embodiment, adjacent two substituents among R1 to R8 bond to each other to form a ring unsubstituted or substituted with an aryl group or an alkyl group.

In another embodiment, adjacent two substituents among R1 to R8 bond to each other to form an aromatic hydrocarbon ring or heteroring unsubstituted or substituted with an aryl group or an alkyl group.

In another embodiment, adjacent two substituents among R1 to R8 bond to each other to form an aromatic hydrocarbon ring or heteroring unsubstituted or substituted with a phenyl group or a methyl group.

In another embodiment, adjacent two substituents among R1 to R8 bond to each other to form a benzene ring; an indole ring unsubstituted or substituted with a phenyl group; a benzothiophene ring; a benzofuran ring; or an indene ring unsubstituted or substituted with a methyl group.

In another embodiment,

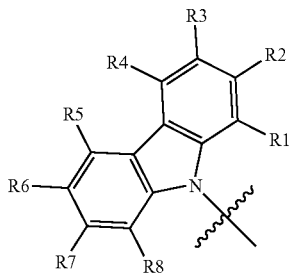

may be represented by the following Chemical Formula 17. Herein,

is a site linked to a dibenzofuran structure.

[Chemical Formula 17]

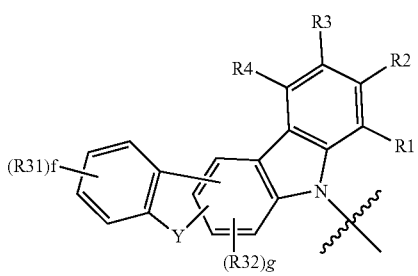

In Chemical Formula 17,

R1 to R4 have the same definitions as in Chemical Formula 1,

Y is O, S, NR or CR'R",

R, R', R", R31 and R32 are the same as or different from each other, and selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, f is an integer of 0 to 4, and when f is 2 or greater, R31s are the same as or different from each other, g is an integer of 0 to 2, and when g is 2 or greater, R32s are the same as or different from each other.

In another embodiment, Chemical Formula 17 may be selected from among the following structural formulae.

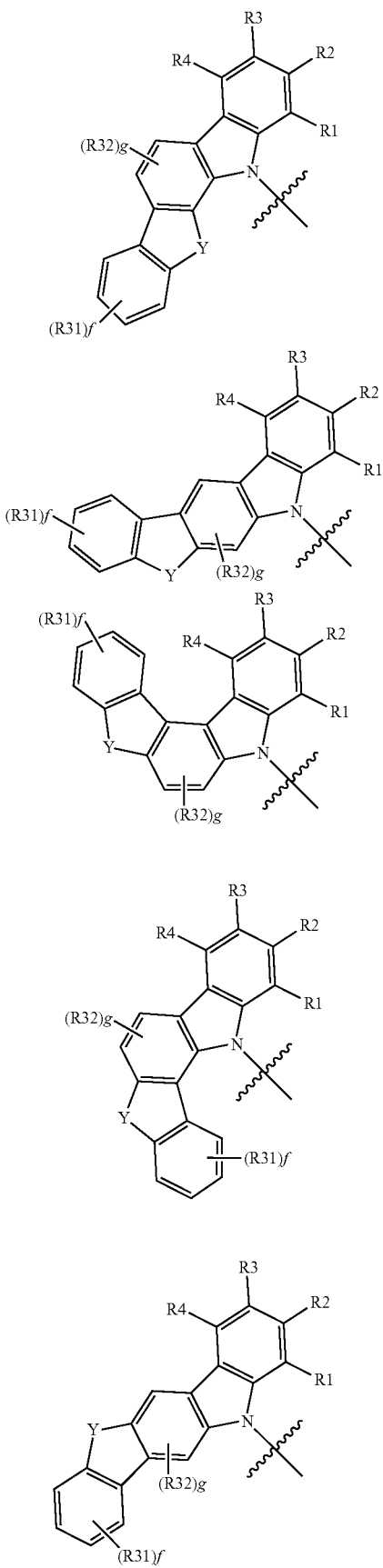

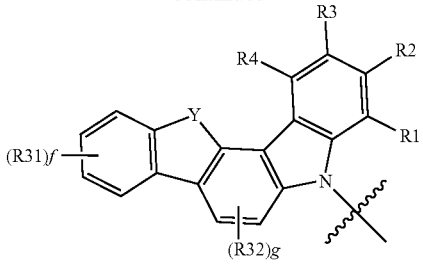

In another embodiment, R18 to R21 are the same as or different from each other, and each independently hydrogen; deuterium; an aryl group; or a heteroaryl group.

In another embodiment, R18 to R21 are the same as or different from each other, and each independently hydrogen; or deuterium.

In another embodiment, R18 to R21 are hydrogen.

In another embodiment, R17 and R22 are the same as or different from each other, and each independently hydrogen; deuterium; an aryl group; or a heteroaryl group.

In another embodiment, R17 and R22 are the same as or different from each other, and each independently an aryl group; or a heteroaryl group.

In another embodiment, R17 and R22 are the same as or different from each other, and each independently an aryl group.

In another embodiment, R17 and R22 are a phenyl group.

In another embodiment, R11 to R15 are the same as or different from each other, and each independently hydrogen; deuterium; an aryl group unsubstituted or substituted with an alkyl group; or a substituted or unsubstituted heteroaryl group.

In another embodiment, R11 to R15 are the same as or different from each other, and each independently hydrogen; deuterium; an aryl group unsubstituted or substituted with an alkyl group; or a heteroaryl group.

In another embodiment, R11 to R15 are the same as or different from each other, and each independently hydrogen; an aryl group unsubstituted or substituted with a methyl group; or a heteroaryl group.

In another embodiment, R11 to R15 are the same as or different from each other, and each independently hydrogen; a phenyl group; a biphenylyl group; a naphthyl group; a dimethylfluorenyl group; a dibenzofuran group; or a d benzothiophene group.

In another embodiment, R12 and R14 are the same as or different from each other, and each independently an aryl group unsubstituted or substituted with an alkyl group; or a heteroaryl group.

In another embodiment, R12 and R14 are the same as or different from each other, and each independently a phenyl group, a biphenylyl group, a naphthyl group, a dimethylfluorenyl group; a dibenzofuran group; or a dibenzothiophene group.

In another embodiment, R23 to R26 are the same as or different from each other, and each independently hydrogen; deuterium; an aryl group; or a heteroaryl group.

In another embodiment, R23 to R26 are the same as or different from each other, and each independently hydrogen; deuterium; or an aryl group.

In another embodiment, R23 to R26 are the same as or different from each other, and each independently hydrogen; or an aryl group.

In another embodiment, R23 to R26 are the same as or different from each other, and each independently hydrogen; a phenyl group; or a biphenylyl group.

In another embodiment, R27 is hydrogen; deuterium; an aryl group; or a heteroaryl group.

In another embodiment, R27 is hydrogen; deuterium; or an aryl group.

In another embodiment, R27 is hydrogen; or an aryl group.

In another embodiment, R27 is hydrogen; or a phenyl group.

In another embodiment, Y is O or S.

In another embodiment, Y is NR, and R is an aryl group.

In another embodiment, Y is NR, and R is a phenyl group.

In another embodiment, Y is CR'R", and R' and R" are an alkyl group.

In another embodiment, Y is CR'R", and R' and R" are a methyl group.

In another embodiment, R31 is hydrogen; deuterium; an aryl group; or a heteroaryl group.

In another embodiment, R31 is hydrogen; deuterium; or an aryl group.

In another embodiment, R31 is hydrogen; or a phenyl group.

In another embodiment, R32 is hydrogen; or deuterium.

In another embodiment, R32 is hydrogen.

According to one embodiment of the present application, Chemical Formula 1 may be represented by any one of the following compounds, but is not limited thereto.

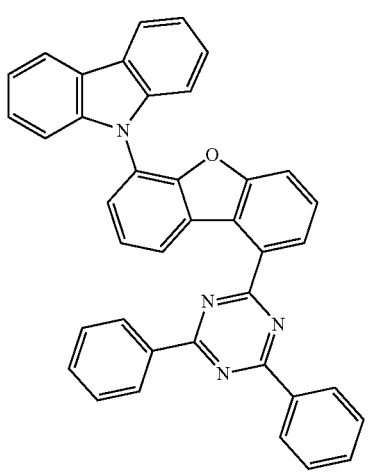

1

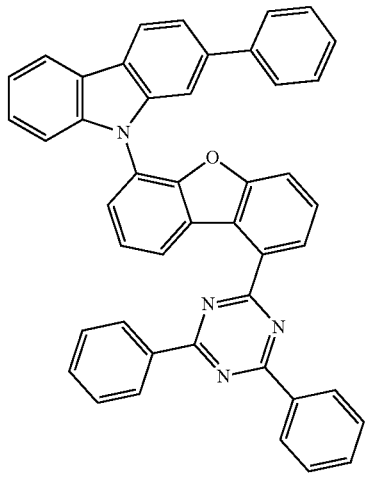 [SMILES: c1ccc(-c2ccc3c4ccccc4n(-c4cccc5c4oc4cccc(-c6nc(-c7ccccc7)nc(-c7ccccc7)n6)c45)c3c2)cc1]

2

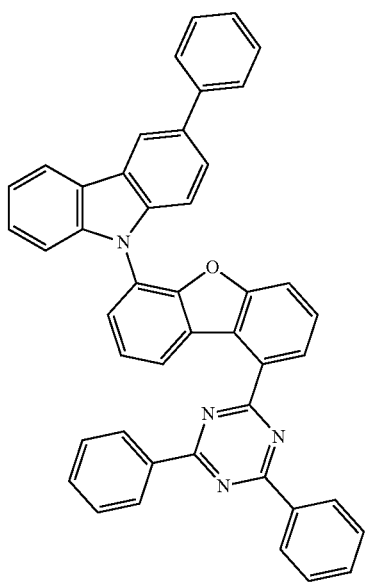

3

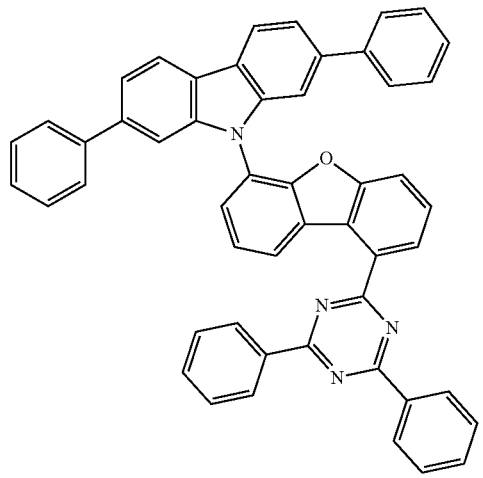

4

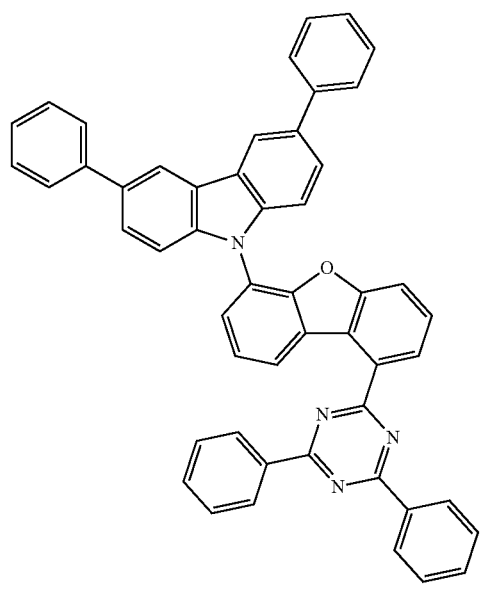
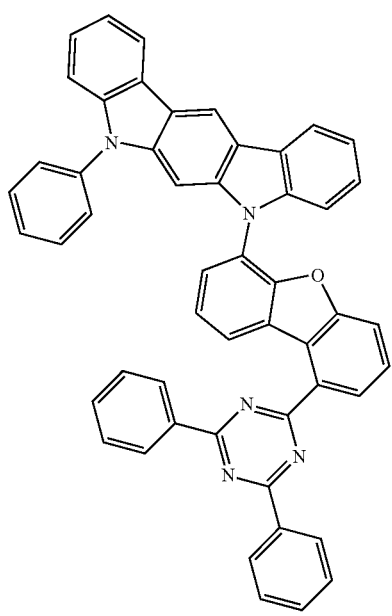
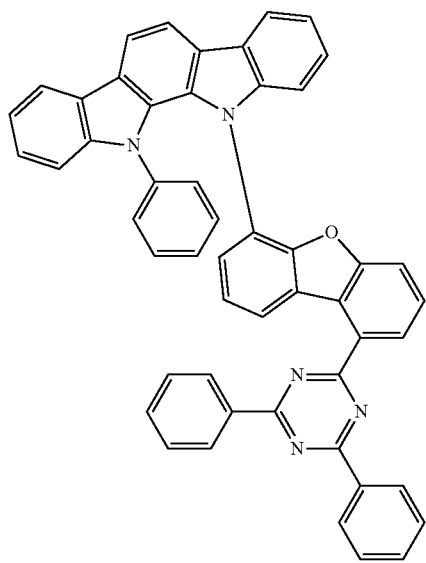
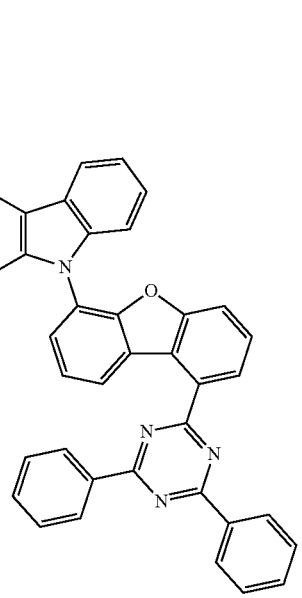

9
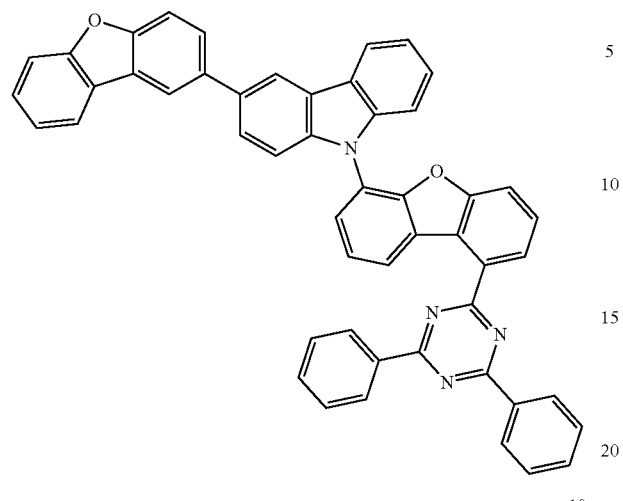
10
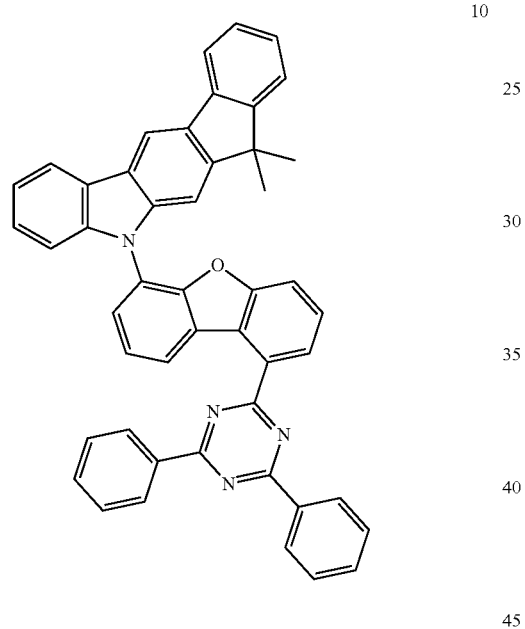
11
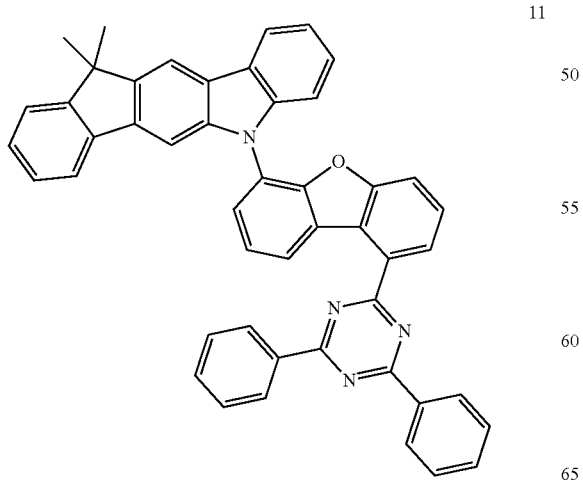
12
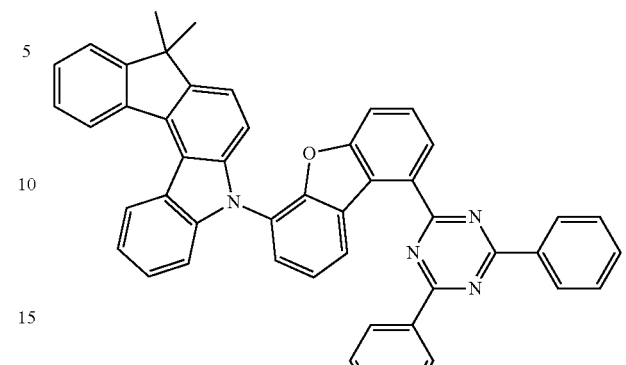
13
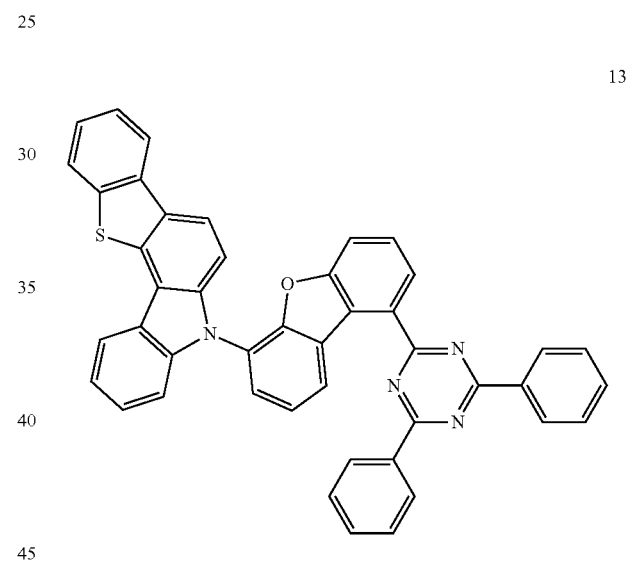
14
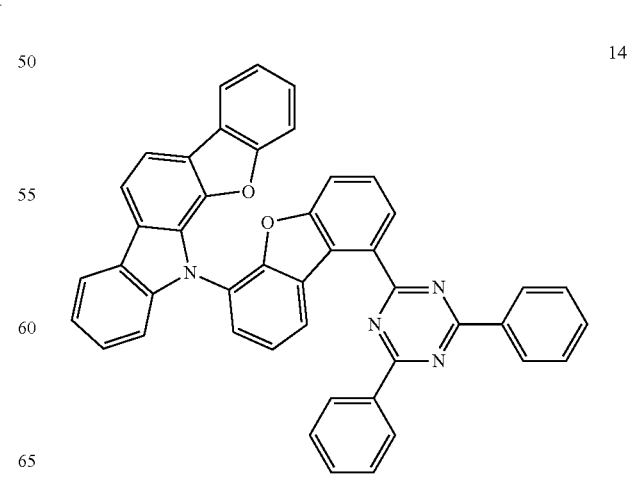

15
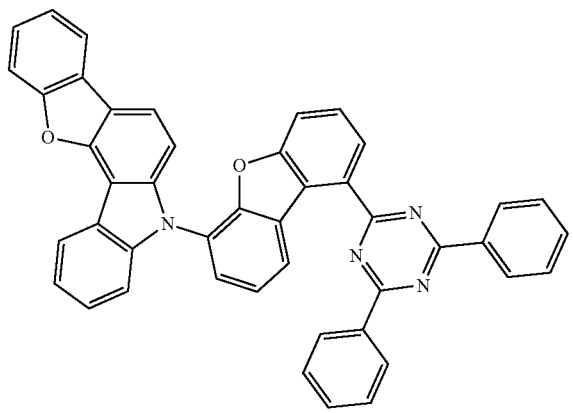
16
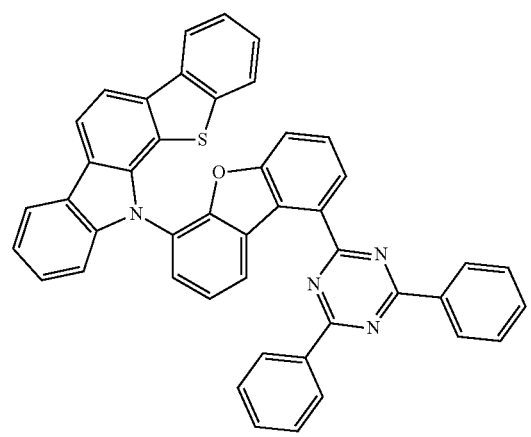
17
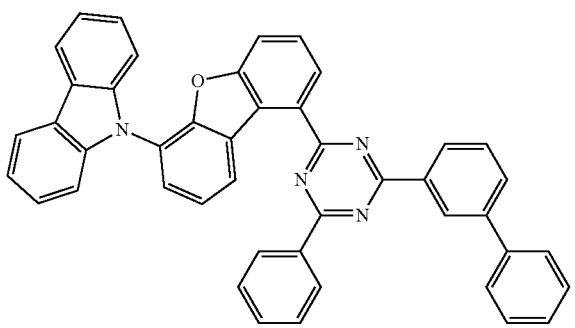
17
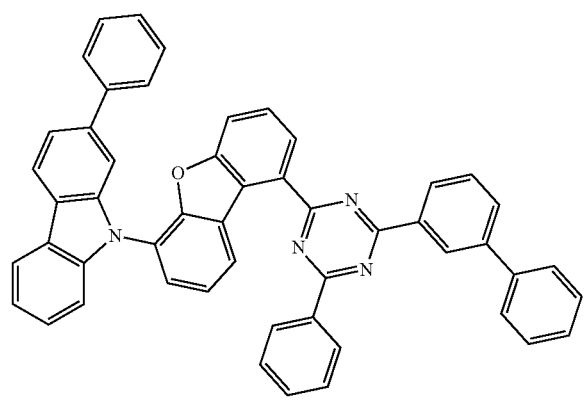
19
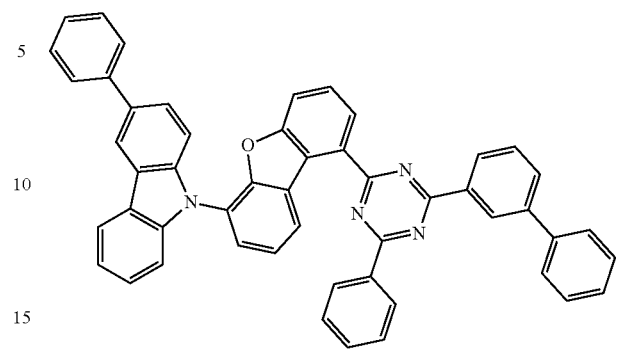
20
21
22
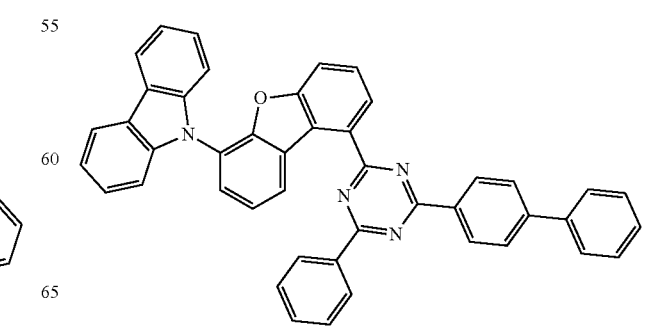

23
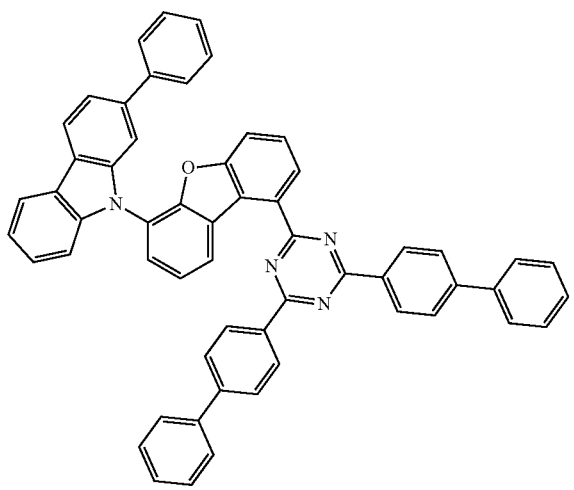
24
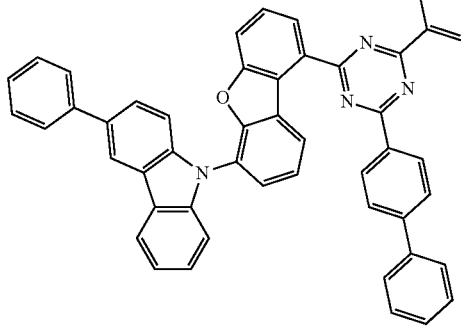
25
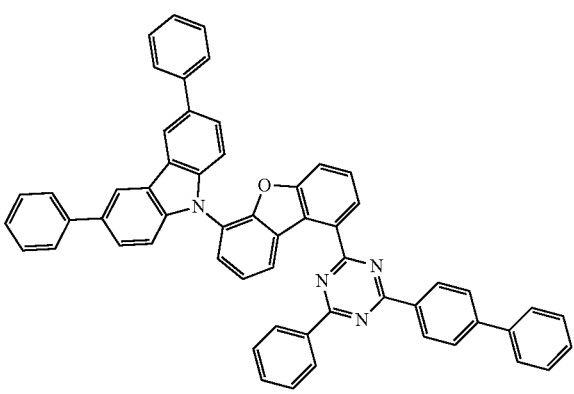
26
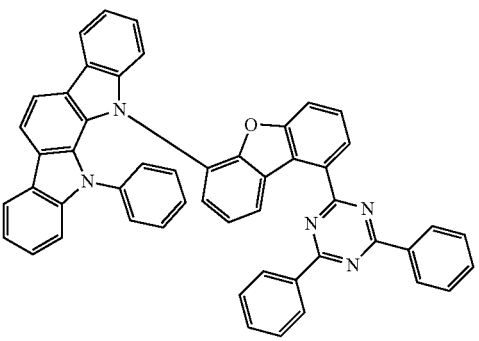
27
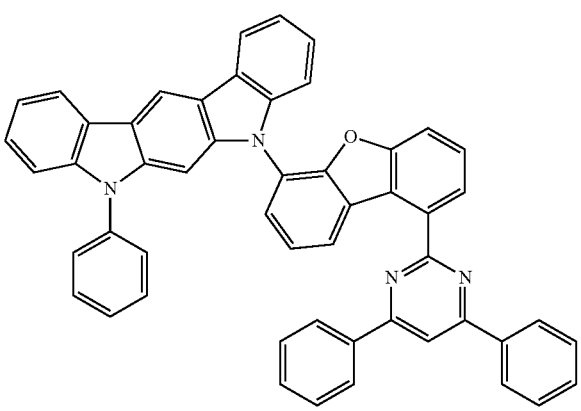
28
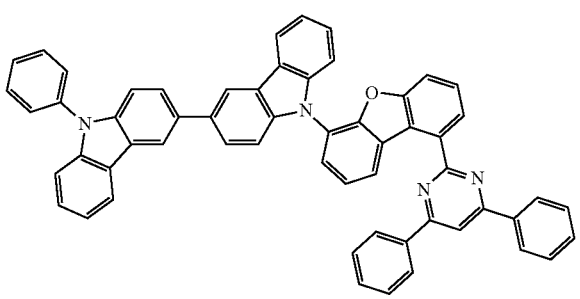
29
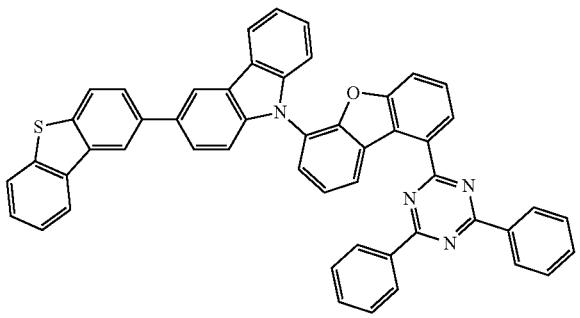

30
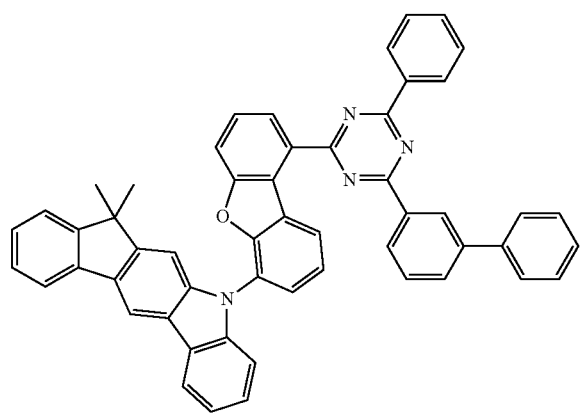
31
34
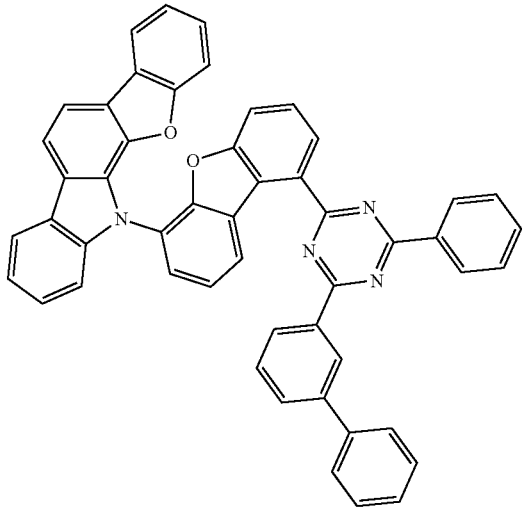
32
35
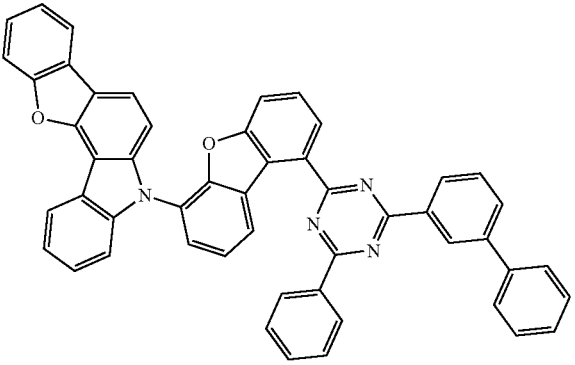
33
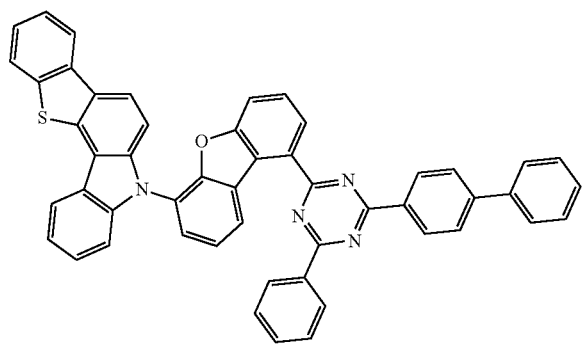
36

37
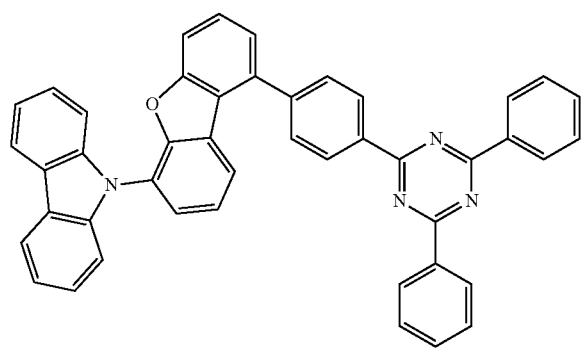
38
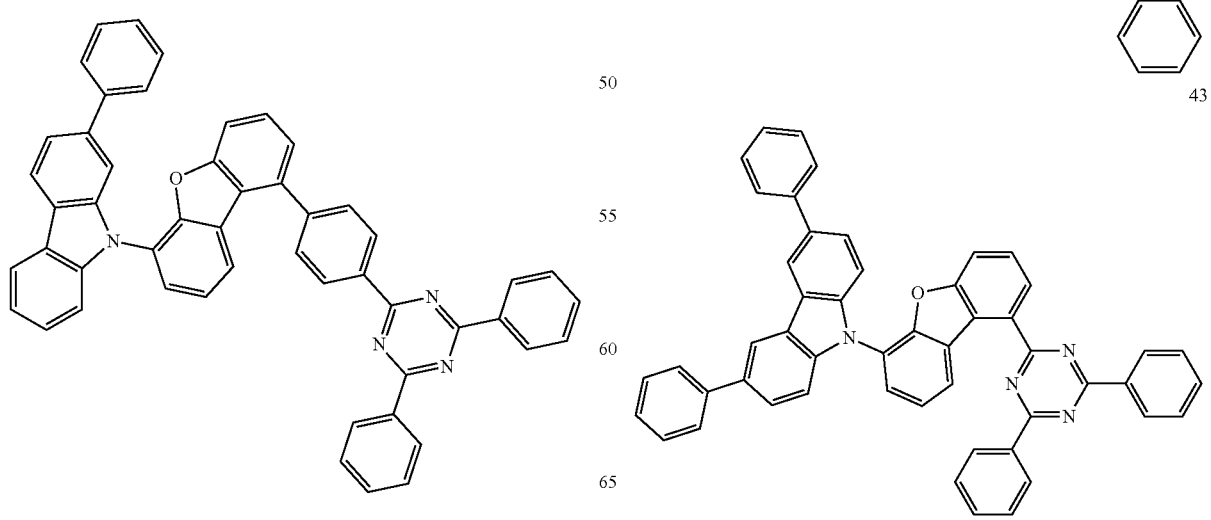
39
40
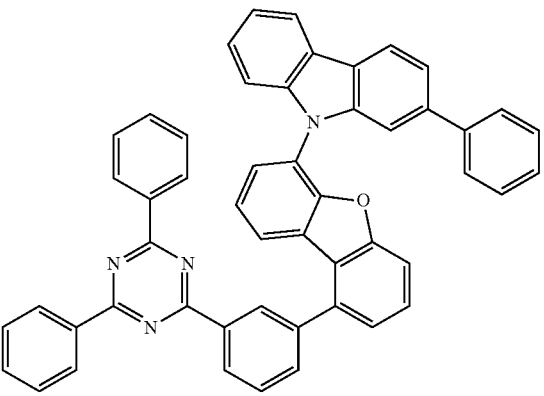
41
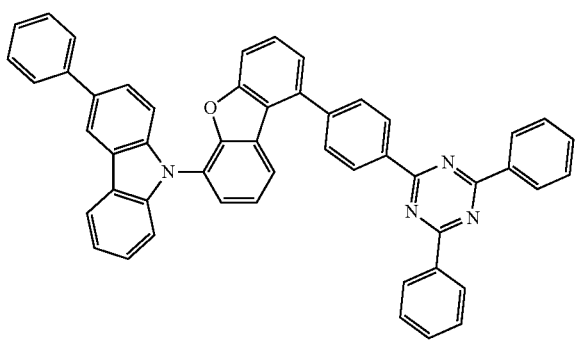
42
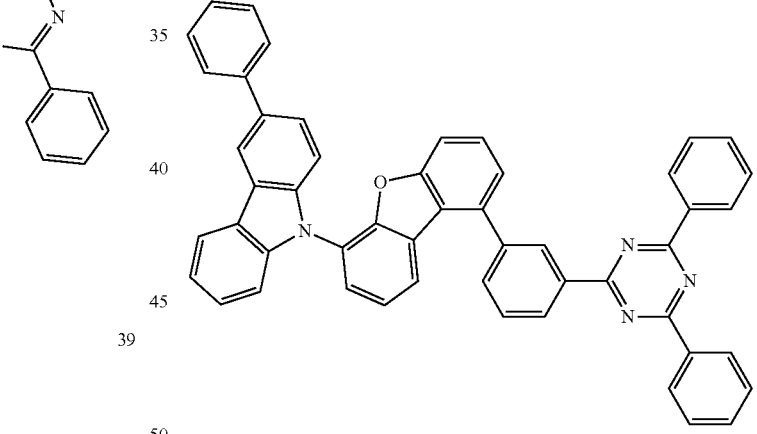
43

44
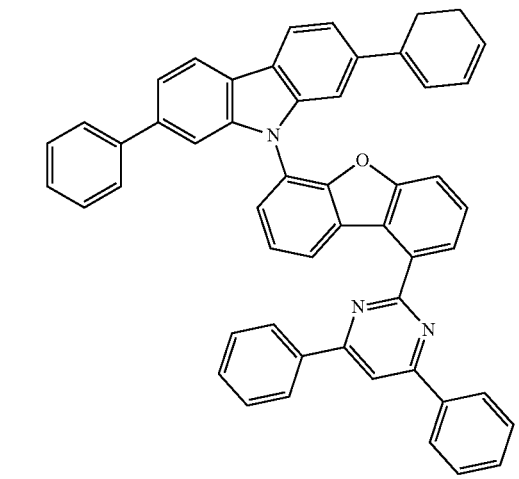
45

46
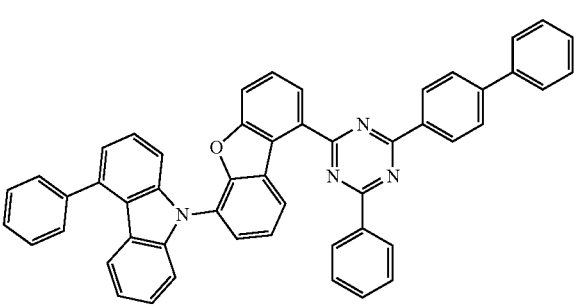
47
48
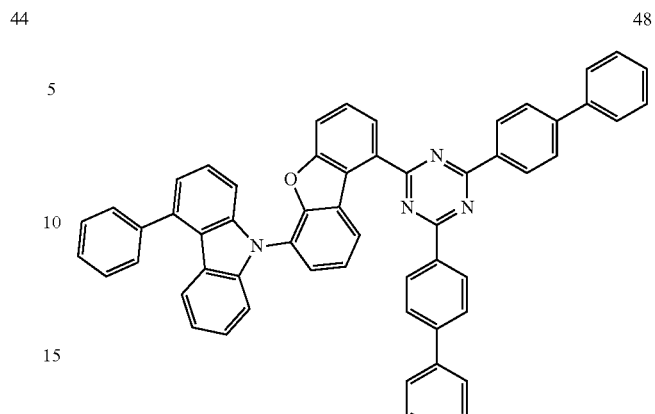
49
50
51

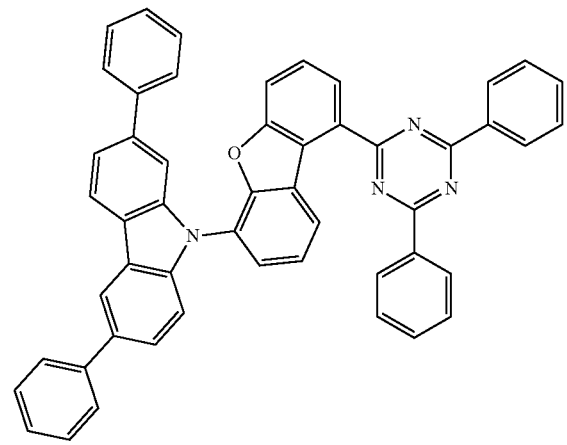
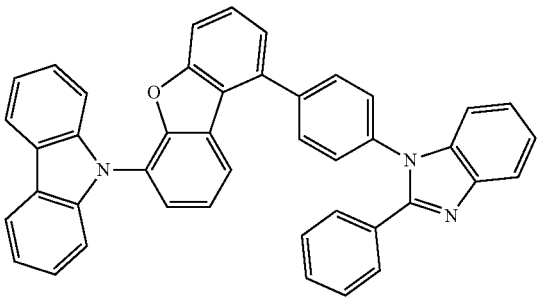
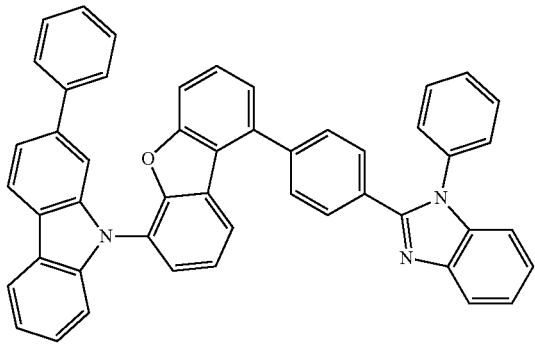
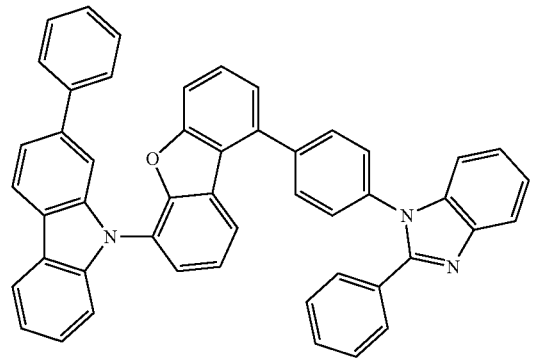
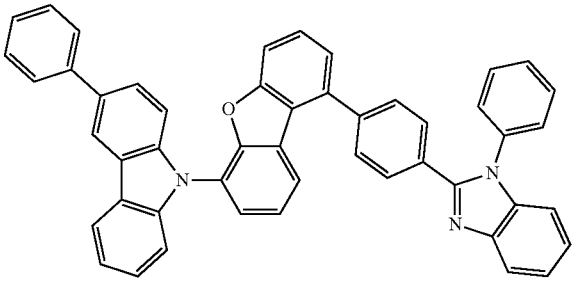

-continued
60
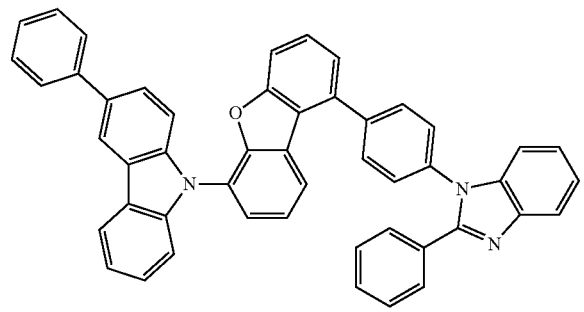
61
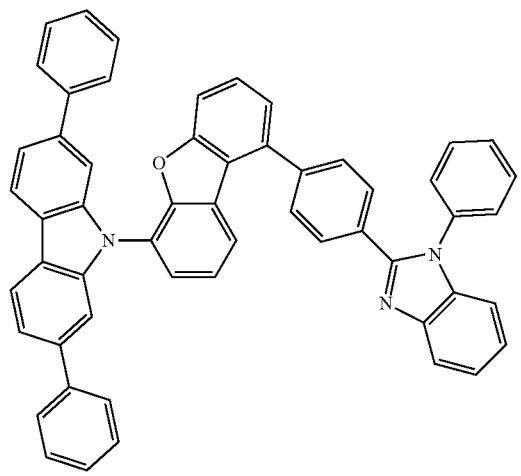
62
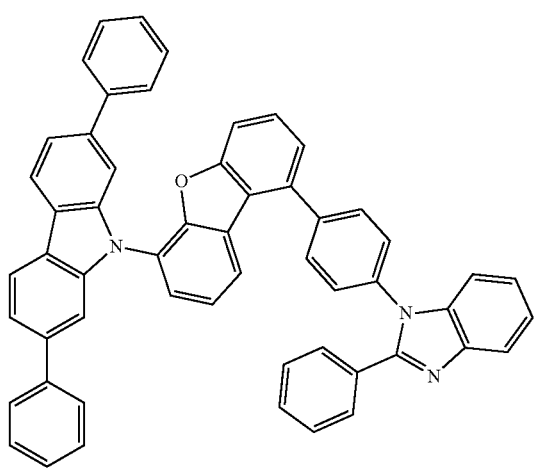
-continued
63
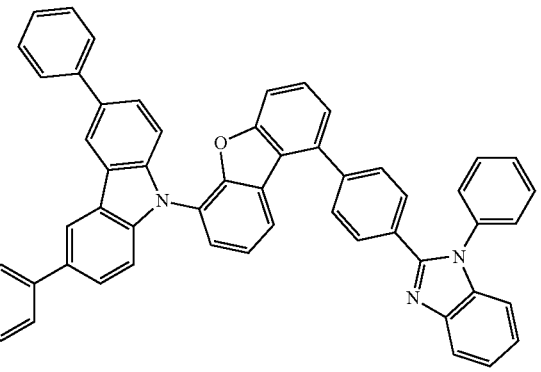
64
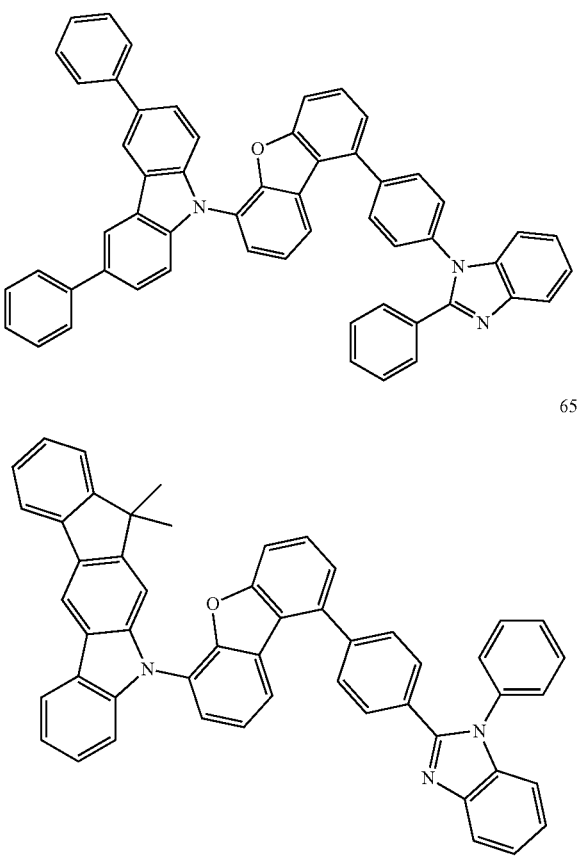
65
66
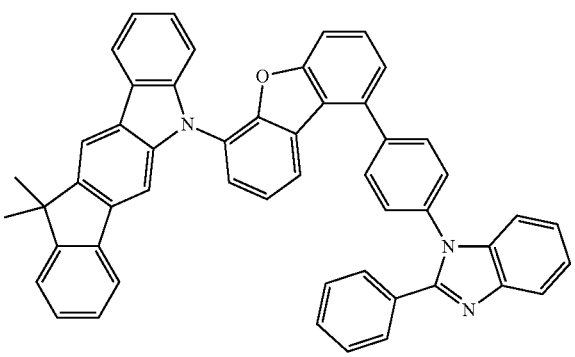

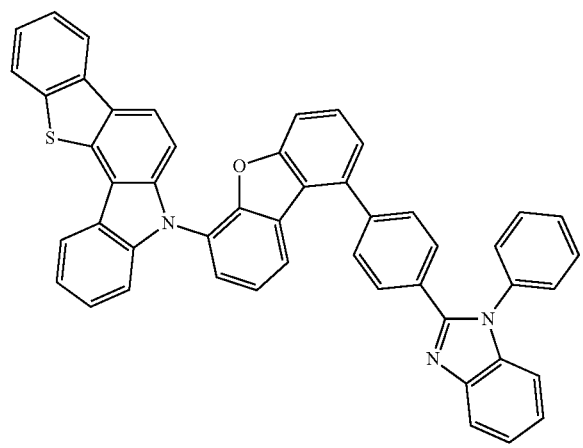
67
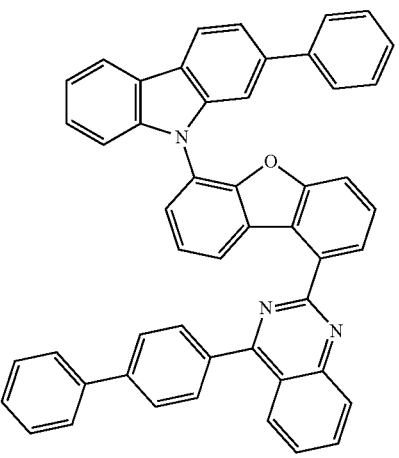
70
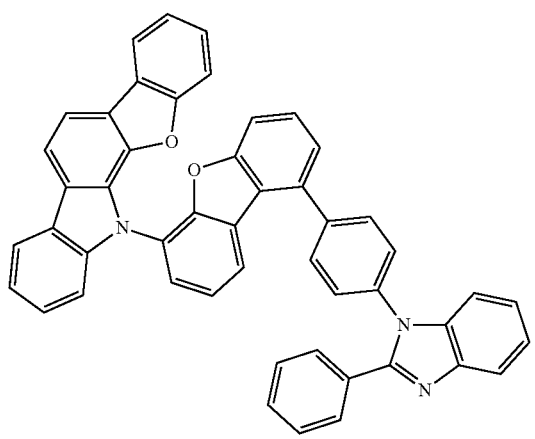
68
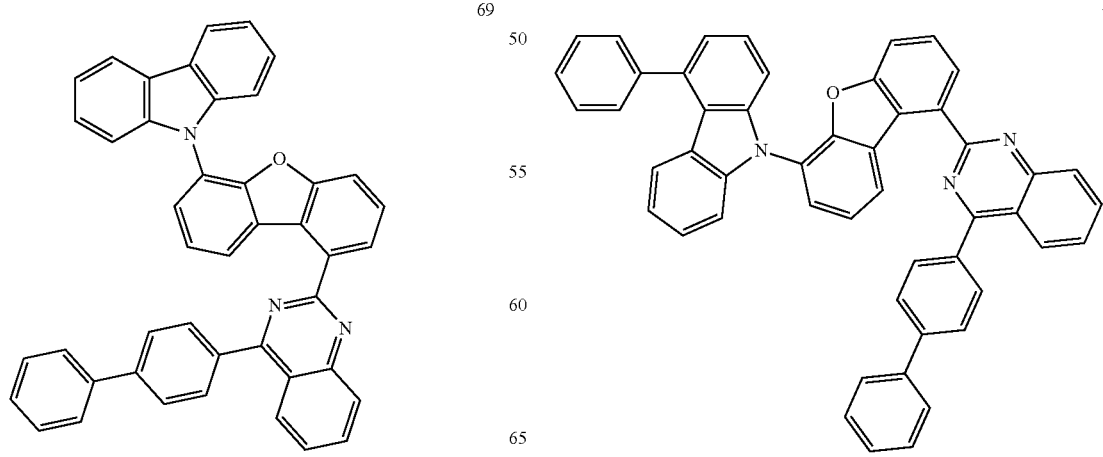
69
72

73
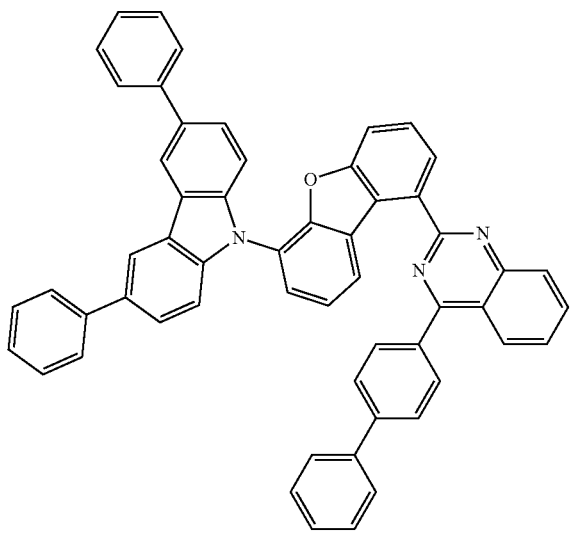
74
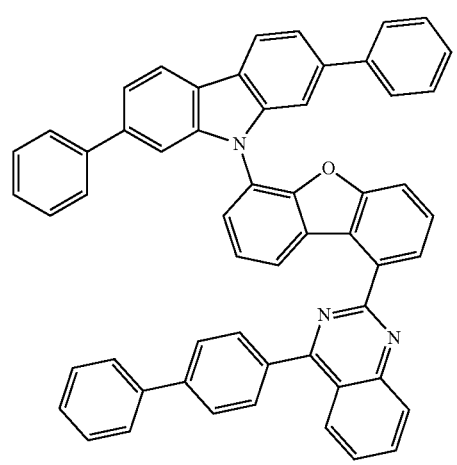
75
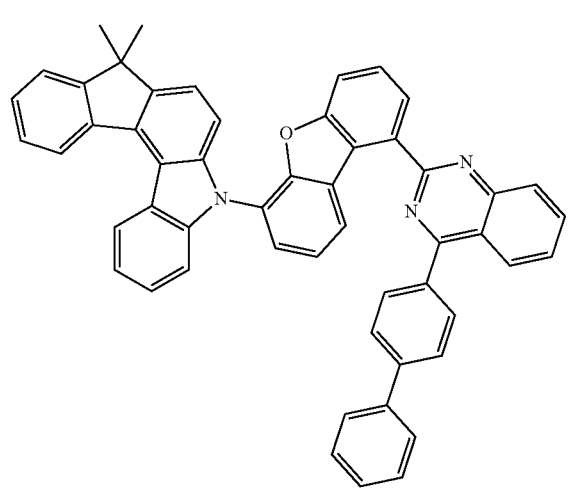
76
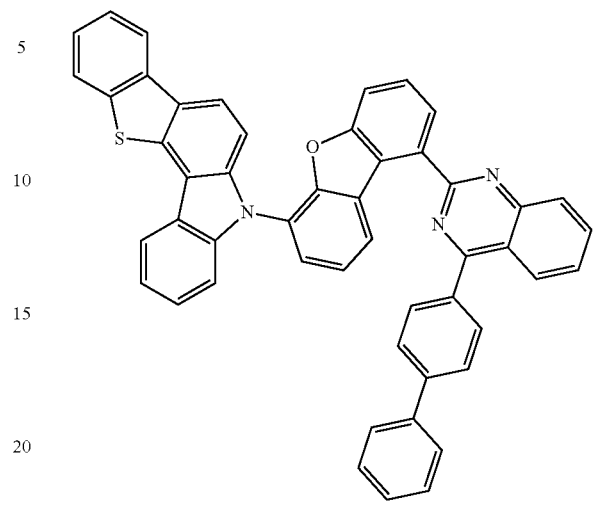
77
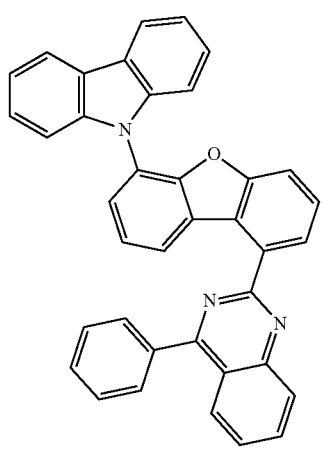
78
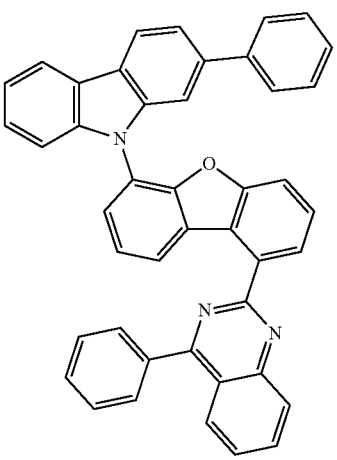

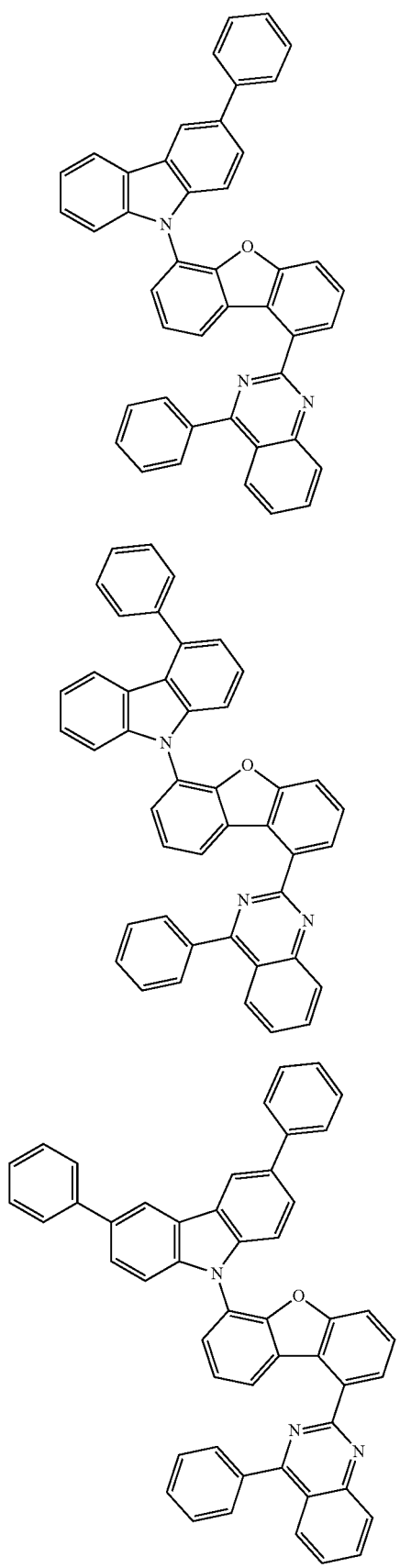
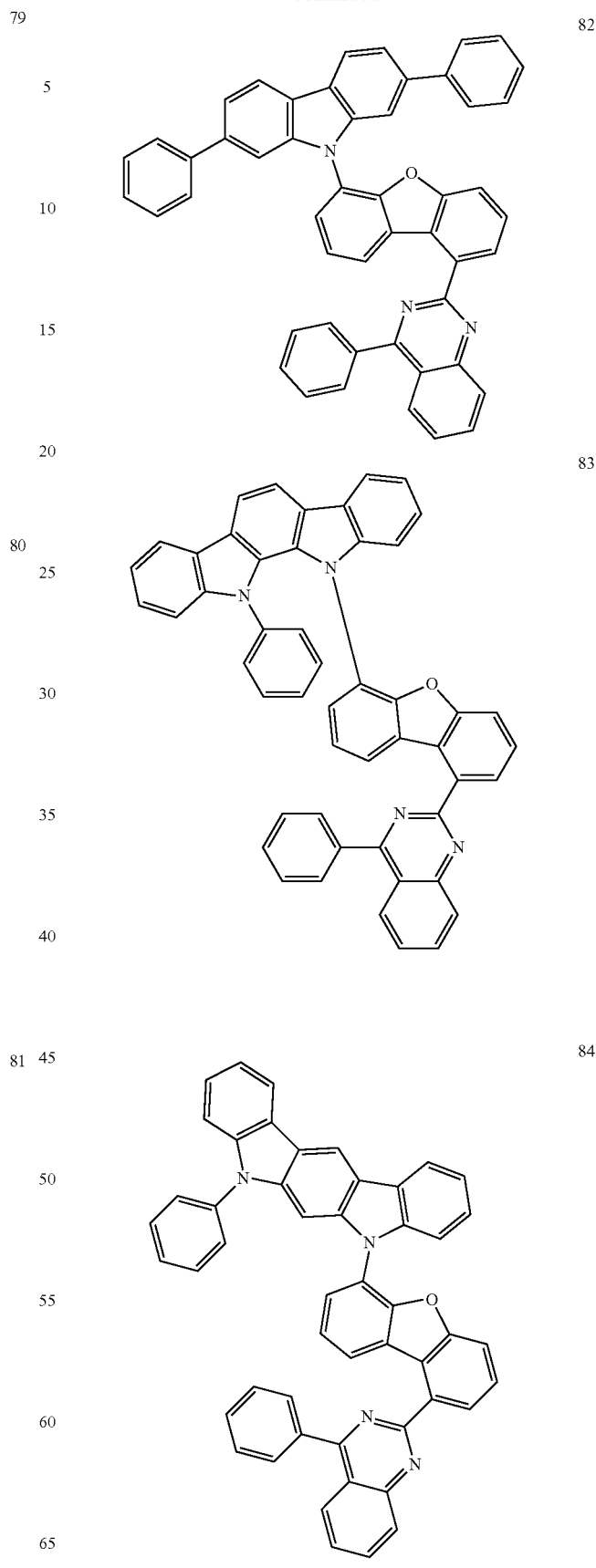

85
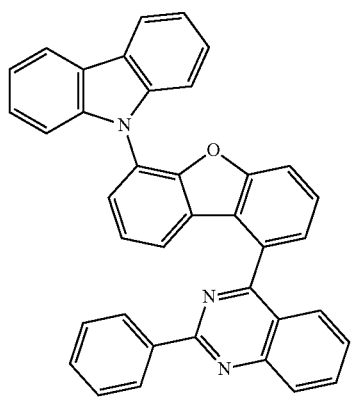
86
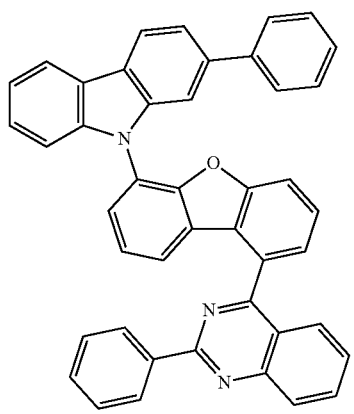
87
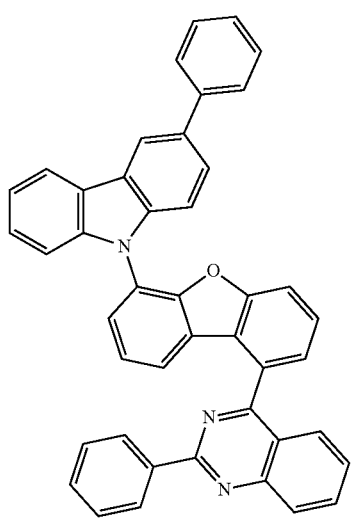
88
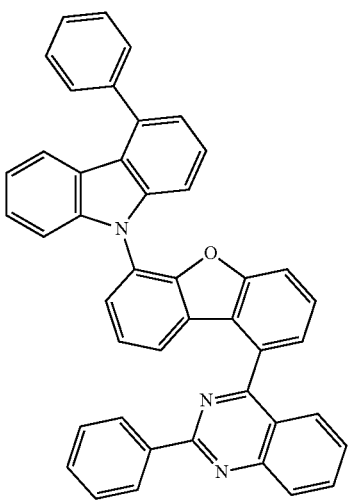
89
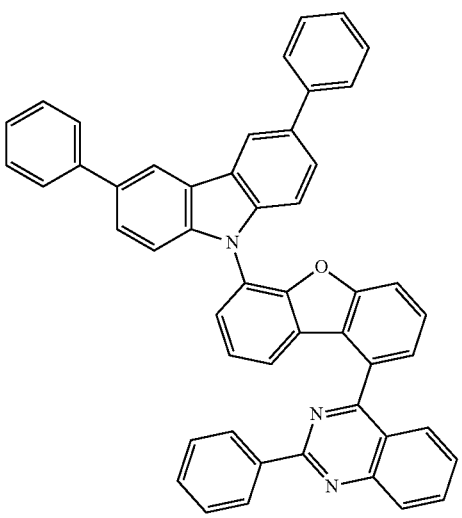
90
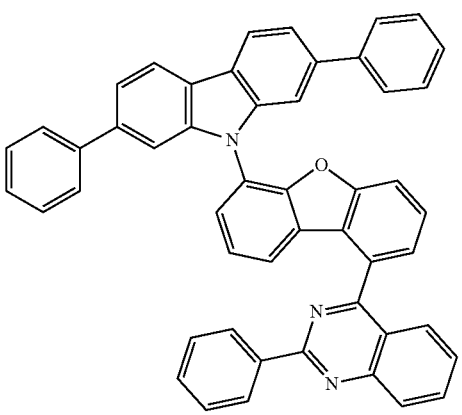

91
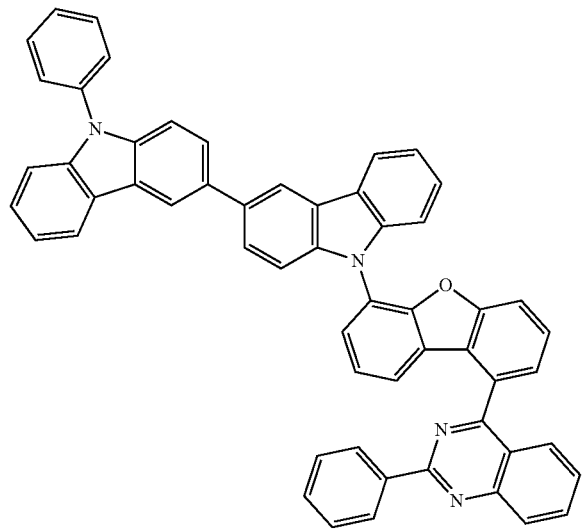
92
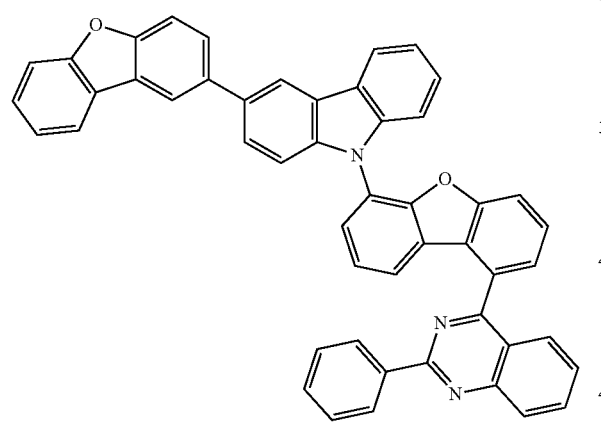
93
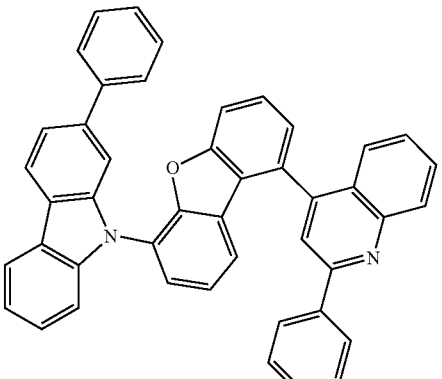
94
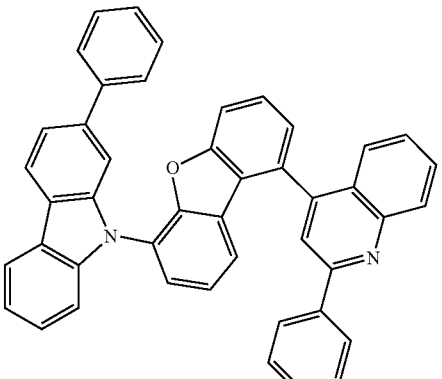
95
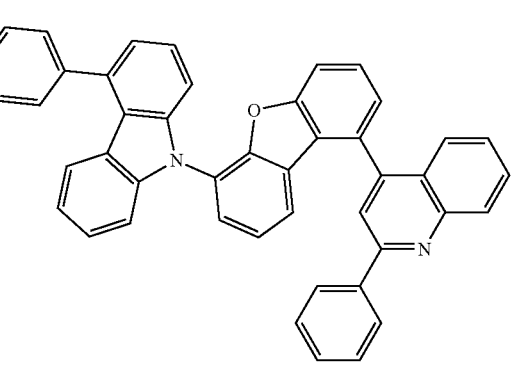
96
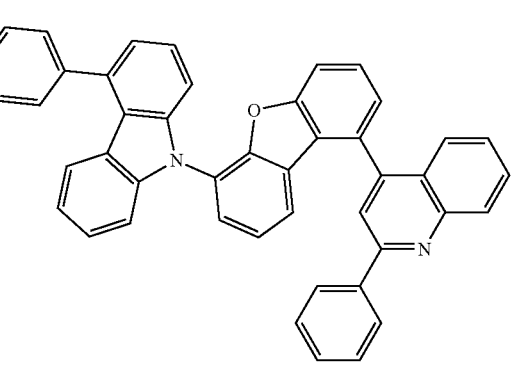
97
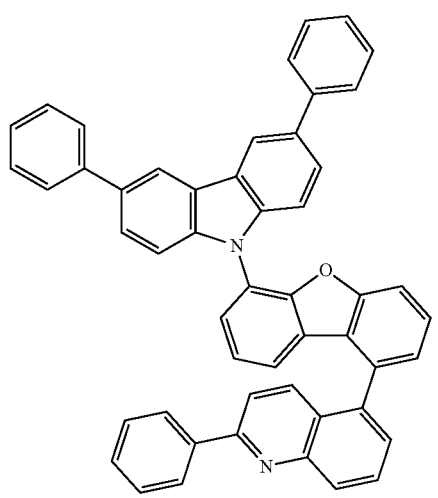

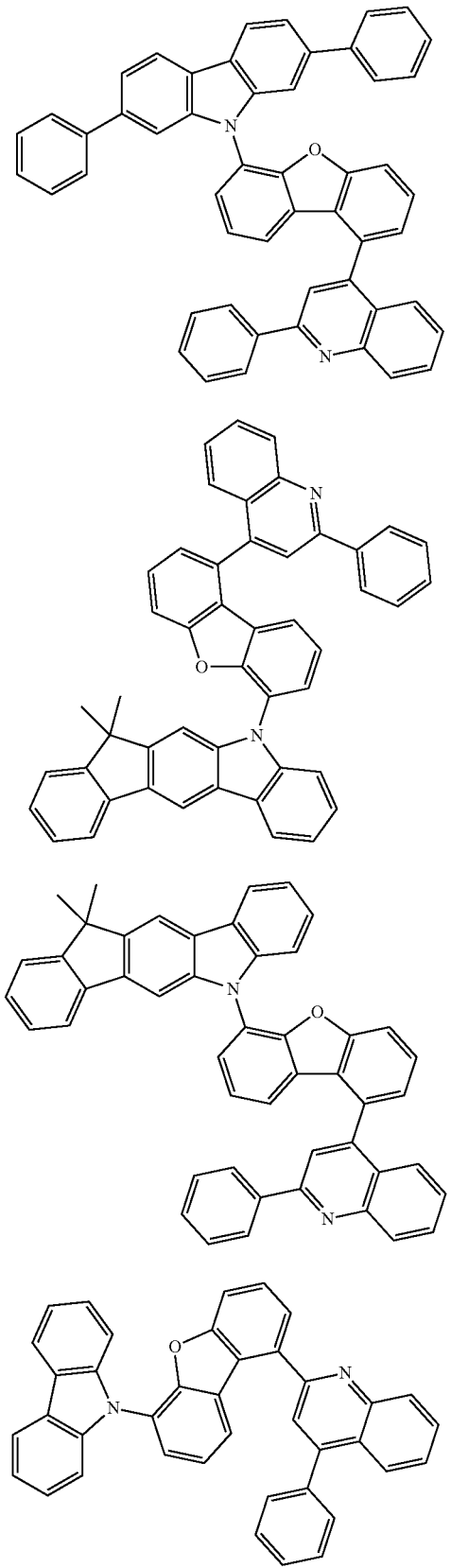
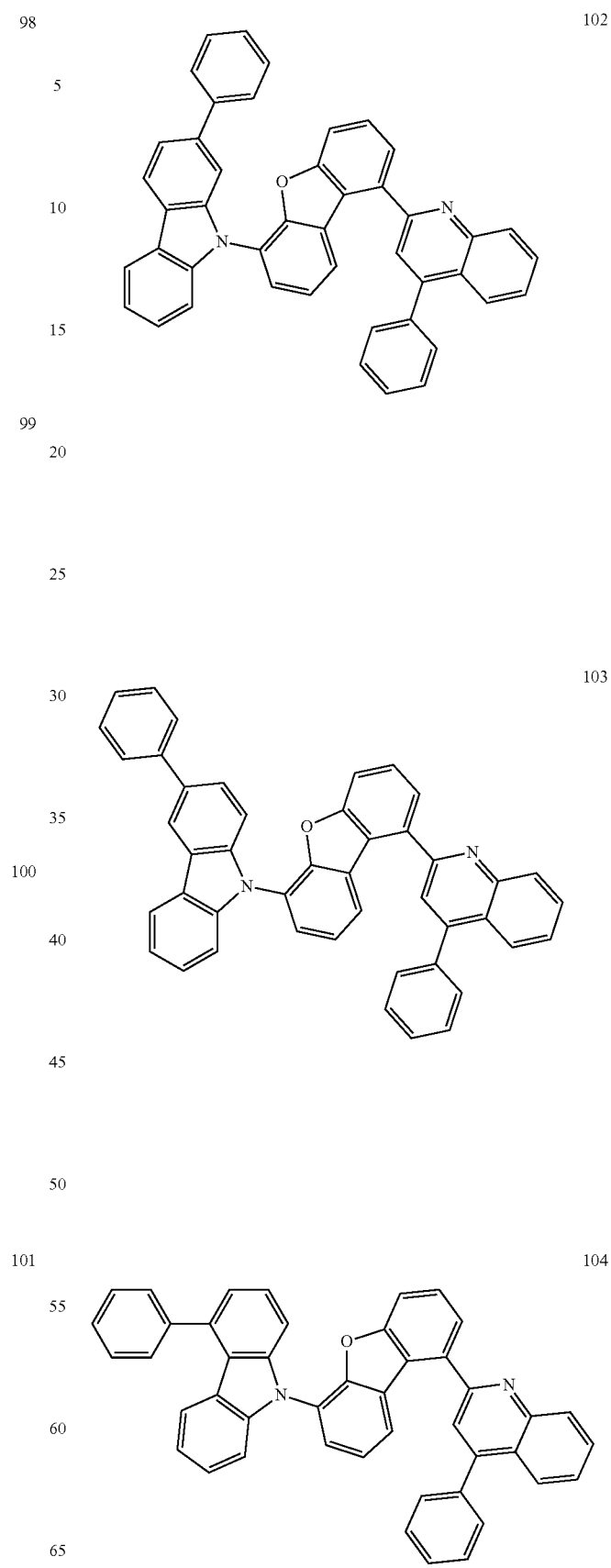

105
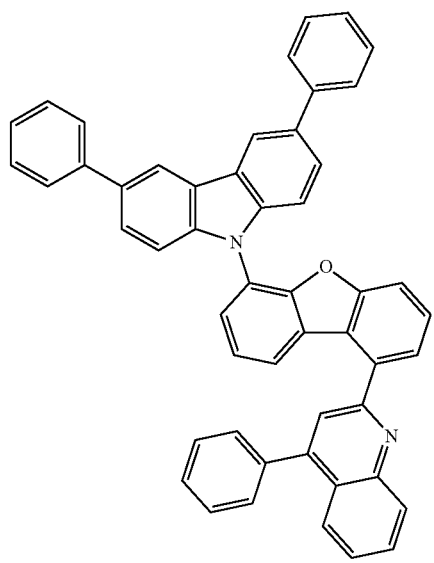
106
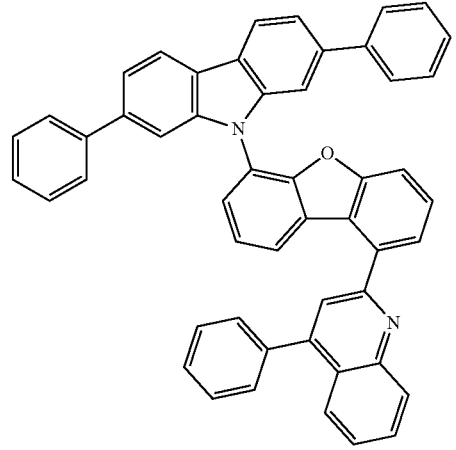
107
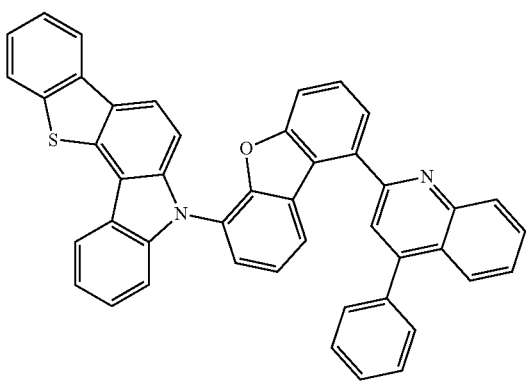
108
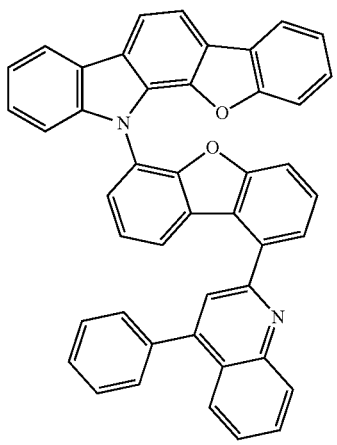
109
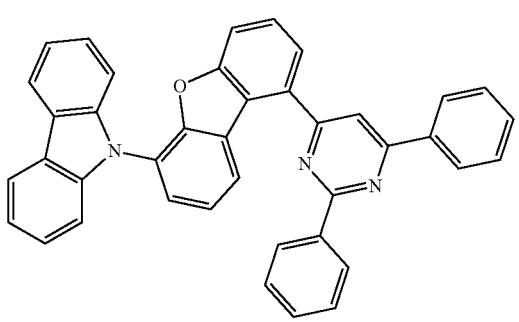
110
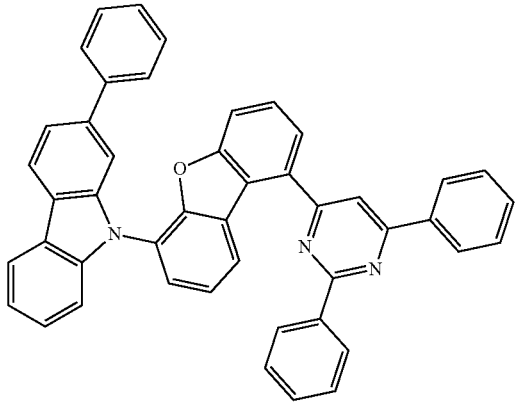
111
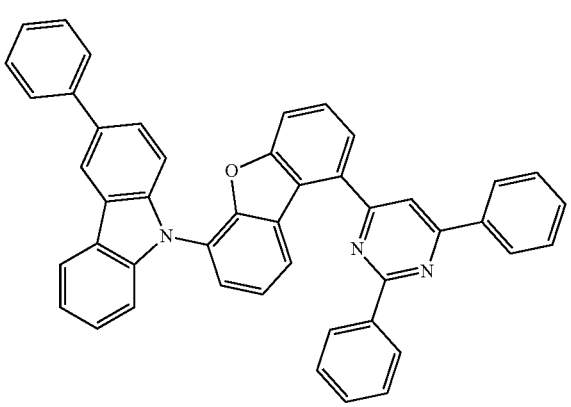

51
-continued

52
-continued

118
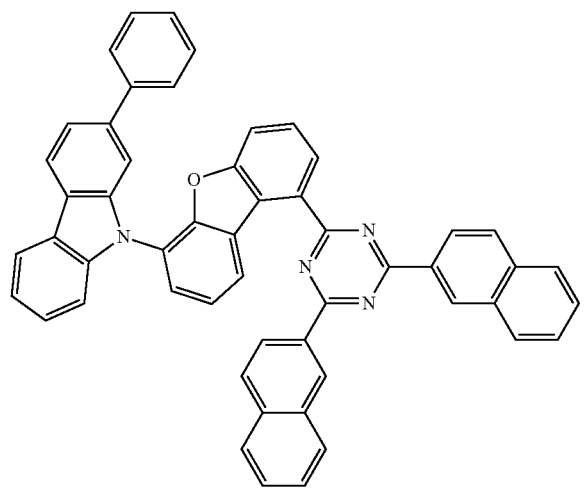
119
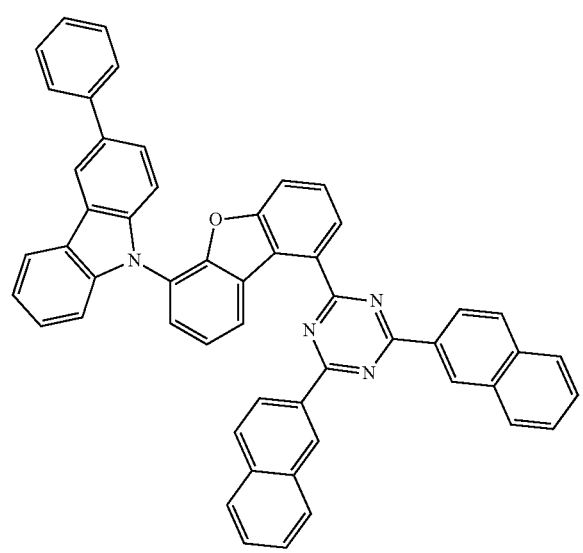
120
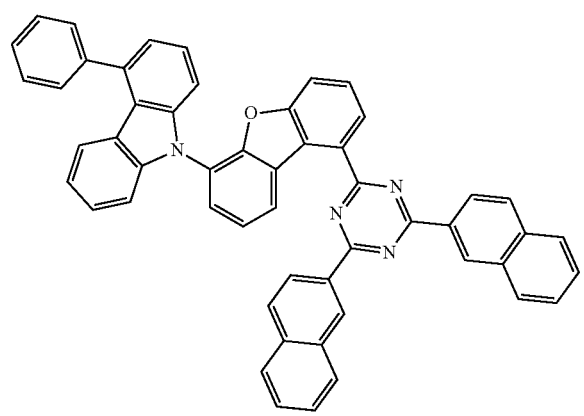
121
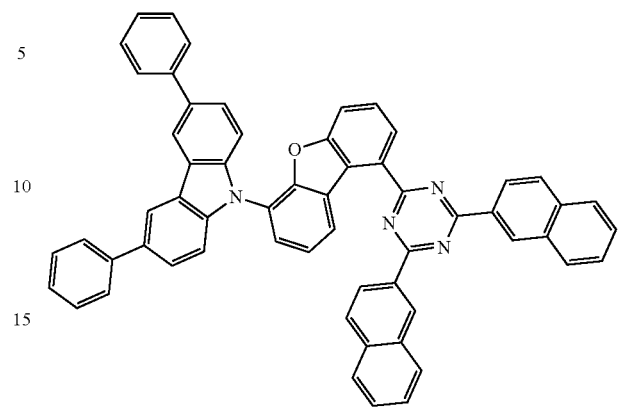
122
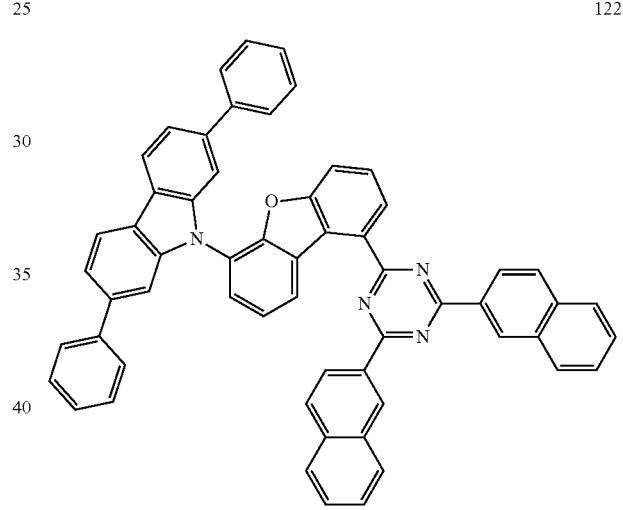
123
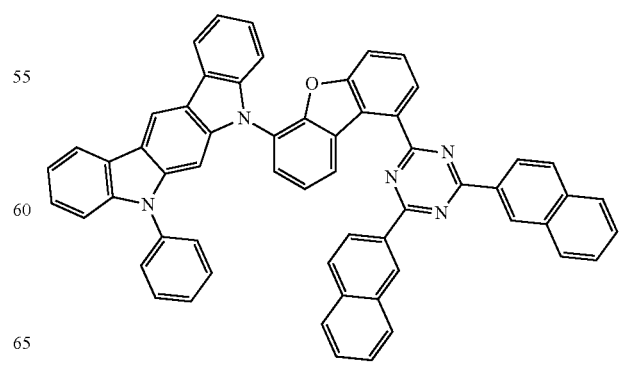

124
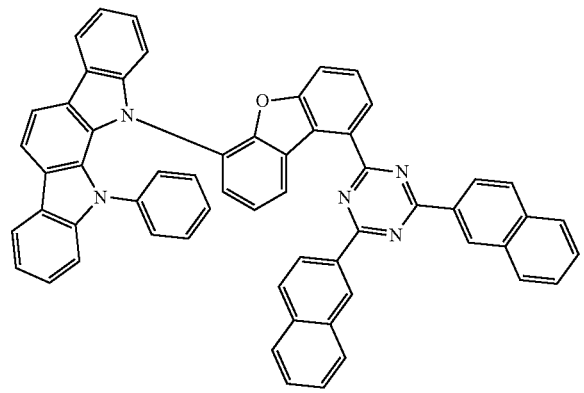
125
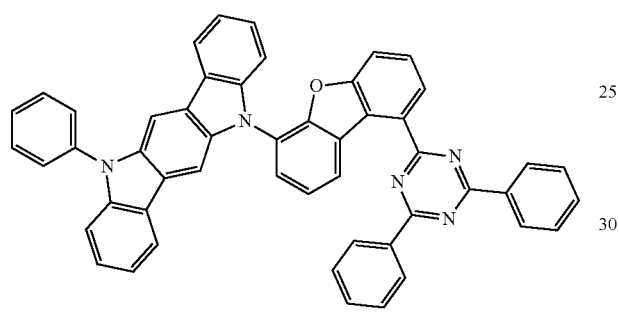
126
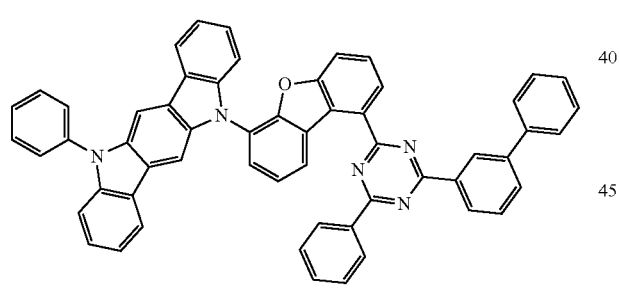
127
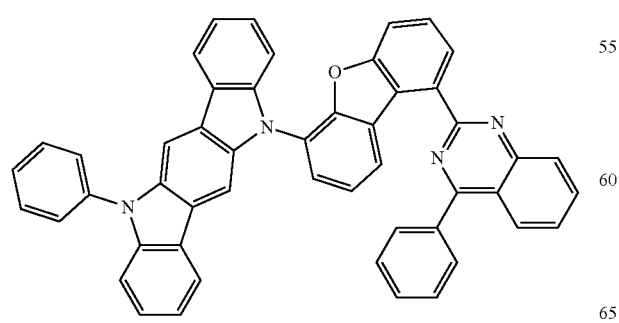
128
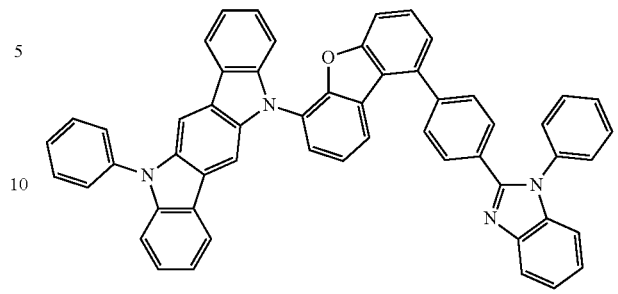
129
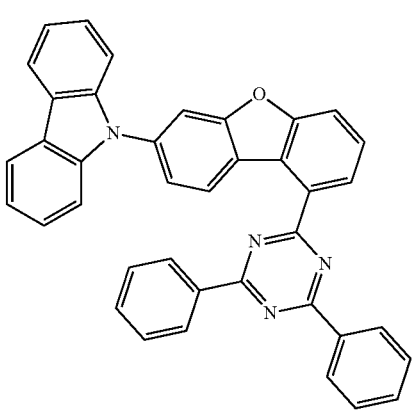
130
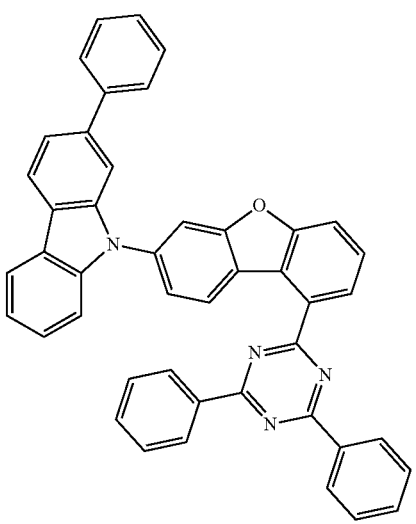

131 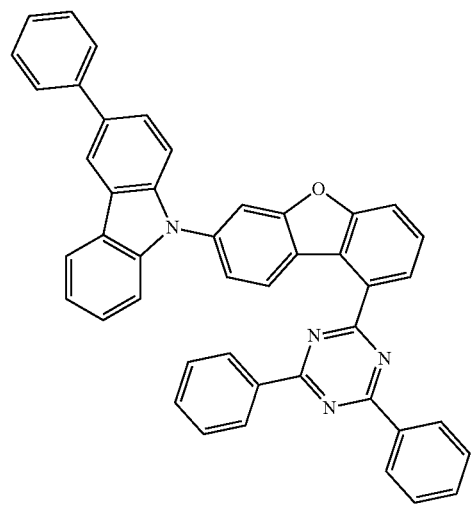
132 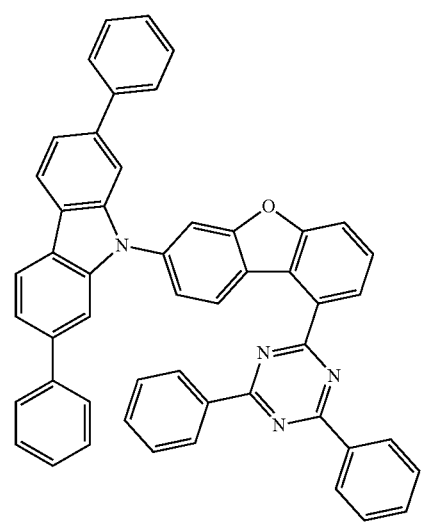
133 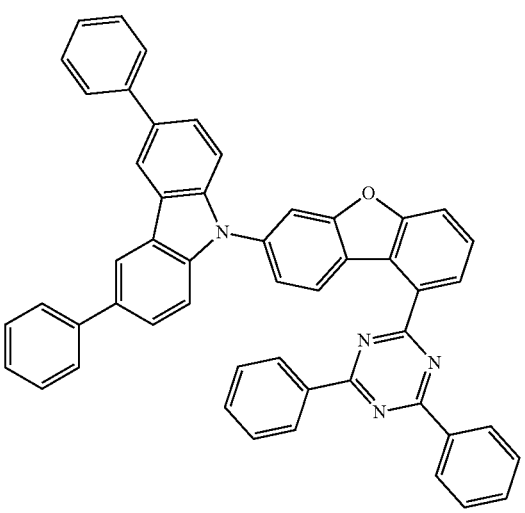
134 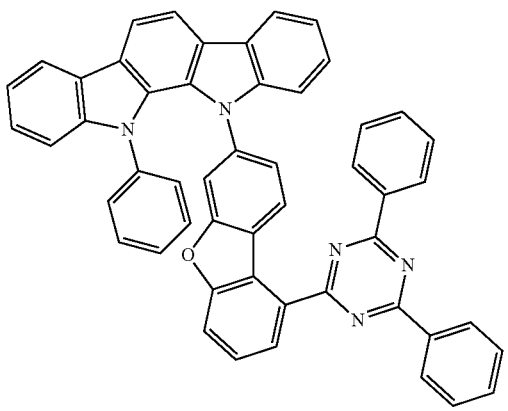
135 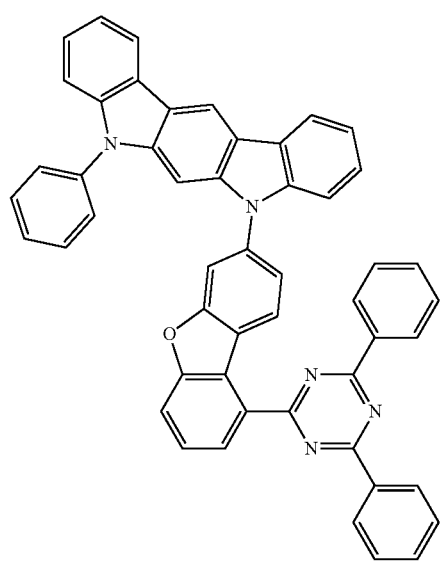
136 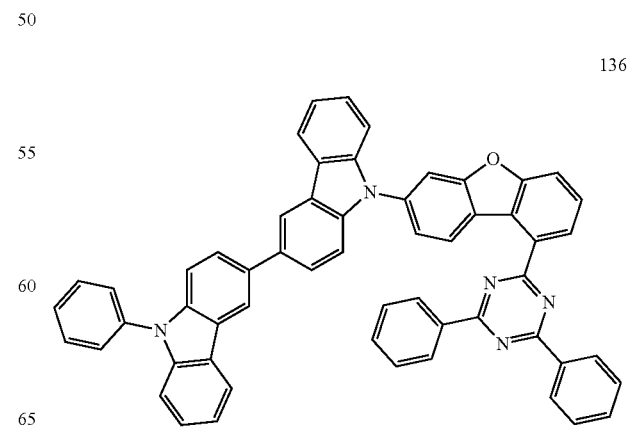

137
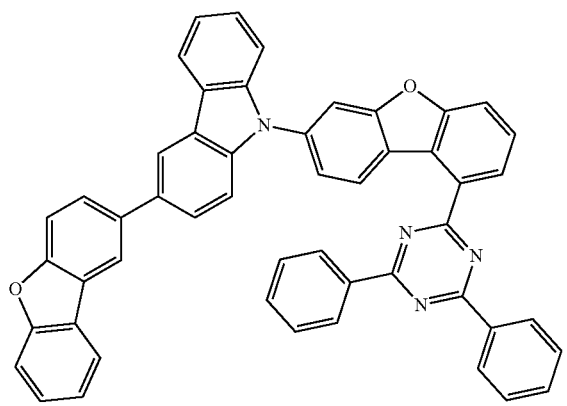
138
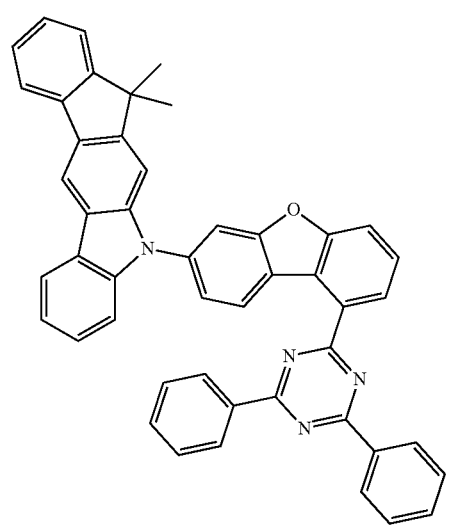
139
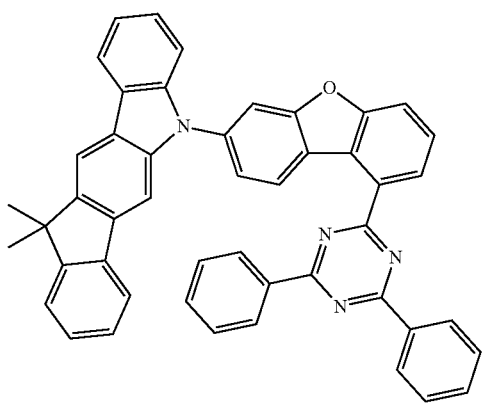
140
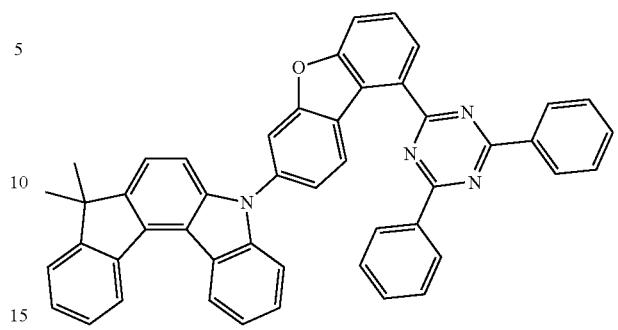
141
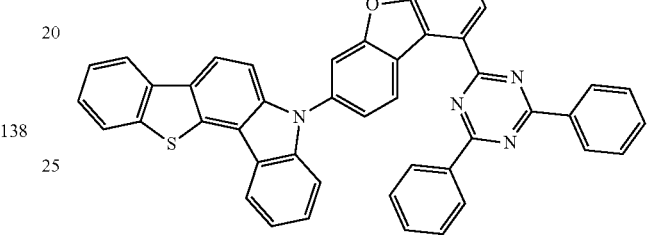
142
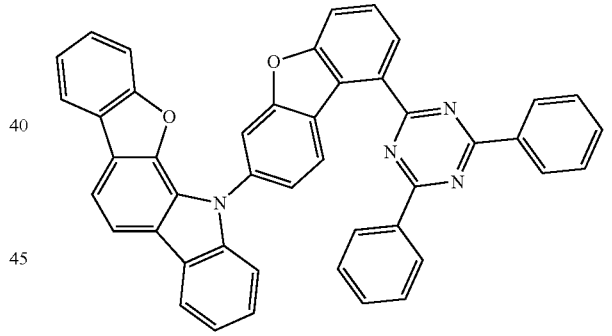
143
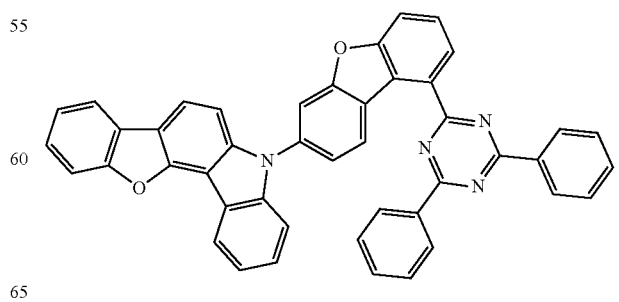

144
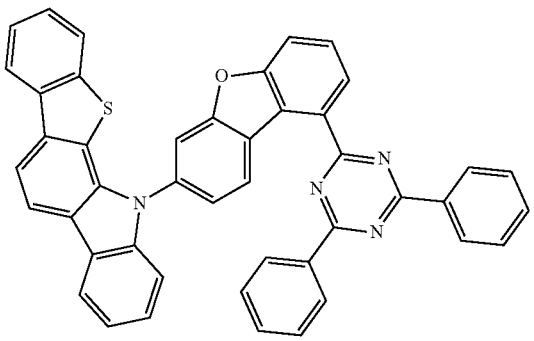
145
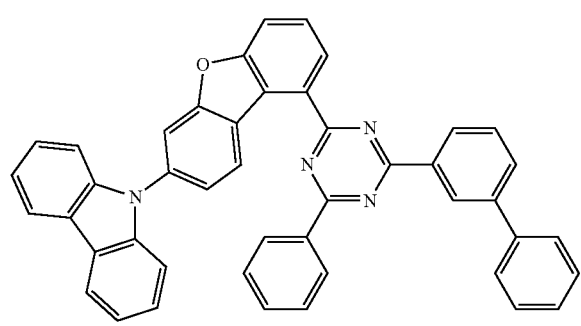
146
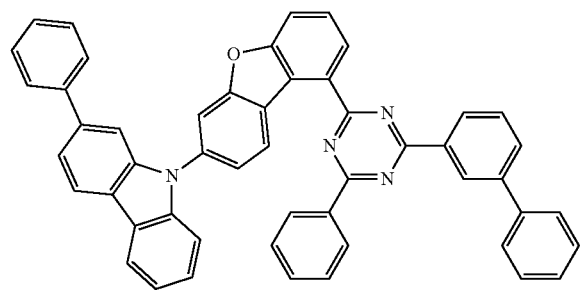
147
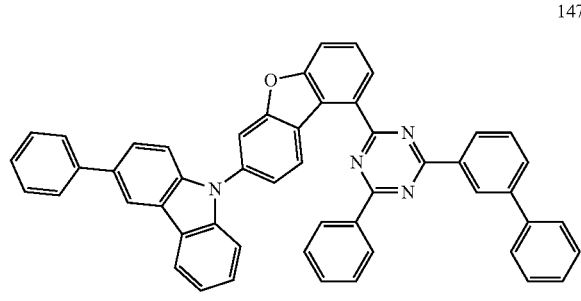
148
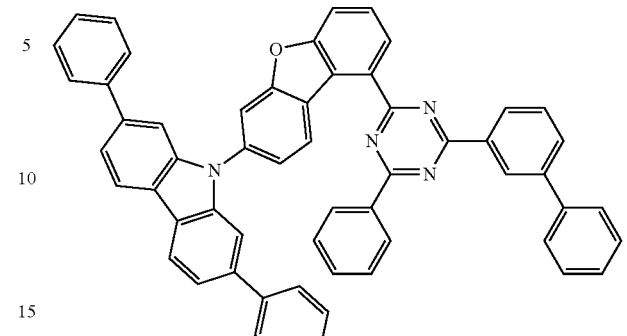
149
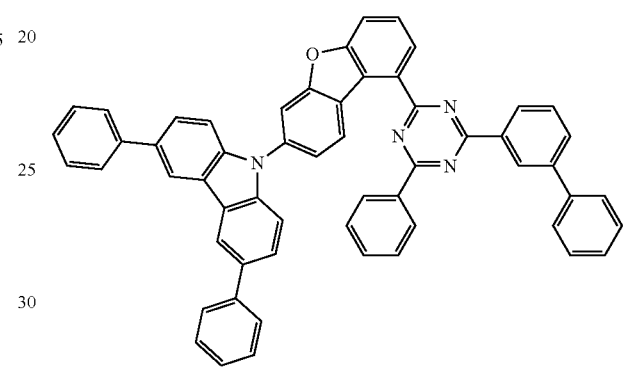
150
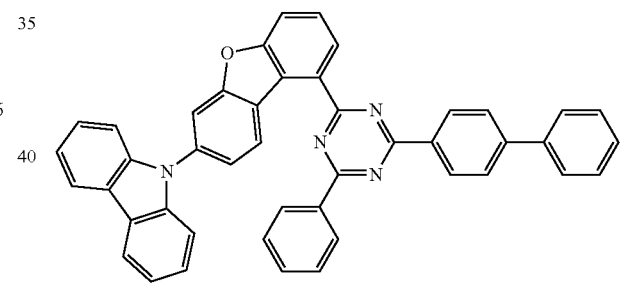
151
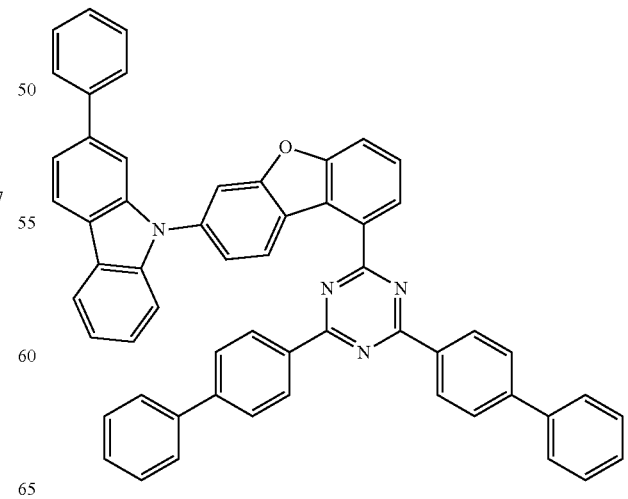

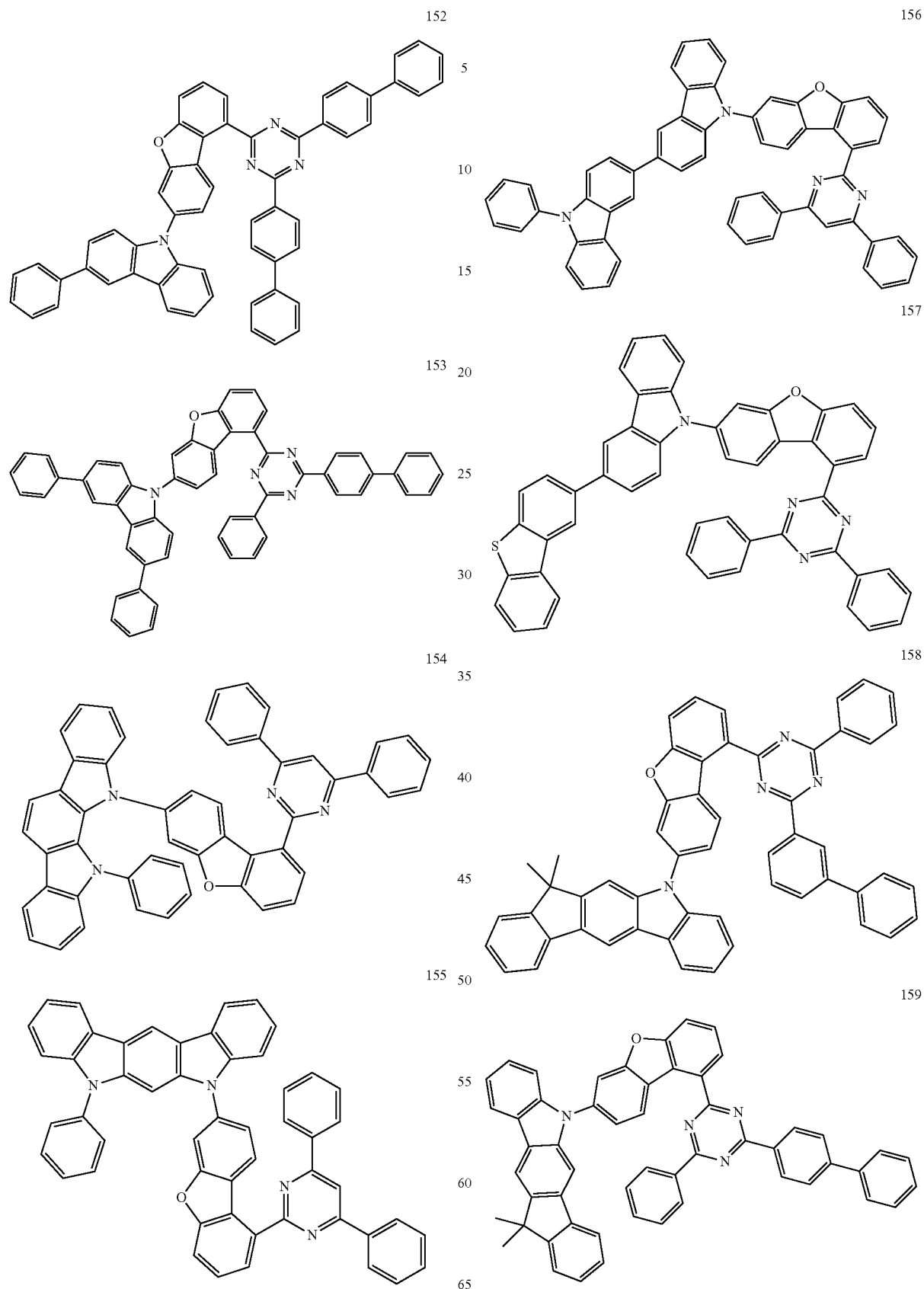

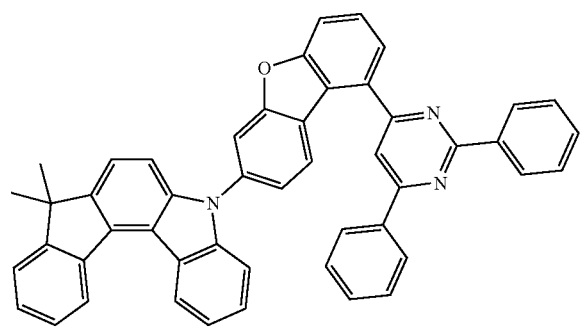
160
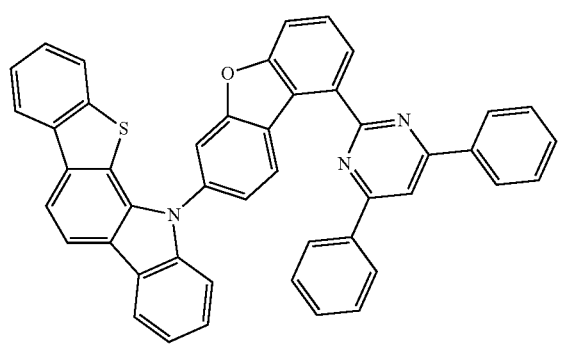
164
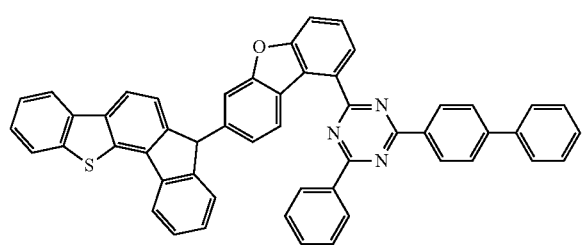
161
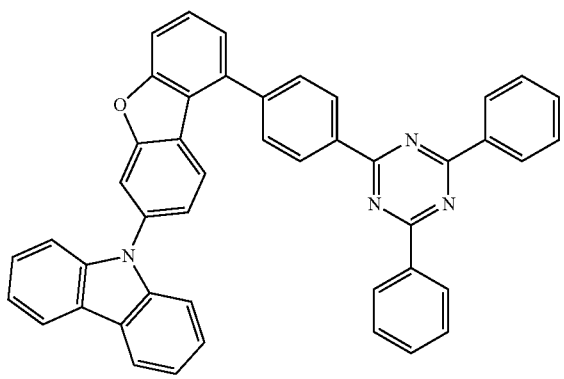
165
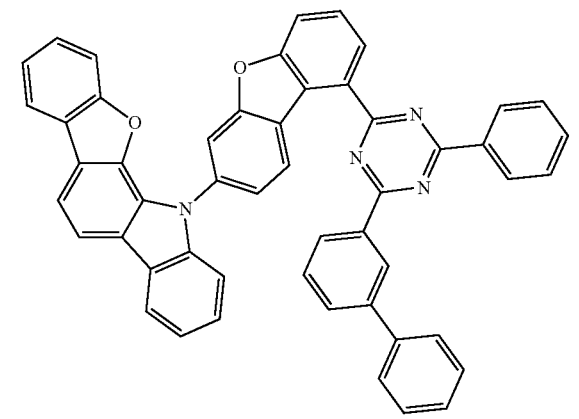
162
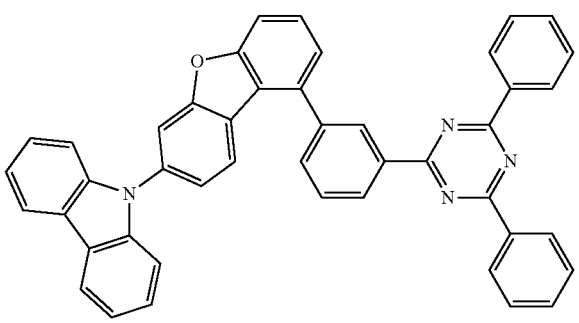
166
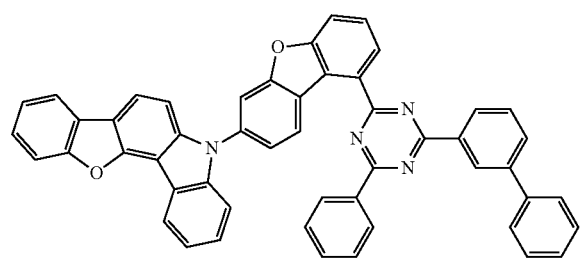
163
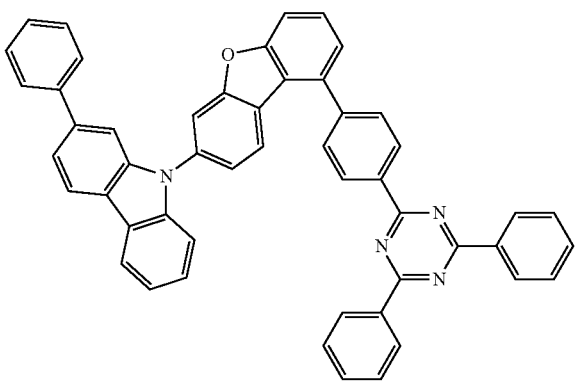
167

168 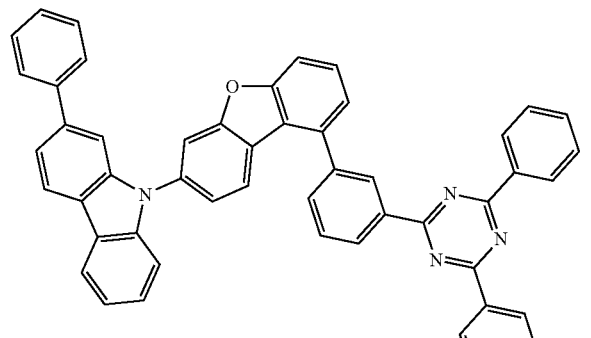
169 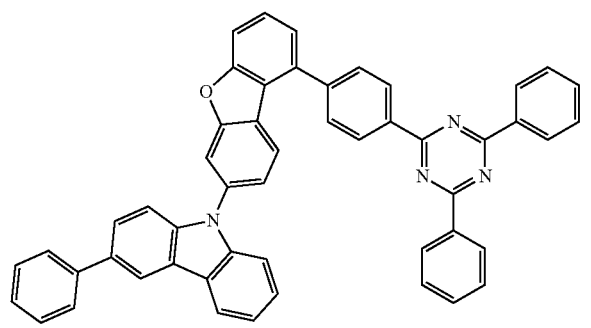
170 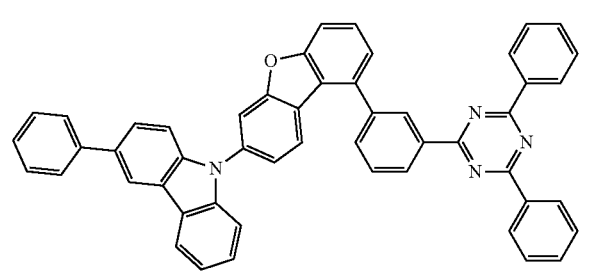
171 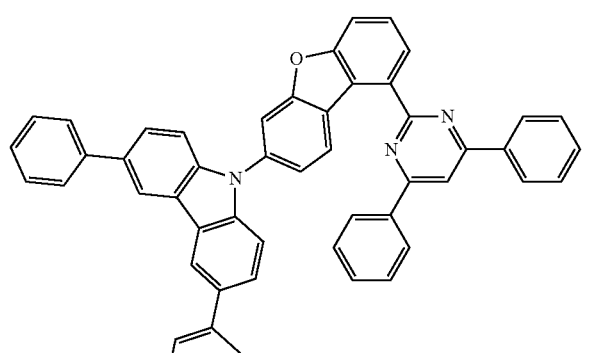
172 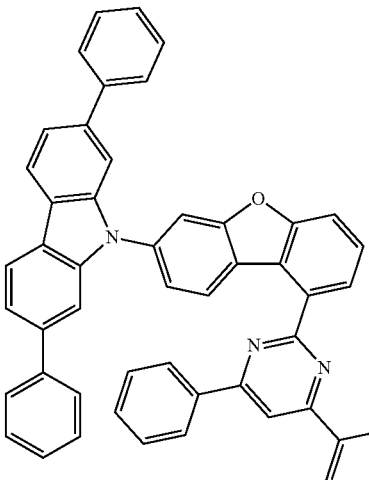
173 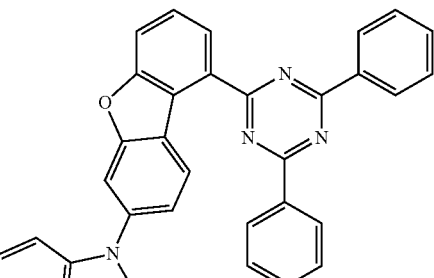
174 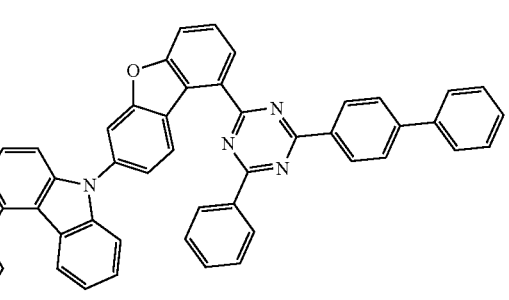
175 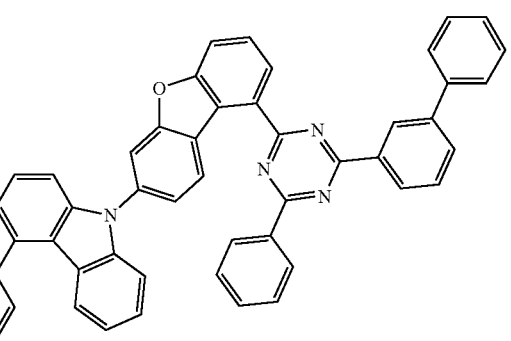

176
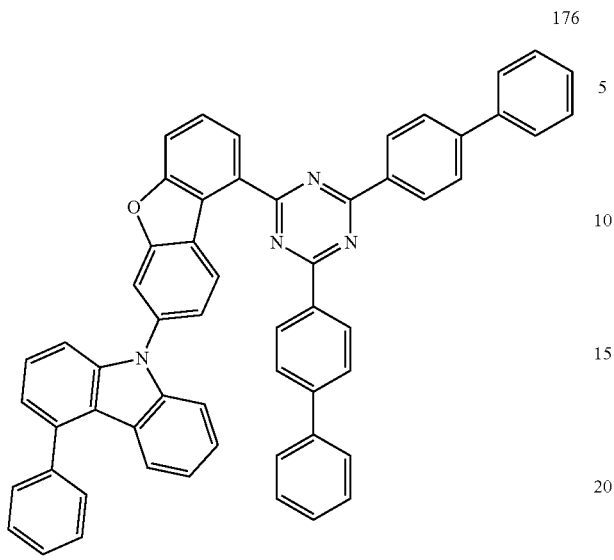
177
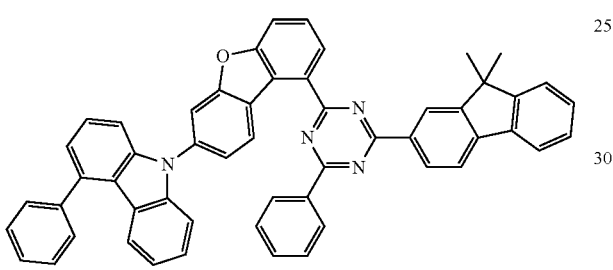
178
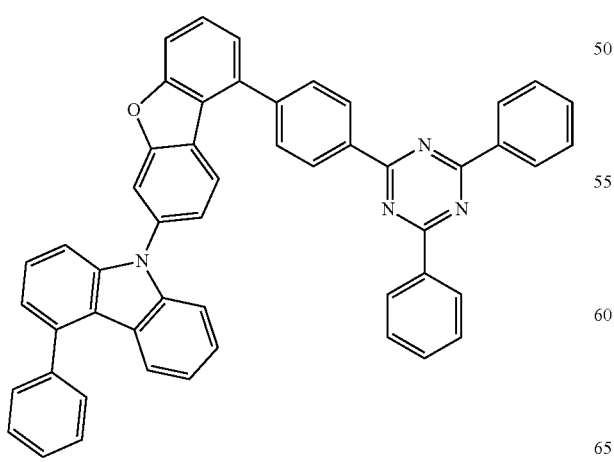
179
180
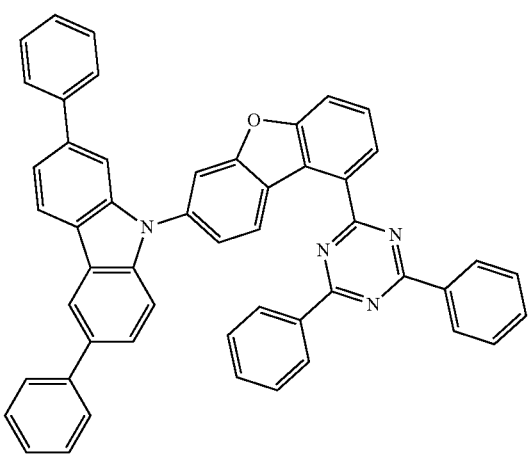
181
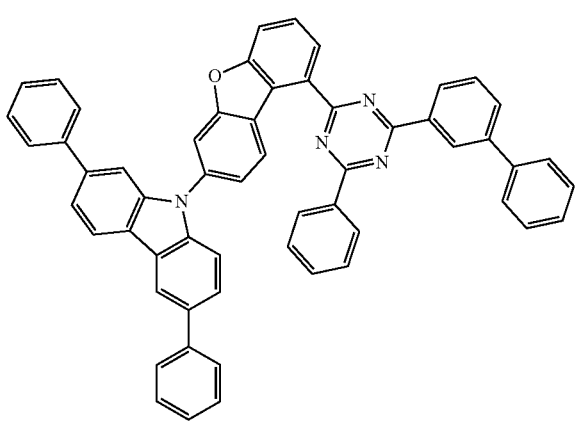
182
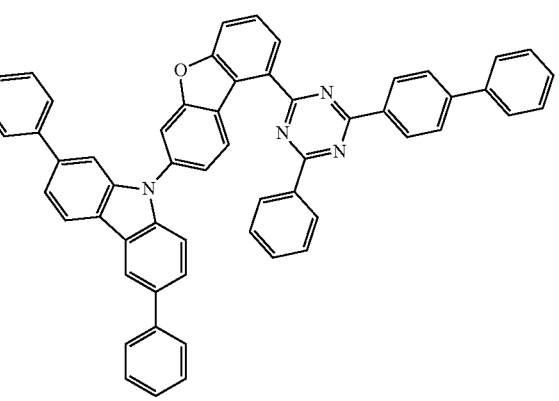

-continued
183
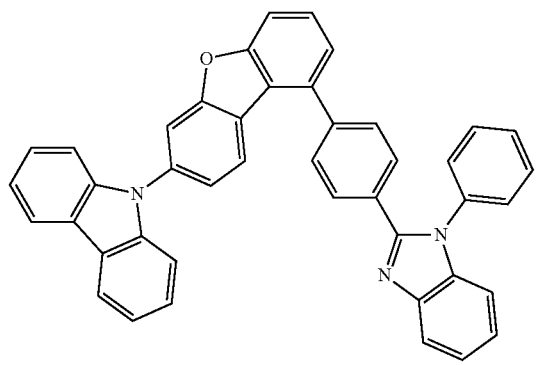
184
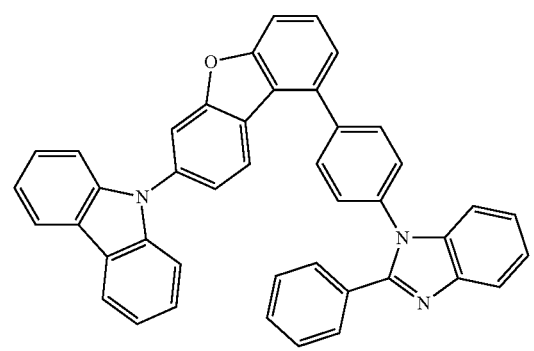
185
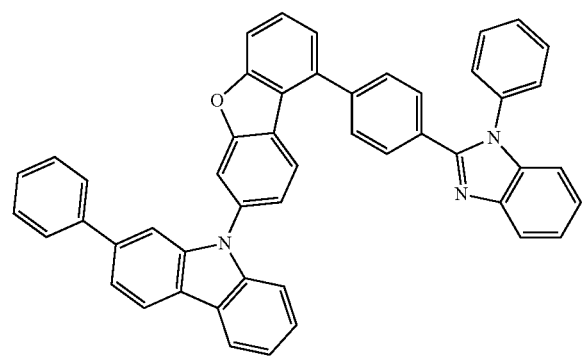
186
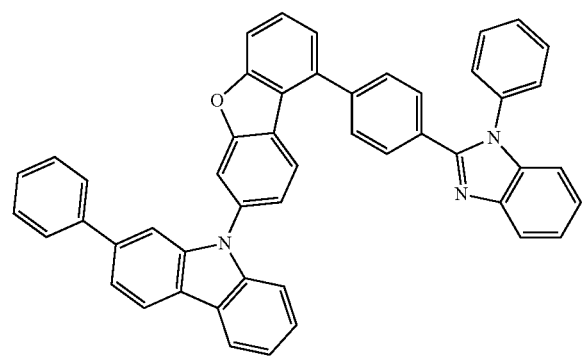
-continued
187
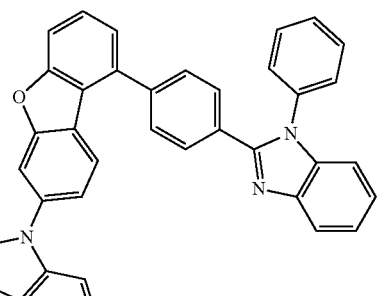
188
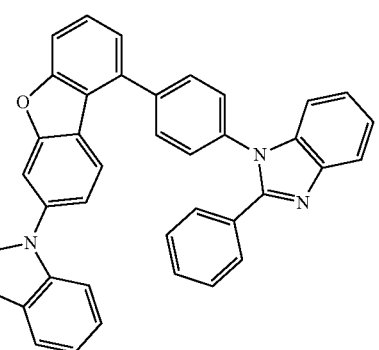
189
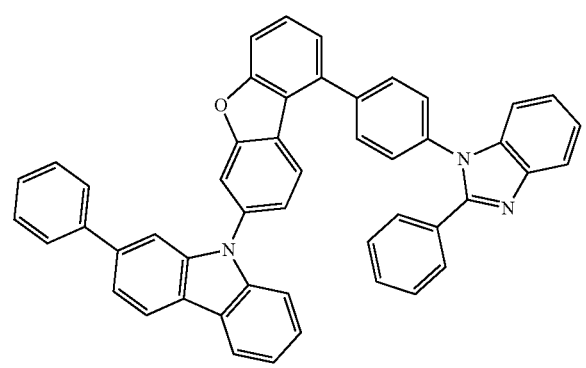
190
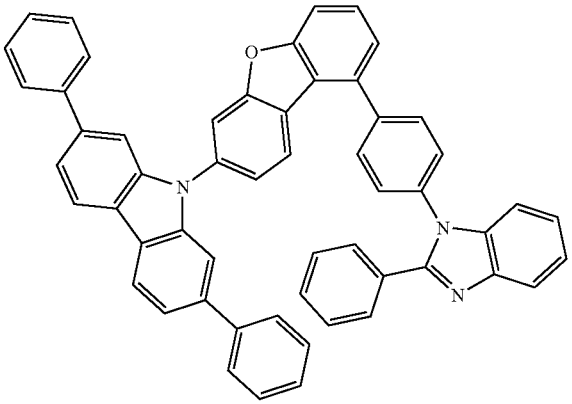

191
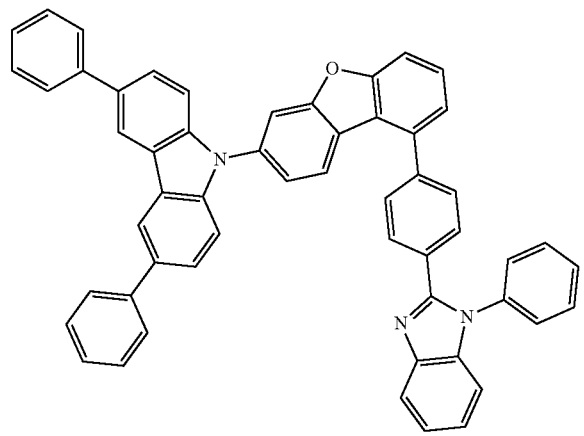
192
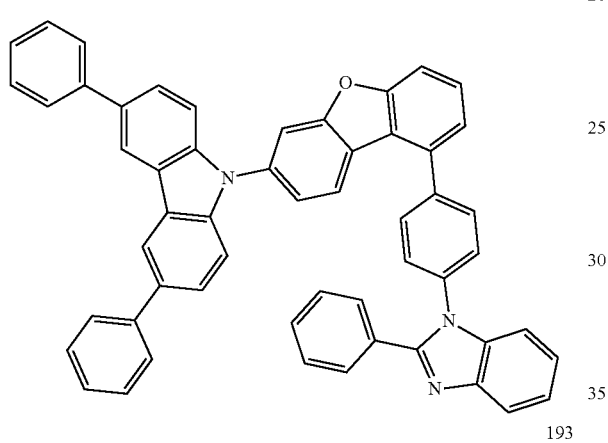
193
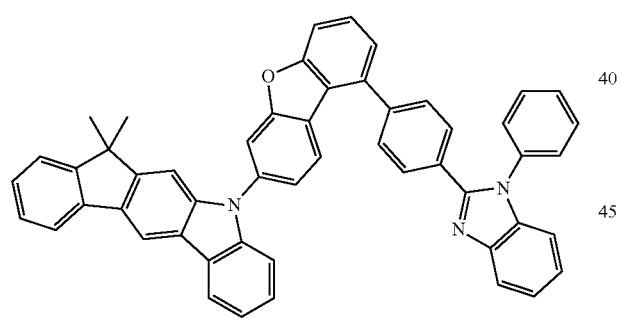
194
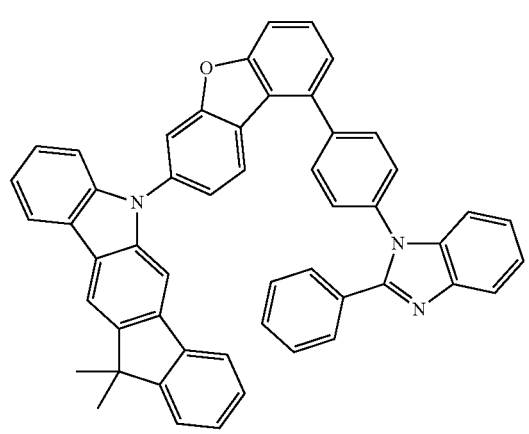
195
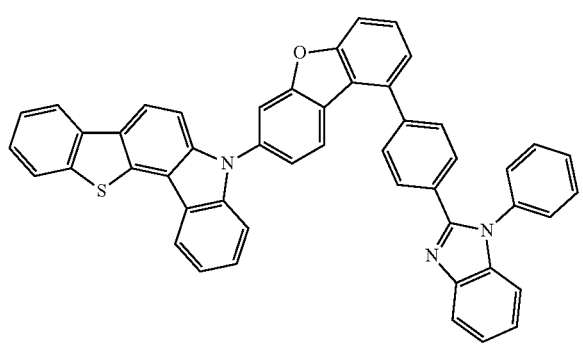
196
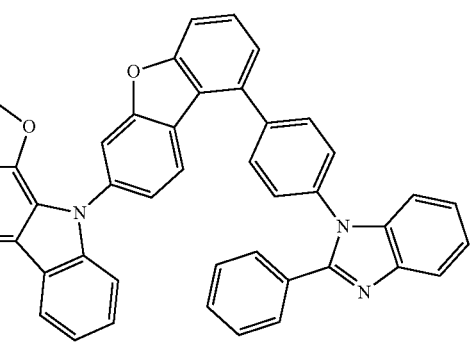
197
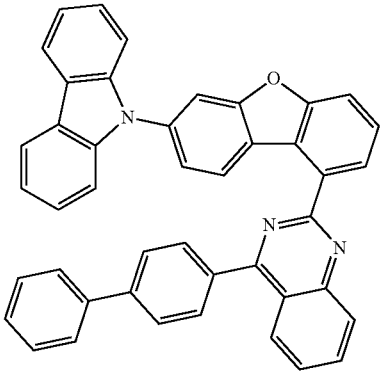
198
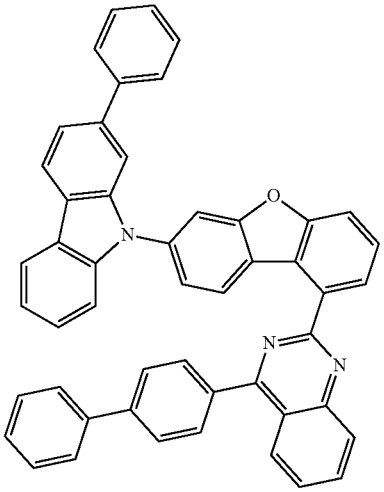

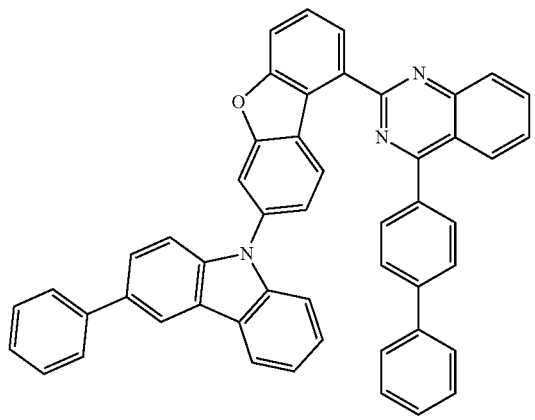
199
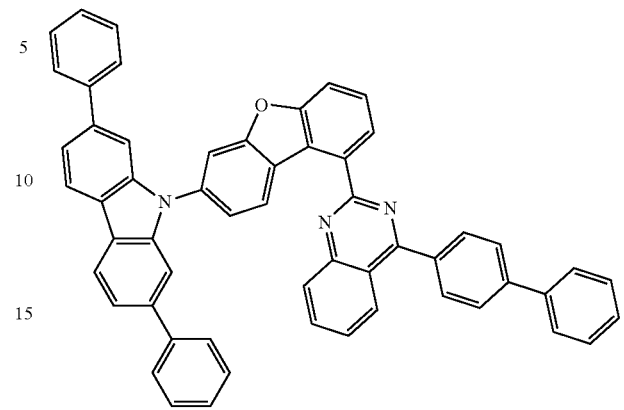
202
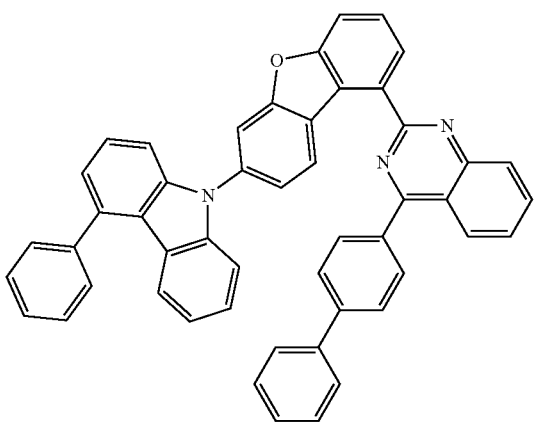
200
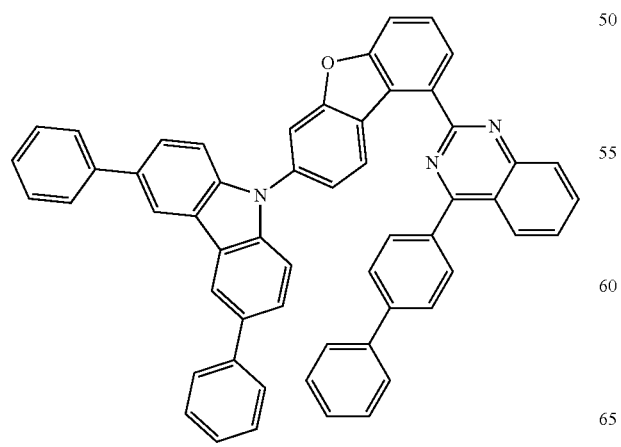
201
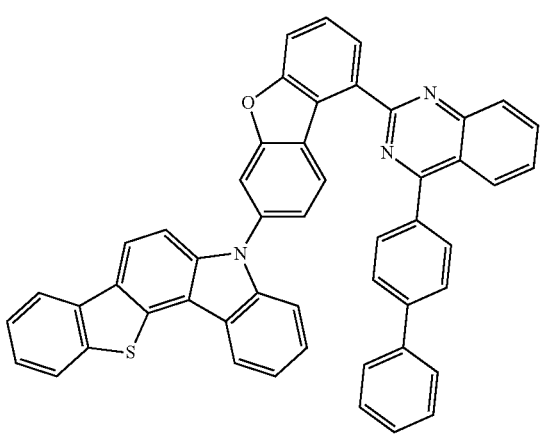
203
204

205 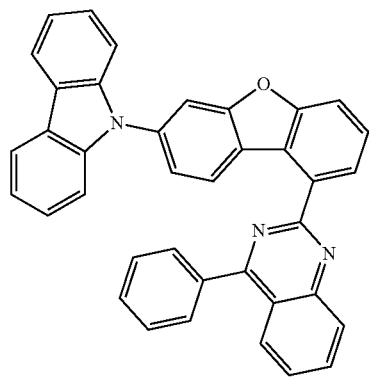
206 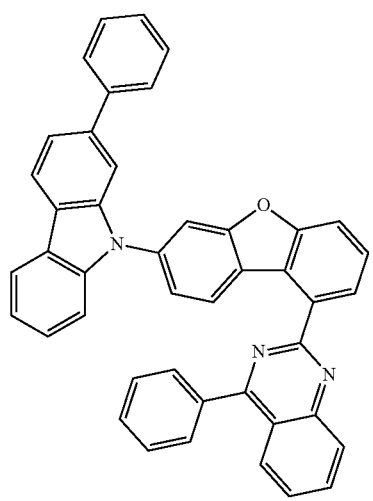
207 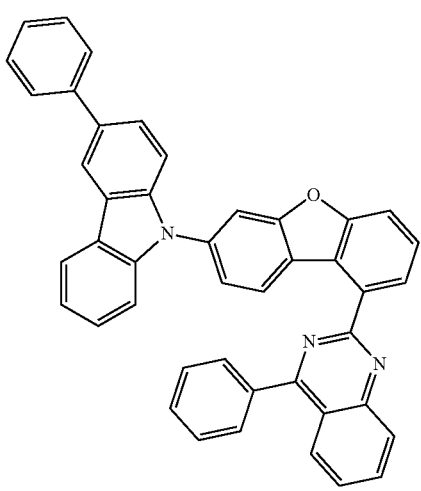
208 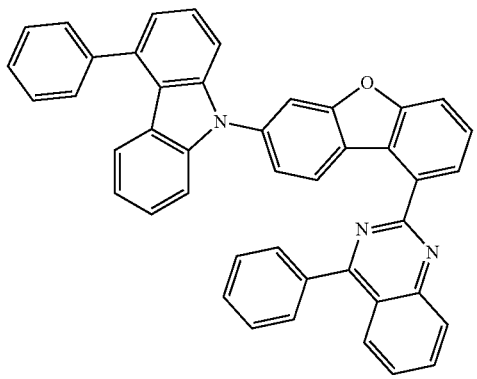
209 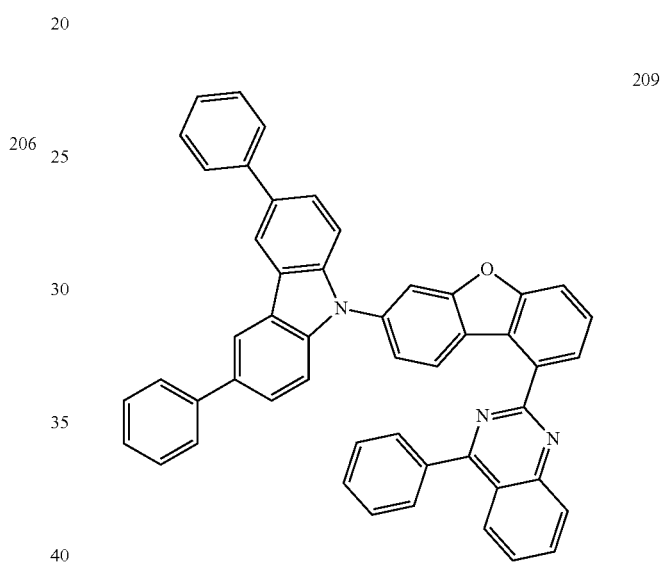
210 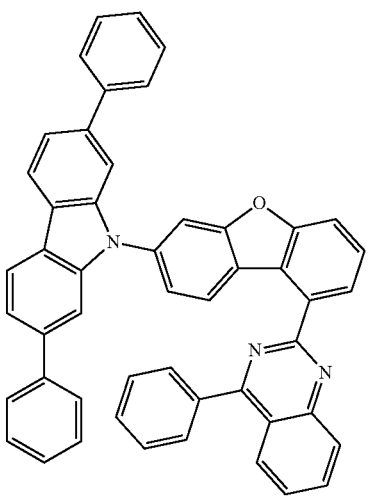

211
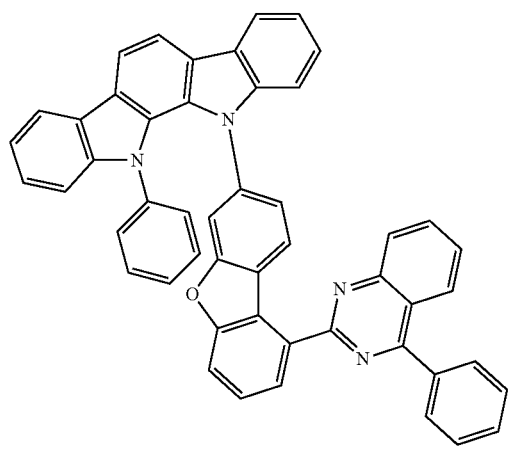
212
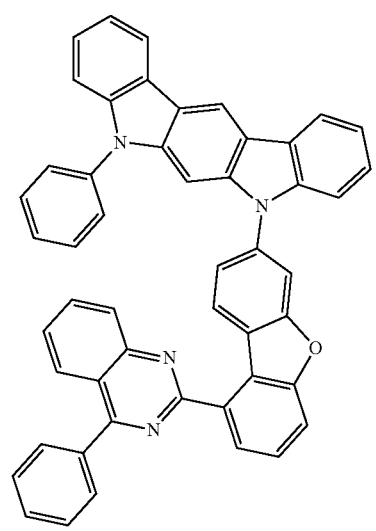
213
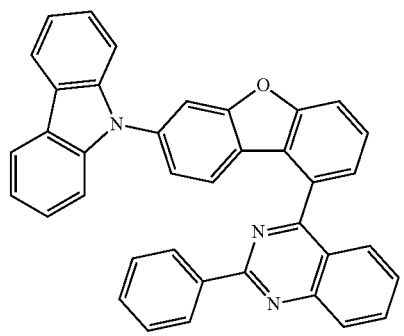
214
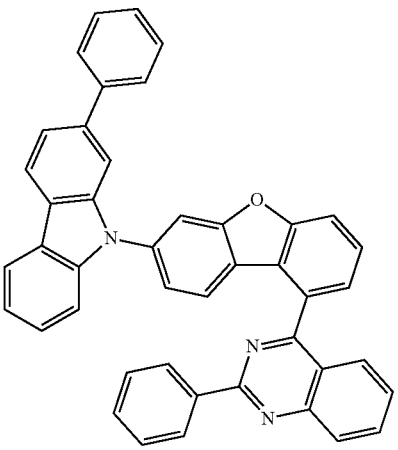
215
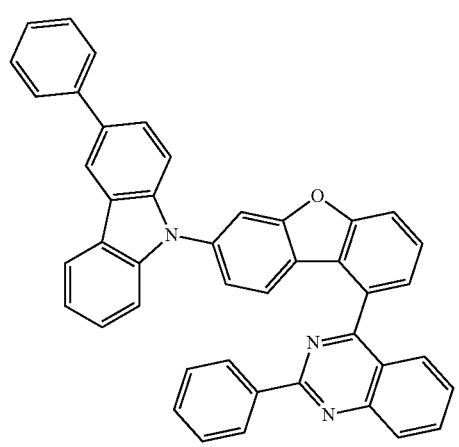
216
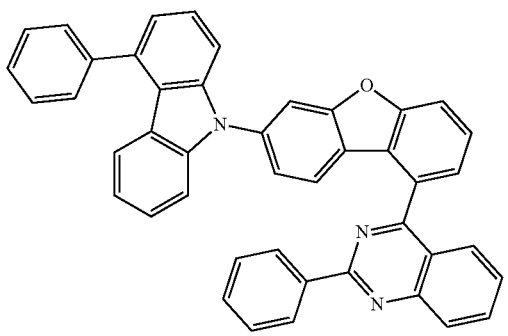
217
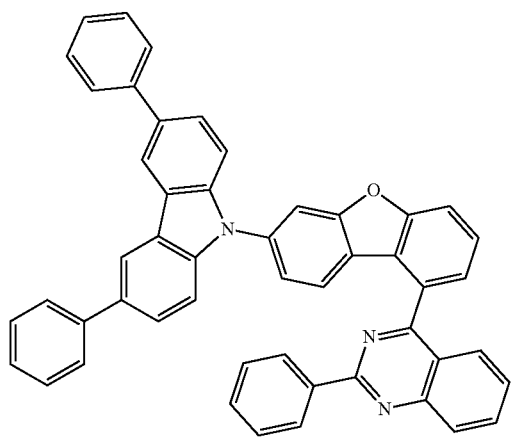

81
-continued
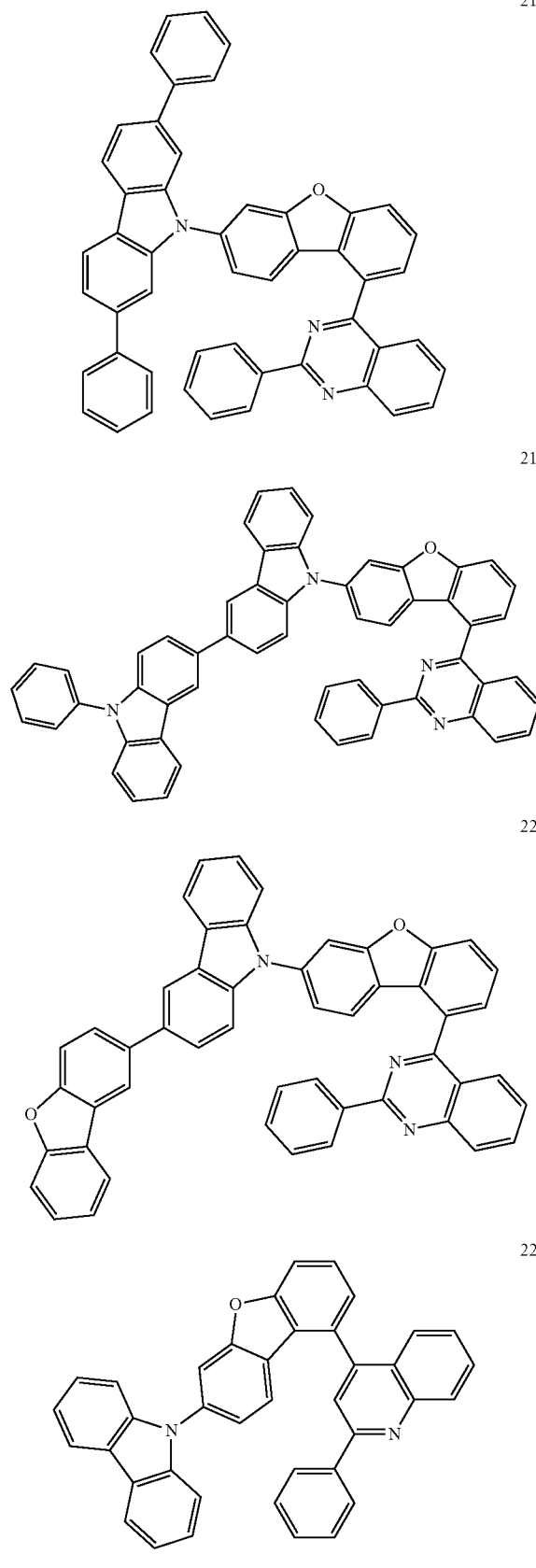
218
219
220
221
82
-continued
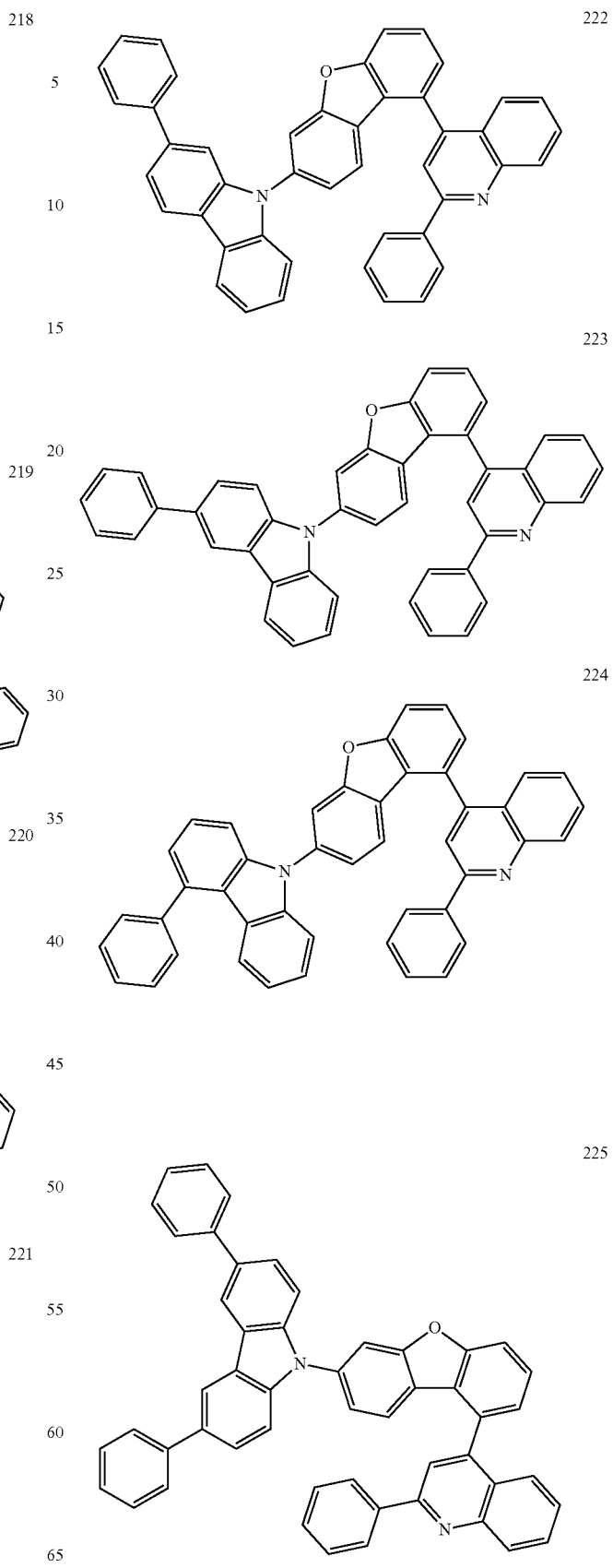
222
223
224
225

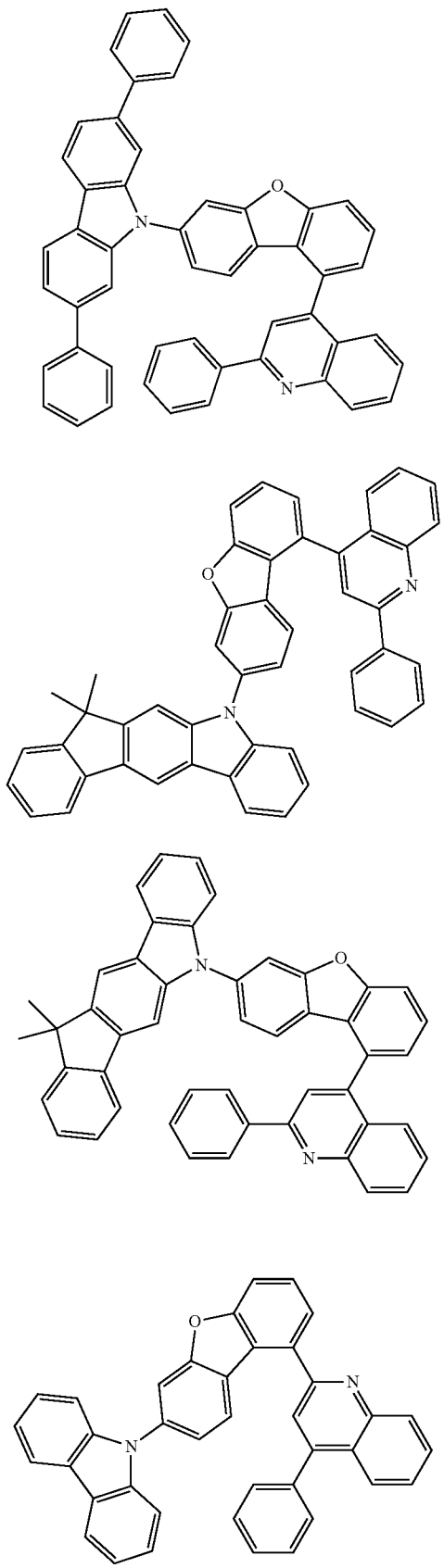
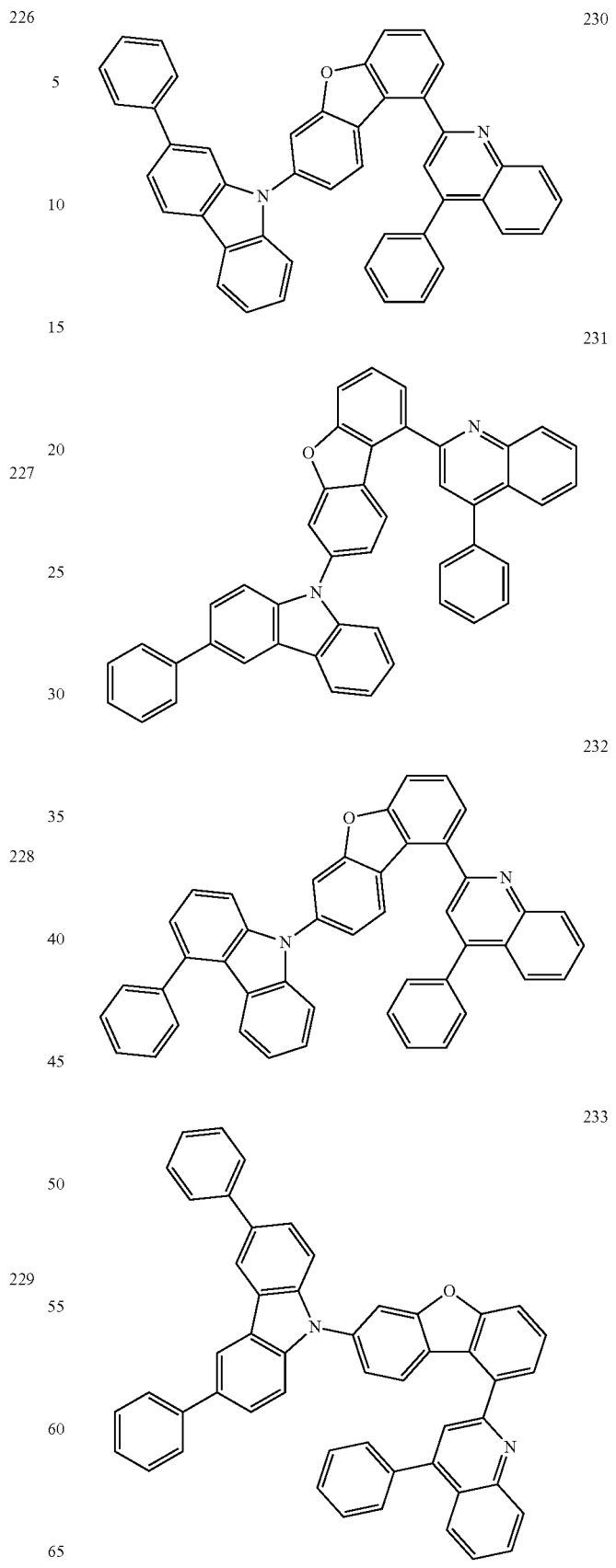

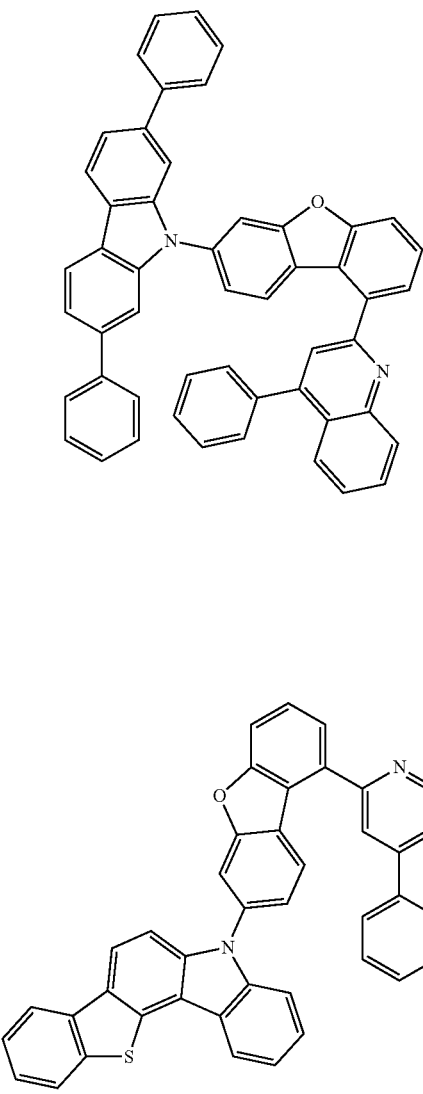
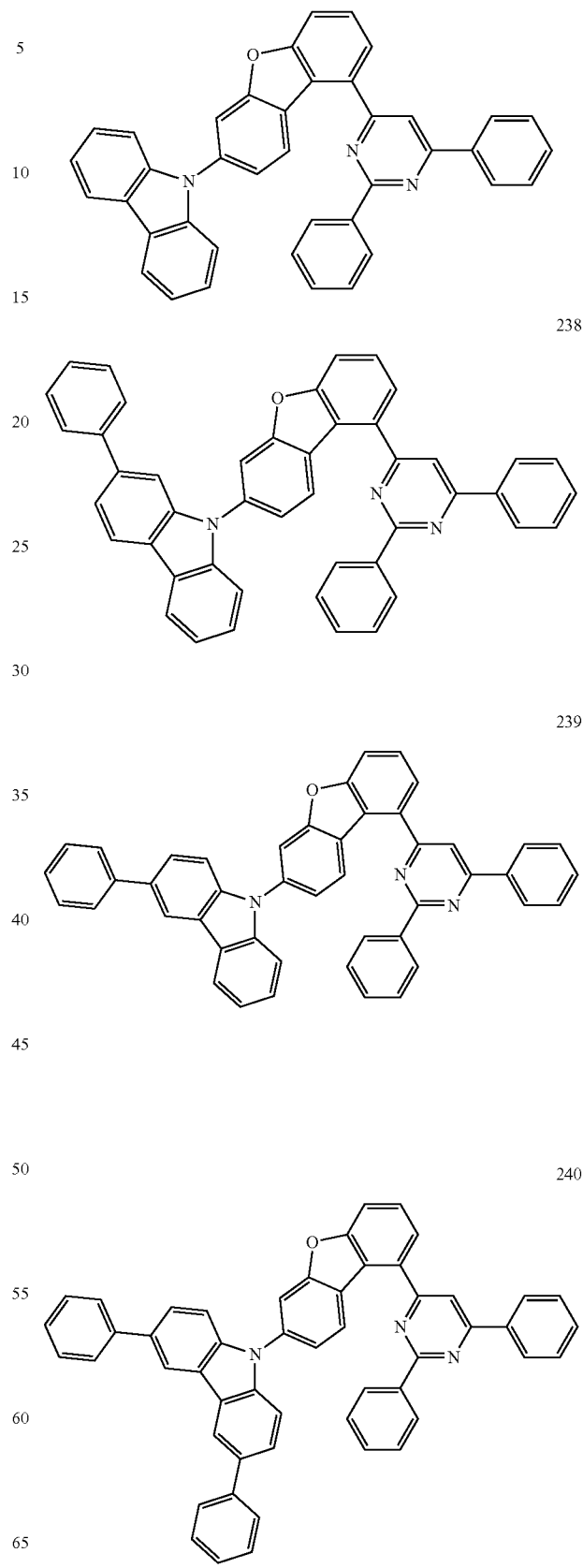

241
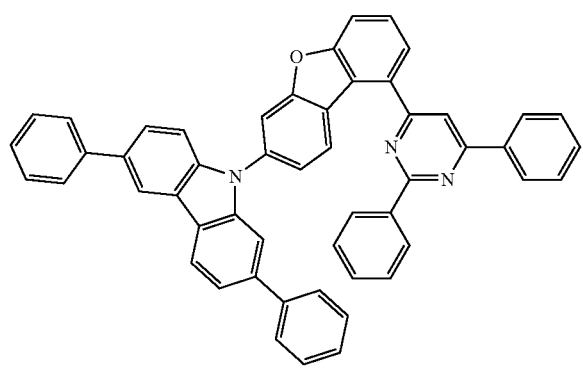
242
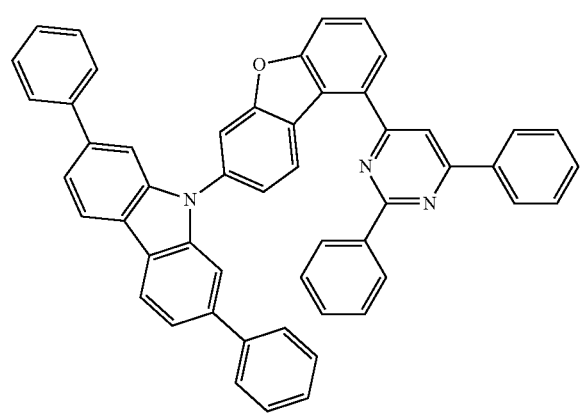
243
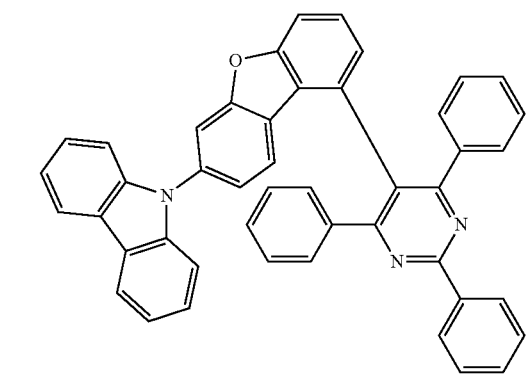
244
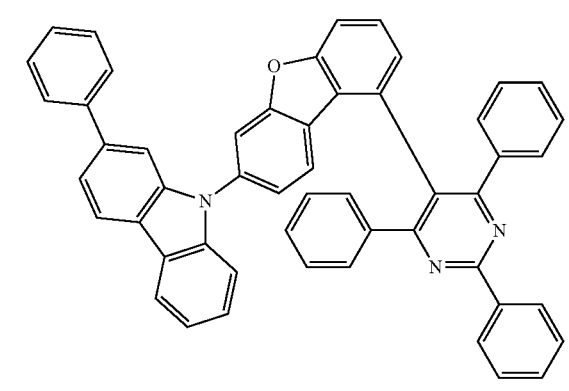
245
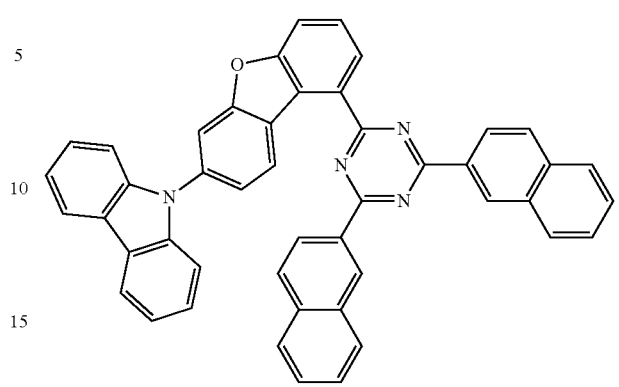
246
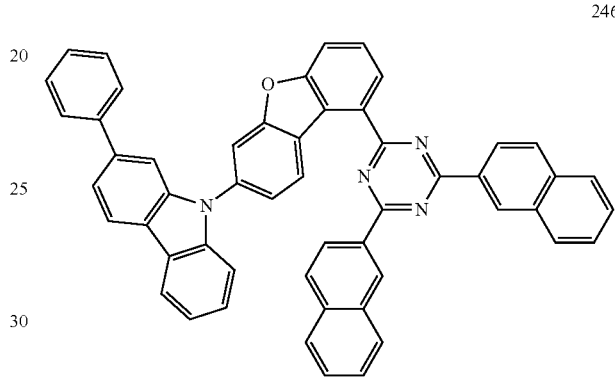
247
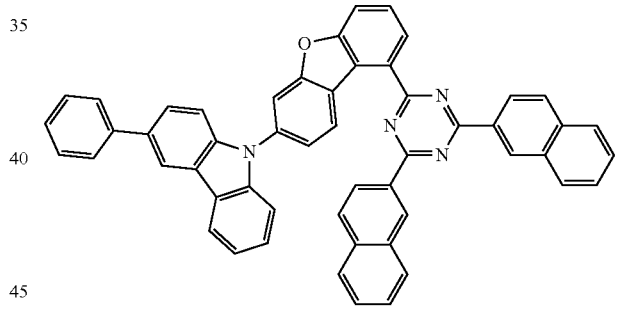
248

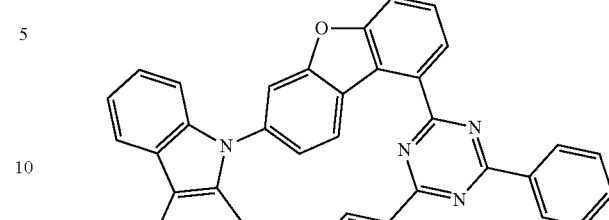
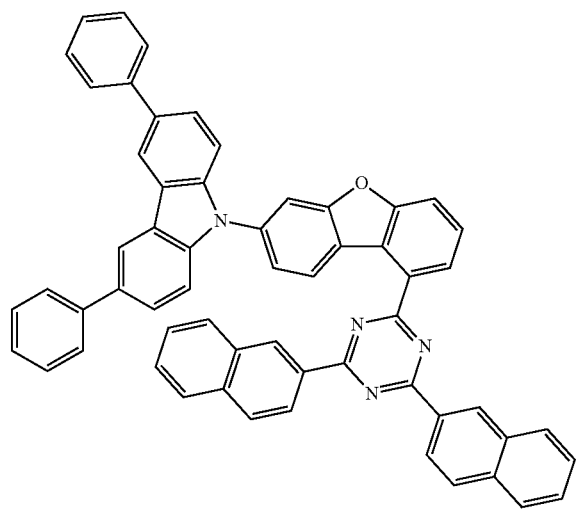
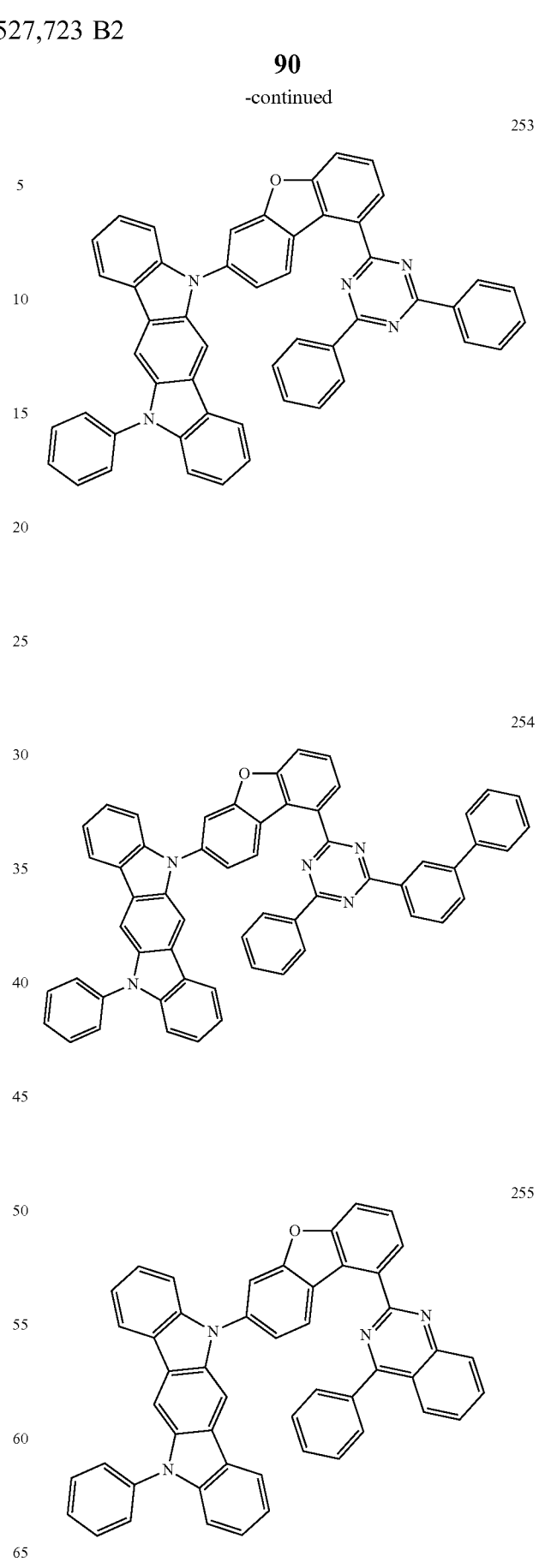

256
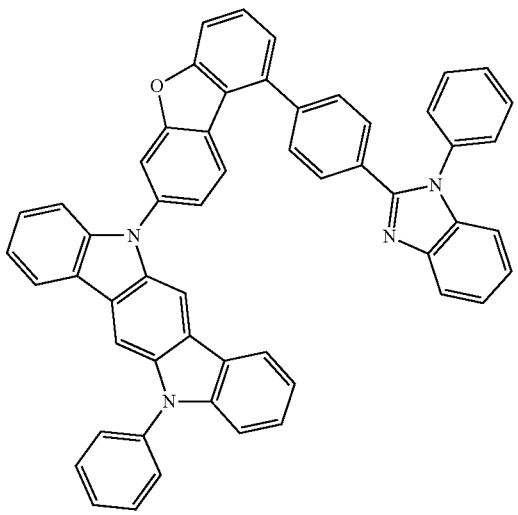
257
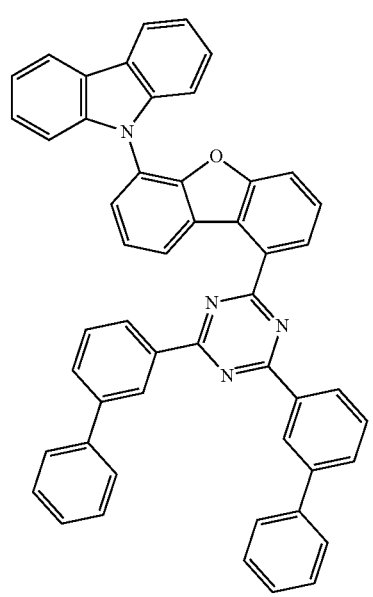
258
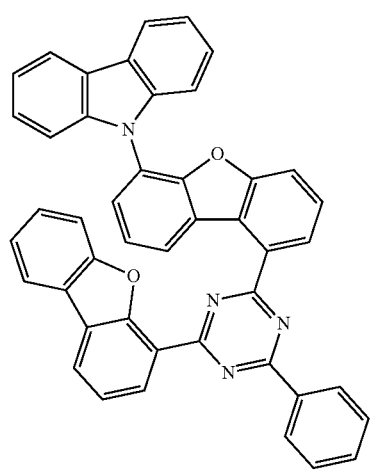
259
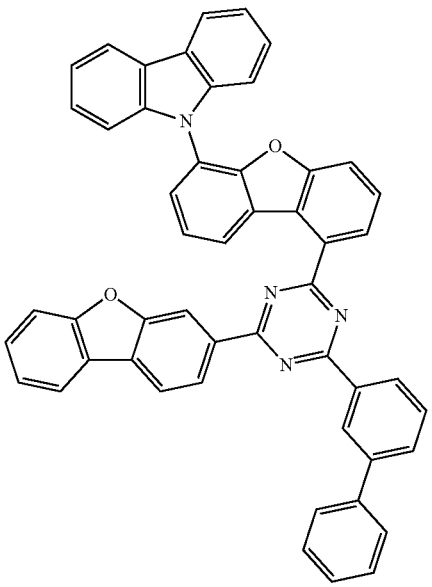
260
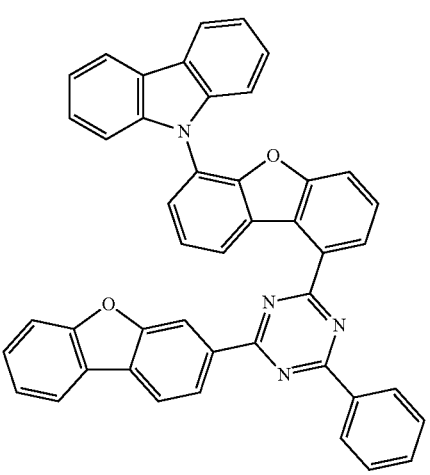
261
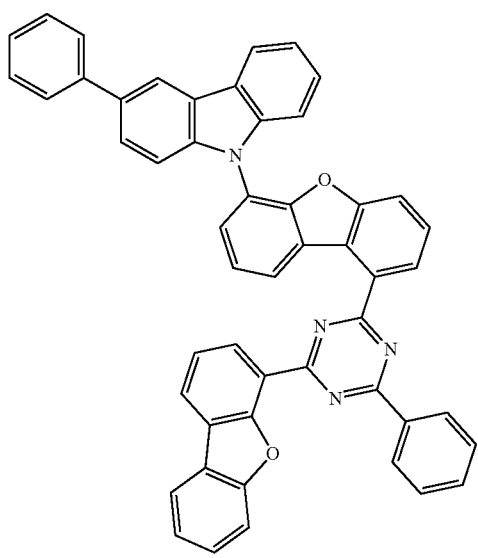

262
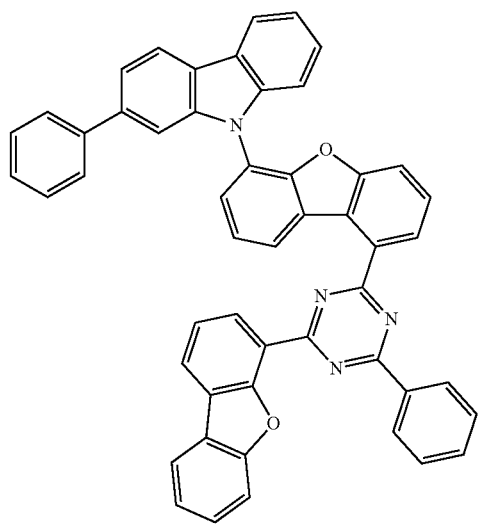
263
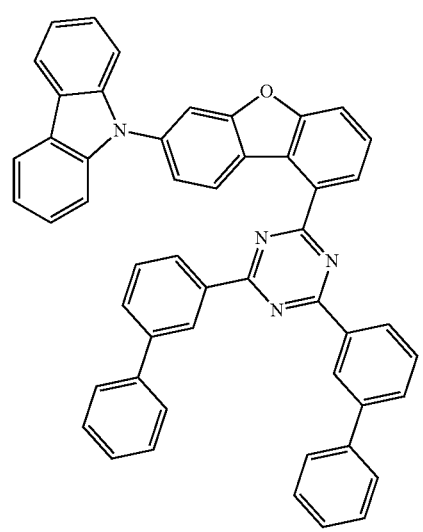
264
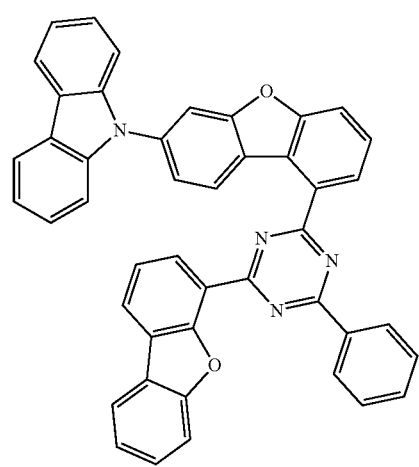
265
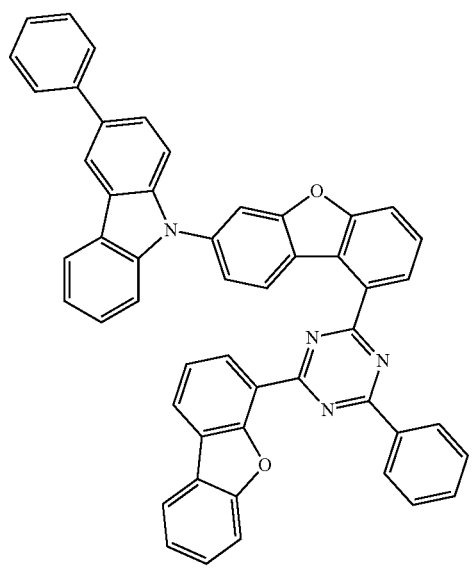
266
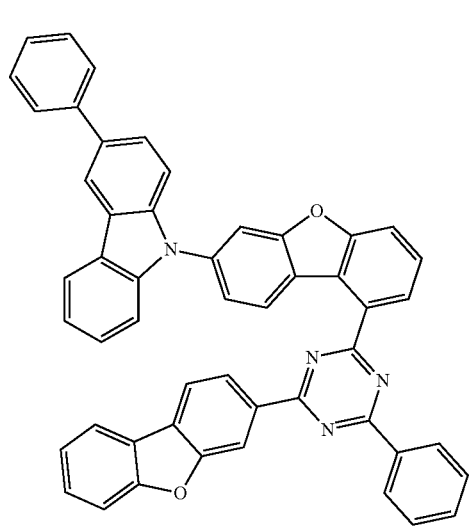
267
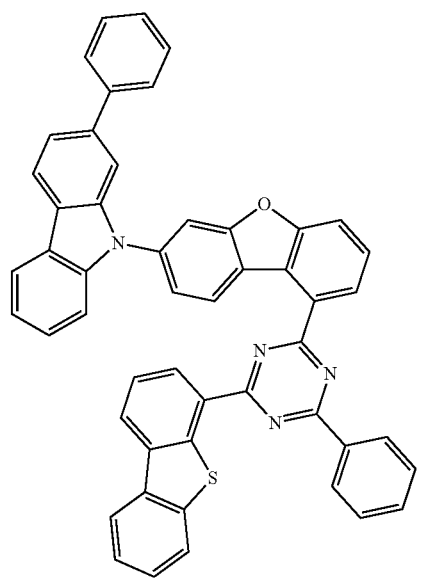

95
-continued
268
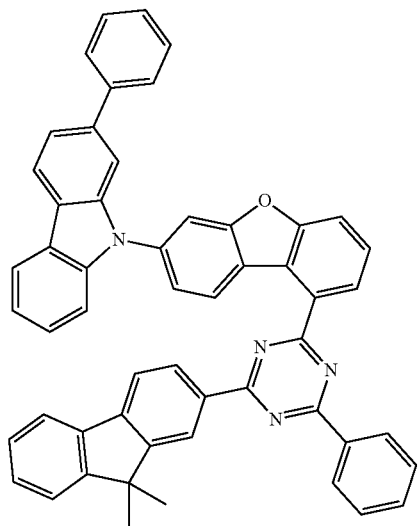
269
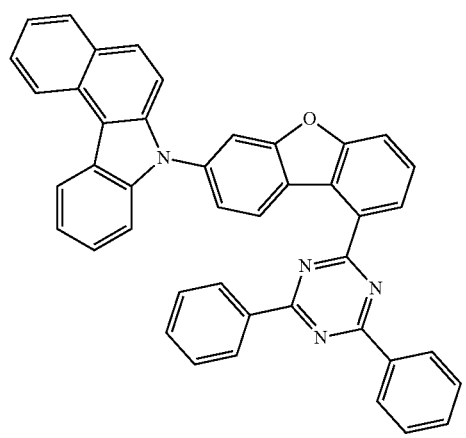
270
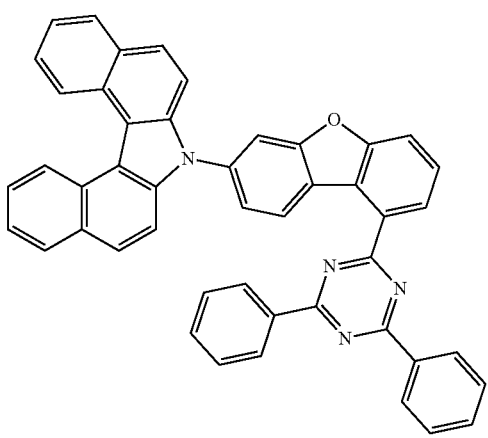
96
-continued
271
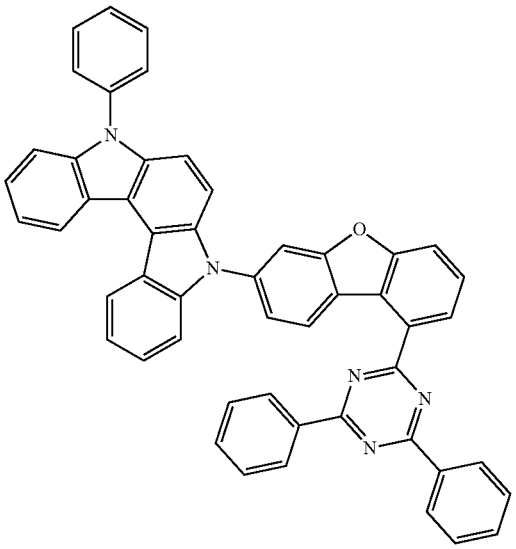
272
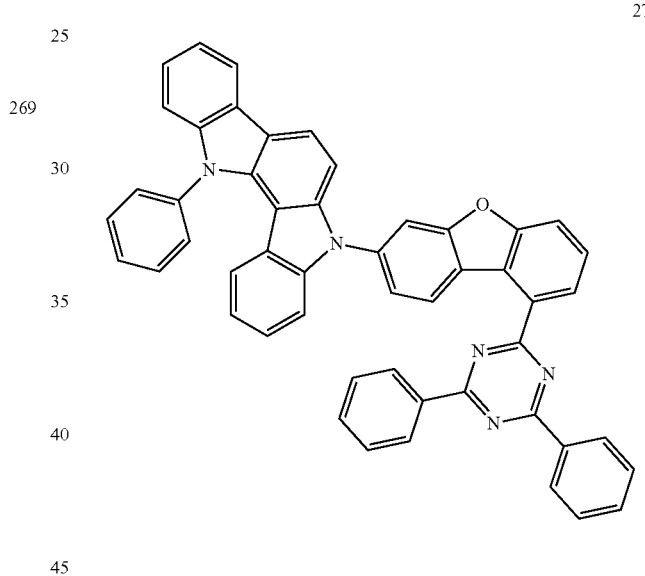
273
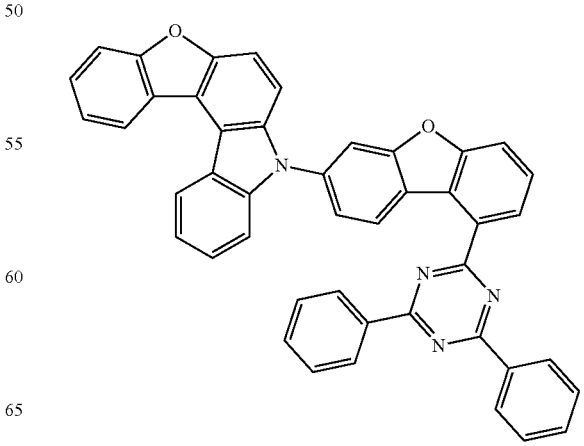

274
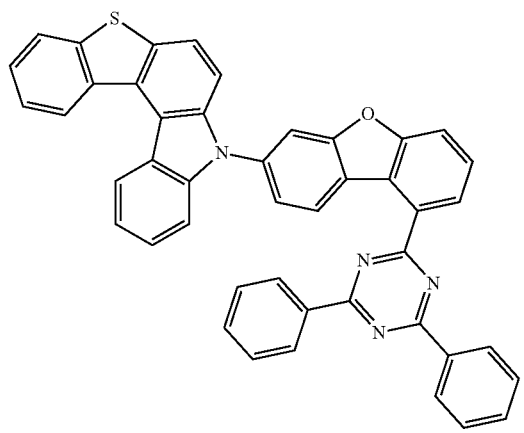
275
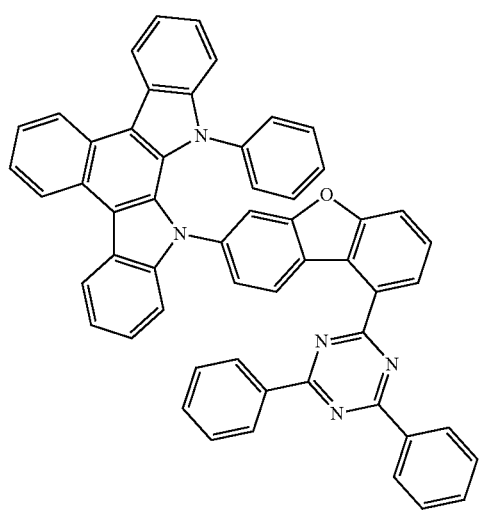
276
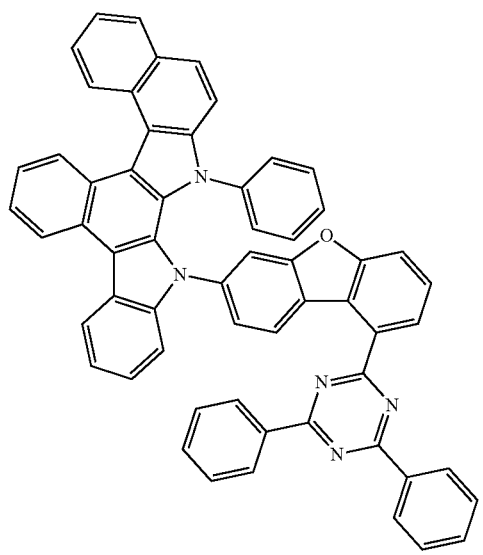
277
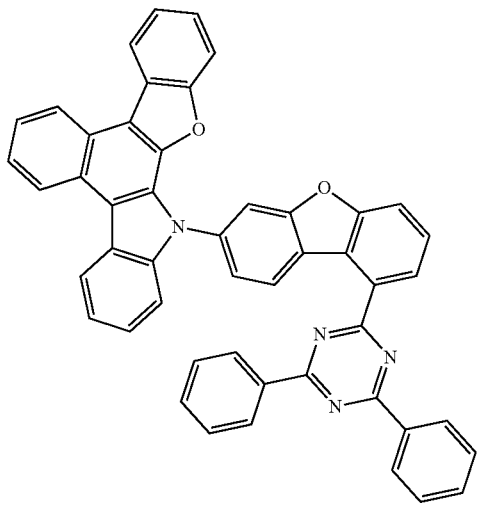
278
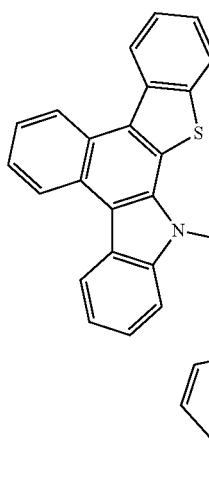
279
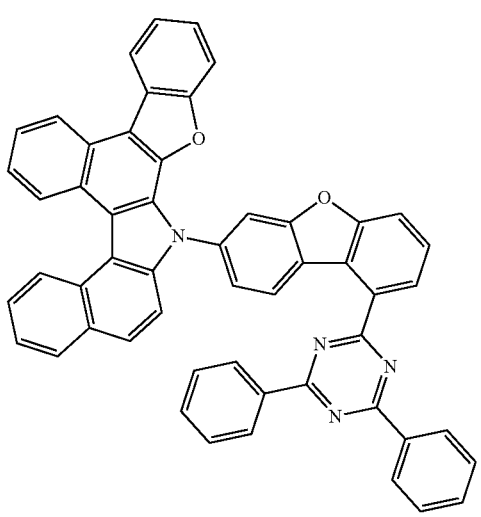

280

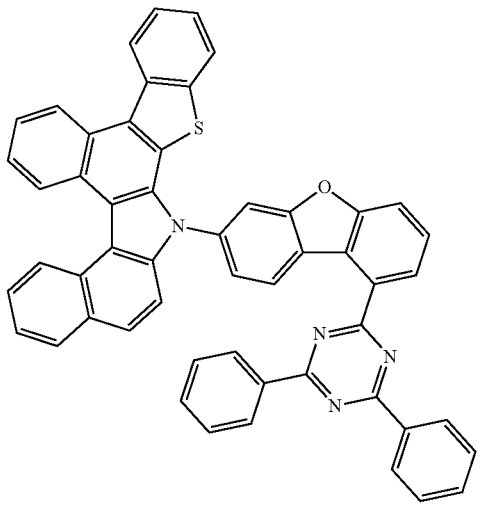

281

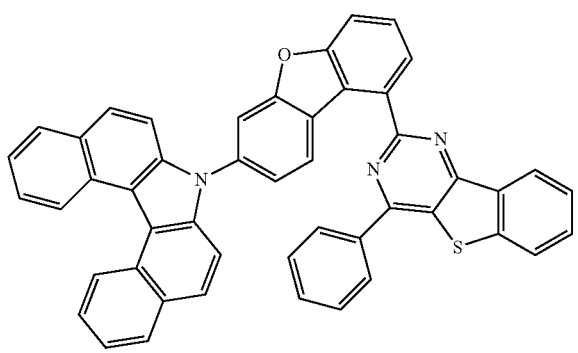

282

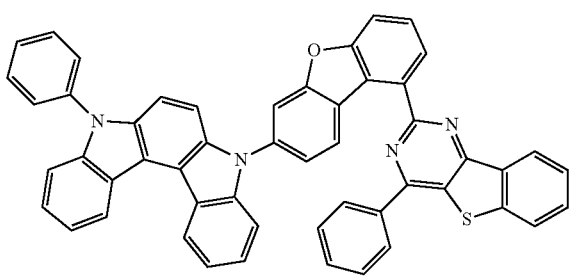

283

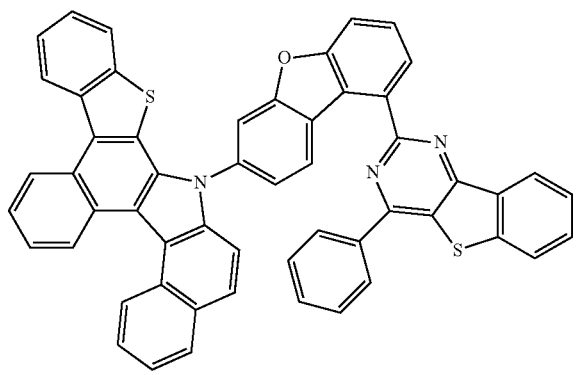

284

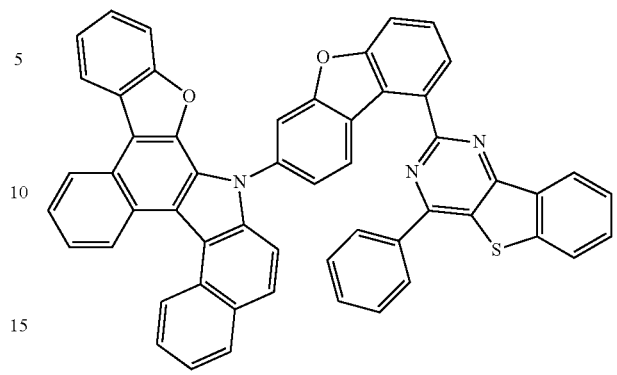

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

In addition, one embodiment of the present application provides, as an organic electronic device, an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Specific descriptions on the heterocyclic compound represented by Chemical Formula 1 are the same as described above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a blue light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a blue light emitting layer of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In the organic light emitting device of the present disclosure, the organic material layer may comprise a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another example, the organic material layer comprising the heterocyclic compound comprises the heterocyclic compound represented by Chemical Formula 1 as a host, and may be used together with an iridium-based dopant.

In the organic light emitting device of the present disclosure, the organic material layer comprises an electron injection layer or an electron transfer layer, and the electron transfer layer or the electron injection layer may comprise the heterocyclic compound.

In another organic light emitting device, the organic material layer comprises an electron blocking layer or a hole blocking layer, and the electron blocking layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed and used, or different series hosts may be mixed and used. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

BEST MODE FOR DISCLOSURE

Hereinafter, the present specification will be described in more detail with reference to examples, however, these are for illustrative purposes only, and the scope of the present application is not limited thereto.

[Preparation Example 1] Preparation of Compound 1(C)

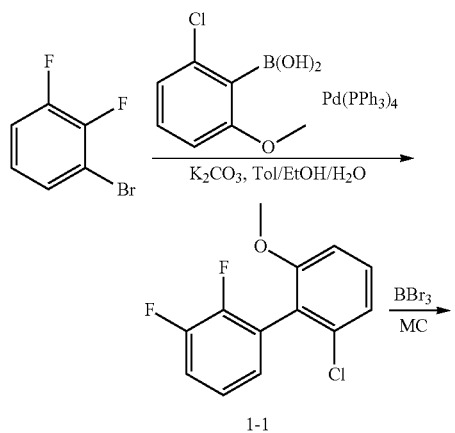
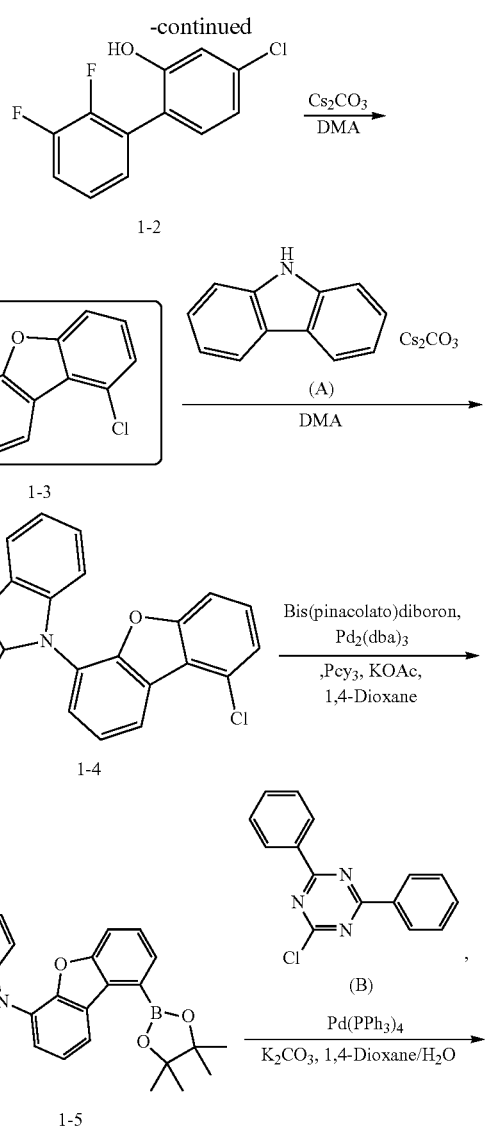

Preparation of Compound 1-1

In a one neck round bottom flask, a mixture of 1-bromo-2,3-difluorobenzene (40.5 g, 209 mmol), (2-chloro-6-methoxyphenyl)boronic acid (43 g, 230 mmol), tetrakis(triphenylphosphine)palladium(0) (24 g, 20.9 mmol), potassium carbonate (57.9 g, 419 mmol) and toluene/ethanol/water (500 ml/100 ml/100 ml) was refluxed at 110° C. The result was extracted with dichloromethane, and dried with $MgSO_4$. The result was silica gel filtered and then concentrated to obtain Compound 1-1 (40.8 g, 76%).

Preparation of Compound 1-2

In a one neck round bottom flask, a mixture of 2'-chloro-2,3-difluoro-6'-methoxy-1,1'-biphenyl (40.8 g, 160 mmol) and MC (600 ml) was cooled to a temperature of 0° C., $BBr_3$ (30 mL, 320 mmol) was added dropwise thereto, the temperature was raised to room temperature, and the result was stirred for 1 hour. The reaction was terminated using distilled water, and the result was extracted with dichloromethane and dried with $MgSO_4$. The result was column purified (MC:HX=1:1) to obtain Compound 1-2 (21 g, 54%).

Preparation of Compound 1-3

In a one neck round bottom flask, a dimethylacetamide (200 ml) mixture of 4-chloro-2',3'-difluoro-[1,1'-biphenyl]-2-ol (21 g, 87.2 mmol) and $Cs_2CO_3$ (71 g, 218 mmol) was stirred at 120° C. The result was cooled and filtered, the solvent of the filtrate was removed, and then the result was column purified (HX:MC=4:1) to obtain Compound 1-3 (17 g, 88%).

Preparation of Compound 1-4

In a one neck round bottom flask, a dimethylacetamide (60 ml) mixture of 1-chloro-6-fluorodibenzo[b,d]furan (6 g, 27.19 mmol), 9H-carbazole (5 g, 29.9 mmol) and $Cs_2CO_3$ (22 g, 101.7 mmol) was refluxed for 12 hours at 170° C. The result was cooled and filtered, the solvent of the filtrate was removed, and then the result was column purified (HX:MC=3:1) to obtain Compound 1-4 (9 g, 90%).

Preparation of Compound 1-5

In a one neck round bottom flask, a 1,4-dioxane (100 ml) mixture of 9-(9-chlorodibenzo[b,d]furan-4-yl)-9H-carbazole (9 g, 24.4 mmol), bis(pinacolato)diboron (12.4 g, 48.9 mmol), Pcy3 (1.37 g, 4.89 mmol), potassium acetate (7.1 g, 73 mmol) and $Pd_2(dba)_3$ (2.2 g, 2.44 mmol) was refluxed at 140° C. The result was cooled, then the filtered filtrate was concentrated, and column purified (HX:MC=3:1) to obtain Compound 1-5 (7.2 g, 64%).

Preparation of Compound 1

In a one neck round bottom flask, a mixture of 9-(9-(4,4,5,5-tetramethyl-1,3,2-dioxaborolan-2-yl)dibenzo[b,d]furan-4-yl)-9H-carbazole (7.2 g, 15.6 mmol), 2-chloro-4,6-diphenyl-1,3,5-triazine (5 g, 18.8 mmol), tetrakis(triphenylphosphine)palladium(0) (1.8 g, 1.56 mmol), potassium carbonate (4.3 g, 31.2 mmol) and 1,4-dioxane/water (100 ml/25 ml) was refluxed for 4 hours at 120° C. After filtering at 120° C., the result was washed with 1,4-dioxane, distilled water and MeOH to obtain Compound 1(C) (6.6 g, 75%).

The following Compound C was synthesized in the same manner as in the preparation of Compound 1 in Preparation Example 1 except that A and B of the following [Table 1] to [Table 7] were used as intermediates.

TABLE 1

| Compound | A | B | C | Yield (1-3 to C) |
|---|---|---|---|---|
| 2 | (2-phenyl-9H-carbazole) | (2-chloro-4,6-diphenyl-1,3,5-triazine) | (2-phenyl-carbazole linked to dibenzofuran with diphenyltriazine) | 69% |

TABLE 1-continued
| Compound | A | B | C | Yield (1-3 to C) |
|---|---|---|---|---|
| 3 | 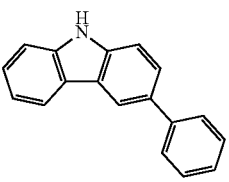 | 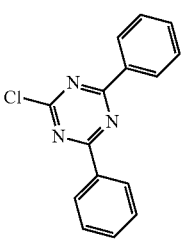 | 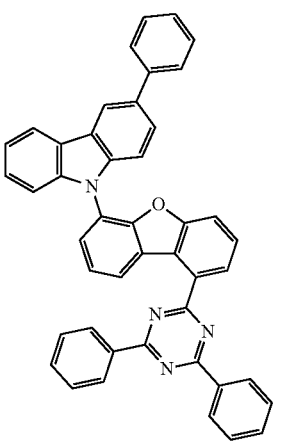 | 72% |
| 5 | 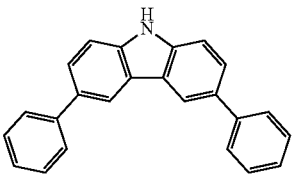 | 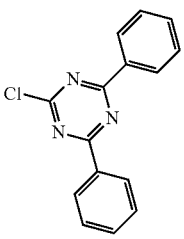 | 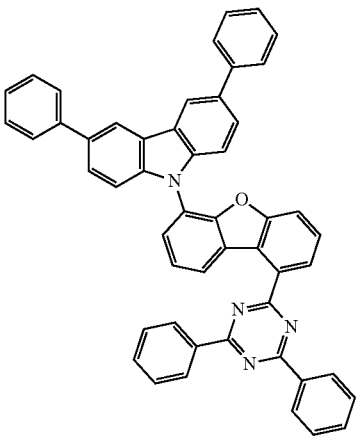 | 70% |
| 7 | 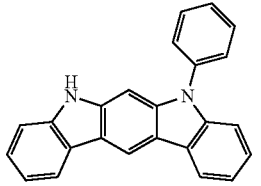 | 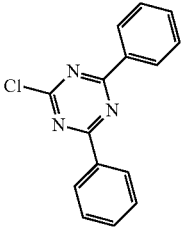 | 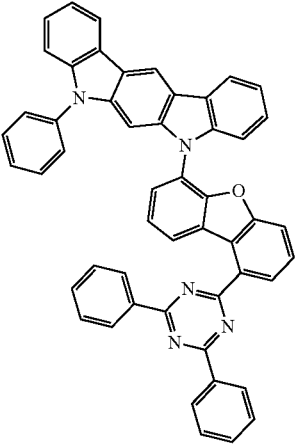 | 61% |

TABLE 1-continued

| Compound | A | B | C | Yield (1-3 to C) |
|---|---|---|---|---|
| 10 | (structure) | (structure) | (structure) | 63% |
| 17 | (structure) | (structure) | (structure) | 64% |

TABLE 2

| Compound | A | B | C | Yield (1-3 to C) |
|---|---|---|---|---|
| 18 | (structure) | (structure) | (structure) | 70% |

TABLE 2-continued
| Compound | A | B | C | Yield (1-3 to C) |
|---|---|---|---|---|
| 19 | 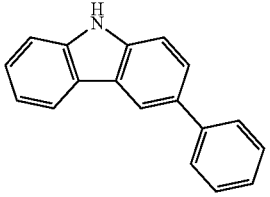 | 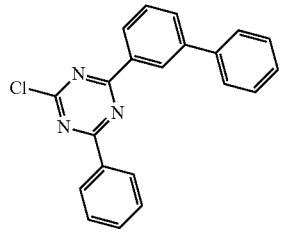 | 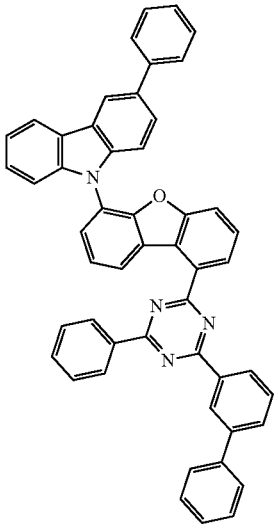 | 68% |
| 22 | 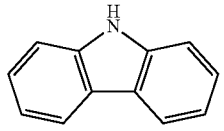 | 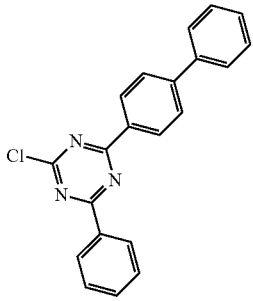 | 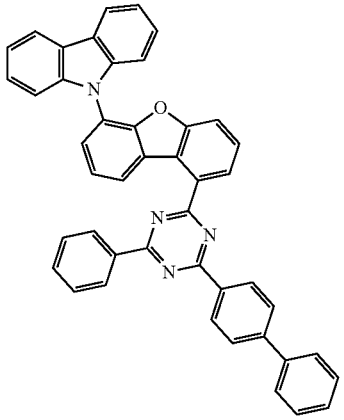 | 66% |
| 28 | 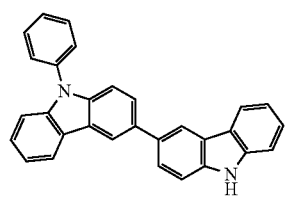 | 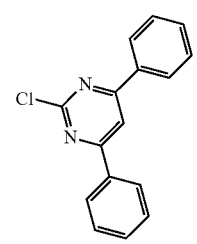 | 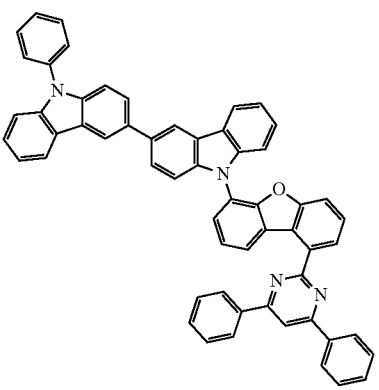 | 69% |

TABLE 2-continued
| Compound | A | B | C | Yield (1-3 to C) |
|---|---|---|---|---|
| 29 | 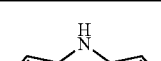 | | | 58% |
| 34 | | | | 62% |
TABLE 3
| Compound | A | B | C | Yield (1-3 to C) |
|---|---|---|---|---|
| 38 | 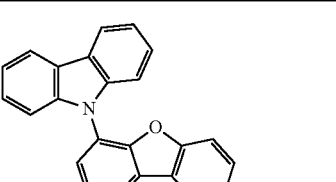 | | | 70% |

TABLE 3-continued
| Compound | A | B | C | Yield (1-3 to C) |
|---|---|---|---|---|
| 39 | 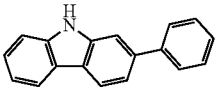 | 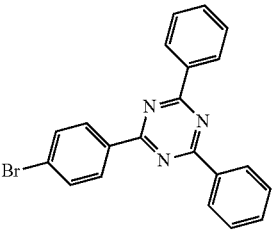 | 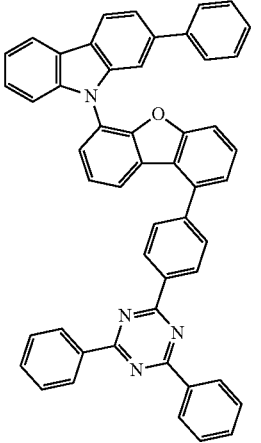 | 71% |
| 43 | 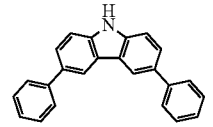 | 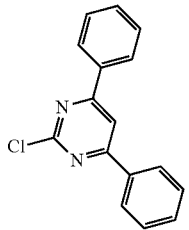 | 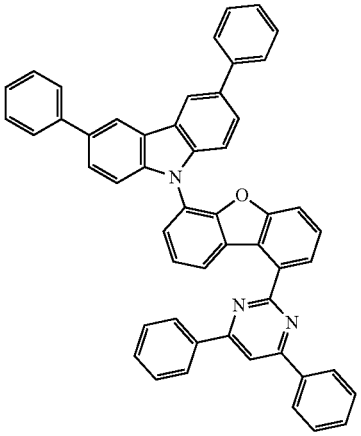 | 68% |
| 45 | 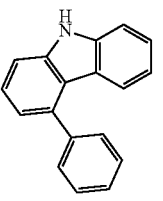 | 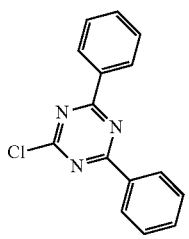 | 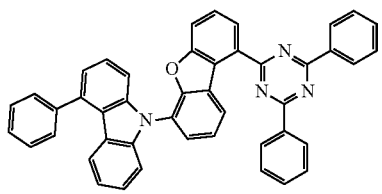 | 42% |
| 48 | 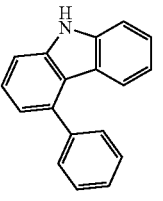 | 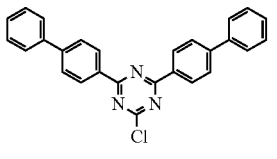 | 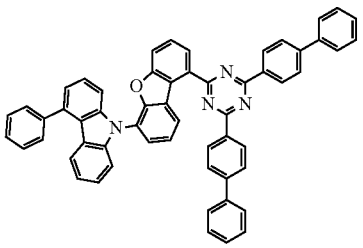 | 48% |

TABLE 3-continued

| Compound | A | B | C | Yield (1-3 to C) |
|---|---|---|---|---|
| 51 | (structure) | (structure) | (structure) | 53% |

TABLE 4

| Compound | A | B | C | Yield (1-3 to C) |
|---|---|---|---|---|
| 53 | (structure) | (structure) | (structure) | 51% |
| 59 | (structure) | (structure) | (structure) | 66% |
| 62 | (structure) | (structure) | (structure) | 65% |

TABLE 4-continued

| Compound | A | B | C | Yield (1-3 to C) |
|---|---|---|---|---|
| 65 | | | | 67% |
| 67 | | | | 61% |
| 70 | | | | 69% |

TABLE 5
| Compound | A | B | C | Yield (1-3 to C) |
|---|---|---|---|---|
| 71 | 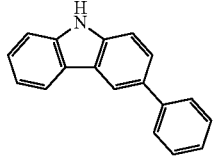 | 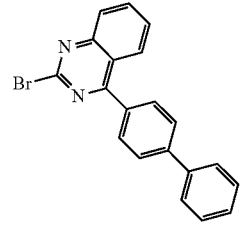 | 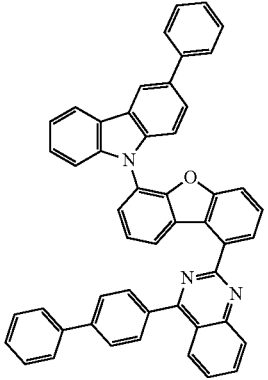 | 63% |
| 75 | 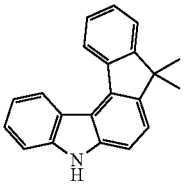 | 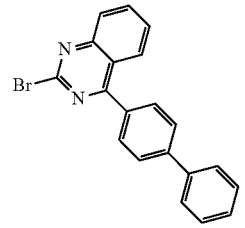 | 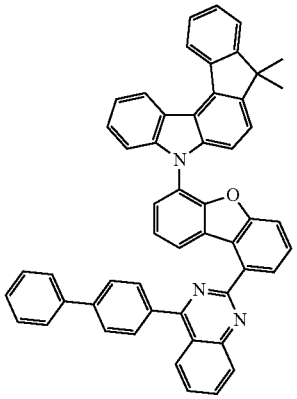 | 64% |
| 77 | 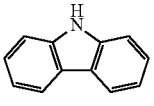 | 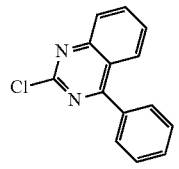 | 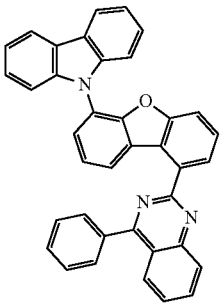 | 64% |
| 80 | 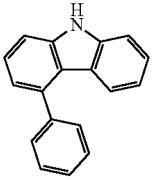 | 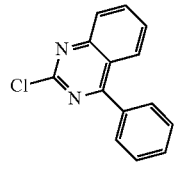 | 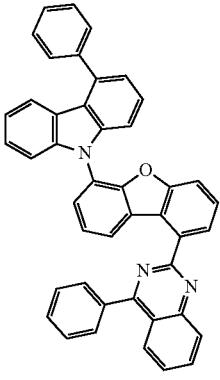 | 70% |

TABLE 5-continued

| Compound | A | B | C | Yield (1-3 to C) |
|---|---|---|---|---|
| 83 | | | | 68% |
| 86 | | | | 60% |

TABLE 6

| Compound | A | B | C | Yield (1-3 to C) |
|---|---|---|---|---|
| 90 | | | | 66% |
| 92 | | | | 61% |

TABLE 6-continued
| Compound | A | B | C | Yield (1-3 to C) |
|---|---|---|---|---|
| 95 | 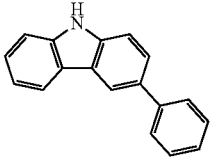 | 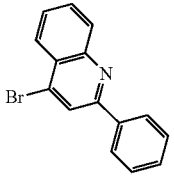 | 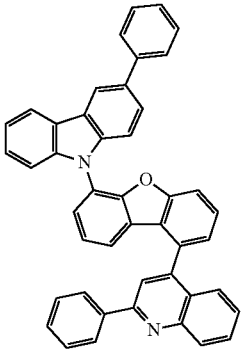 | 51% |
| 100 | 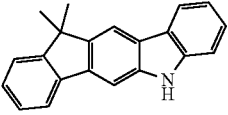 |  | 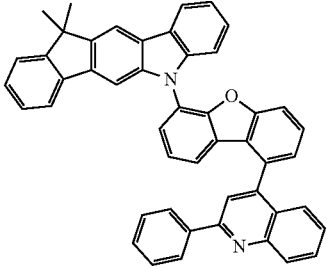 | 54% |
| 101 | 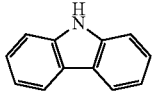 | 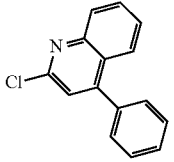 | 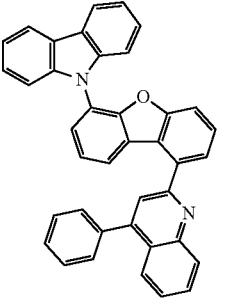 | 49% |
| 110 | 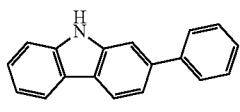 | 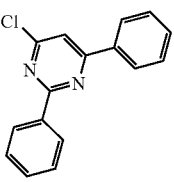 | 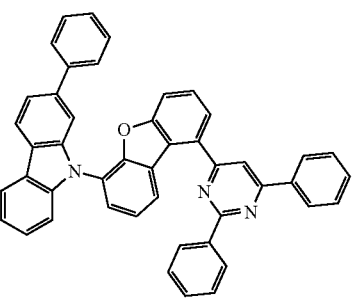 | 54% |

TABLE 7

| Compound | A | B | C | Yield (1-3 to C) |
|---|---|---|---|---|
| 113 | | | | 69% |
| 118 | | | | 60% |
| 119 | | | | 62% |

TABLE 7-continued
| Compound | A | B | C | Yield (1-3 to C) |
|---|---|---|---|---|
| 121 | 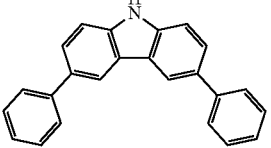 | 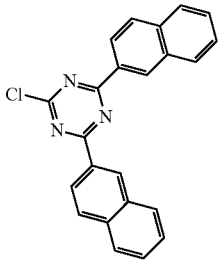 | 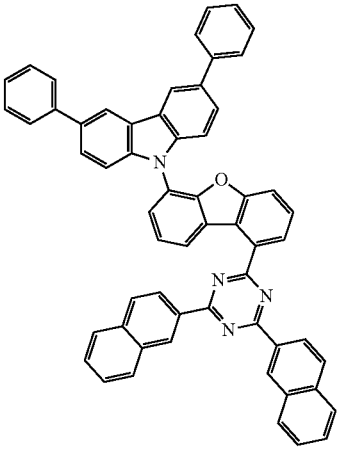 | 63% |
| 125 | 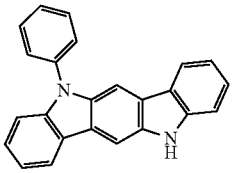 | 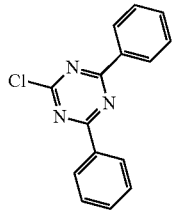 | 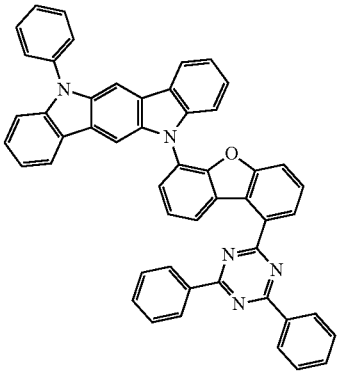 | 70% |
| 127 | 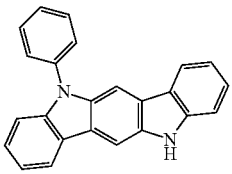 | 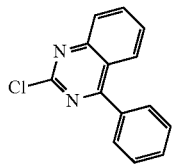 | 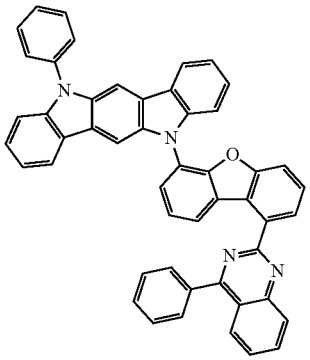 | 64% |

TABLE 7-continued
| Compound | A | B | C | Yield (1-3 to C) |
|---|---|---|---|---|
| 257 | 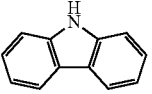 | 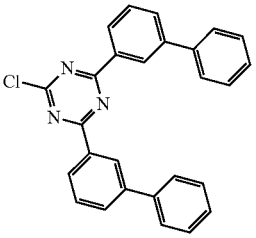 | 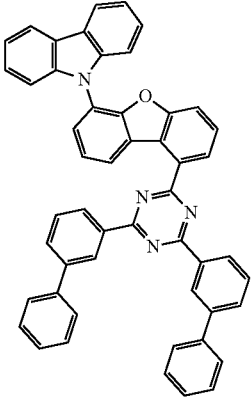 | 63% |
| 258 | 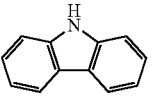 | 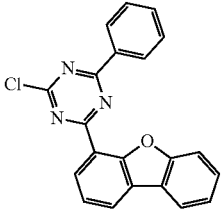 | 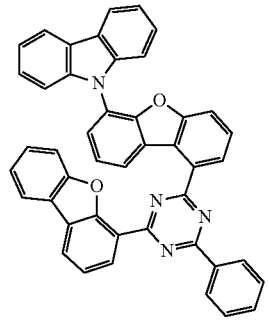 | 69% |
| 261 | 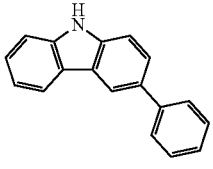 | 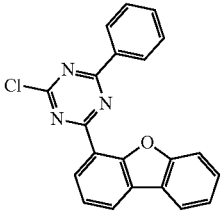 | 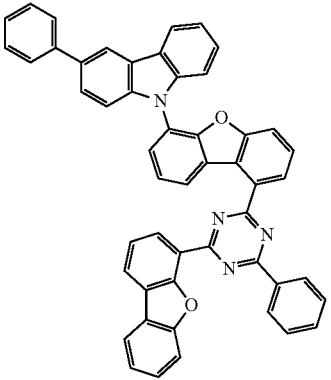 | 68% |

[Preparation Example 2] Preparation of Compound 129(F)

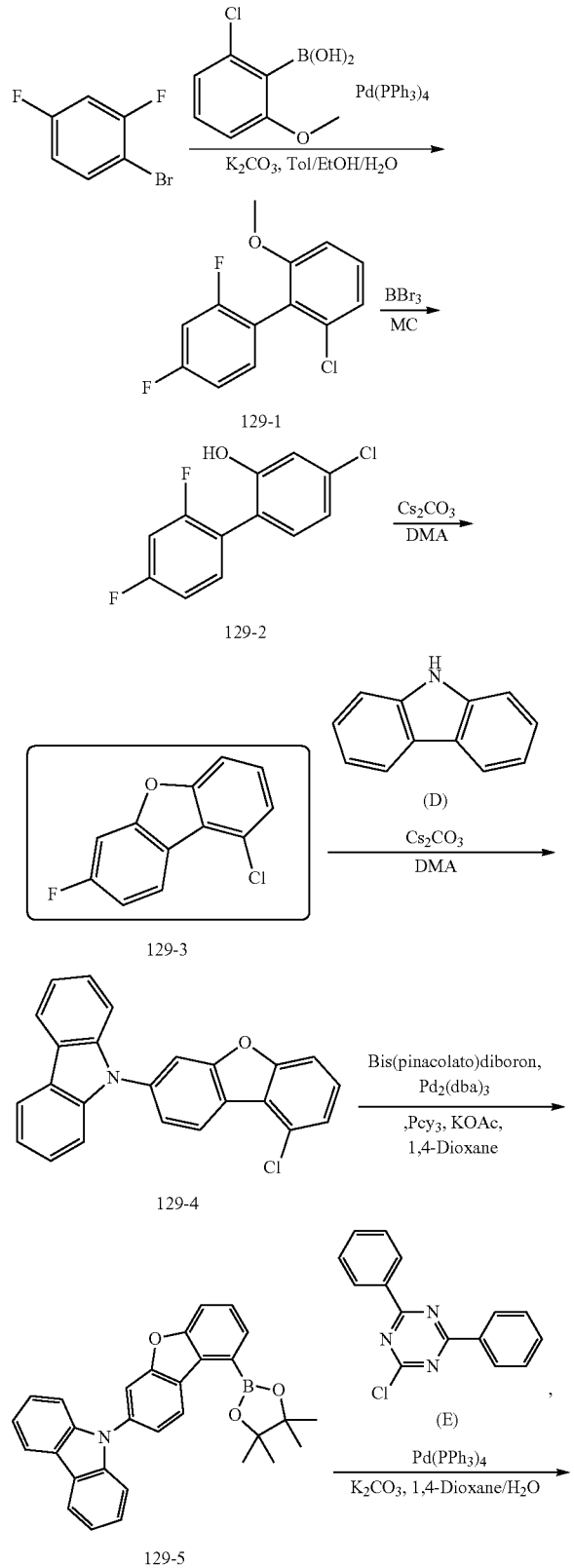

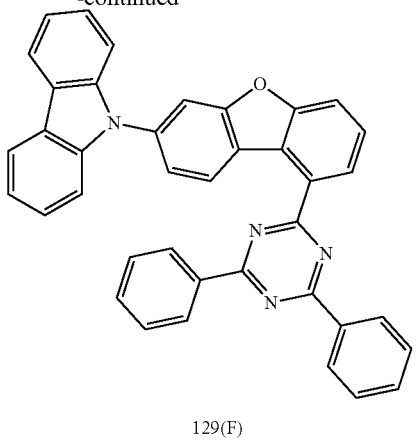

129(F)

Preparation of Compound 129-1

In a one neck round bottom flask, a mixture of 1-bromo-2,4-difluorobenzene (40 g, 207 mmol), (2-chloro-6-methoxyphenyl)boronic acid (42.4 g, 227 mmol), tetrakis(triphenylphosphine)palladium(0) (23 g, 20.7 mmol), potassium carbonate (57 g, 414 mmol) and toluene/ethanol/water (600 ml/150 ml/150 ml) was refluxed at 110° C.

The result was extracted with dichloromethane, and dried with MgSO$_4$. The result was silica gel filtered and then concentrated to obtain Compound 129-1 (50 g, 94%).

Preparation of Compound 129-2

In a one neck round bottom flask, a mixture of 2'-chloro-2,4-difluoro-6'-methoxy-1,1'-biphenyl (50 g, 196 mmol) and dichloromethane (700 ml) was cooled to a temperature of 0° C., BBr$_3$ (28.3 mL, 294 mmol) was added dropwise thereto, the temperature was raised to room temperature, and the result was stirred for 2 hours.

The reaction was terminated using distilled water, and the result was extracted with dichloromethane and dried with MgSO$_4$. The result was silica gel filtered to obtain Compound 129-2 (27.5 g, 58%).

Preparation of Compound 129-3

In a one neck round bottom flask, a dimethylacetamide (300 ml) mixture of 4-chloro-2',4'-difluoro-[1,1'-biphenyl]-2-ol (27 g, 114 mmol) and Cs$_2$CO$_3$ (83 g, 285 mmol) was stirred at 120° C. The result was cooled and filtered, the solvent of the filtrate was removed, and then the result was silica gel filtered to obtain Compound 129-3 (23 g, 92%).

Preparation of Compound 129-4

In a one neck round bottom flask, a dimethylacetamide (60 ml) mixture of 1-chloro-7-fluorodibenzo[b,d]furan (5.5 g, 24.9 mmol), 9H-carbazole (4.58 g, 27.4 mmol) and Cs$_2$CO$_3$ (20 g, 62 mmol) was refluxed for 6 hours at 170° C. The result was cooled and filtered, the solvent of the filtrate was removed, and then the result was column purified (HX:MC=3:1) to obtain Compound 129-4 (7.6 g, 83%).

Preparation of Compound 129-5

In a one neck round bottom flask, a 1,4-dioxane (80 ml) mixture of 9-(9-chlorodibenzo[b,d]furan-3-yl)-9H-carbazole (7.5 g, 20.3 mmol), bis(pinacolato)diboron (10.3 g, 40.7 mmol), Pcy3 (1.14 g, 4.07 mmol), potassium acetate (5.97 g, 60.9 mmol) and Pd$_2$(dba)$_3$ (1.85 g, 2.03 mmol) was refluxed at 140° C. The result was cooled, then the filtered filtrate was concentrated, and column purified (HX:MC=2:1) to obtain Compound 129-5 (6.5 g, 70%).

Preparation of Compound 129

In a one neck round bottom flask, a mixture of 9-(9-(4,4,5,5-tetramethyl-1,3,2-dioxaborolan-2-yl)dibenzo[b,d]furan-3-yl)-9H-carbazole (6.5 g, 14.1 mmol), 2-chloro-4,6-diphenyl-1,3,5-triazine (4.54 g, 16.9 mmol), tetrakis(triphenylphosphine)palladium(0) (1.6 g, 1.41 mmol), potassium carbonate (3.9 g, 28.2 mmol) and 1,4-dioxane/water (80 ml/28.2 ml) was refluxed for 4 hours at 120° C. After filtering at 120° C., the result was washed with 1,4-dioxane, distilled water and MeOH to obtain Compound 129(F) (5.4 g, 68%).

The following Compound F was synthesized in the same manner as in the preparation of Compound 129 in Preparation Example 2 except that D and E of the following [Table 8] to [Table 14] were used as intermediates.

TABLE 8

| Compound | D | E | F | Yield (129-3 to F) |
|---|---|---|---|---|
| 130 | | | | 69% |
| 131 | | | | 72% |
| 133 | | | | 70% |

TABLE 8-continued

| Compound | D | E | F | Yield (129-3 to F) |
|---|---|---|---|---|
| 135 | | | | 61% |
| 138 | | | | 63% |
| 145 | | | | 64% |

TABLE 9

| Compound | D | E | F | Yield (129-3 to F) |
|---|---|---|---|---|
| 146 | | | | 70% |
| 147 | | | | 68% |
| 150 | | | | 66% |
| 156 | | | | 69% |

TABLE 9-continued
| Compound | D | E | F | Yield (129-3 to F) |
|---|---|---|---|---|
| 157 | 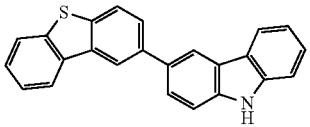 | 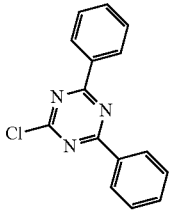 | 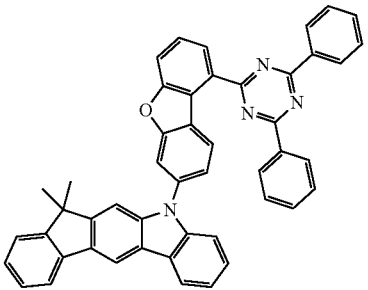 | 58% |
| 162 | 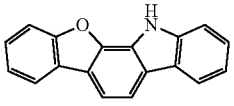 | 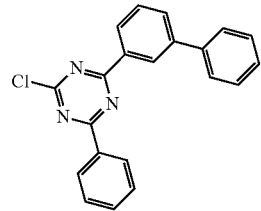 | 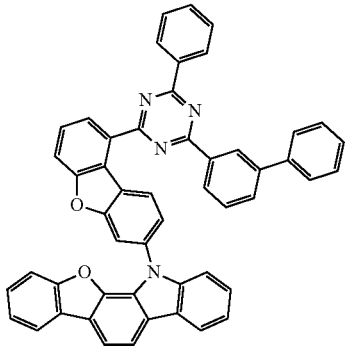 | 62% |
TABLE 10
| Compound | D | E | F | Yield (129-3 to F) |
|---|---|---|---|---|
| 166 | 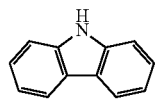 | 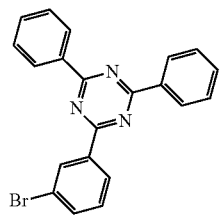 | 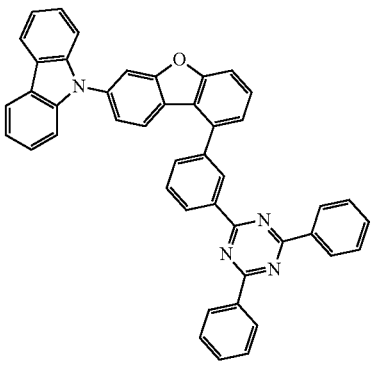 | 70% |

TABLE 10-continued
| Compound | D | E | F | Yield (129-3 to F) |
|---|---|---|---|---|
| 167 | 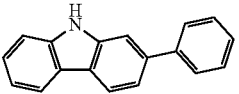 | 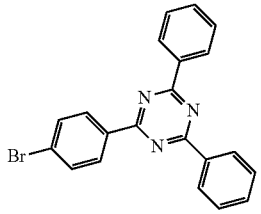 | 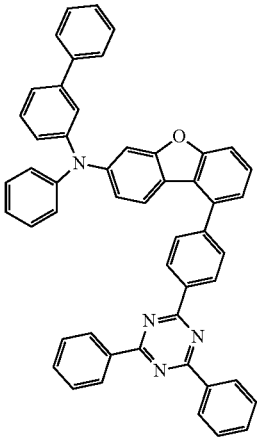 | 71% |
| 171 | 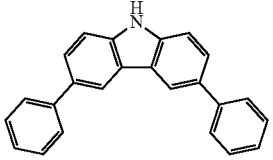 | 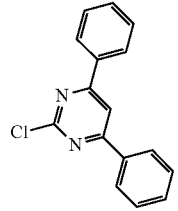 | 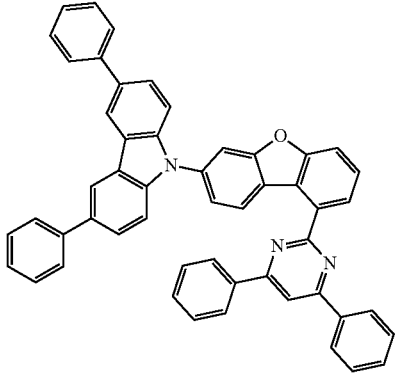 | 68% |
| 173 | 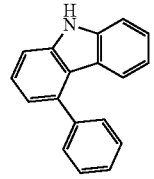 | 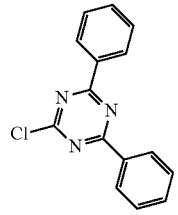 | 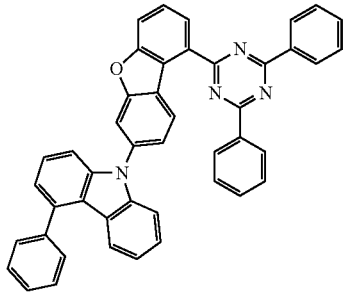 | 42% |
| 176 | 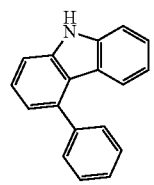 | 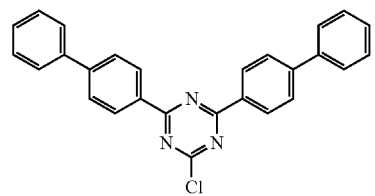 | 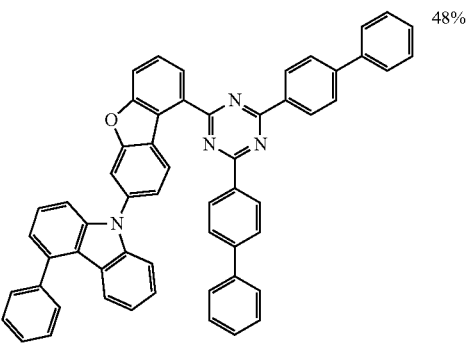 | 48% |

TABLE 10-continued

| Compound | D | E | F | Yield (129-3 to F) |
|---|---|---|---|---|
| 179 | (carbazole structure) | (chlorotriazine structure) | (product structure) | 53% |

TABLE 11

| Compound | D | E | F | Yield (129-3 to F) |
|---|---|---|---|---|
| 181 | (diphenylcarbazole structure) | (chlorotriazine structure) | (product structure) | 51% |
| 187 | (phenylcarbazole structure) | (bromophenyl benzimidazole structure) | (product structure) | 66% |

TABLE 11-continued
| Compound | D | E | F | Yield (129-3 to F) |
|---|---|---|---|---|
| 190 | 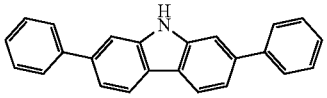 | 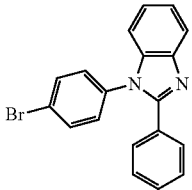 | 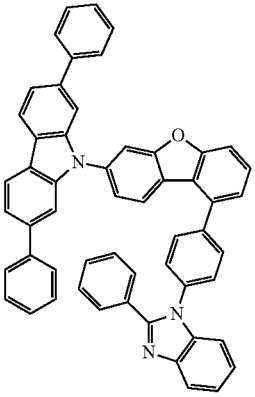 | 65% |
| 193 | 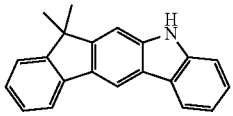 | 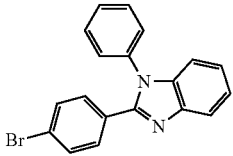 | 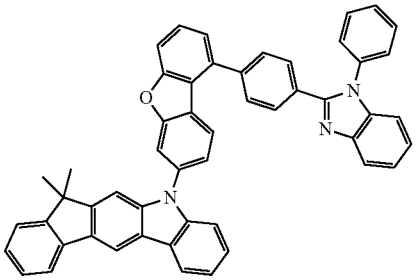 | 67% |
| 195 | 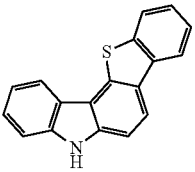 | 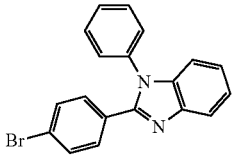 | 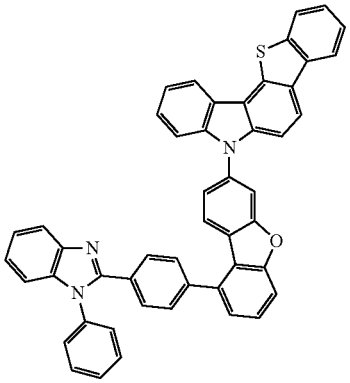 | 61% |
| 198 | 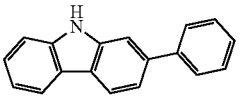 | 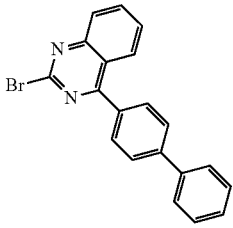 | 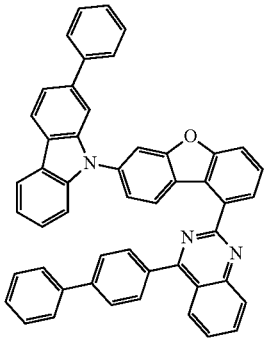 | 69% |

TABLE 12
| Compound | D | E | F | Yield (129-3 to F) |
|---|---|---|---|---|
| 199 | 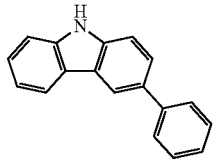 | 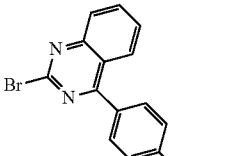 | 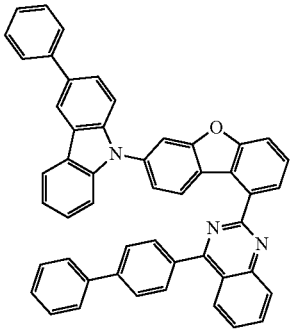 | 63% |
| 203 | 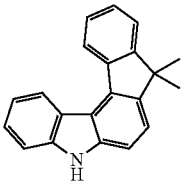 | 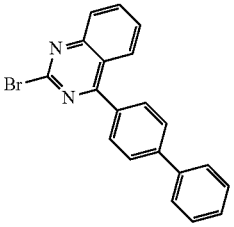 | 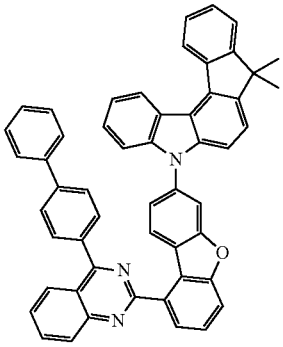 | 64% |
| 205 | 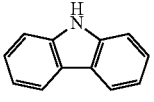 | 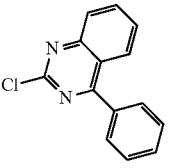 | 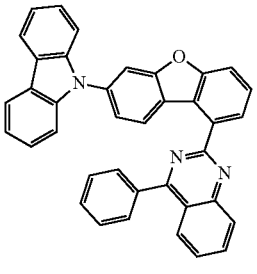 | 64% |
| 208 |  | 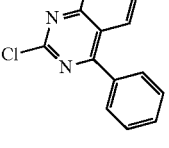 | 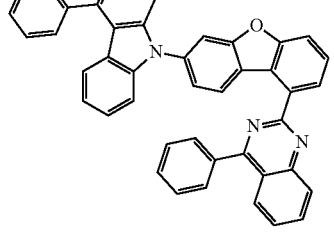 | 70% |
| 211 | 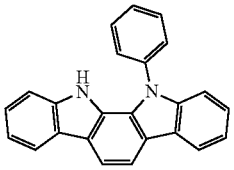 | 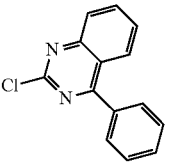 | 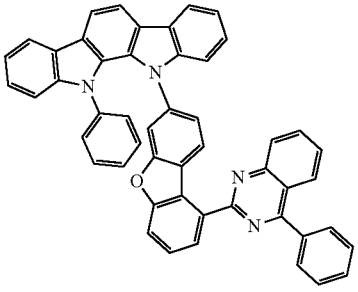 | 68% |

TABLE 12-continued
| Compound | D | E | F | Yield (129-3 to F) |
|---|---|---|---|---|
| 214 | 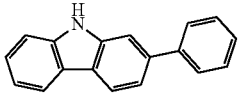 | 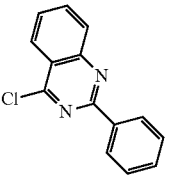 | 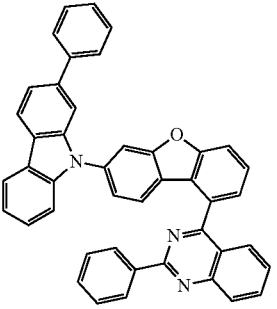 | 60% |
TABLE 13
| Compound | D | E | F | Yield (129-3 to F) |
|---|---|---|---|---|
| 218 | 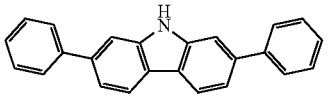 | 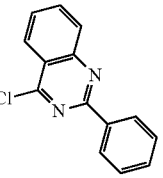 | 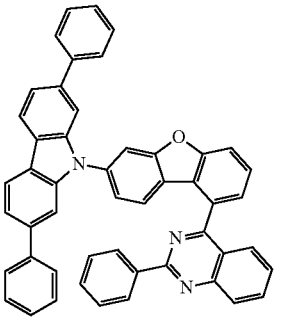 | 66% |
| 220 | 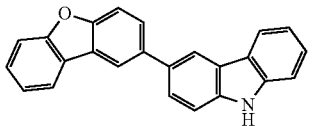 | 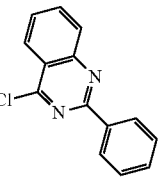 | 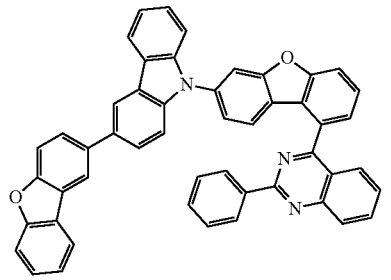 | 61% |
| 223 | 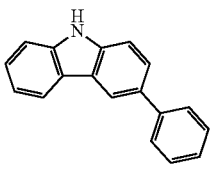 | 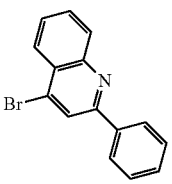 | 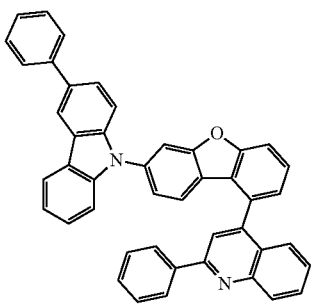 | 51% |

TABLE 13-continued
| Compound | D | E | F | Yield (129-3 to F) |
|---|---|---|---|---|
| 228 | 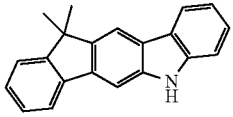 | 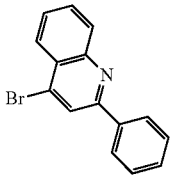 | 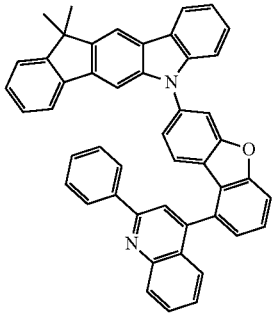 | 54% |
| 229 | 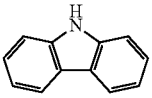 | 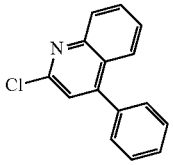 | 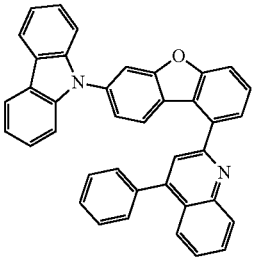 | 49% |
| 238 | 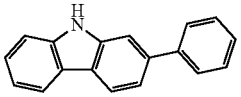 | 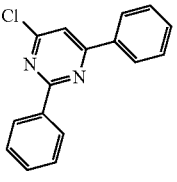 | 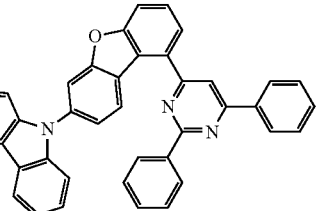 | 54% |
TABLE 14
| Compound | D | E | F | Yield (129-3 to F) |
|---|---|---|---|---|
| 241 | 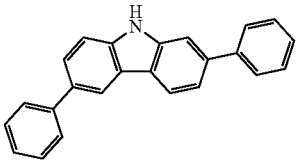 | 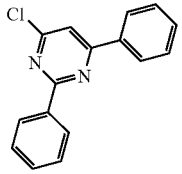 | 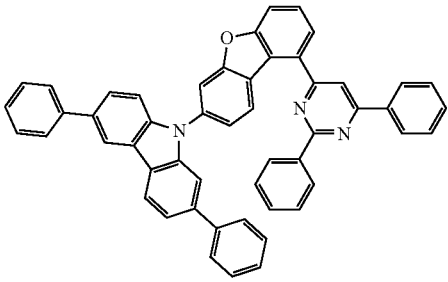 | 69% |

TABLE 14-continued
| Compound | D | E | F | Yield (129-3 to F) |
|---|---|---|---|---|
| 246 | 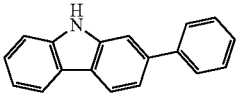 | 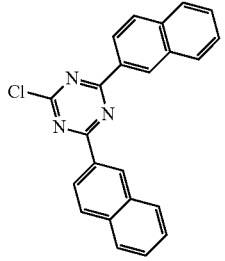 | 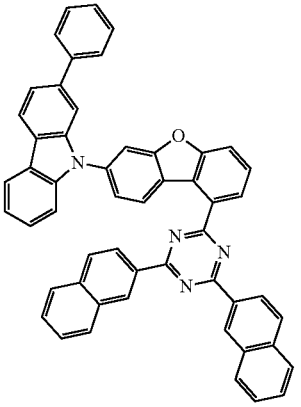 | 60% |
| 247 | 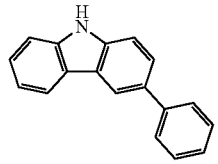 | 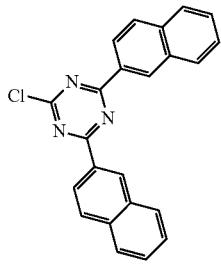 | 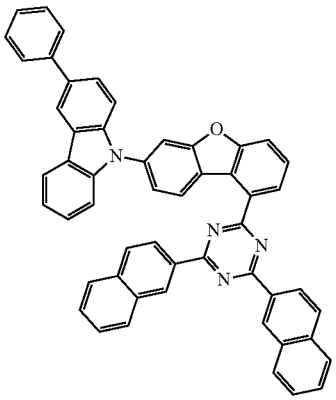 | 62% |
| 249 | 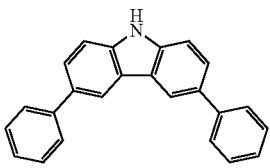 | 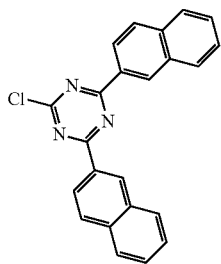 | 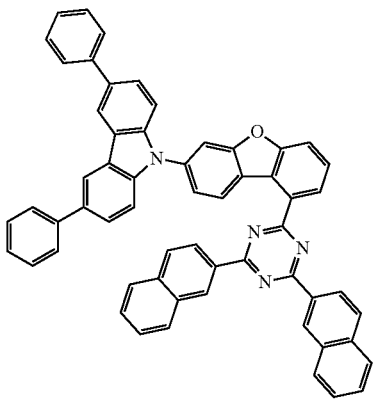 | 63% |

TABLE 14-continued

| Compound | D | E | F | Yield (129-3 to F) |
|---|---|---|---|---|
| 253 | | | | 70% |
| 255 | | | | 64% |
| 263 | | | | 68% |
| 264 | | | | 71% |

TABLE 14-continued

| Compound | D | E | F | Yield (129-3 to F) |
|---|---|---|---|---|
| 265 | | | | 62% |
| 271 | | | | 60% |
| 272 | | | | 67% |
| 282 | | | | 62% |

Compounds 1 to 284 other than the compounds described in Tables 1 to 14 were prepared in the same manner as described in the preparation examples described above.

Synthesis identification results of the compounds prepared above are as described in the following Table 15 and Table 16.

TABLE 15

| Compound | FD-Mass | Compound | FD-Mass |
|---|---|---|---|
| 1 | m/z = 564.63(C39H24N4O = 564.20) | 2 | m/z = 640.73(C45H28N4O = 640.23) |
| 3 | m/z = 640.73(C45H28N4O = 640.23) | 4 | m/z = 716.83(C51H32N4O = 717.26) |

TABLE 15-continued

| Compound | FD-Mass | Compound | FD-Mass |
|---|---|---|---|
| 5 | m/z = 716.83(C51H32N4O = 717.26) | 6 | m/z = 729.82(C51H31N5O = 729.25) |
| 7 | m/z = 729.82(C51H31N5O = 729.25) | 8 | m/z = 805.92(C57H35N5O = 805.28) |
| 9 | m/z = 730.81(C51H30N4O2 = 730.81) | 10 | m/z = 680.79(C48H32N4O = 680.26) |
| 11 | m/z = 680.79(C48H32N4O = 680.26) | 12 | m/z = 680.79(C48H32N4O = 680.26) |
| 13 | m/z = 670.78(C45H26N4OS = 670.18) | 14 | m/z = 654.71(C45H26N4O2 = 654.21) |
| 15 | m/z = 654.71(C45H26N4O2 = 654.21) | 16 | m/z = 670.78(C45H26N4OS = 670.18) |
| 17 | m/z = 640.73(C45H2N4O = 640.23) | 18 | m/z = 716.83(C51H32N4O = 716.26) |
| 19 | m/z = 716.83(C51H32N4O = 716.26) | 20 | m/z = 792.92(C57H36N4O = 792.29) |
| 21 | m/z = 792.92(C57H36N4O = 792.29) | 22 | m/z = 640.73(C45H2N4O = 640.23) |
| 23 | m/z = 792.92(C57H36N4O = 792.29) | 24 | m/z = 792.92(C57H36N4O = 792.29) |
| 25 | m/z = 792.92(C57H36N4O = 792.29) | 26 | m/z = 728.84(C52H32N4O = 728.26) |
| 27 | m/z = 728.84(C52H32N4O = 728.26) | 28 | m/z = 804.93(C58H36N4O = 804.29) |
| 29 | m/z = 746.21(C51H30N4OS = 746.21) | 30 | m/z = 756.89(C54H36N4O = 756.29) |
| 31 | m/z = 756.89(C54H36N4O = 756.29) | 32 | m/z = 679.81(C49H33N3O = 679.26) |
| 33 | m/z = 746.88(C51H30N4OS = 746.21) | 34 | m/z = 730.81(C51H30N4O2 = 730.24) |
| 35 | m/z = 730.81(C51H30N4O2 = 730.24) | 36 | m/z = 669.79(C46H27N3OS = 669.19) |
| 37 | m/z = 640.73(C45H28N4O = 640.23) | 38 | m/z = 640.73(C45H28N4O = 640.23) |
| 39 | m/z = 716.83(C51H32N4O = 717.26) | 40 | m/z = 716.83(C51H32N4O = 717.26) |
| 41 | m/z = 716.83(C51H43N4O = 716.26) | 42 | m/z = 716.83(C51H32N4O = 717.26) |
| 43 | m/z = 715.84(C52H33N3O = 715.26) | 44 | m/z = 715.84(C52H33N3O = 715.26) |
| 45 | m/z = 640.73(C45H28N4O = 640.23 | 46 | m/z = 716.83(C51H32N4O = 716.26) |
| 47 | m/z = 716.83(C51H32N4O = 716.26) | 48 | m/z = 792.92(C57H36N4O = 792.29) |
| 49 | m/z = 756.89(C54H36N4O = 756.29) | 50 | m/z = 716.83(C51H32N4O = 716.26) |
| 51 | m/z = 716.83(C51H32N4O = 716.26) | 52 | m/z = 716.83(C51H32N4O = 716.26) |
| 53 | m/z = 792.92(C57H36N4O = 792.29) | 54 | m/z = 792.92(C57H36N4O = 792.29) |
| 55 | m/z = 601.69(C43H27N3O = 601.69) | 56 | m/z = 601.69(C43H27N3O = 601.69) |
| 57 | m/z = 677.79(C49H31N3O = 677.25) | 58 | m/z = 677.79(C49H31N3O = 677.25) |
| 59 | m/z = 677.79(C49H31N3O = 677.25) | 60 | m/z = 677.79(C49H31N3O = 677.25) |
| 61 | m/z = 753.89(C55H35N3O = 753.28) | 62 | m/z = 753.89(C55H35N3O = 753.28) |
| 63 | m/z = 753.89(C55H35N3O = 753.28) | 64 | m/z = 753.89(C55H35N3O = 753.28) |
| 65 | m/z = 717.85(C52H35N3O = 717.28) | 66 | m/z = 717.85(C52H35N3O = 717.28) |
| 67 | m/z = 707.84(C49H29N3OS = 707.20) | 68 | m/z = 691.77(C49H29N3O2 = 691.23) |
| 69 | m/z = 613.70(C44H27N3O = 613.22) | 70 | m/z = 689.80(C50H31N3O = 689.25) |
| 71 | m/z = 689.80(C50H31N3O = 689.25) | 72 | m/z = 689.80(C50H31N3O = 689.25) |
| 73 | m/z = 765.90(C56H35N3O = 765.28) | 74 | m/z = 765.90(C56H35N3O = 765.28) |
| 75 | m/z = 729.86(C53H35N3O = 729.28) | 76 | m/z = 719.20(C50H29N3OS = 719.20) |
| 77 | m/z = 537.61(C38H23N3O = 537.18) | 78 | m/z = 613.70(C44H27N3O = 613.22) |
| 79 | m/z = 613.70(C44H27N3O = 613.22) | 80 | m/z = 613.70(C44H27N3O = 613.22) |
| 81 | m/z = 689.80(C50H31N3O = 689.25) | 82 | m/z = 689.80(C50H31N3O = 689.25) |
| 83 | m/z = 702.80(C50H30N4O = 702.24) | 84 | m/z = 702.80(C50H30N4O = 702.24) |
| 85 | m/z = 537.61(C38H23N3O = 537.18) | 86 | m/z = 613.70(C44H27N3O = 613.22) |
| 87 | m/z = 613.70(C44H27N3O = 613.22) | 88 | m/z = 613.70(C44H27N3O = 613.22) |
| 89 | m/z = 689.80(C50H31N3O = 689.25) | 90 | m/z = 689.80(C50H31N3O = 689.25) |
| 91 | m/z = 778.90(C56H34N4O = 78.27) | 92 | m/z = 703.78(C50H29N3O2 = 703.23) |
| 93 | m/z = 536.62(C39H24N2O = 536.19) | 94 | m/z = 612.72(C45H28N2O = 612.22) |
| 95 | m/z = 612.72(C45H28N2O = 612.22) | 96 | m/z = 612.72(C45H28N2O = 612.22) |
| 97 | m/z = 688.81(C51H32N2O = 688.25) | 98 | m/z = 688.81(C51H32N2O = 688.25) |
| 99 | m/z = 652.78(C48H32N2O = 652.25) | 100 | m/z = 652.78(C48H32N2O = 652.25) |
| 101 | m/z = 536.62(C39H24N2O = 536.19) | 102 | m/z = 612.72(C45H28N2O = 612.22) |
| 103 | m/z = 612.72(C45H28N2O = 612.22) | 104 | m/z = 612.72(C45H28N2O = 612.22) |
| 105 | m/z = 688.81(C51H32N2O = 688.25) | 106 | m/z = 688.81(C51H32N2O = 688.25) |
| 107 | m/z = 642.77(C45H26N2OS = 642.18) | 108 | m/z = 626.70(C45H27N2O2 = 626.20) |
| 109 | m/z = 563.65(C40H25N3O = 563.20) | 110 | m/z = 639.73(C46H29N3O = 639.23) |
| 111 | m/z = 639.73(C46H29N3O = 639.23) | 112 | m/z = 715.84(C52H33N3O = 715.26) |
| 113 | m/z = 715.84(C52H33N3O = 715.26) | 114 | m/z = 715.84(C52H33N3O = 715.26) |
| 115 | m/z = 639.74(C46H29N3O = 639.23) | 116 | m/z = 715.84(C52H33N3O = 715.26) |
| 117 | m/z = 664.75(C47H28N4O = 664.23) | 118 | m/z = 740.85(C53H32N4O = 740.26) |
| 119 | m/z = 740.85(C53H32N4O = 740.26) | 120 | m/z = 740.85(C53H32N4O = 740.26) |
| 121 | m/z = 816.94(C59H36N4O = 816.29) | 122 | m/z = 816.94(C59H36N4O = 816.29) |
| 123 | m/z = 829.94(C59H35N5O = 829.28) | 124 | m/z = 829.94(C59H35N5O = 829.28) |
| 125 | m/z = 729.82(C51H31N5O = 729.25) | 126 | m/z = 805.92(C57H35N5O = 805.28) |
| 127 | m/z = 702.80(C50H30N4O = 702.24) | 128 | m/z = 766.27(C55H34N4O = 766.27) |
| 129 | m/z = 564.63(C39H24N4O = 564.20) | 130 | m/z = 640.73(C45H28N4O = 640.23) |
| 131 | m/z = 640.73(C45H28N4O = 640.23) | 132 | m/z = 716.83(C51H32N4O = 717.26) |
| 133 | m/z = 716.83(C51H32N4O = 717.26) | 134 | m/z = 729.82(C51H31N5O = 729.25) |
| 135 | m/z = 729.82(C51H31N5O = 729.25) | 136 | m/z = 805.92(C57H35N5O = 805.28) |
| 137 | m/z = 730.81(C51H30N4O2 = 730.81) | 138 | m/z = 680.79(C48H32N4O = 680.26) |
| 139 | m/z = 680.79(C48H32N4O = 680.26) | 140 | m/z = 680.79(C48H32N4O = 680.26) |
| 141 | m/z = 670.78(C45H26N4OS = 670.18) | 142 | m/z = 654.71(C45H26N4O2 = 654.21) |
| 143 | m/z = 654.71(C45H26N4O2 = 654.21) | 144 | m/z = 670.78(C45H26N4OS = 670.18) |
| 145 | m/z = 640.73(C45H2N4O = 640.23) | 146 | m/z = 716.83(C51H32N4O = 716.26) |
| 147 | m/z = 716.83(C51H32N4O = 716.26) | 148 | m/z = 792.92(C57H36N4O = 792.29) |
| 149 | m/z = 792.92(C57H36N4O = 792.29) | 150 | m/z = 640.73(C45H2N4O = 640.23) |
| 151 | m/z = 792.92(C57H36N4O = 792.29) | 152 | m/z = 792.92(C57H36N4O = 792.29) |
| 153 | m/z = 792.92(C57H36N4O = 792.29) | 154 | m/z = 728.84(C52H32N4O = 728.26) |
| 155 | m/z = 728.84(C52H32N4O = 728.26) | 156 | m/z = 804.93(C58H36N4O = 804.29) |
| 157 | m/z = 746.21(C51H30N4OS = 746.21) | 158 | m/z = 756.89(C54H36N4O = 756.29) |
| 159 | m/z = 756.89(C54H36N4O = 756.29) | 160 | m/z = 679.81(C49H33N3O = 679.26) |

TABLE 15-continued

| Compound | FD-Mass | Compound | FD-Mass |
|---|---|---|---|
| 161 | m/z = 746.88(C51H30N4OS = 746.21) | 162 | m/z = 730.81(C51H30N4O2 = 730.24 |
| 163 | m/z = 730.81(C51H30N4O2 = 730.24 | 164 | m/z = 669.79(C46H27N3OS = 669.19) |
| 165 | m/z = 640.73(C45H28N4O = 640.23) | 166 | m/z = 640.73(C45H28N4O = 640.23) |
| 167 | m/z = 716.83(C51H32N4O = 717.26) | 168 | m/z = 716.83(C51H32N4O = 717.26) |
| 169 | m/z = 716.83(C51H43N4O = 716.26) | 170 | m/z = 716.83(C51H32N4O = 717.26) |
| 171 | m/z = 715.84(C52H33N3O = 715.26) | 172 | m/z = 715.84(C52H33N3O = 715.26) |
| 173 | m/z = 640.73(C45H28N4O = 640.23 | 174 | m/z = 716.83(C51H32N4O = 716.26) |
| 175 | m/z = 716.83(C51H32N4O = 716.26) | 176 | m/z = 792.92(C57H36N4O = 792.29) |
| 177 | m/z = 756.89(C54H36N4O = 756.29) | 178 | m/z = 716.83(C51H32N4O = 716.26) |
| 179 | m/z = 716.83(C51H32N4O = 716.26) | 180 | m/z = 716.83(C51H32N4O = 716.26) |
| 181 | m/z = 792.92(C57H36N4O = 792.29) | 182 | m/z = 792.92(C57H36N4O = 792.29) |
| 183 | m/z = 601.69(C43H27N3O = 601.69) | 184 | m/z = 601.69(C43H27N3O = 601.69) |
| 185 | m/z = 677.79(C49H31N3O = 677.25) | 186 | m/z = 677.79(C49H31N3O = 677.25) |
| 187 | m/z = 677.79(C49H31N3O = 677.25) | 188 | m/z = 677.79(C49H31N3O = 677.25) |
| 189 | m/z = 753.89(C55H35N3O = 753.28) | 190 | m/z = 753.89(C55H35N3O = 753.28) |
| 191 | m/z = 753.89(C55H35N3O = 753.28) | 192 | m/z = 753.89(C55H35N3O = 753.28) |
| 193 | m/z = 717.85(C52H35N3O = 717.28) | 194 | m/z = 717.85(C52H35N3O = 717.28) |
| 195 | m/z = 707.84(C49H29N3OS = 707.20) | 196 | m/z = 691.77(C49H29N3O2 = 691.23) |
| 197 | m/z = 613.70(C44H27N3O = 613.22) | 198 | m/z = 689.80(C50H31N3O = 689.25) |
| 199 | m/z = 689.80(C50H31N3O = 689.25) | 200 | m/z = 689.80(C50H31N3O = 689.25) |
| 201 | m/z = 765.90(C56H35N3O = 765.28) | 202 | m/z = 765.90(C56H35N3O = 765.28) |
| 203 | m/z = 729.86(C53H35N3O = 729.28) | 204 | m/z = 719.20(C50H29N3OS = 719.20) |
| 205 | m/z = 537.61(C38H23N3O = 537.18) | 206 | m/z = 613.70(C44H27N3O = 613.22) |
| 207 | m/z = 613.70(C44H27N3O = 613.22) | 208 | m/z = 613.70(C44H27N3O = 613.22) |
| 209 | m/z = 689.80(C50H31N3O = 689.25) | 210 | m/z = 689.80(C50H31N3O = 689.25) |
| 211 | m/z = 702.80(C50H30N4O = 702.24) | 212 | m/z = 702.80(C50H30N4O = 702.24) |
| 213 | m/z = 537.61(C38H23N3O = 537.18) | 214 | m/z = 613.70(C44H27N3O = 613.22) |
| 215 | m/z = 613.70(C44H27N3O = 613.22) | 216 | m/z = 613.70(C44H27N3O = 613.22) |
| 217 | m/z = 689.80(C50H31N3O = 689.25) | 218 | m/z = 689.80(C50H31N3O = 689.25) |
| 219 | m/z = 778.90(C56H34N4O = 78.27) | 220 | m/z = 703.78(C50H29N3O2 = 703.23) |
| 221 | m/z = 536.62(C39H24N2O = 536.19) | 222 | m/z = 612.72(C45H28N2O = 612.22) |
| 223 | m/z = 612.72(C45H28N2O = 612.22) | 224 | m/z = 612.72(C45H28N2O = 612.22) |
| 225 | m/z = 688.81(C51H32N2O = 688.25) | 226 | m/z = 688.81(C51H32N2O = 688.25) |
| 227 | m/z = 652.78(C48H32N2O = 652.25) | 228 | m/z = 652.78(C48H32N2O = 652.25) |
| 229 | m/z = 536.62(C39H24N2O = 536.19) | 230 | m/z = 612.72(C45H28N2O = 612.22) |
| 231 | m/z = 612.72(C45H28N2O = 612.22) | 232 | m/z = 612.72(C45H28N2O = 612.22) |
| 233 | m/z = 688.81(C51H32N2O = 688.25) | 234 | m/z = 688.81(C51H32N2O = 688.25) |
| 235 | m/z = 642.77(C45H26N2OS = 642.18) | 236 | m/z = 626.70(C45H27N2O2 = 626.20) |
| 237 | m/z = 563.65(C40H25N3O = 563.20) | 238 | m/z = 639.73(C46H29N3O = 639.23) |
| 239 | m/z = 639.73(C46H29N3O = 639.23) | 240 | m/z = 715.84(C52H33N3O = 715.26) |
| 241 | m/z = 715.84(C52H33N3O = 715.26) | 242 | m/z = 715.84(C52H33N3O = 715.26) |
| 243 | m/z = 639.74(C46H29N3O = 639.23) | 244 | m/z = 715.84(C52H33N3O = 715.26) |
| 245 | m/z = 664.75(C47H28N4O = 664.23) | 246 | m/z = 740.85(C53H32N4O = 740.26) |
| 247 | m/z = 740.85(C53H32N4O = 740.26) | 248 | m/z = 740.85(C53H32N4O = 740.26) |
| 249 | m/z = 816.94(C59H36N4O = 816.29) | 250 | m/z = 816.94(C59H36N4O = 816.29) |
| 251 | m/z = 829.94(C59H35N5O = 829.28) | 252 | m/z = 829.94(C59H35N5O = 829.28) |
| 253 | m/z = 729.82(C51H31N5O = 729.25) | 254 | m/z = 805.92(C57H35N5O = 805.28) |
| 255 | m/z = 702.80(C50H30N4O = 702.24) | 256 | m/z = 766.27(C55H34N4O = 766.27) |
| 257 | m/z = 716.83(C51H32N4O = 716.26) | 258 | m/z = 654.71(C45H26N4O2 = 654.21) |
| 259 | m/z = 730.81(C51H30N4O2 = 730.24) | 260 | m/z = 654.71(C45H26N4O2 = 654.21) |
| 261 | m/z = 730.81(C51H30N4O2 = 730.24) | 262 | m/z = 730.81(C51H30N4O2 = 730.24) |
| 263 | m/z = 716.83(C51H32N4O = 716.26) | 264 | m/z = 654.71(C45H26N4O2 = 654.21) |
| 265 | m/z = 730.81(C51H30N4O2 = 730.24) | 266 | m/z = 730.81(C51H30N4O2 = 730.24) |
| 267 | m/z = 746.88(C51H30N4OS = 741.21) | 268 | m/z = 756.89(C54H36N4O = 756.29) |
| 269 | m/z = 614.71(C43H26N4O = 614.21) | 270 | m/z = 664.77(C47H28N4O = 664.23) |
| 271 | m/z = 729.84(C51H31N5O = 729.25) | 272 | m/z = 729.84(C51H31N5O = 729.25) |
| 273 | m/z = 654.73(C45H26N4O2 = 654.21) | 274 | m/z = 670.79(C45H26N4OS = 670.18) |
| 275 | m/z = 779.90(C55H33N5O = 779.27) | 276 | m/z = 829.96(C59H35N5O = 829.28) |
| 277 | m/z = 704.79(C49H28N4O2 = 704.22) | 278 | m/z = 720.85(C49H28N4OS = 720.20) |
| 279 | m/z = 754.85(C53H30N4O2 = 754.24) | 280 | m/z = 770.91(C53H30N4OS = 770.21) |
| 281 | m/z = 693.82(C48H27N3OS = 693.19) | 282 | m/z = 758.90(C52H30N4OS = 758.21) |
| 283 | m/z = 799.97(C54H29N3OS2 = 799.18) | 284 | m/z = 783.90(C54H29N3O2S = 783.20) |

TABLE 16

| Compound | $^1$H NMR (CDCl$_3$, 200 Mz) |
|---|---|
| 1 | δ = 8.55 (1h, d), 8.28 (4h, d), 8.12 (1H, d), 7.94~7.89 (2H, q), 7.75 (1H, d), 7.63~7.62 (2H, m), 7.51~7.25 (13H, m) |
| 2 | δ = 8.55 (1H, d), 8.28 (4H, d), 8.18 (1H, d), 7.94~7.89 (2H, q), 7.79~7.75 (2H, q), 7.62 (2H, m), 7.52~7.5 (16H, m) |
| 3 | δ = 8.55 (1H, d), 8.28 (4H, d), 7.94~7.87 (3H, q), 7.77~7.69 (4H, m), 7.52~7.2 (16H, m) |
| 5 | δ = 8.28 (4H, d), 8.18 (1H, d), 8.00 (1H, d), 7.89~7.87 (2H, t), 7.77~7.69 (4H, m), 7.52~7.25 (16H, m) |
| 10 | δ = 8.39 (1H, s), 8.28 (4H, d), 8.12~8.059 (2H, t), 7.89 (1H, d), 7.75 (1H, d), 7.69 (1H, s), 7.63~7.61 (3H, m), 7.51~7.24 (13H, m) |

TABLE 16-continued

| Compound | $^1$H NMR (CDCl$_3$, 200 Mz) |
|---|---|
| 17 | δ = 8.52 (1H, d), 8.28~8.24 (3H, m), 8.12 (1H, d), 7.94~7.89 (2H, d), 7.75~7.70 (2H, m), 7.62~7.25 (19H, m) |
| 18 | δ = 8.53 (1H, d), 8.28~8.18 (4H, m), 7.94~7.89 (2H, q), 7.79~7.70 (3H, m), 7.62~7.25 (22H, m) |
| 129 | δ = 8.55 (1H, d), 8.28 (4H, d), 8.12 (1H, d), 7.94~7.89 (2H, q), 7.75 (2H, d), 7.73 (1H, s), 7.63~7.62 (2H, m), 7.51~7.25 (12H, m) |
| 130 | δ = 8.55 (1H, d), 8.28 (4H, d), 8.18 (1H, d), 7.94~7.89 (2H, q), 7.79~7.73 (3H, m), 7.62 (2H, m), 7.52~7.25 (15H, m) |
| 131 | δ = 8.55 (1H, d), 8.28 (4H, d), 7.94~7.87 (3H, m), 7.77~7.73 (5H, m), 7.52~7.25 (15H, m) |
| 133 | δ = 8.28 (4H, d), 8.18 (1H, d), 8.0 (1H, d), 7.89~7.87 (2H, t), 7.77~7.73 (5H, m), 7.62 (1H, m), 7.52~7.41 (18H, m) |
| 138 | δ = 8.39 (1H, d), 8.28 (4H, d), 8.12~8.09 (2H, t), 7.89 (1H, d), 7.75~7.61 (6H, m), 7.51~7.41 (10H, m), |
| 145 | δ = 8.55 (1H, d), 8.28~8.24 (3H, m), 8.12 (1H, d), 7.94~7.89 (2H, q), 7 75~7.70 (3H, t), 7.63~7.25 (18H, m) |
| 146 | δ = 8.55 (1H, d), 8.28~8.18 (4H, m), 7.94~7.89 (2H, d), 7.79~7.70 (4H, m), 7.62~7.25 (21H, m) |
| 257 | δ = 8.55 (1H, d), 8.24 (2H, d), 8.12 (1H, d), 7.94~7.89 (2H, q), 7.75~7.70 (3H, m), 7.63~7.25 (23H, m) |
| 265 | δ = 8.28 (2H, d), 8.18~8.12 (2H, q), 8.00 (1H, d), 7.89~7.73 (7H, m), 7.66~7.62 (3H, m), 7.52~7.29 (15H, m) |
| 271 | δ = 8.55 (2H, d), 8.36 (4H, t), 7.98~7.94 (3H, m), 7.82 (1H, d), 7.69~7.50 (15H, m), 7.35 (2H, t), 7.26~7.25 (2H, d), 7.16 (2H, t) |
| 272 | δ = 8.55 (2H, d), 8.36 (4H, t), 8.12 (1H, d), 7.98~7.94 (3H, m), 7.82 (1H, d), 7.69~7.50 (14H, m), 7.35 (2H, t), 7.25~7.16 (4H, m) |
| 282 | δ = 8.55 (2H, d), 8.05 (1H, d), 7.98~7.82 (7H, m), 7.69~7.35 (16H, m), 7.26~7.25 (2H, d), 7.16 (2H, t) |

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), a hole injection layer 4,4',4"-tris[2-naphthyl(phenyl)amino]triphenylamine (2-TNATA) and a hole transfer layer N,N'-di(1-naphthyl)-N,N'-diphenyl-(1,1'-biphenyl)-4,4'-diamine (NPB), which are common layers, were formed.

A light emitting layer was thermal vacuum deposited thereon as follows. The light emitting layer was deposited to 400 Å using the compound described in the following [Table 17] as a host and tris(2-phenylpyridine)iridium (Ir(ppy)$_3$) as a green phosphorescent dopant and by doping the Ir(ppy)$_3$ to the host to a thickness of 7% of the light emitting layer deposition. After that, BCP was deposited to 60 Å as a hole blocking layer, and Alq$_3$ was deposited to 200 Å as an electron transfer layer thereon. Lastly, lithium fluoride (LiF) was deposited to a thickness of 10 Å on the electron transfer layer to form an electron injection layer, and then an aluminum (Al) cathode was deposited to a thickness of 1200 Å on the electron injection layer to form a cathode, and as a result, an organic electroluminescent device was manufactured.

Meanwhile, all the organic compounds required to manufacture the OLED device were vacuum sublimation purified under $10^{-6}$ torr to $10^{-8}$ torr by each material to be used in the OLED manufacture.

2) Driving Voltage and Light Emission Efficiency of Organic Electroluminescent Device For the organic electroluminescent devices manufactured as above, electroluminescent light emission (EL) properties were measured using M7000 manufactured by McScience Inc., and with the measurement results, $T_{90}$ when standard luminance was 6,000 cd/m$^2$ was measured using a lifetime test system (M6000) manufactured by McScience Inc. Properties of the organic electroluminescent device of the present disclosure are as shown in [Table 17].

[Comparative Example 1]

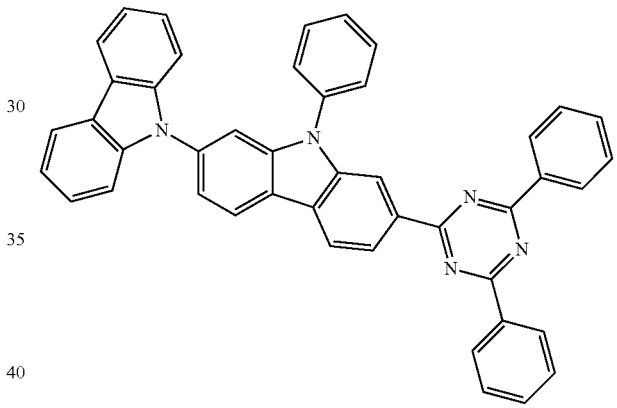

A

[Comparative Example 2]

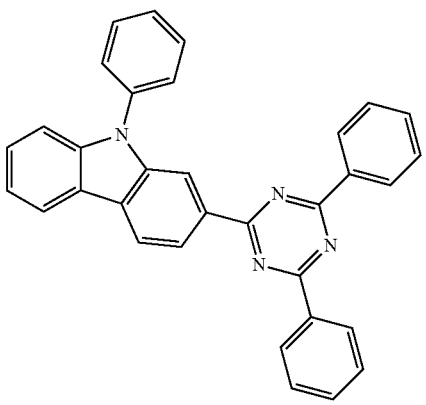

B

[Comparative Example 3]

C

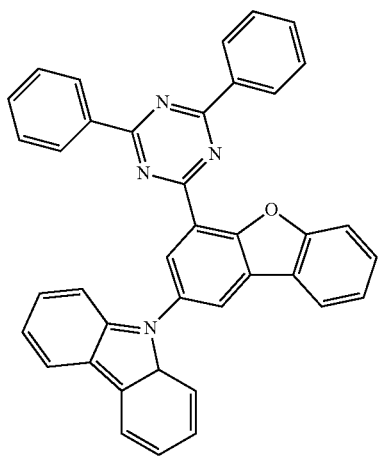

[Comparative Example 4]

D

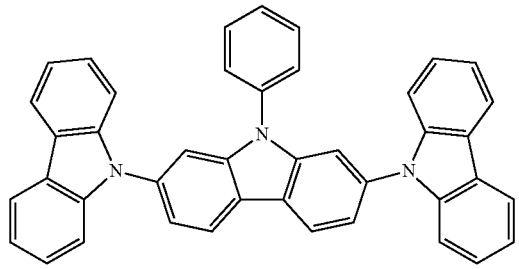

[Comparative Example 5]

E

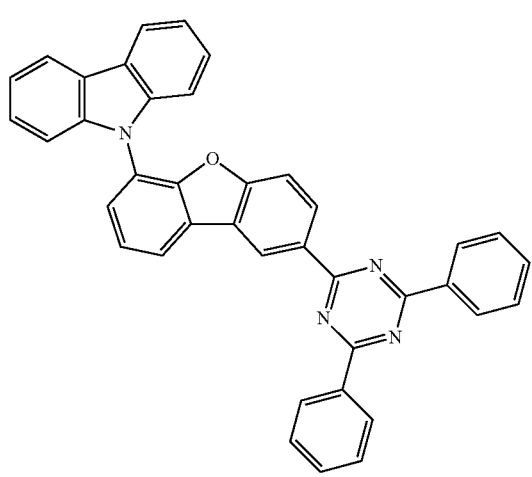

[Comparative Example 6]

F

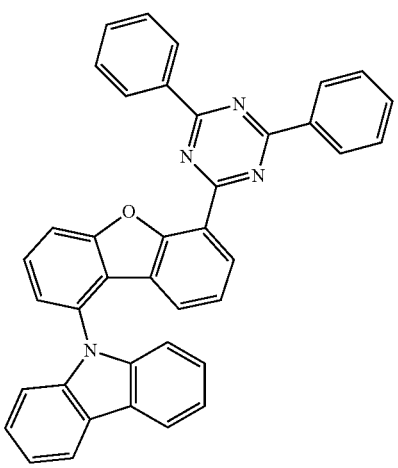

[Comparative Example 7]

G

TABLE 17

| Compound | | Driving Voltage (V) | Efficiency (cd/A) | Color Coordinate (x, y) | Lifetime ($T_{90}$) |
|---|---|---|---|---|---|
| Comparative Example 1 | A | 5.84 | 44.3 | (0.276, 0.674) | 57 |
| Comparative Example 2 | B | 5.57 | 51.2 | (0.286, 0.673) | 58 |
| Comparative Example 3 | C | 5.43 | 55.4 | (0.286, 0.678) | 77 |
| Comparative Example 4 | D | 5.92 | 57.2 | (0.288, 0.677) | 43 |
| Comparative Example 5 | E | 5.62 | 54.5 | (0.281, 0.674 | 65 |
| Comparative Example 6 | F | 5.33 | 55.5 | (0.285, 0.676) | 71 |
| Comparative Example 7 | G | 5.72 | 56.3 | (0.284, 0.679) | 69 |
| Example 1 | 1 | 5.02 | 56.4 | (0.287, 0.673) | 183 |
| Example 2 | 2 | 3.54 | 80.1 | (0.287, 0.677) | 172 |

TABLE 17-continued

| Compound | Driving Voltage (V) | Efficiency (cd/A) | Color Coordinate (x, y) | Lifetime ($T_{90}$) |
|---|---|---|---|---|
| Example 3 | 3 | 3.53 | 76.2 | (0.289, 0.672) | 177 |
| Example 4 | 5 | 3.82 | 73.4 | (0.287, 0.677) | 161 |
| Example 5 | 7 | 4.42 | 68.4 | (0.287, 0.674) | 141 |
| Example 6 | 10 | 4.44 | 62.3 | (0.289, 0.679) | 138 |
| Example 7 | 17 | 3.92 | 78.2 | (0.276, 0.672) | 147 |
| Example 8 | 18 | 3.75 | 71.3 | (0.278, 0.673) | 173 |
| Example 9 | 19 | 3.72 | 79.1 | (0.280, 0.676) | 175 |
| Example 10 | 22 | 3.88 | 79.3 | (0.278, 0.672) | 178 |
| Example 11 | 28 | 4.23 | 67.2 | (0.283, 0.684) | 142 |
| Example 12 | 29 | 4.12 | 63.4 | (0.287, 0.687) | 139 |
| Example 13 | 34 | 4.03 | 69.2 | (0.274, 0.678) | 146 |
| Example 14 | 38 | 3.88 | 78.1 | (0.277, 0.677) | 151 |
| Example 15 | 39 | 3.76 | 77.2 | (0.277, 0.678) | 132 |
| Example 16 | 43 | 4.12 | 67.3 | (0.276, 0.673) | 145 |
| Example 17 | 48 | 4.32 | 72.3 | (0.284, 0.674) | 157 |
| Example 18 | 51 | 4.12 | 74.2 | (0.283, 0.681) | 154 |
| Example 19 | 53 | 4.33 | 72.3 | (0.274, 0.677) | 155 |
| Example 20 | 59 | 3.99 | 69.2 | (0.276, 0.678) | 156 |
| Example 21 | 62 | 3.89 | 70.2 | (0.289, 0.670) | 142 |
| Example 22 | 65 | 4.12 | 69.6 | (0.286, 0.671) | 132 |
| Example 23 | 67 | 3.87 | 69.4 | (0.288, 0.674) | 152 |
| Example 24 | 70 | 4.03 | 64.2 | (0.285, 0.673) | 142 |
| Example 25 | 71 | 3.76 | 70.3 | (0.273, 0.677) | 144 |
| Example 26 | 75 | 3.65 | 72.2 | (0.287, 0.673) | 156 |
| Example 27 | 77 | 3.99 | 69.9 | (0.288, 0.679) | 165 |
| Example 28 | 80 | 4.21 | 65.2 | (0.286, 0.681) | 154 |
| Example 29 | 83 | 4.13 | 68.3 | (0.275, 0.679) | 167 |
| Example 30 | 86 | 4.21 | 71.3 | (0.283, 0.677) | 153 |
| Example 31 | 90 | 4.32 | 69.2 | (0.286, 0.678) | 152 |
| Example 32 | 92 | 4.12 | 73.2 | (0.284, 0.678) | 157 |
| Example 33 | 95 | 4.22 | 64.2 | (0.271, 0.673) | 143 |
| Example 34 | 100 | 3.75 | 63.2 | (0.283, 0.687) | 144 |
| Example 35 | 101 | 4.11 | 63.1 | (0.283, 0.677) | 173 |
| Example 36 | 109 | 4.21 | 63.6 | (0.289, 0.674) | 153 |
| Example 37 | 115 | 4.32 | 66.3 | (0.287, 0.678) | 154 |
| Example 38 | 118 | 4.32 | 65.2 | (0.271, 0.679) | 144 |
| Example 39 | 121 | 4.34 | 62.4 | (0.273, 0.689) | 149 |
| Example 40 | 125 | 3.66 | 73.1 | (0.274, 0.687) | 162 |
| Example 41 | 127 | 3.79 | 71.4 | (0.279, 0.673) | 170 |
| Example 42 | 129 | 3.80 | 69.9 | (0.275, 0.675) | 170 |
| Example 43 | 130 | 3.90 | 67.4 | (0.282, 0.676) | 167 |
| Example 44 | 131 | 3.81 | 62.9 | (0.283, 0.673) | 155 |
| Example 45 | 133 | 3.99 | 70.6 | (0.274, 0.679) | 169 |
| Example 46 | 135 | 3.82 | 72.4 | (0.272, 0.676) | 168 |
| Example 47 | 138 | 3.72 | 73.6 | (0.273, 0.675) | 174 |
| Example 48 | 145 | 3.67 | 68.7 | (0.274, 0.676) | 166 |
| Example 49 | 146 | 4.42 | 65.2 | (0.273, 0.676) | 143 |
| Example 50 | 147 | 4.43 | 63.4 | (0.283, 0.677) | 132 |
| Example 51 | 150 | 3.89 | 75.9 | (0.284, 0.676) | 142 |
| Example 52 | 156 | 3.71 | 71.4 | (0.283, 0.675) | 164 |
| Example 53 | 157 | 3.72 | 69.4 | (0.279, 0.676) | 169 |
| Example 54 | 162 | 3.98 | 76.6 | (0.291, 0.677) | 174 |
| Example 55 | 166 | 4.59 | 67.3 | (0.293, 0.684) | 142 |
| Example 56 | 167 | 4.42 | 66.5 | (0.282, 0.674) | 133 |
| Example 57 | 171 | 4.52 | 65.1 | (0.281, 0.678) | 131 |
| Example 58 | 173 | 4.10 | 73.9 | (0.283, 0.675) | 165 |
| Example 59 | 176 | 3.91 | 73.4 | (0.288, 0.676) | 158 |
| Example 60 | 179 | 4.13 | 68.4 | (0.288, 0.674) | 149 |
| Example 61 | 181 | 4.42 | 66.1 | (0.287, 0.675) | 143 |
| Example 62 | 187 | 4.67 | 63.5 | (0.277, 0.678) | 165 |
| Example 63 | 190 | 4.32 | 69.4 | (0.287, 0.676) | 166 |
| Example 64 | 193 | 4.65 | 66.8 | (0.275, 0.677) | 142 |
| Example 65 | 195 | 4.32 | 67.8 | (0.285, 0.680) | 142 |
| Example 66 | 198 | 4.21 | 71.3 | (0.287, 0.680) | 135 |
| Example 67 | 199 | 3.93 | 67.4 | (0.278, 0.681) | 149 |
| Example 68 | 203 | 4.12 | 64.6 | (0.281, 0.677) | 132 |
| Example 69 | 205 | 3.95 | 67.8 | (0.287, 0.676) | 142 |
| Example 70 | 208 | 3.89 | 68.8 | (0.284, 0.677) | 138 |
| Example 71 | 211 | 4.23 | 67.4 | (0.273, 0.673) | 163 |
| Example 72 | 214 | 4.42 | 62.2 | (0.279, 0.676) | 164 |
| Example 73 | 218 | 4.33 | 68.3 | (0.279, 0.677) | 131 |
| Example 74 | 220 | 4.53 | 67.8 | (0.282, 0.687) | 141 |
| Example 75 | 223 | 4.23 | 67.4 | (0.283, 0.676) | 153 |
| Example 76 | 228 | 4.32 | 78.3 | (0.284, 0.674) | 163 |
| Example 77 | 229 | 4.12 | 68.4 | (0.289, 0.674) | 142 |
| Example 78 | 238 | 3.78 | 62.8 | (0.284, 0.672) | 141 |

TABLE 17-continued

| Compound | Driving Voltage (V) | Efficiency (cd/A) | Color Coordinate (x, y) | Lifetime ($T_{90}$) |
|---|---|---|---|---|
| Example 79 | 241 | 4.32 | 66.4 | (0.283, 0.681) | 158 |
| Example 80 | 246 | 4.21 | 68.9 | (0.279, 0.680) | 133 |
| Example 81 | 247 | 3.66 | 73.4 | (0.279, 0.674) | 178 |
| Example 82 | 249 | 3.79 | 72.8 | (0.278, 0.671) | 177 |
| Example 83 | 253 | 4.64 | 69.3 | (0.275, 0.677) | 154 |
| Example 84 | 255 | 3.78 | 72.5 | (0.284, 0.673) | 171 |
| Example 85 | 257 | 4.32 | 70.4 | (0.287, 0.676) | 158 |
| Example 86 | 258 | 4.01 | 69.2 | (0.284, 0.678) | 143 |
| Example 87 | 261 | 3.86 | 72.3 | (0.279, 0.675) | 152 |
| Example 88 | 263 | 3.65 | 78.8 | (0.279, 0.670) | 177 |
| Example 89 | 264 | 3.64 | 80.3 | (0.281, 0.669) | 185 |
| Example 90 | 265 | 3.76 | 77.6 | (0.282, 0.673) | 162 |
| Example 91 | 271 | 3.62 | 75.8 | (0.288, 0.671) | 152 |
| Example 92 | 272 | 3.82 | 68.3 | (0.279, 0.674) | 139 |
| Example 93 | 282 | 3.67 | 72.2 | (0.281, 0.668) | 148 |

As a result of device evaluation, it was identified that the heterocyclic compound of the present disclosure had excellent efficiency, particularly, lifetime properties. For commercialization of materials, long lifetime properties are a most important factor. Particularly, a device lifetime may decrease due to an increase in the electron instability of a LUMO site caused by strong electron donating properties of oxygen of the dibenzofuran, and with ortho and para orientation, the effect became higher particularly when an N-containing ring substitutes carbons on the 2 and 4 positions of the dibenzofuran. However, the compound according to the present disclosure is capable of improving a device lifetime by having an N-containing ring positioned on the number 1 carbon.

Particularly, when an N-containing ring such as triazine substitutes a position of number 1 carbon of dibenzofuran, steric hindrance occurs at a rigid site in the dibenzofuran, and the molecular structure is present in a bent form. As a result, empty space is eliminated when the molecule is deposited shortening a conjugation length as well as strengthening electron transfer capability, which results in a high Ti value. Substituting a position of number 2 or 4 carbon of dibenzofuran may bring in factors inhibiting charge transfer capability (Chem. Eur. J. 2013, 19, 1194-1198). This was identifiable through Comparative Examples 5 and 6.

The invention claimed is:
1. A heterocyclic compound represented by one of the following Chemical Formulae 6 to 8:

[Chemical Formula 6]

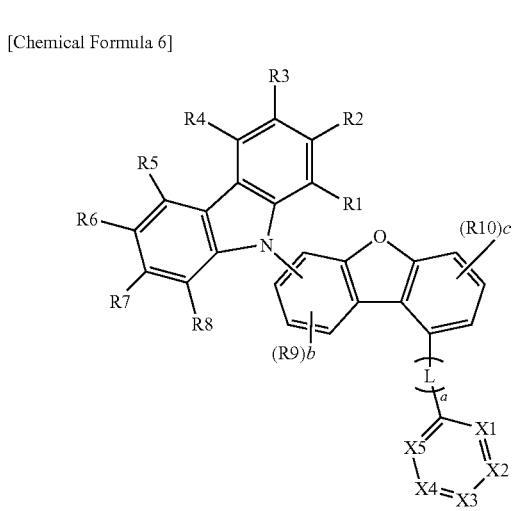

[Chemical Formula 7]

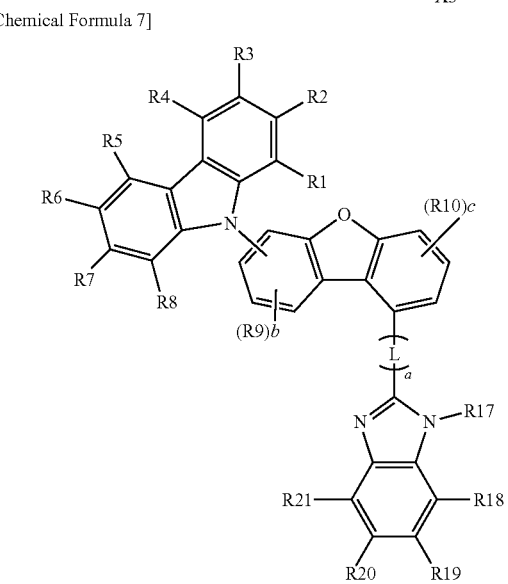

[Chemical Formula 8]

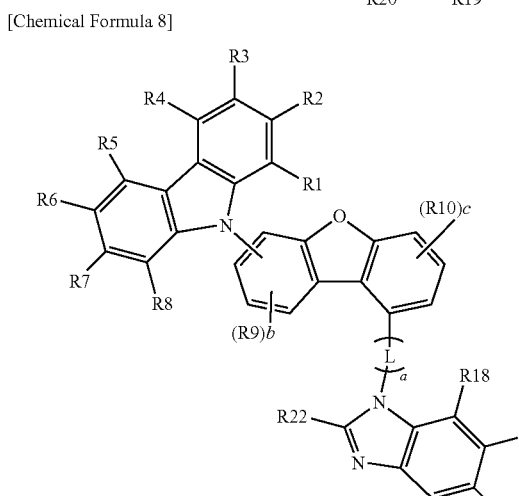

in Chemical Formulae 6 to 8,

L is a direct bond; a substituted or unsubstituted arylene group; or a substituted or unsubstituted heteroarylene group, a is an integer of 1 to 3, and when a is 2 or greater, Ls are the same as or different from each other; and R1 to R10 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heterering, b and c are each an integer of 1 to 3, and when b is 2 or greater, R9s are the same as or different from each other and when c is 2 or greater, R10s are the same as or different from each other, R17 to R22 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heterering, in chemical formula 6, wherein

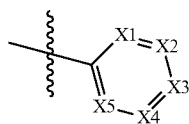

is represented by one of the following Chemical Formulae 9 to 12:

[Chemical Formula 9]

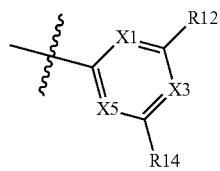

[Chemical Formula 10]

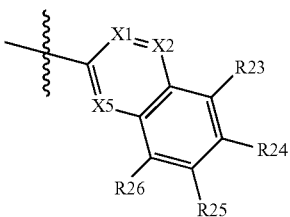

[Chemical Formula 11]

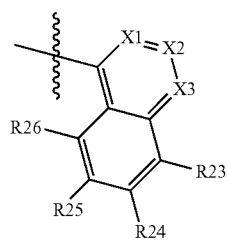

[Chemical Formula 12]

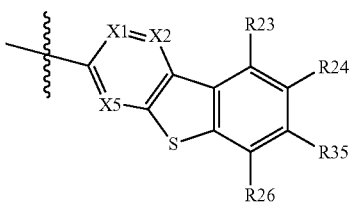

in Chemical Formulas 9 to 12,

X1 is CR11 or N, X2 is CR12 or N, X3 is CR13 or N and X5 is CR15 or N, in Chemical Formula 9, one or more of X1, X3 and X5 are N, in Chemical Formula 10, one or more of X1, X2 and X5 are N, in Chemical Formula 11, one or more of X1 to X3 are N, in Chemical Formula 12, one or more of X1, X2 and X5 are N, R11 to R15 and R23 to R26 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, in chemical formula 6, wherein when R1 to R8 are hydrogen, one of R12 and R14 of chemical formula 9 is a substituted or unsubstituted C10 to C60 aryl group; or a substituted or unsubstituted C2 to C60 heteroaryl group.

2. The heterocyclic compound of claim 1, wherein Chemical Formula 9 is selected from among the following structural formulae:

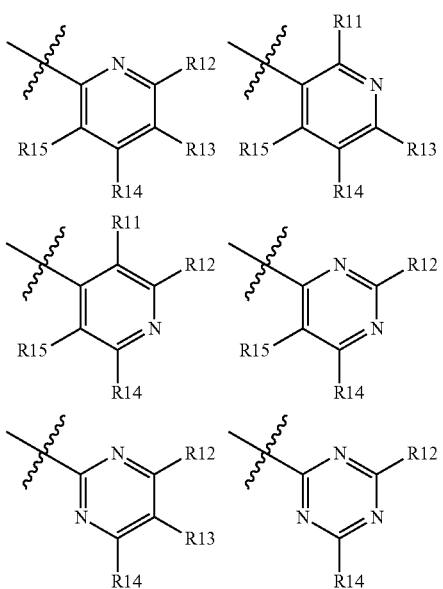

in the structural formulae, R11 to R15 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

3. The heterocyclic compound of claim 1, wherein Chemical Formulae 6 to 8 is represented by any one of the following compounds:

2

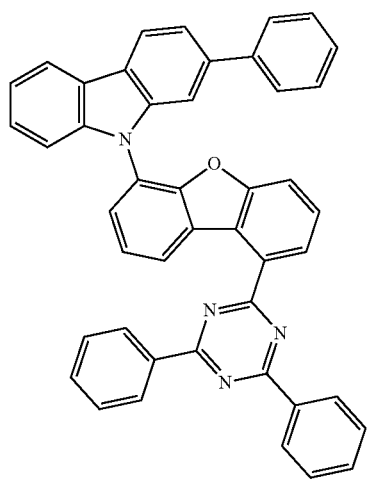

3

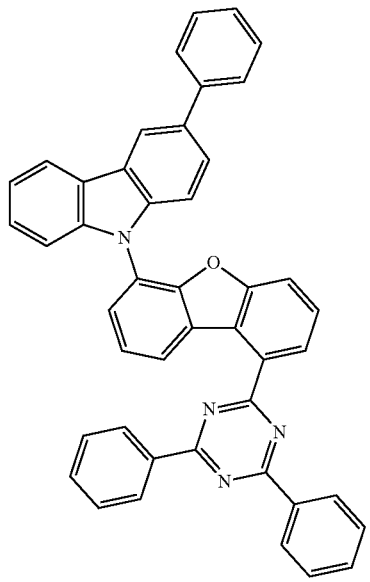

4

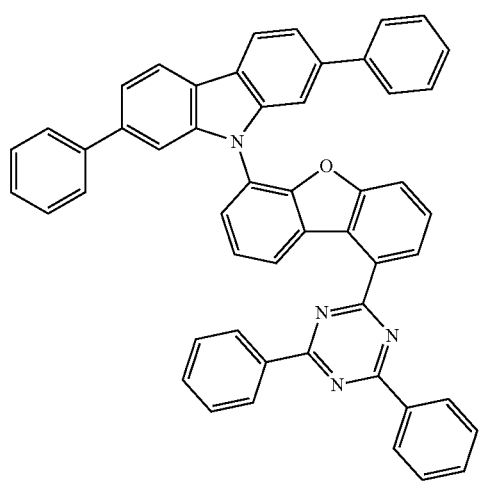

5

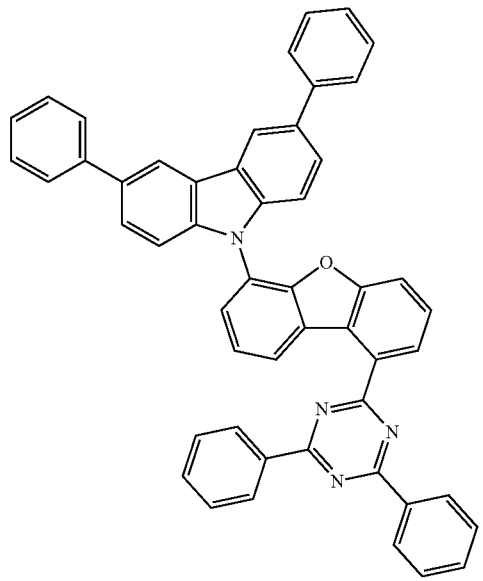

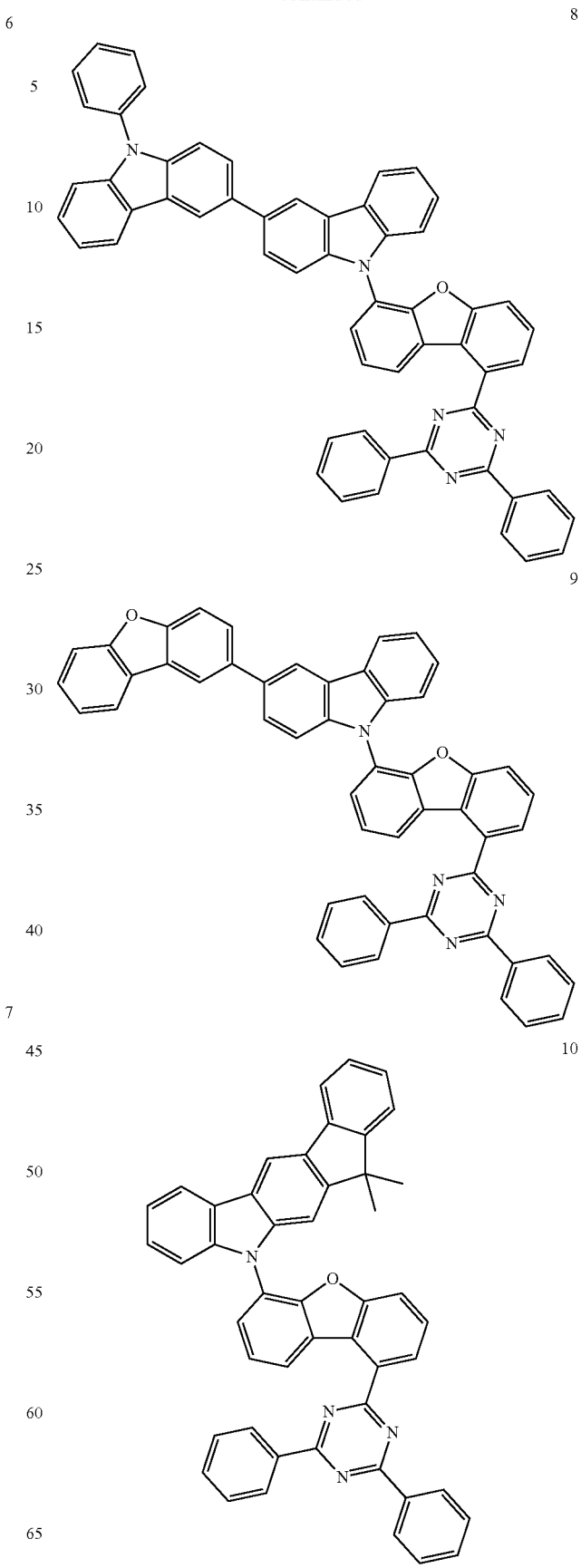

11
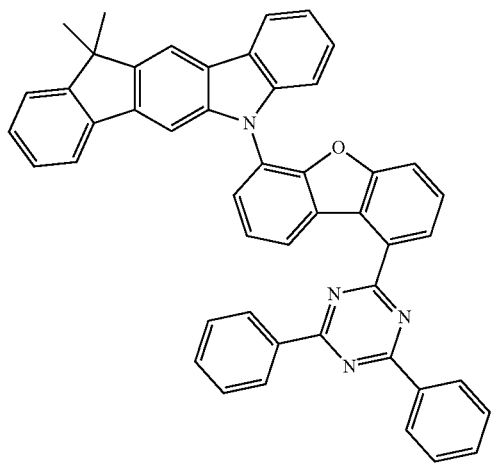
12
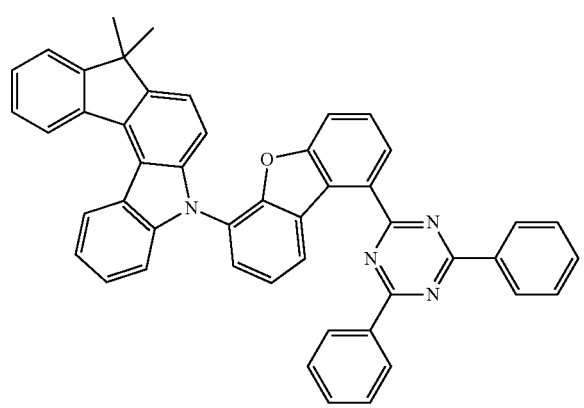
13
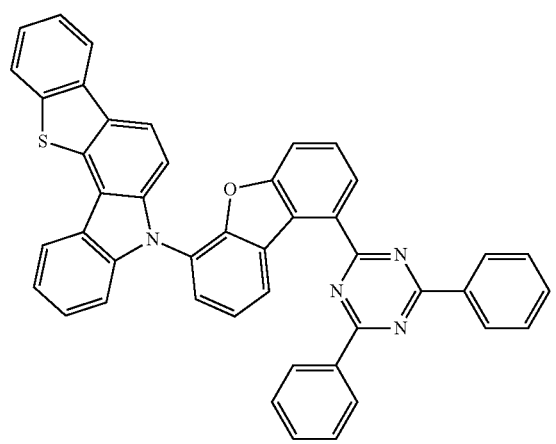
14
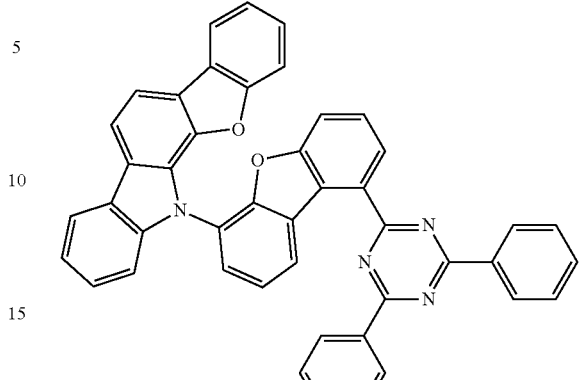
15
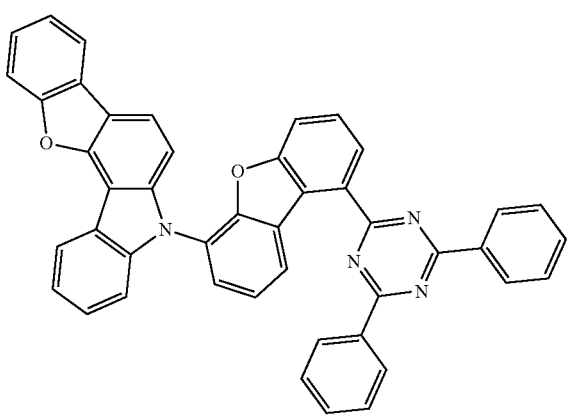
16
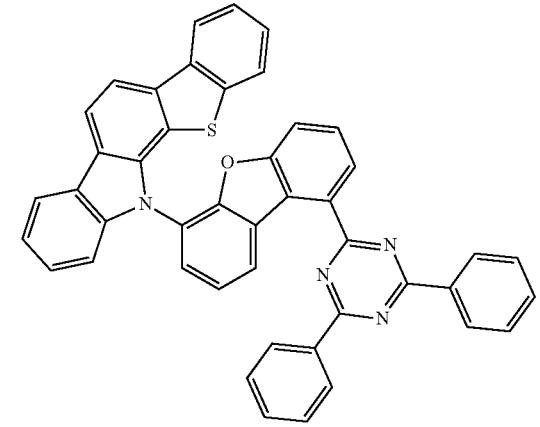
17
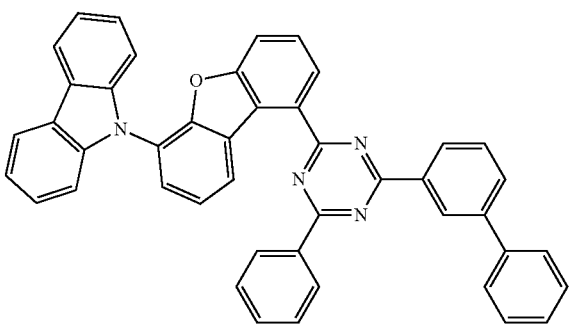

17
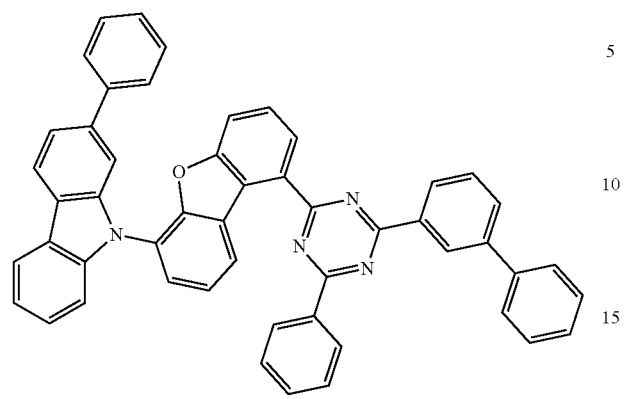
19
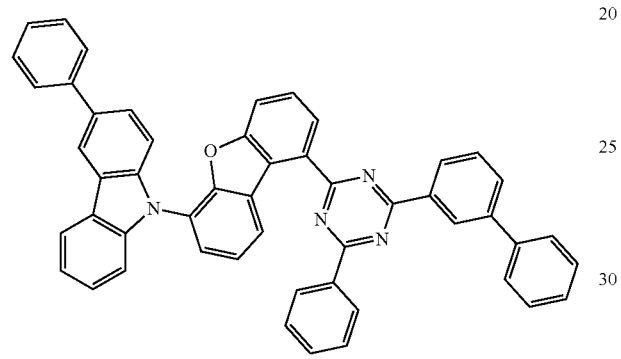
20
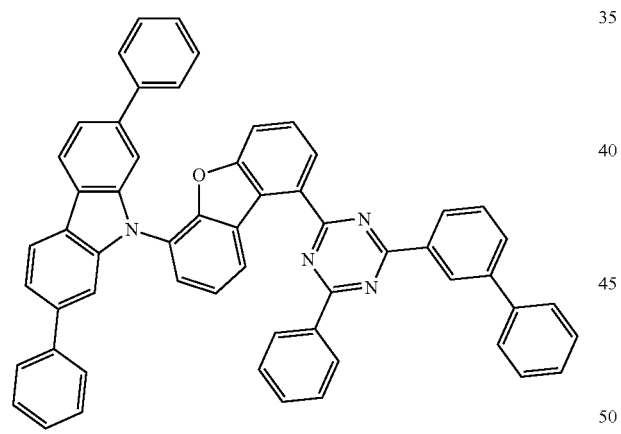
21
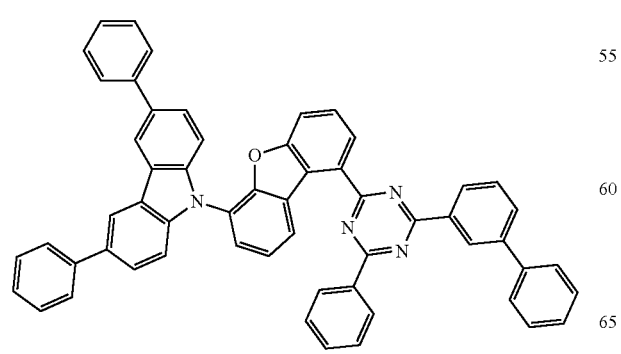
22
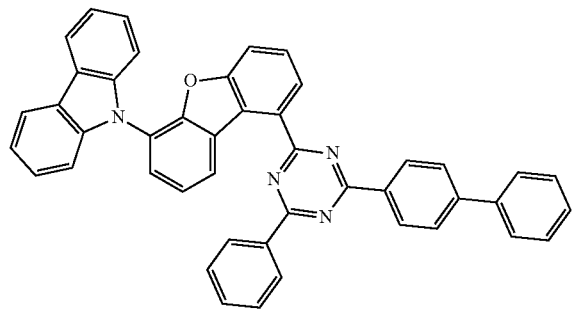
23
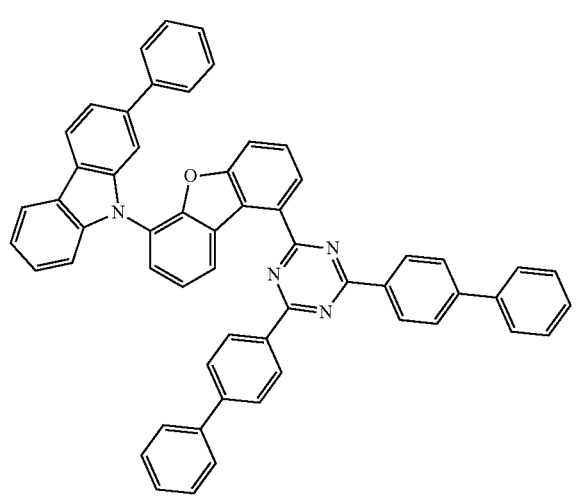
24
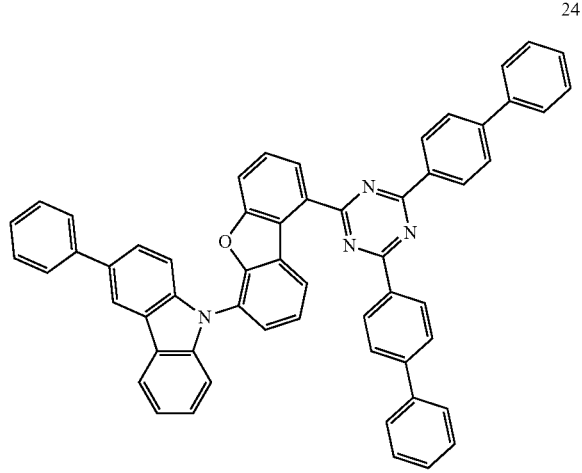

25
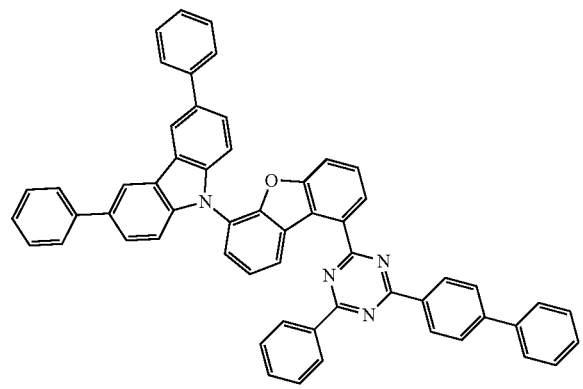
26
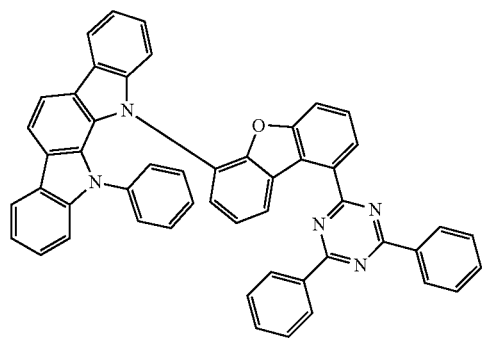
27
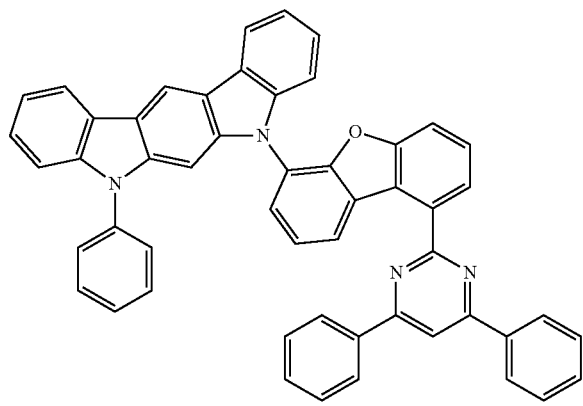
28
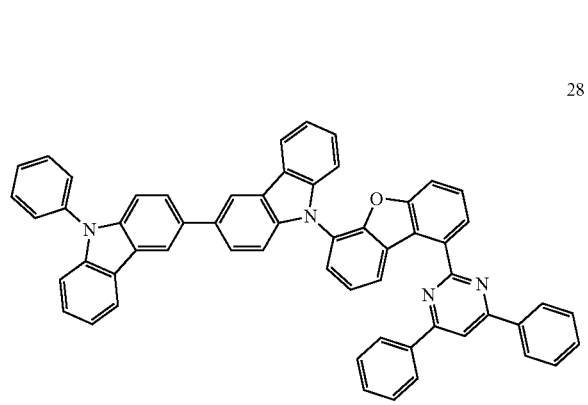
29
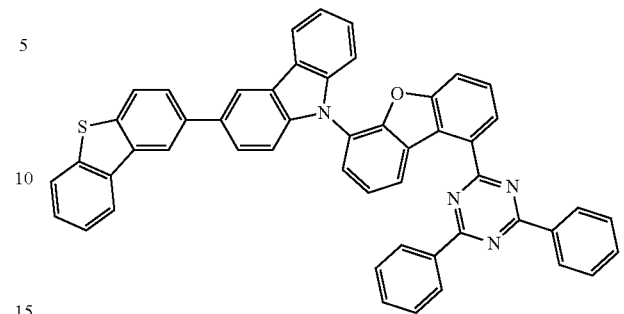
30
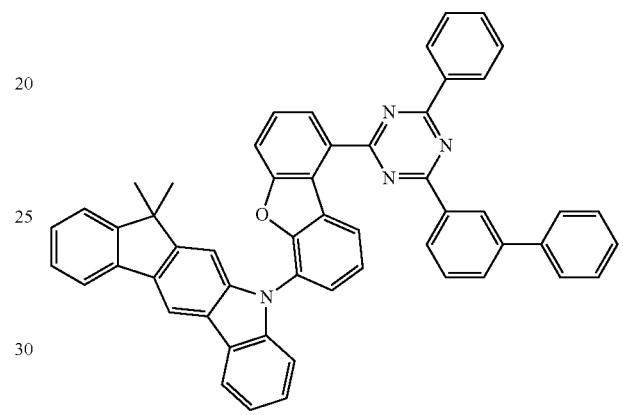
31
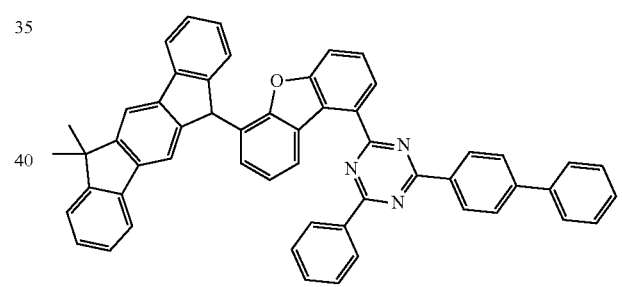
32
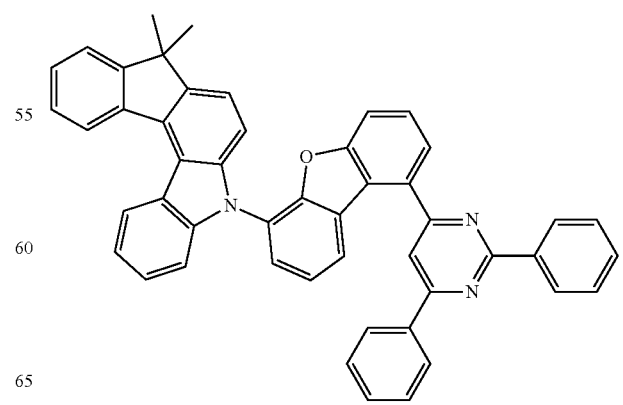

33
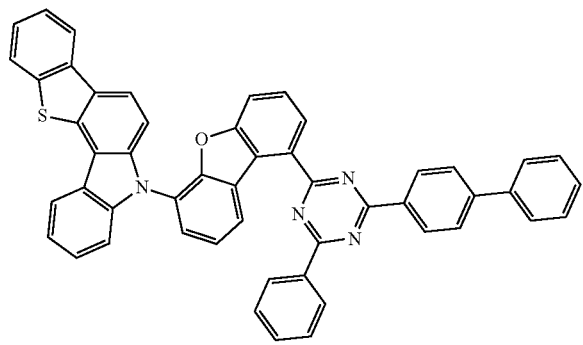
34
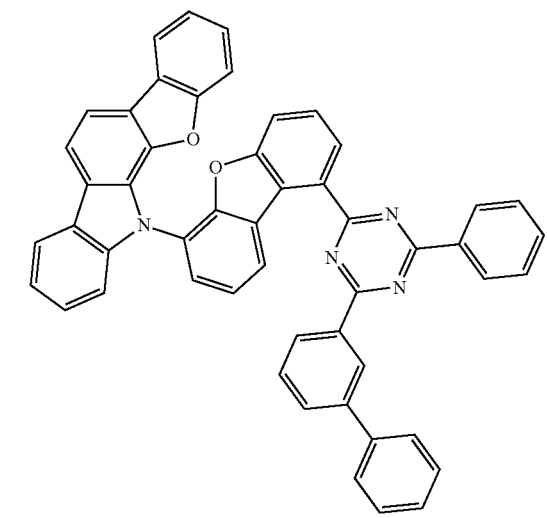
35
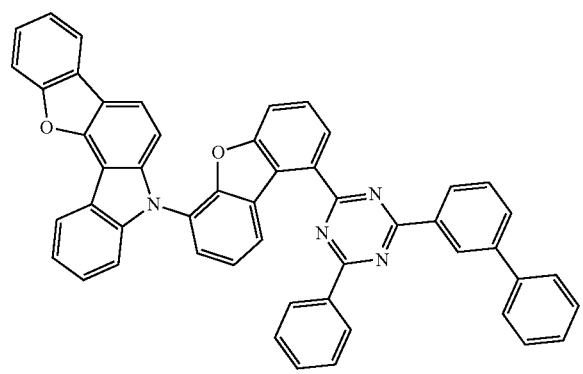
36
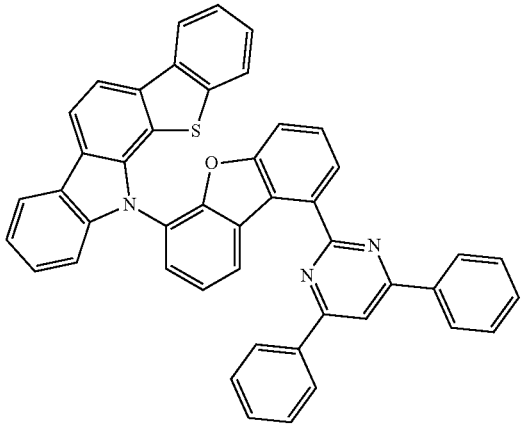
39
40
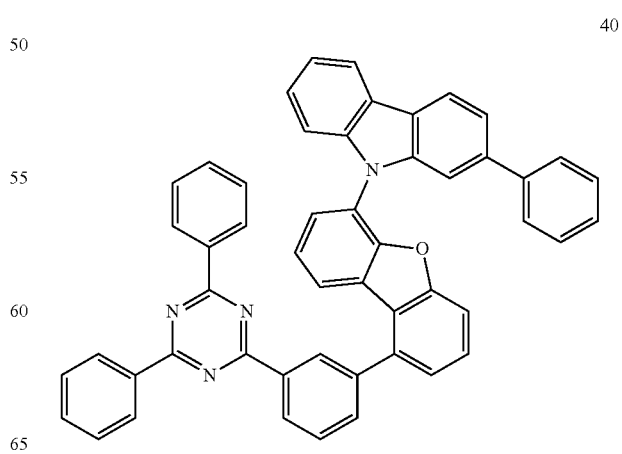

41
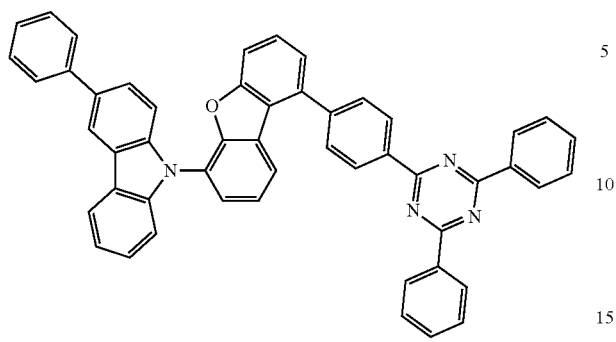
42
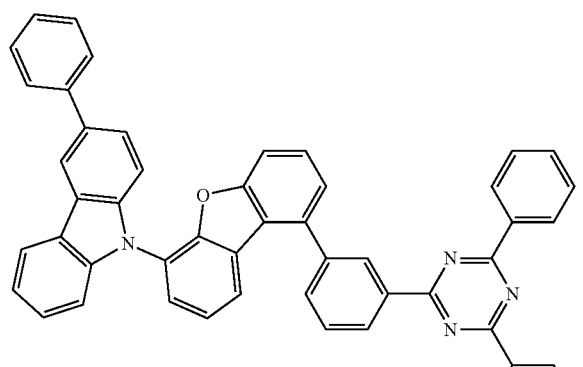
43
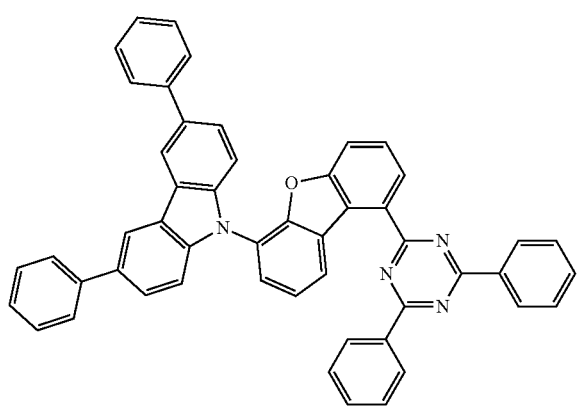
44
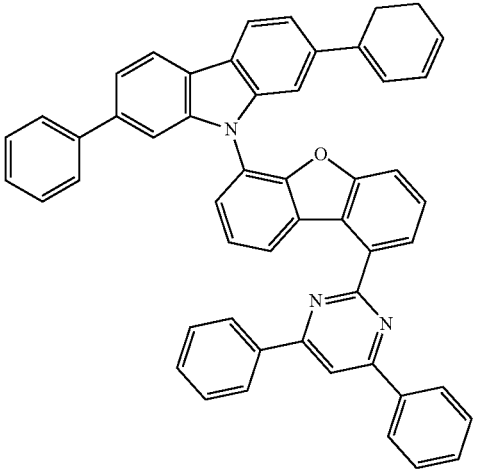
45
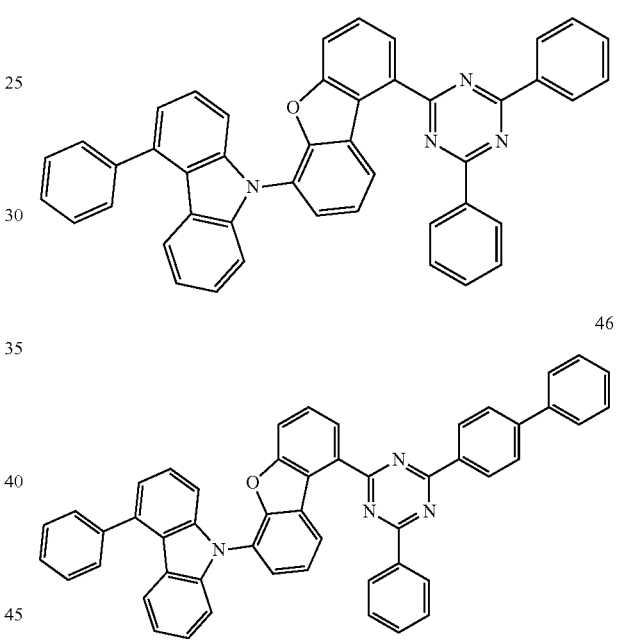
46
47

48
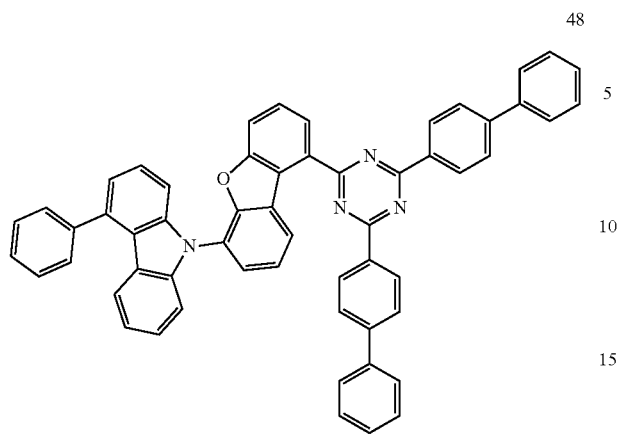
52
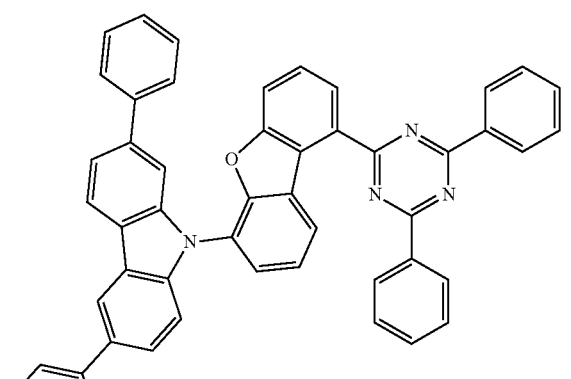
49
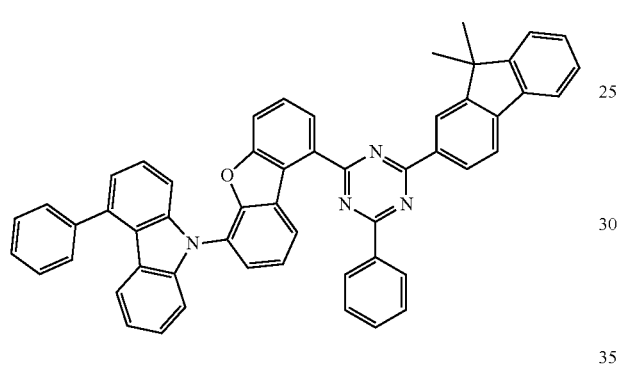
53
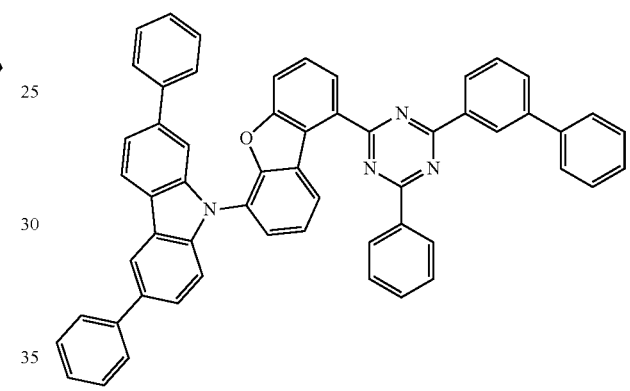
50
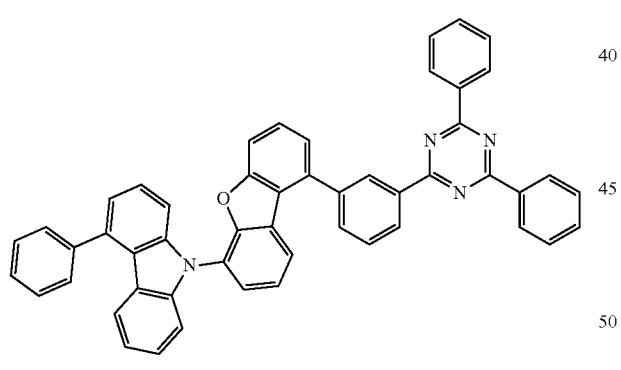
54
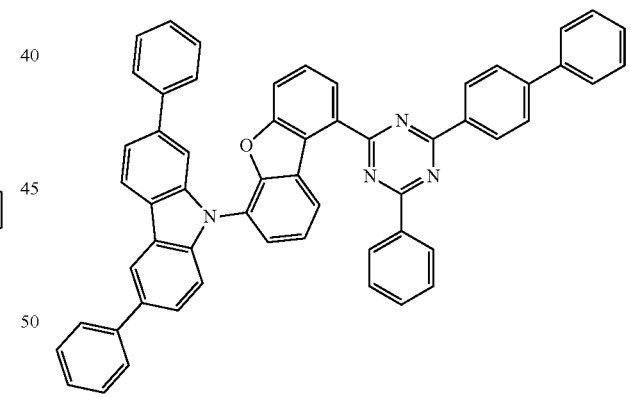
51
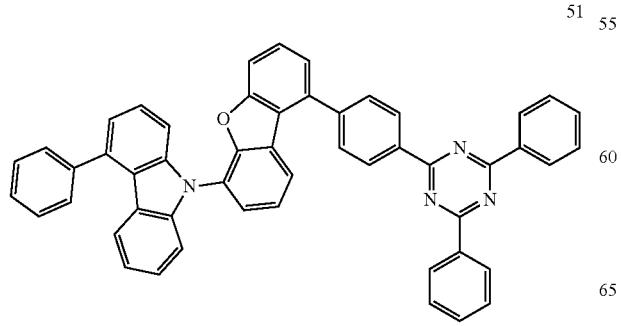
55
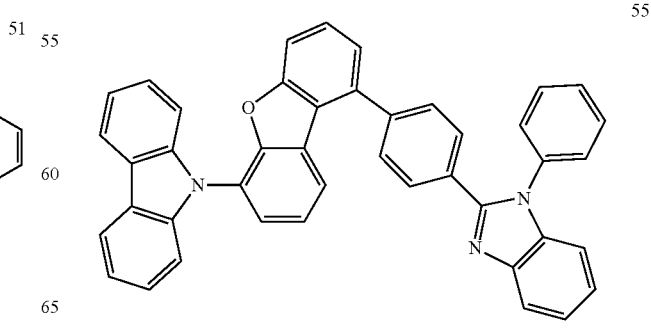

56
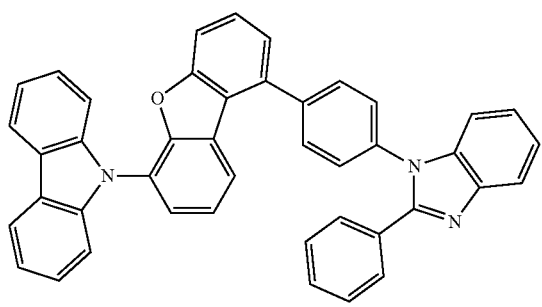
57
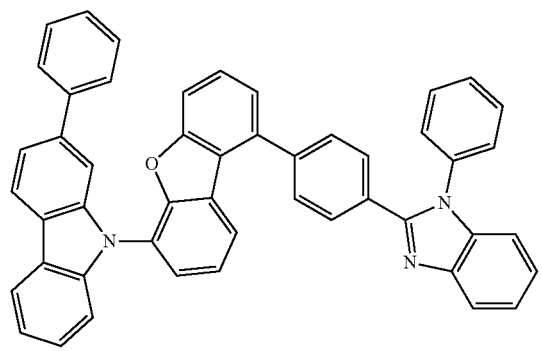
58
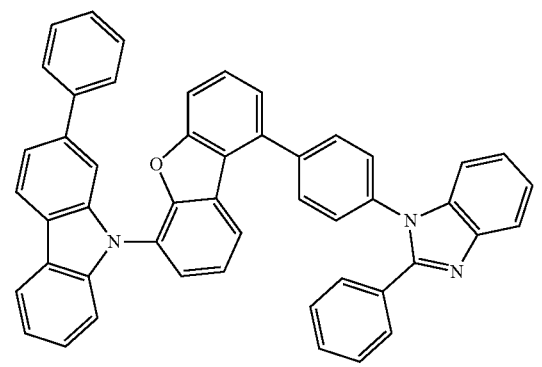
59
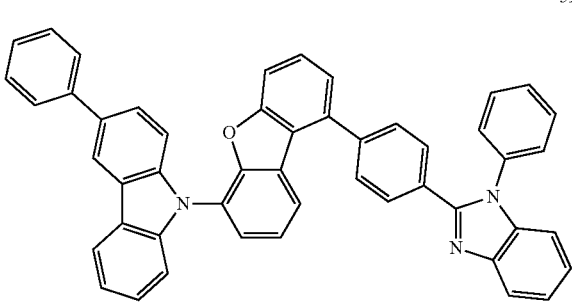
60
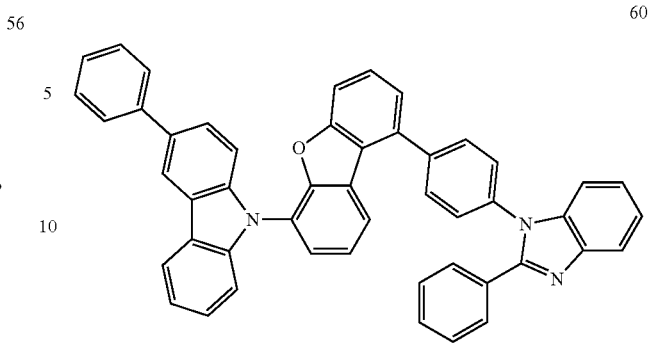
61
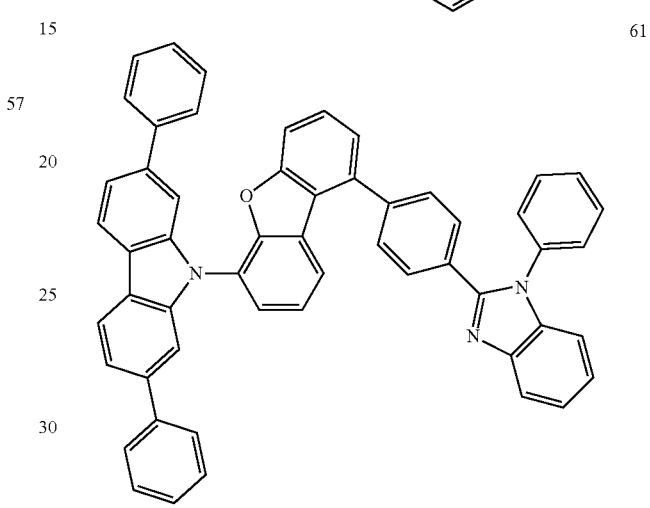
62
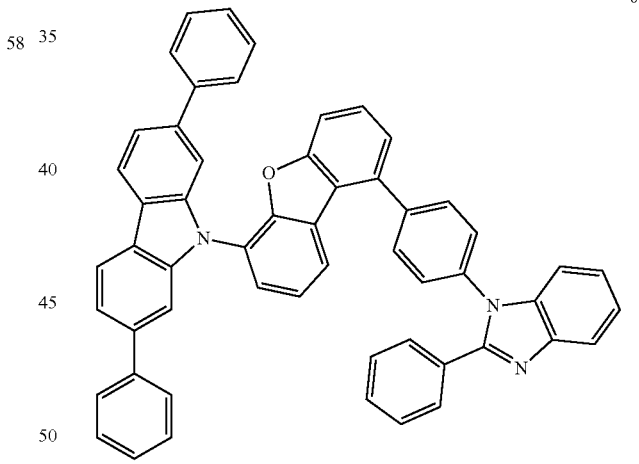
63
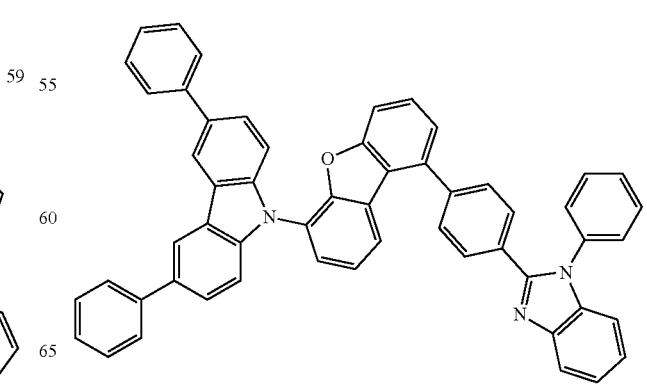

64
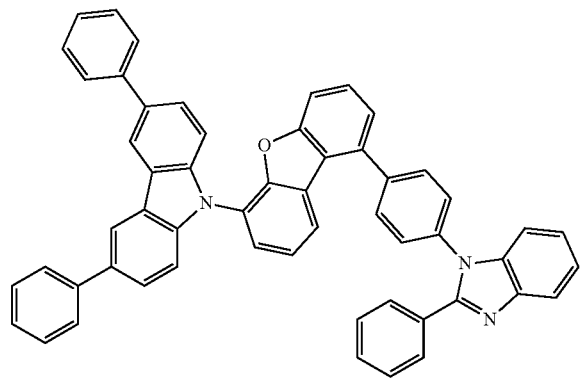
65
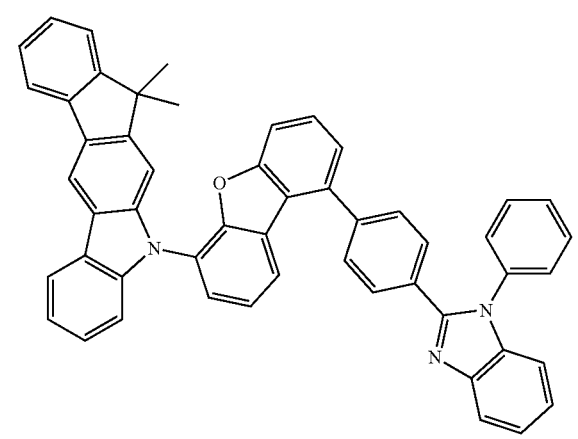
66
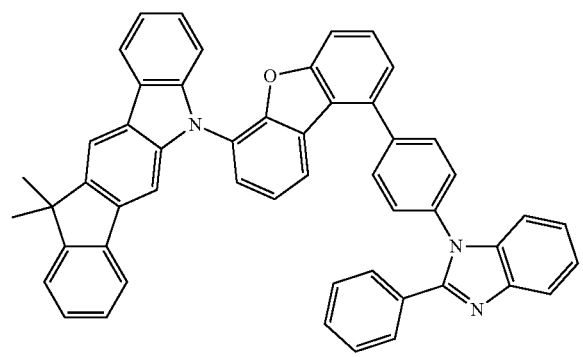
67
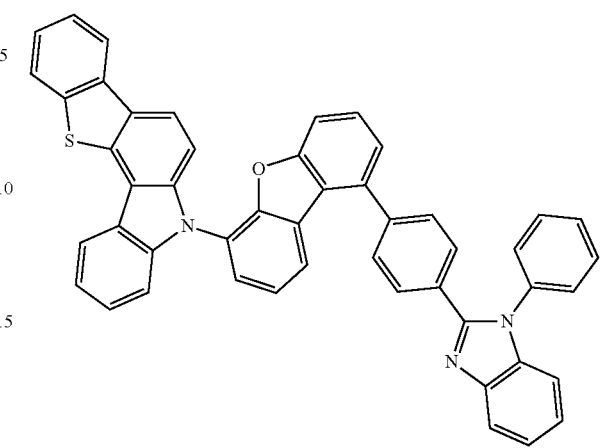
68
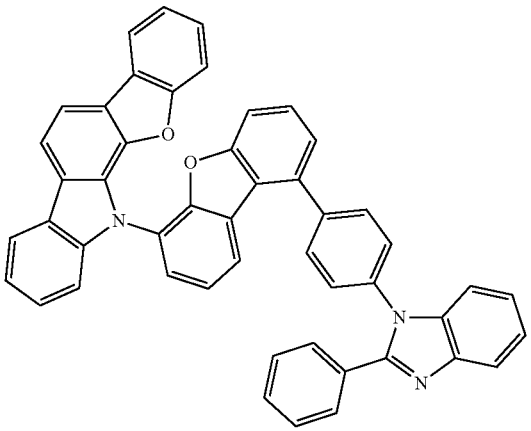
69
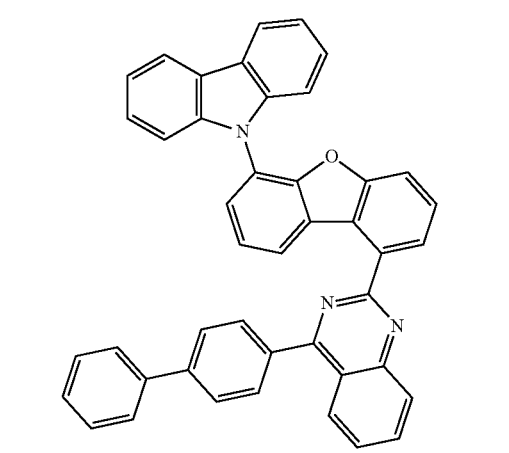

-continued
70
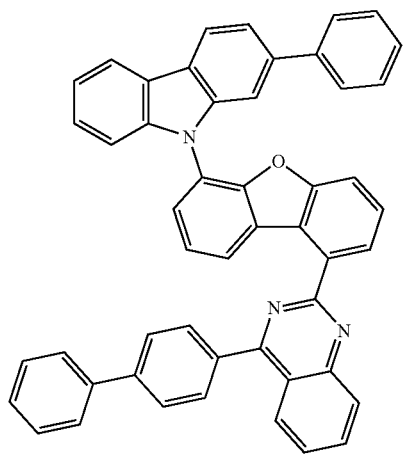
71
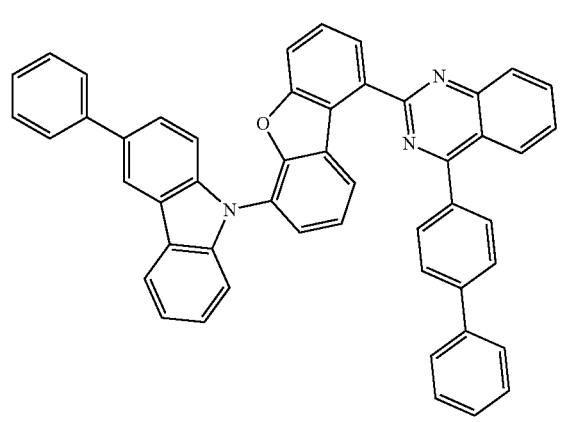
72
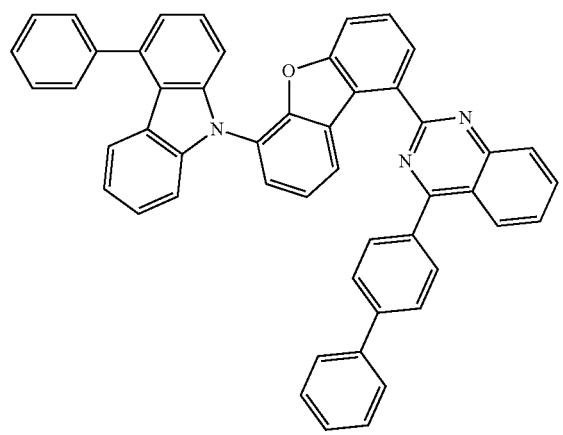
-continued
73
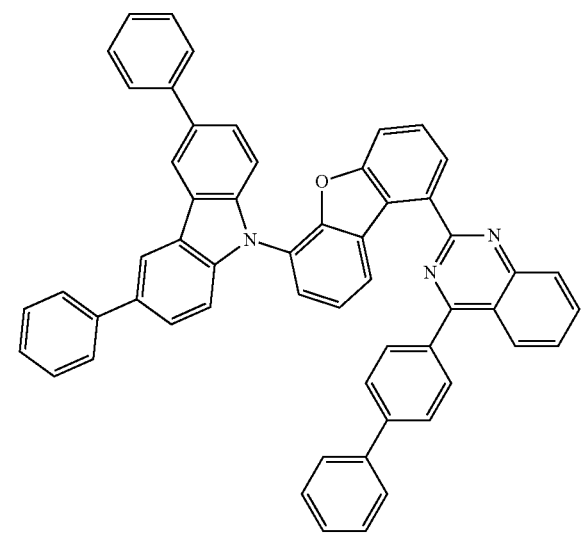
74
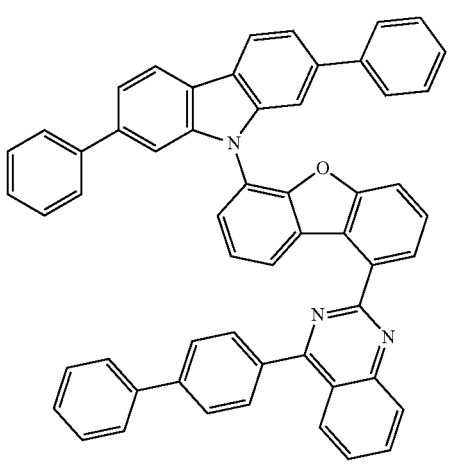
75
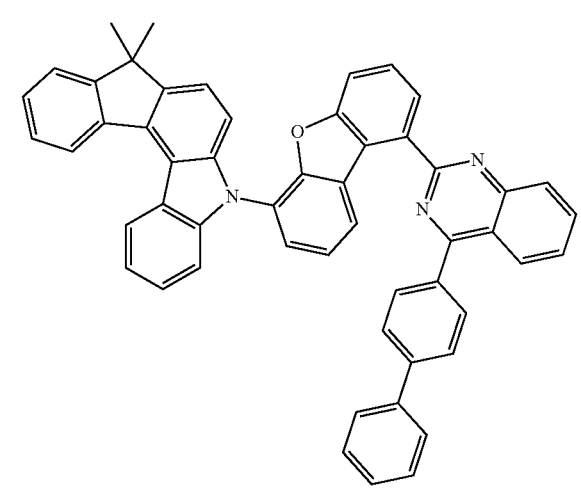

76
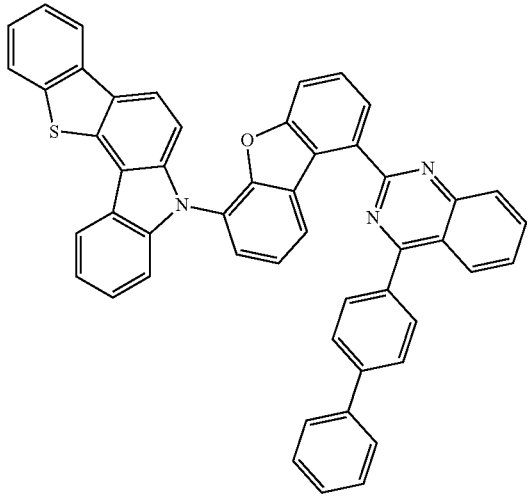
77
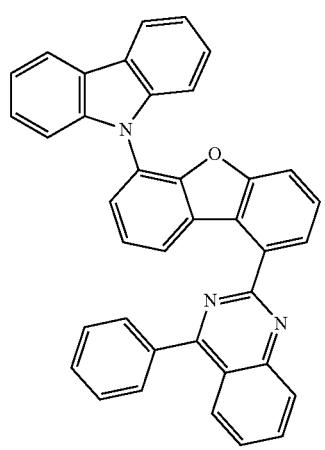
78
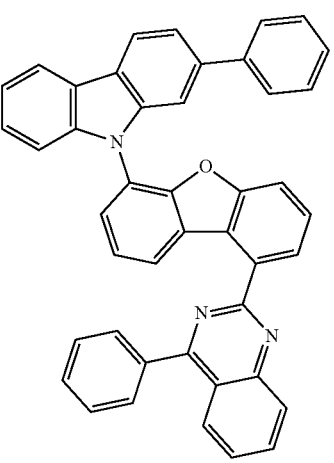
79
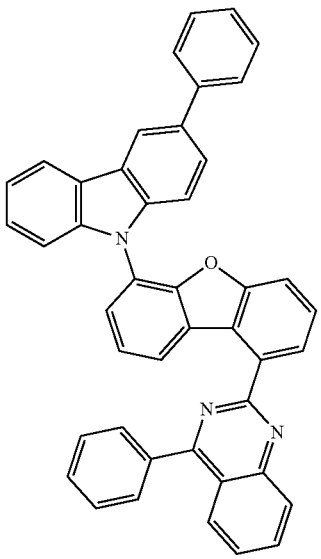
80
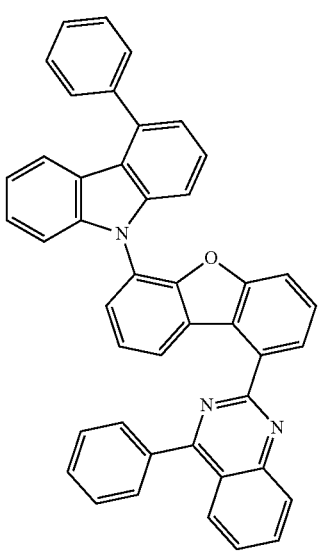
81
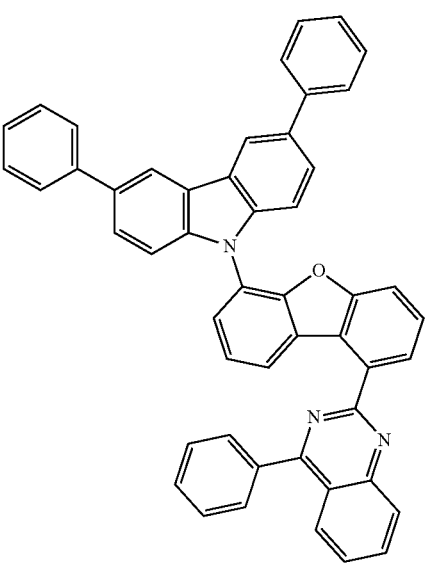

82
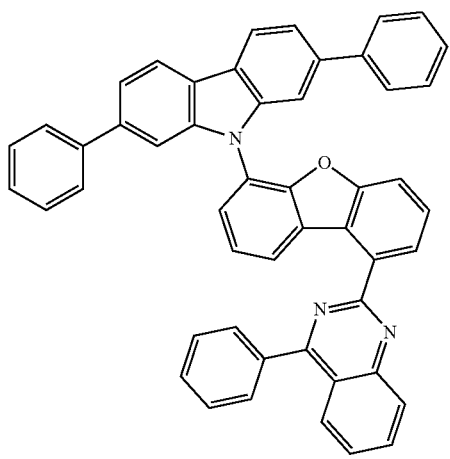
83
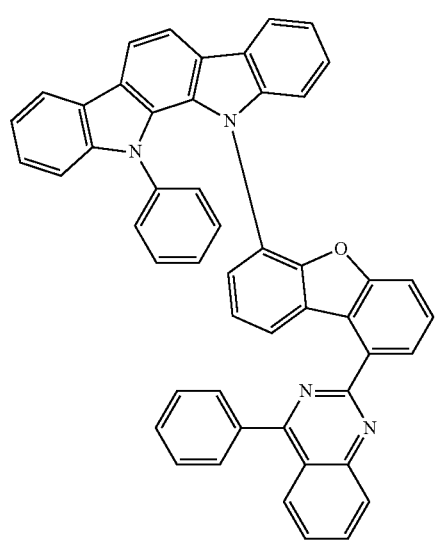
84
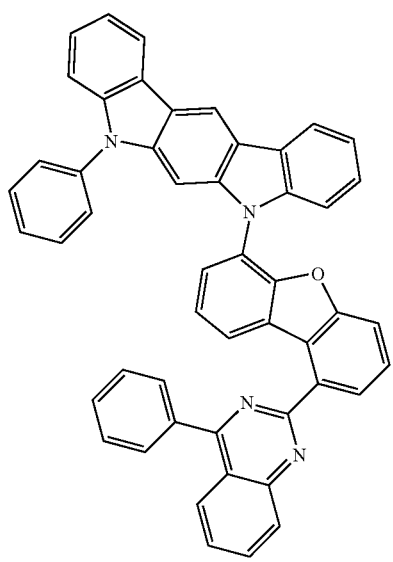
85
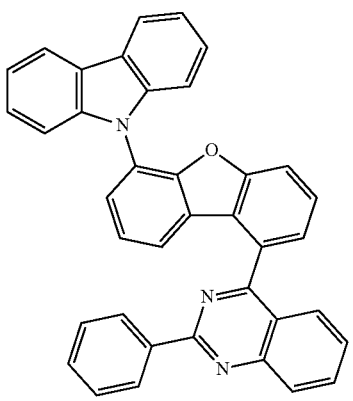
86
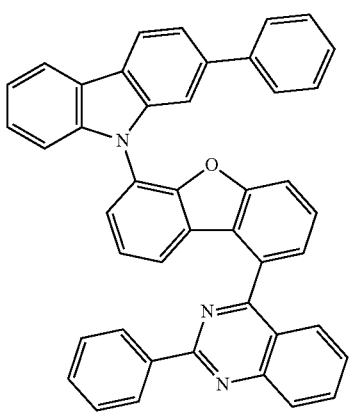
87
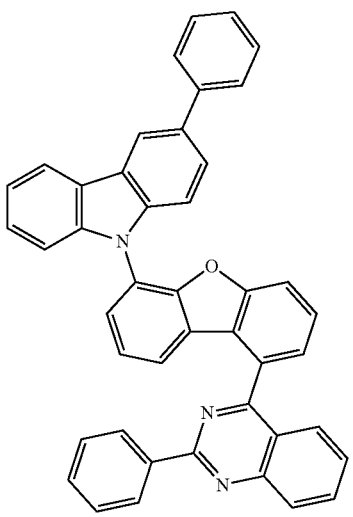

88
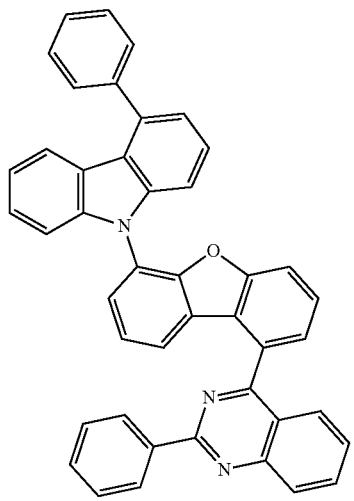
89
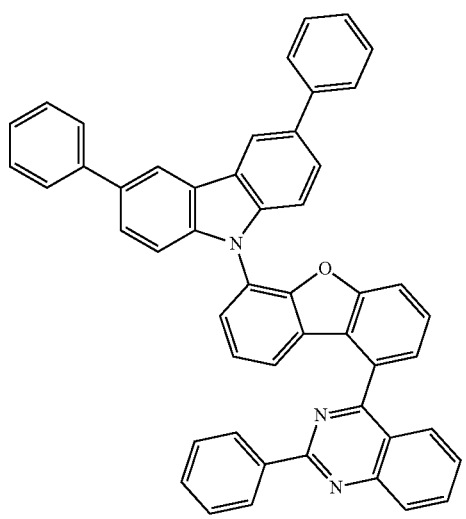
90
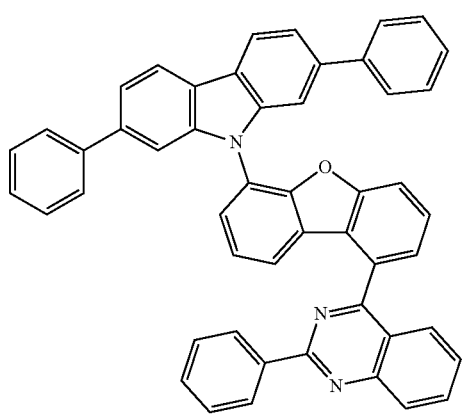
91
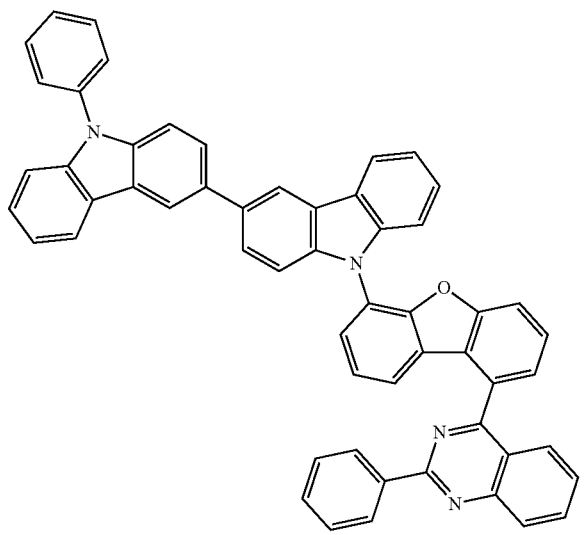
92
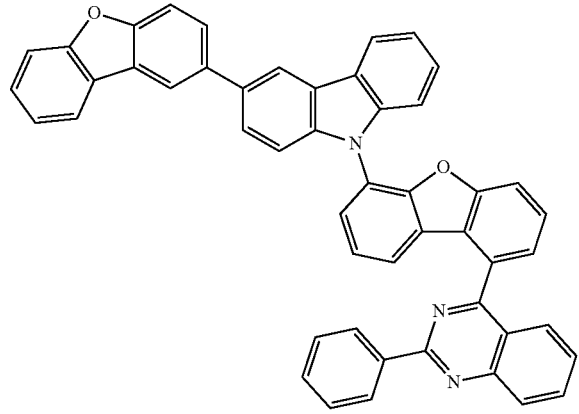
93
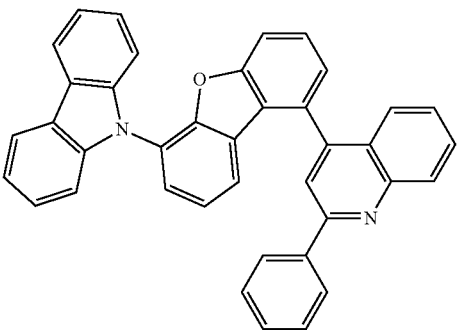

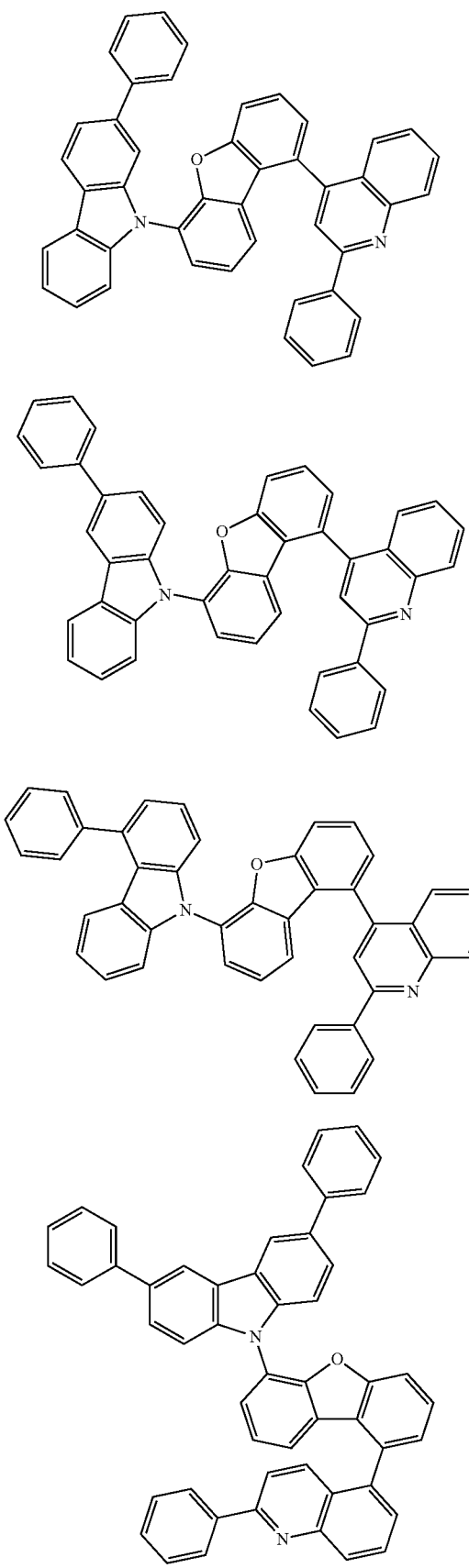
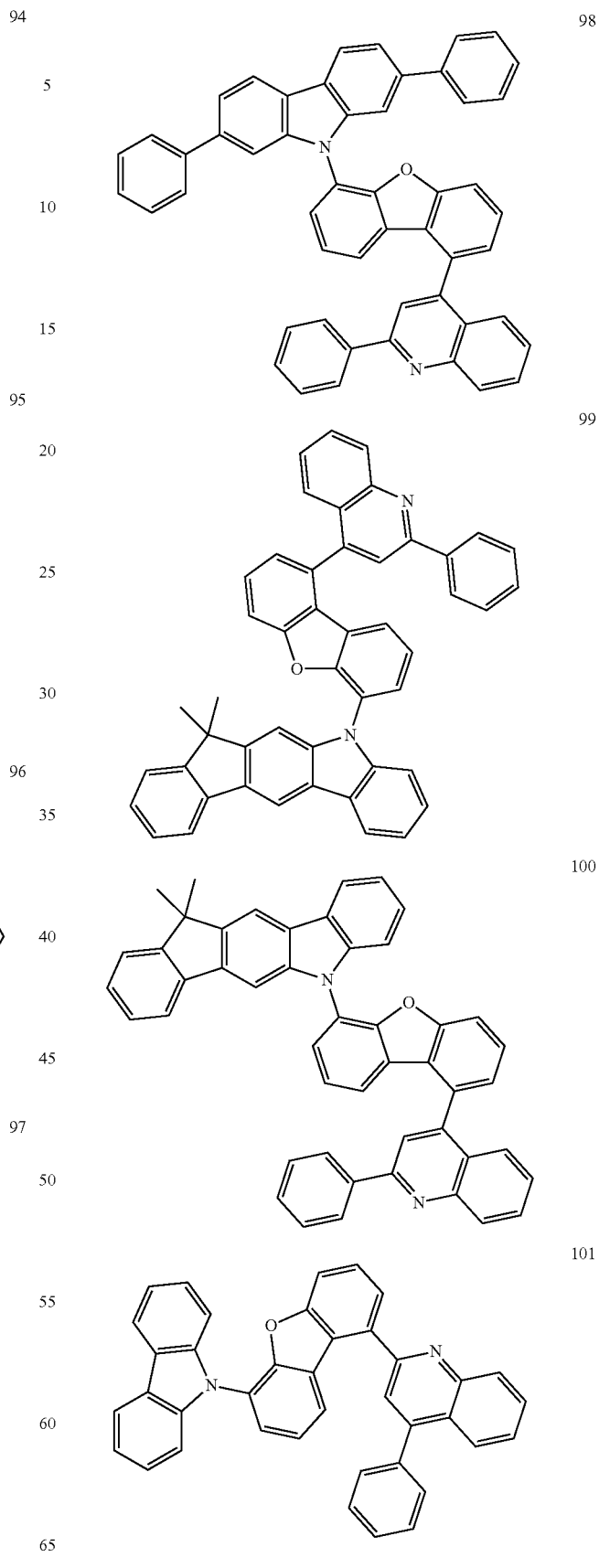

205
-continued
102
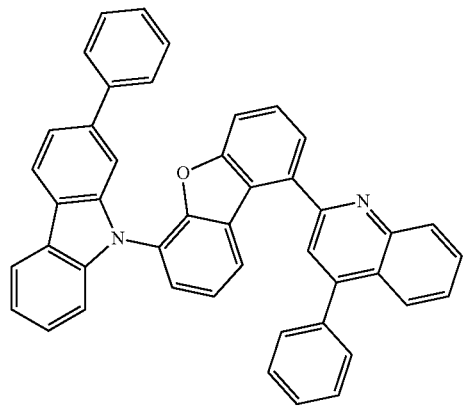
103
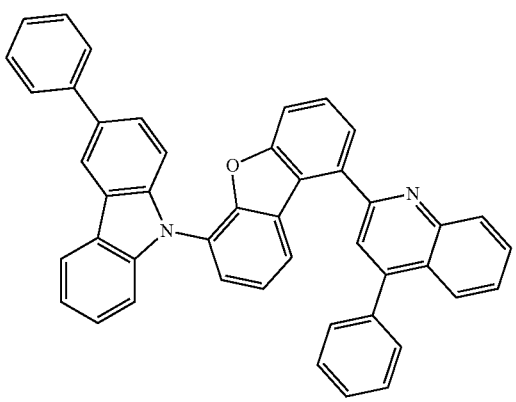
104
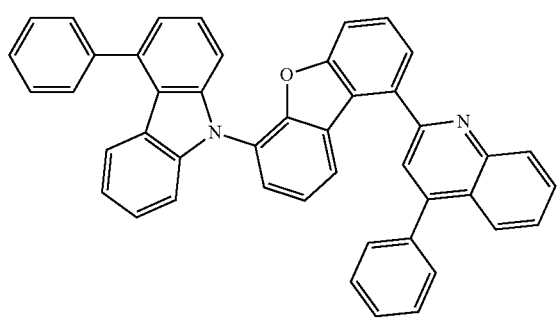
206
-continued
105
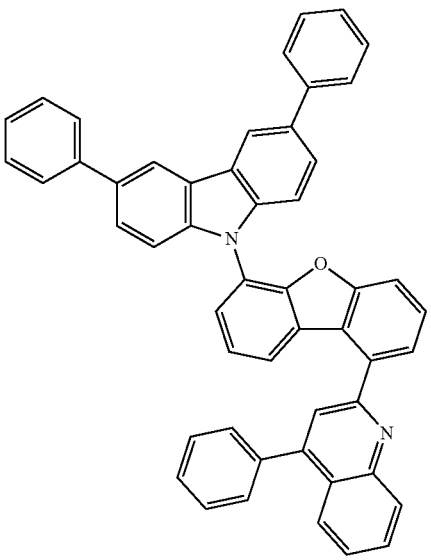
106
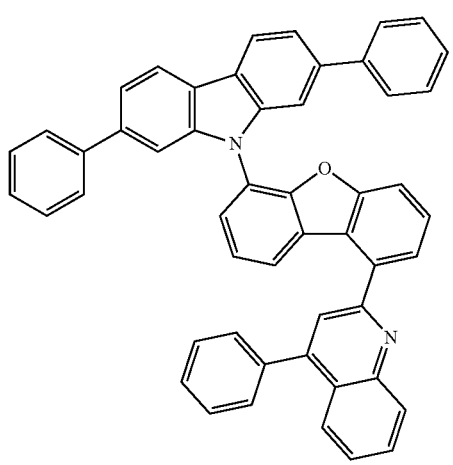
107
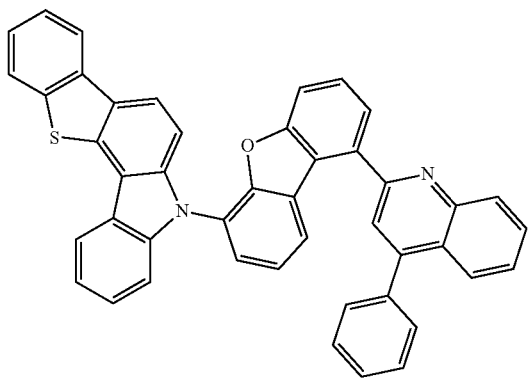

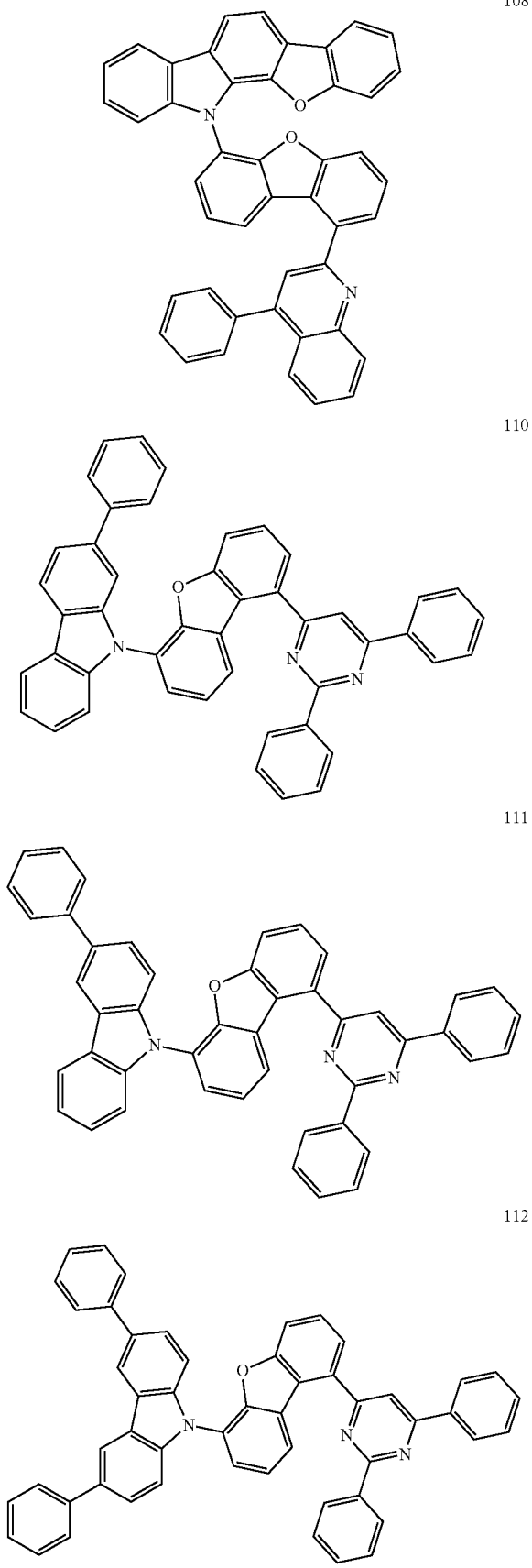
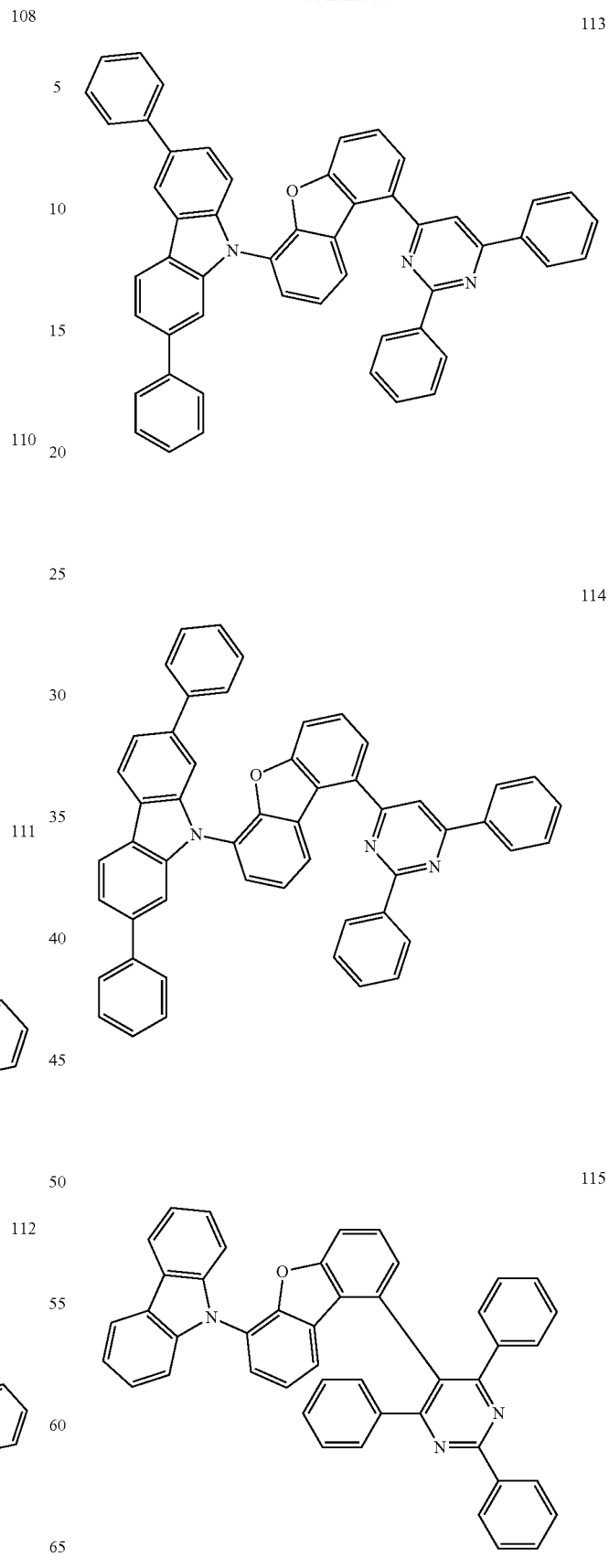

116
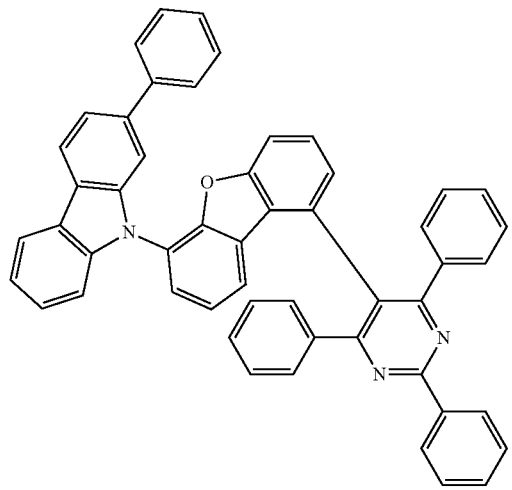
117
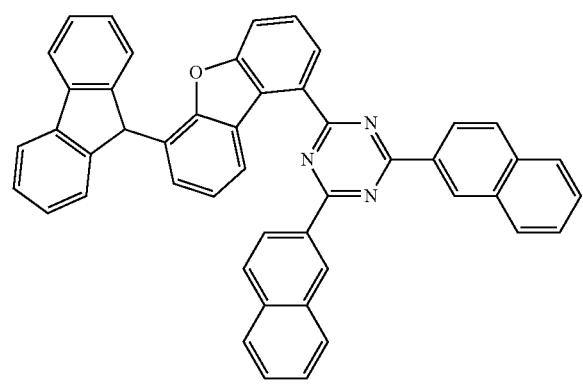
118
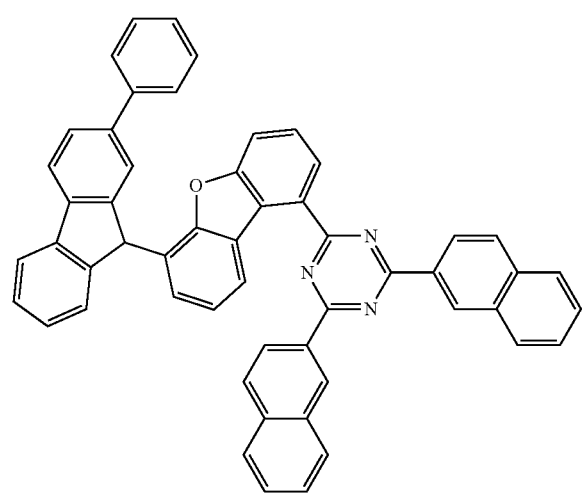
119
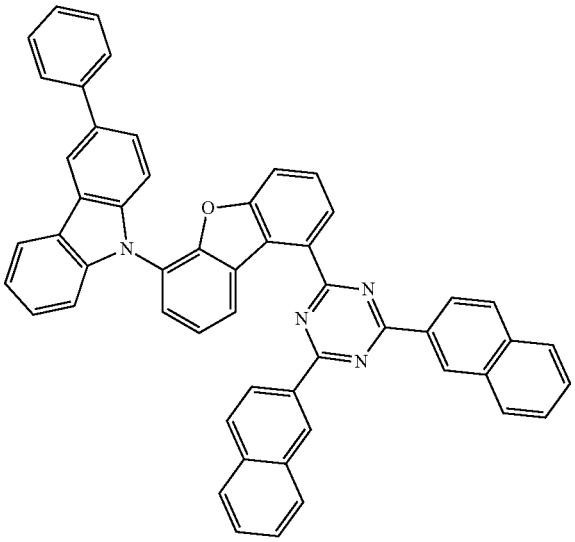
120
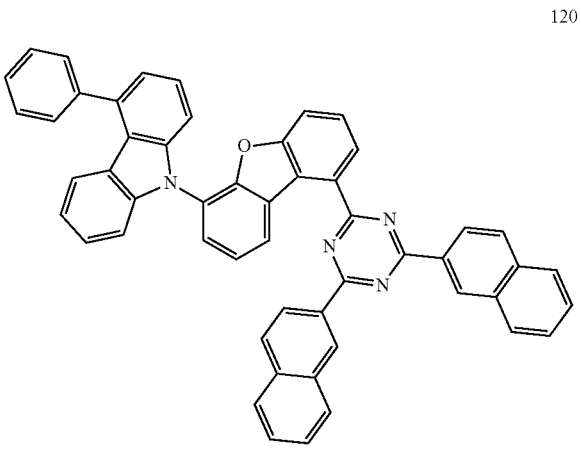
121
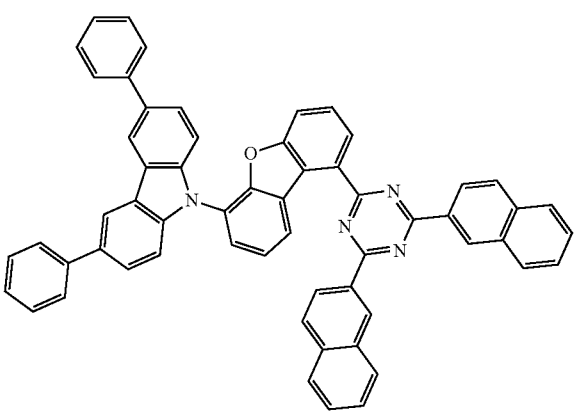

122
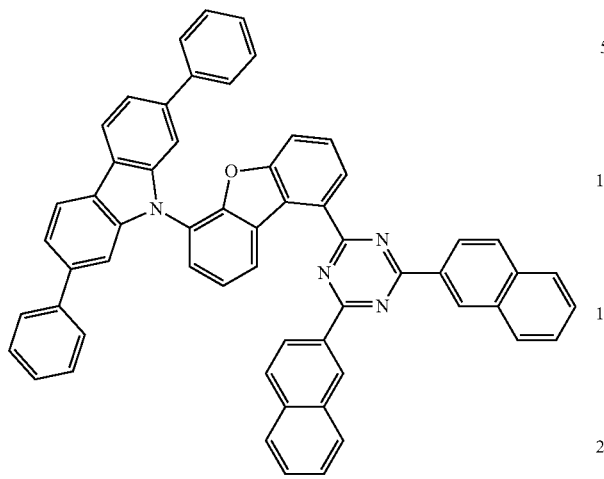
123
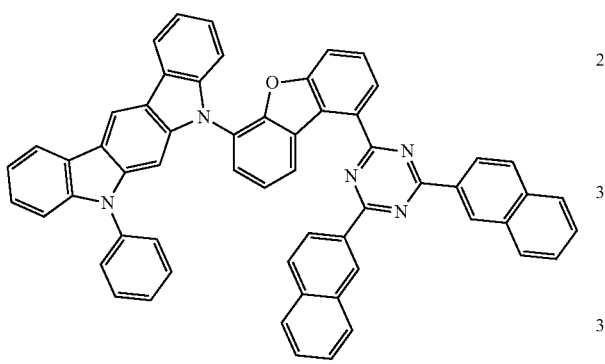
124
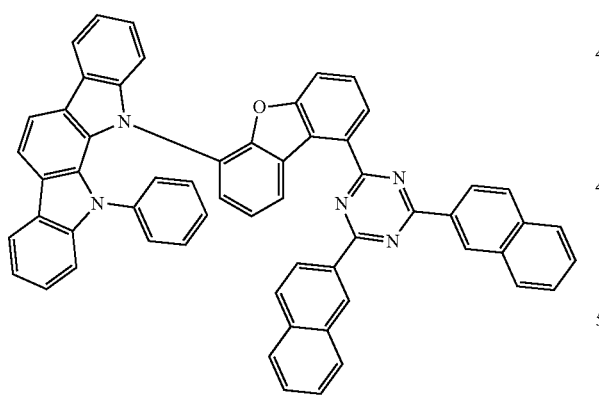
125
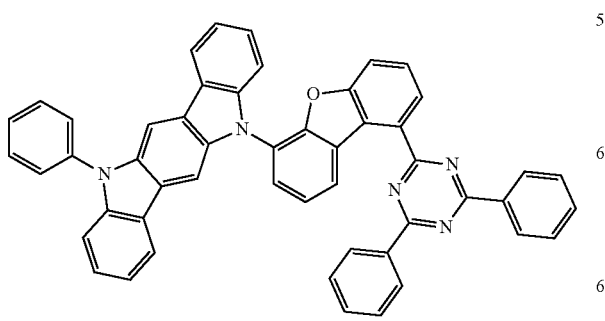
126
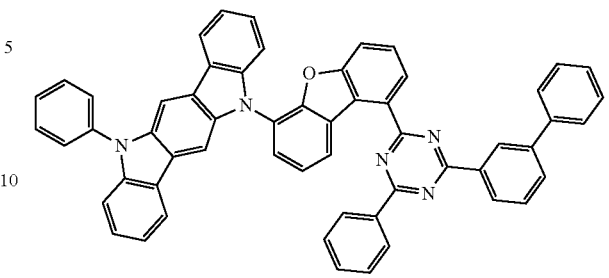
127
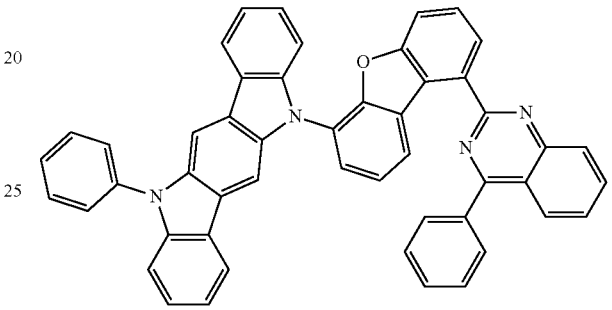
128
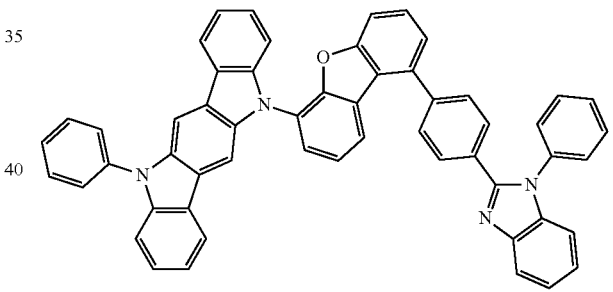
130
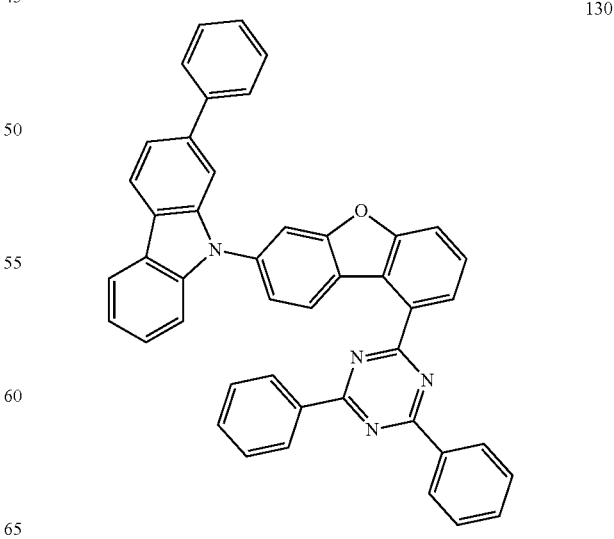

131
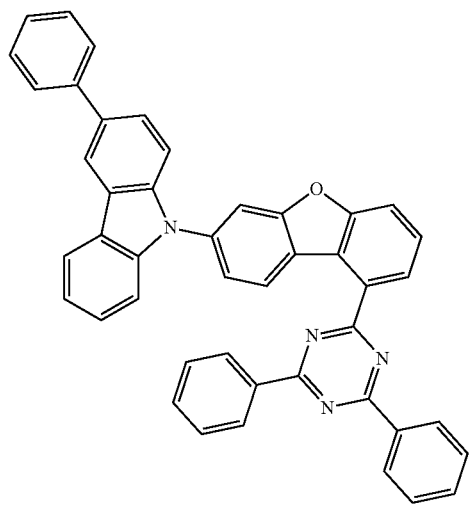
132
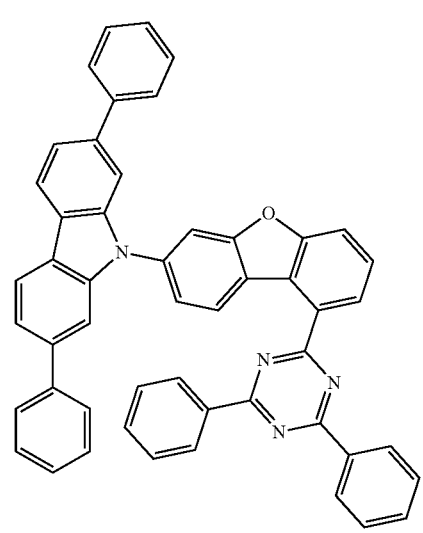
133
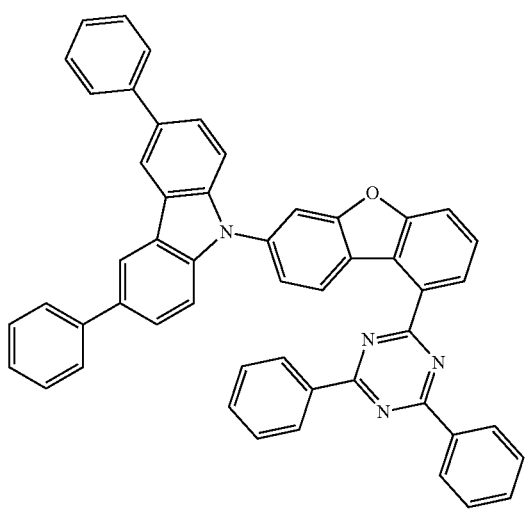
134
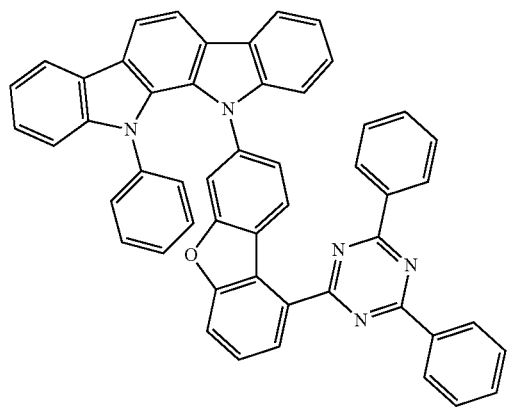
135
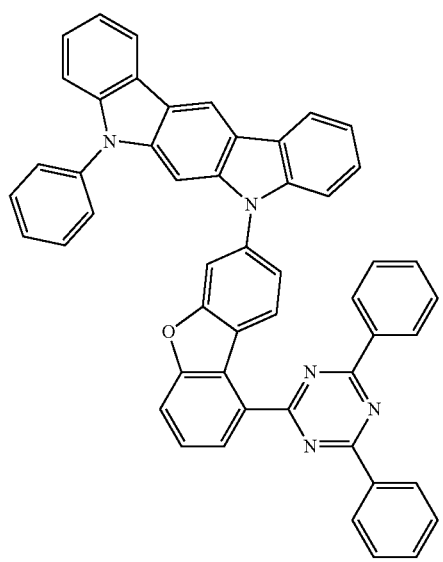
136

137
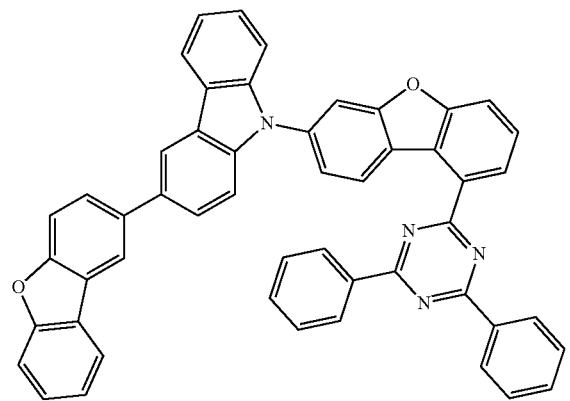
138
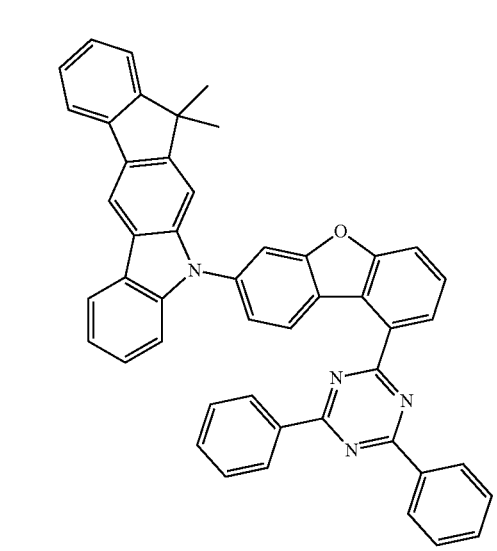
139
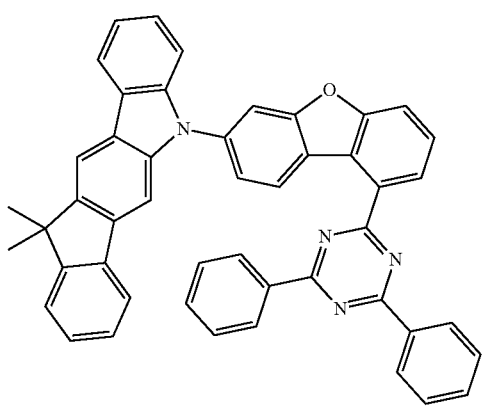
140
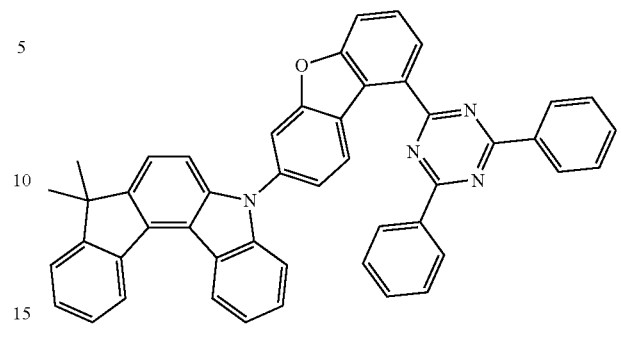
141
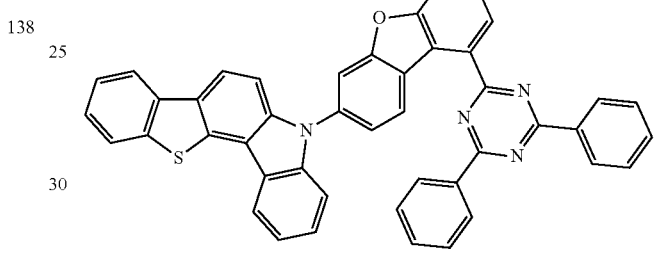
142
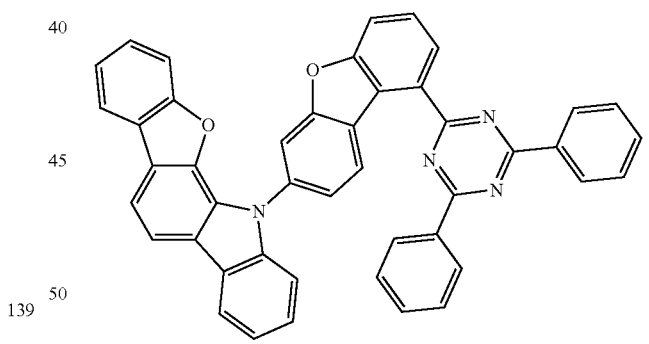
143
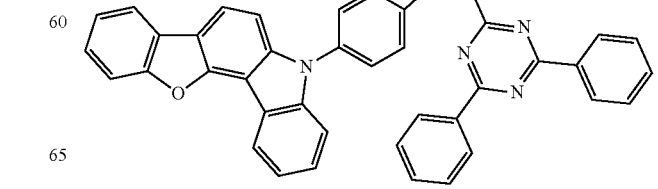

144
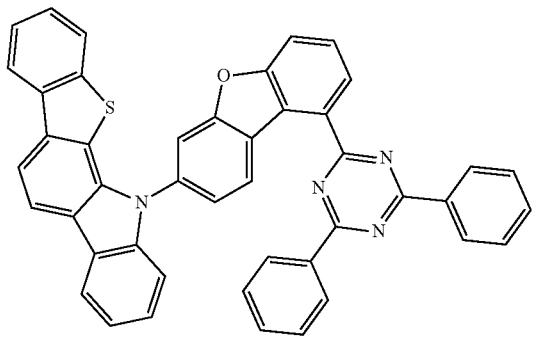
145
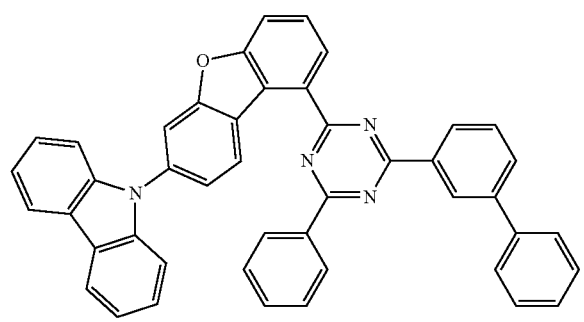
146
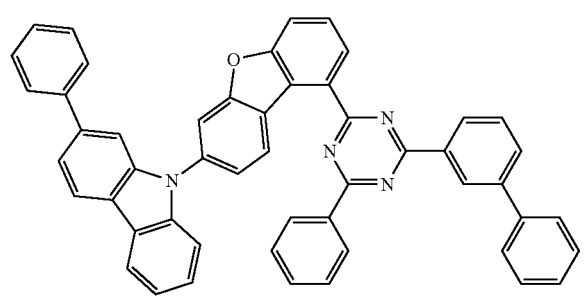
147
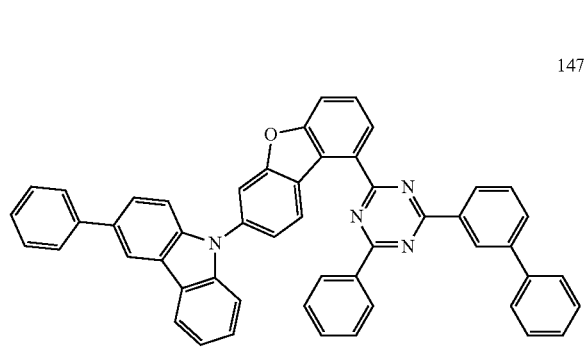
148
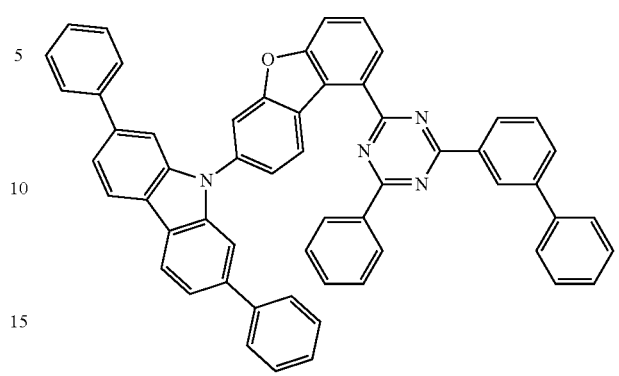
149
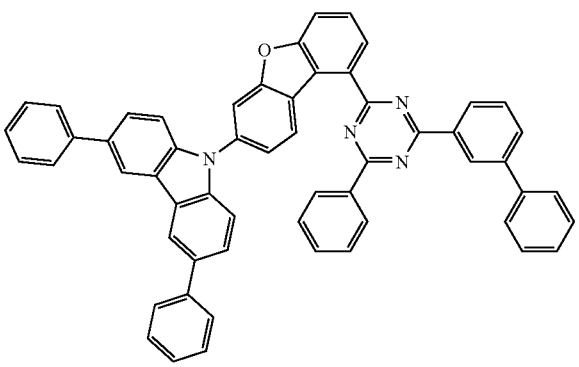
150
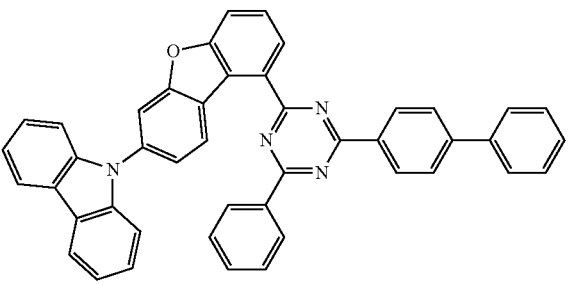
151
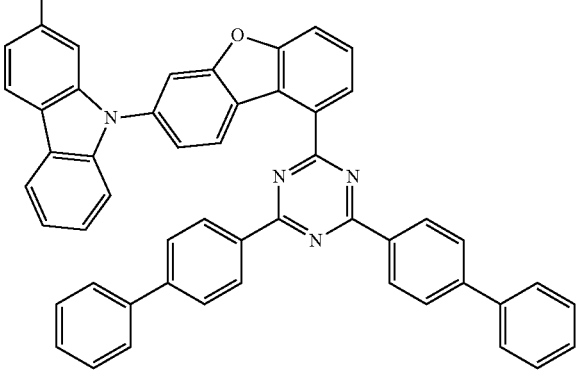

-continued
152
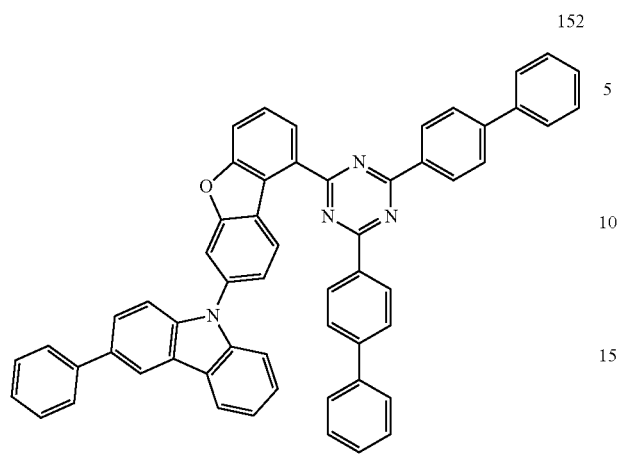
153
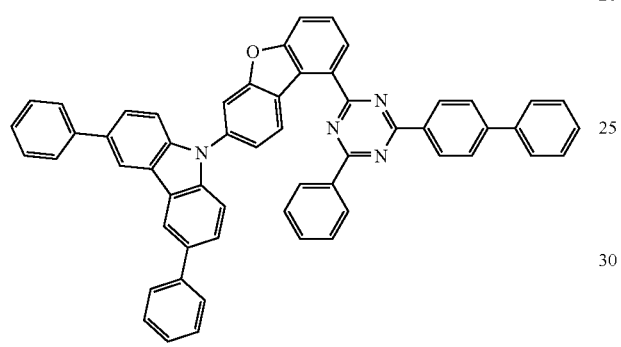
154
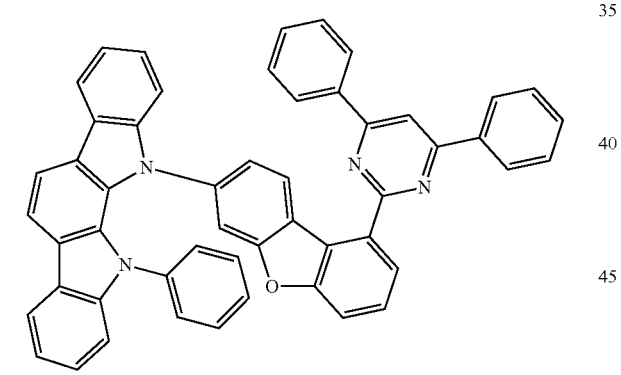
155
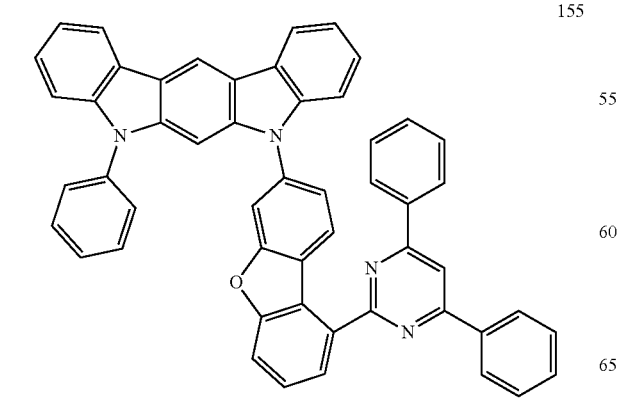
-continued
156
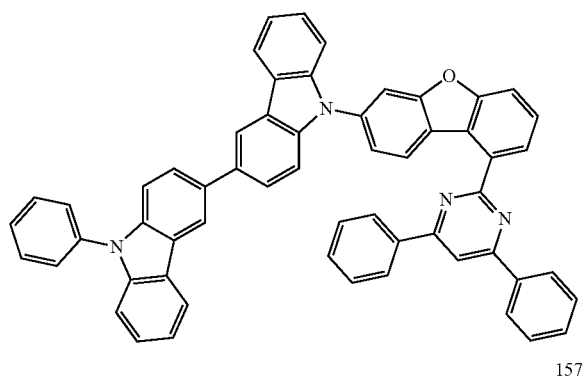
157
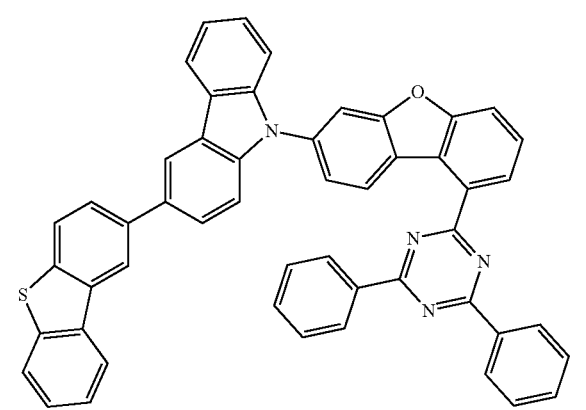
158
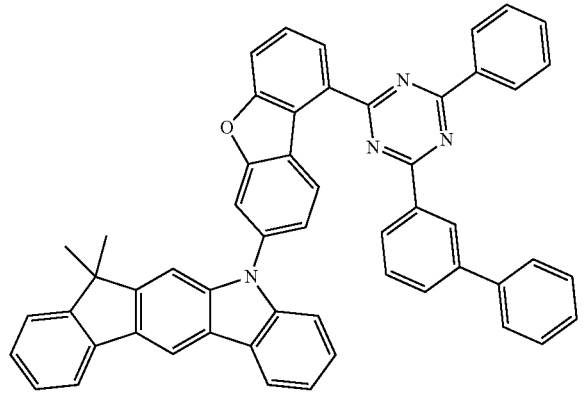
159

160
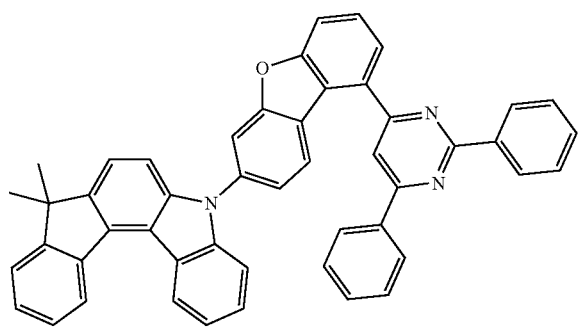
164
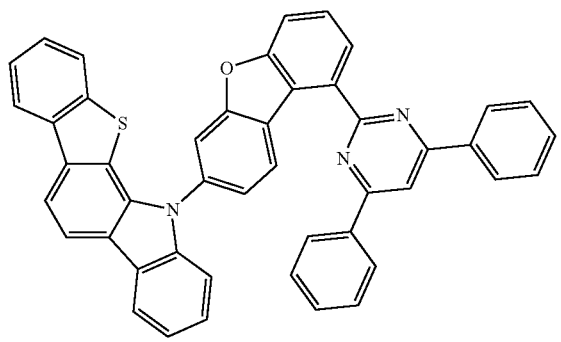
161
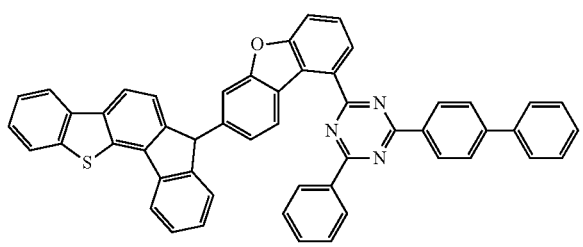
167
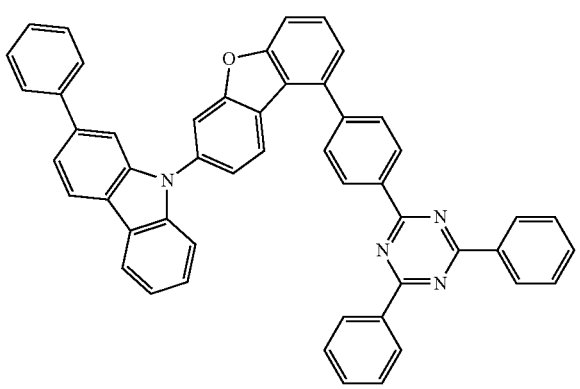
162
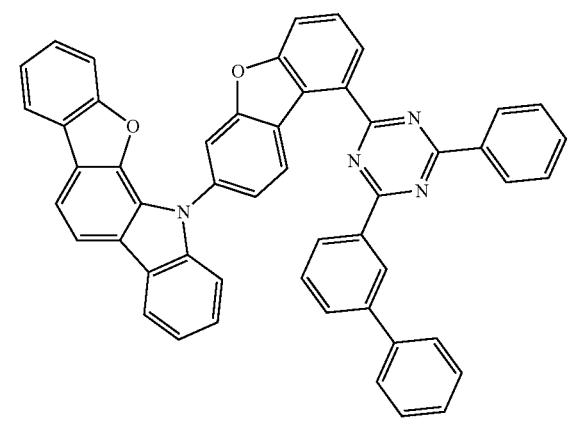
168
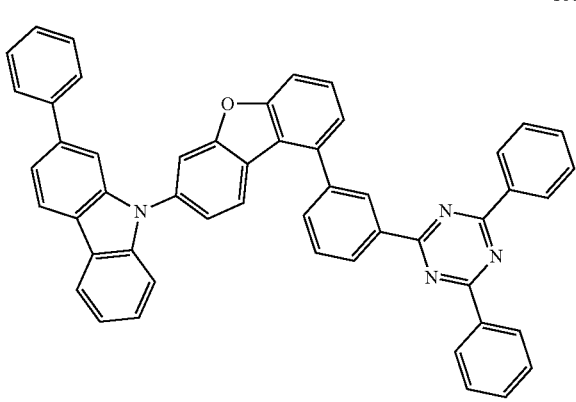
163
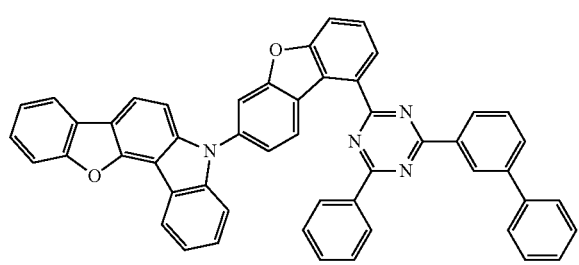
169
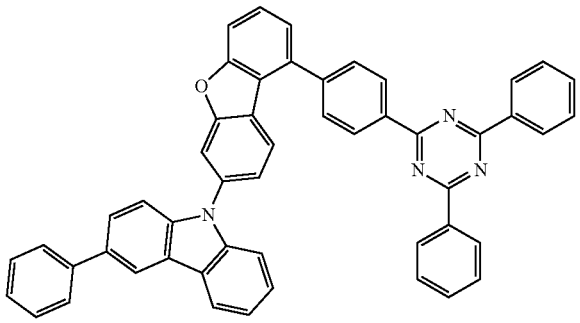

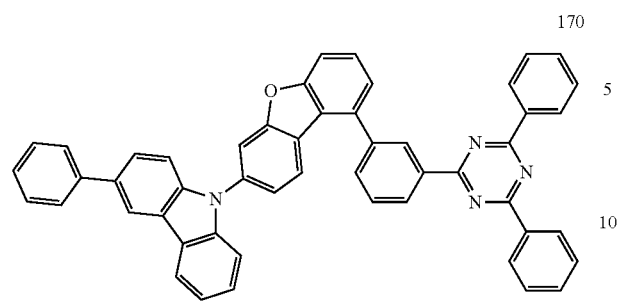
170
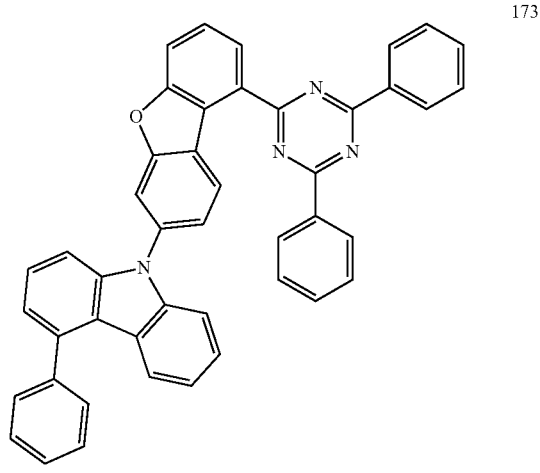
173
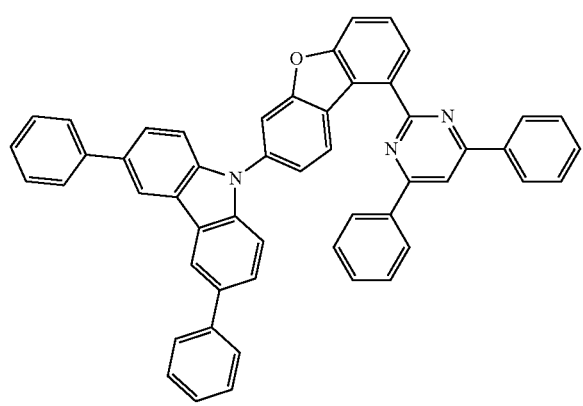
171
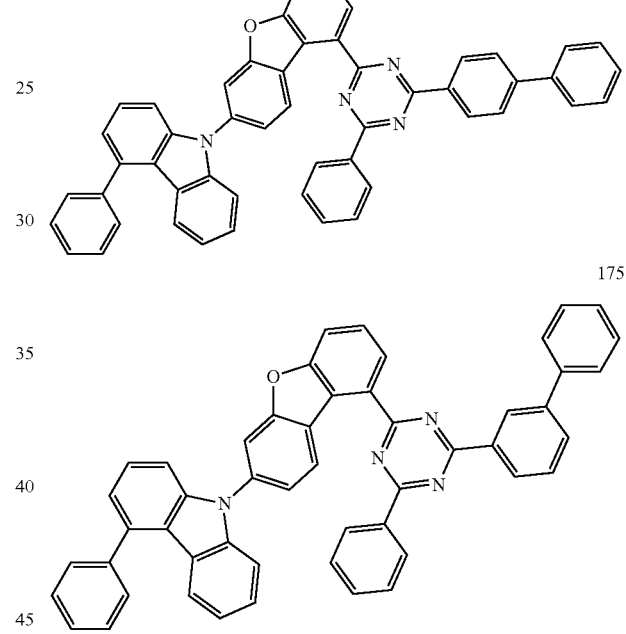
174
175
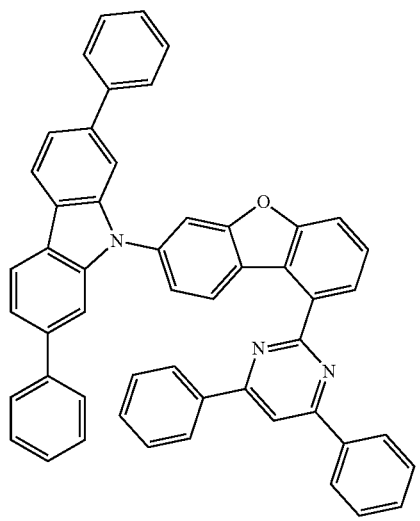
172
176

225
-continued
177
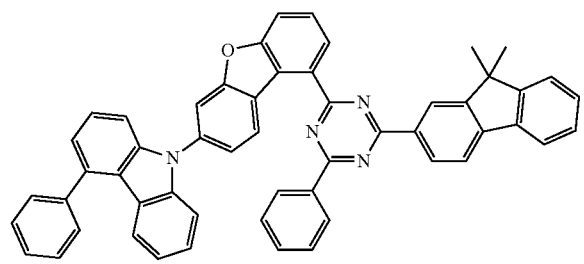
178
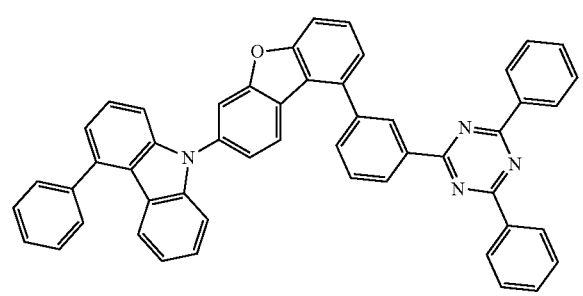
179
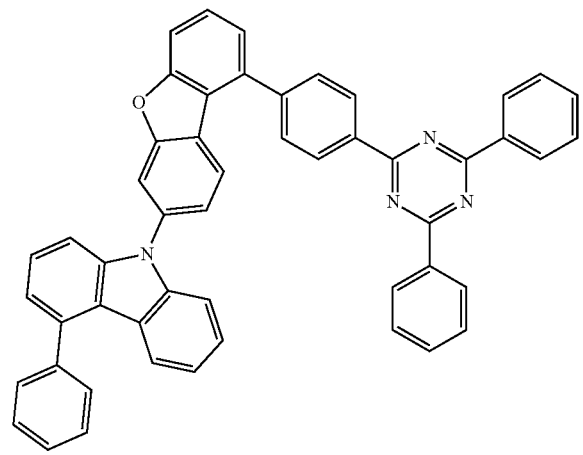
180
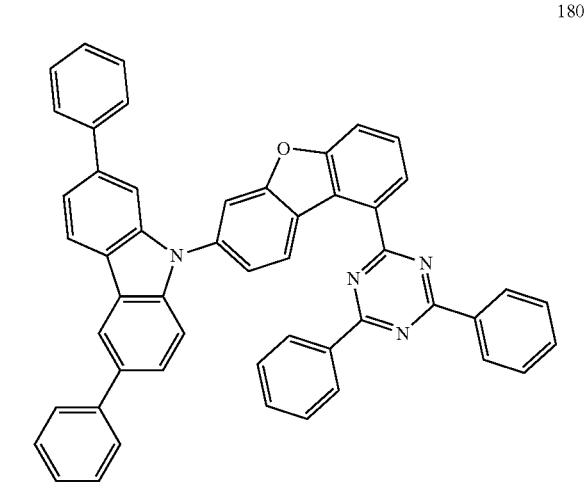
226
-continued
181
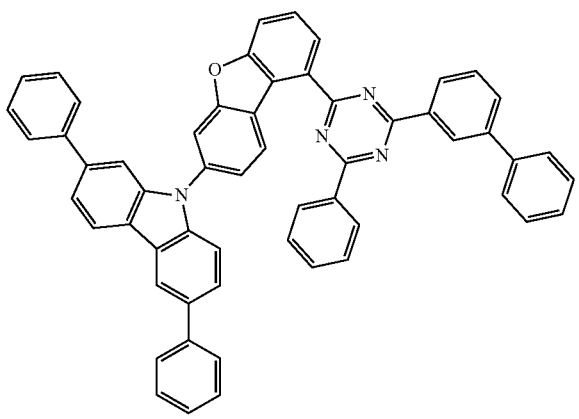
182
183
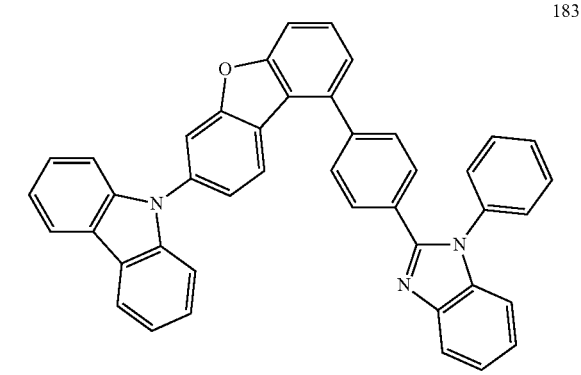
184
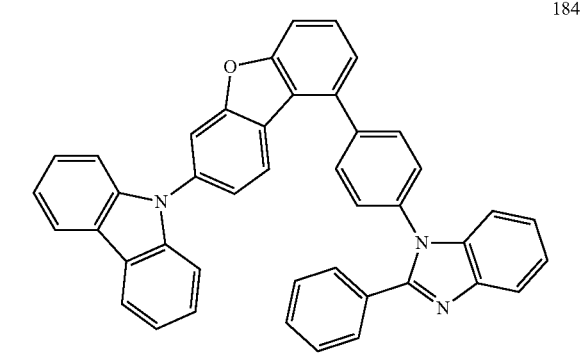

227
-continued
185
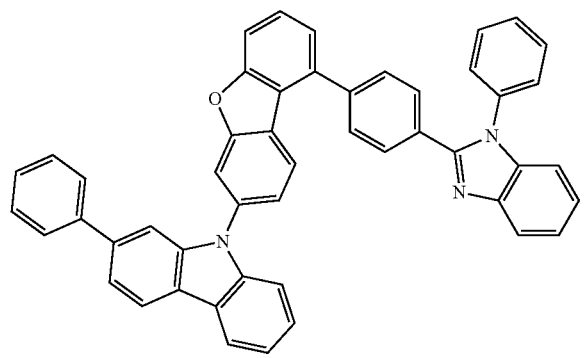
186
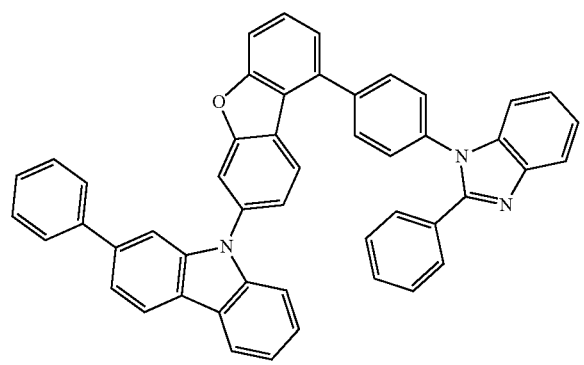
187
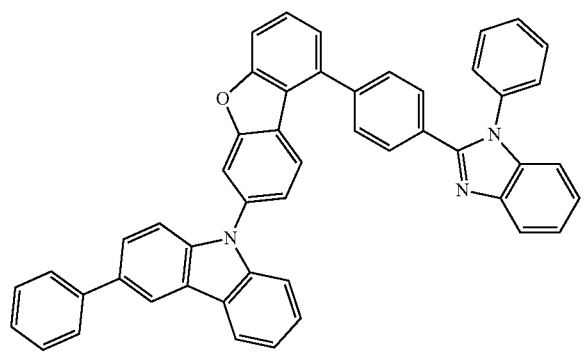
228
-continued
189
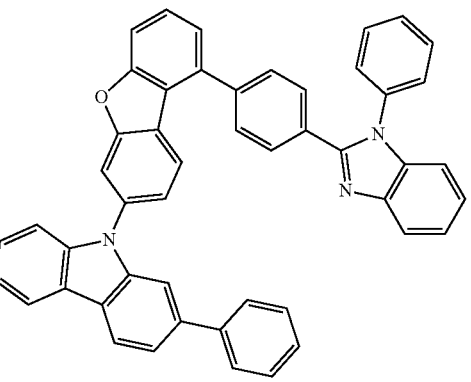
190
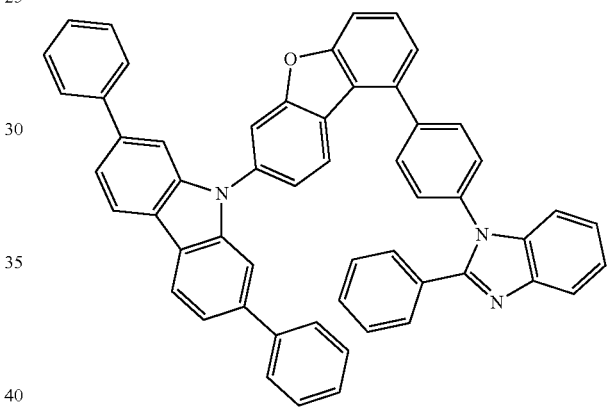
191
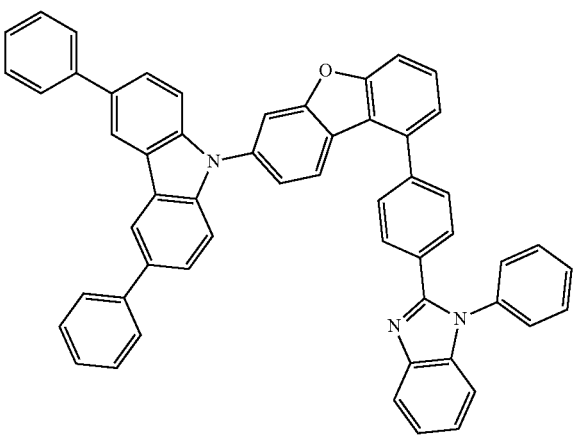
188

192
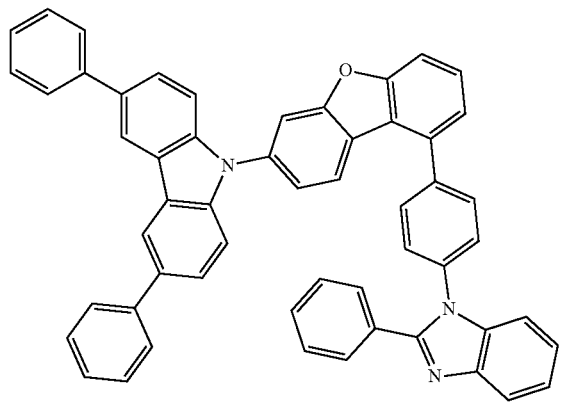
193
197
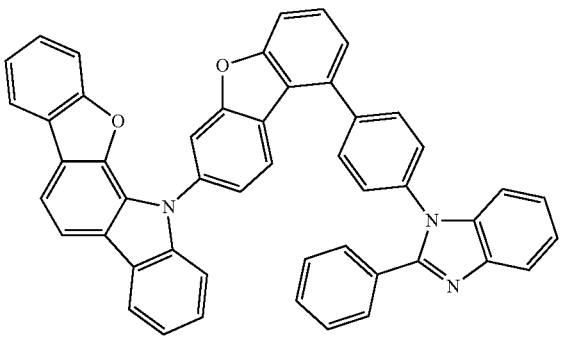
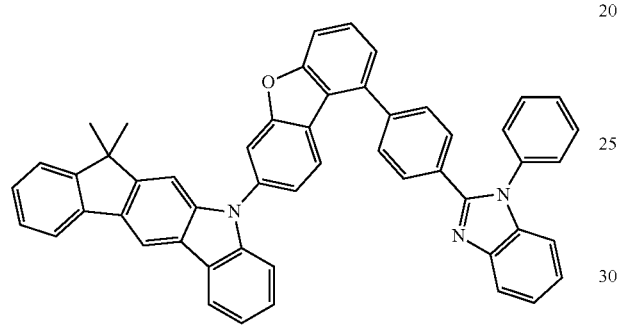
198
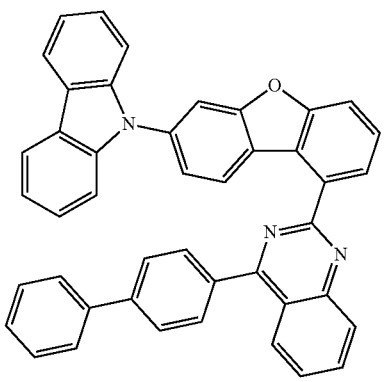
194
195
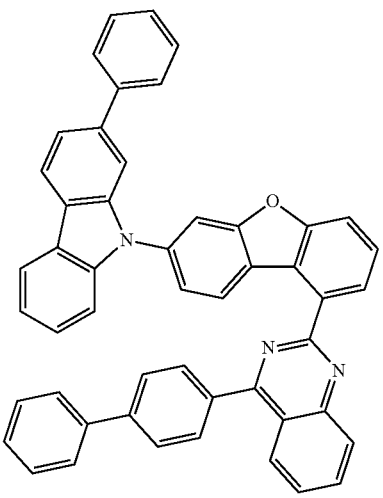

199
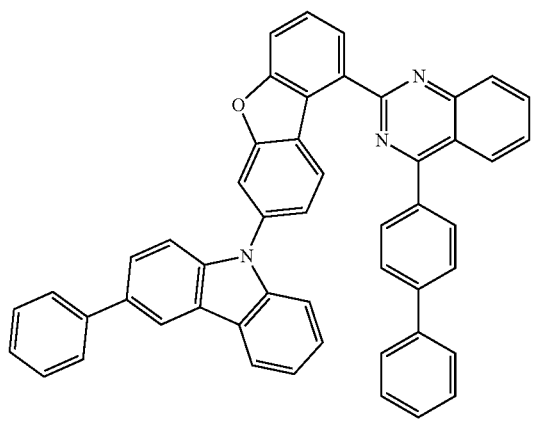
200
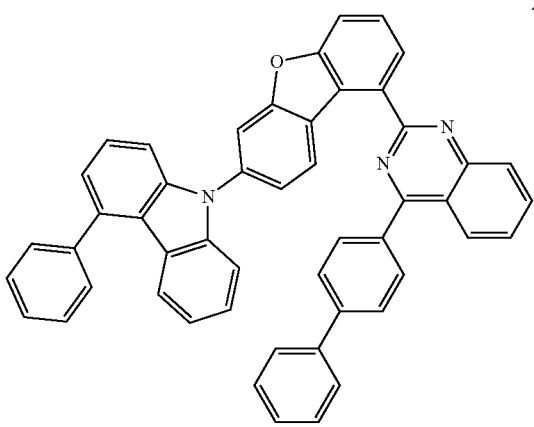
201
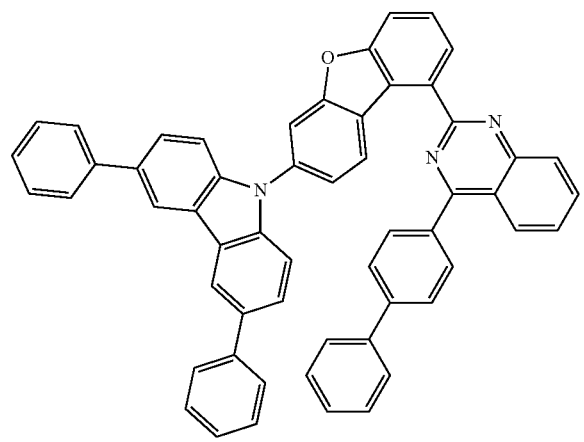
202
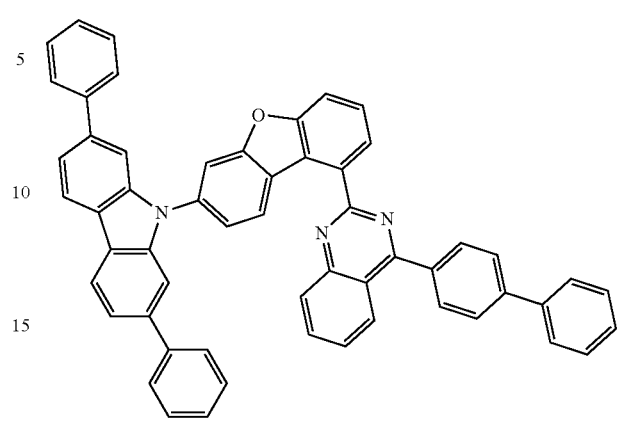
203
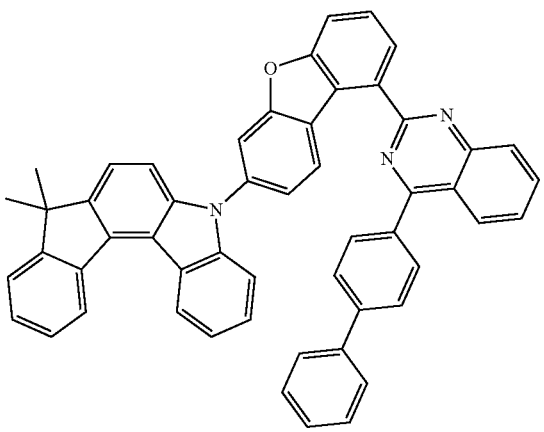
204
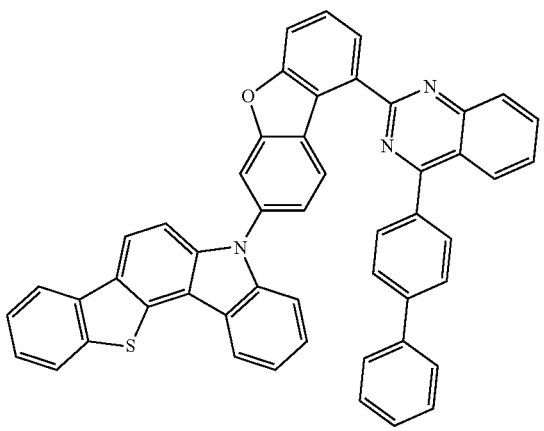

233
-continued
205
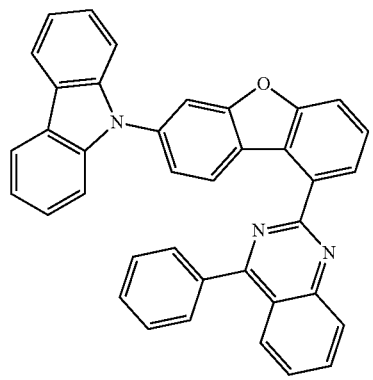
206
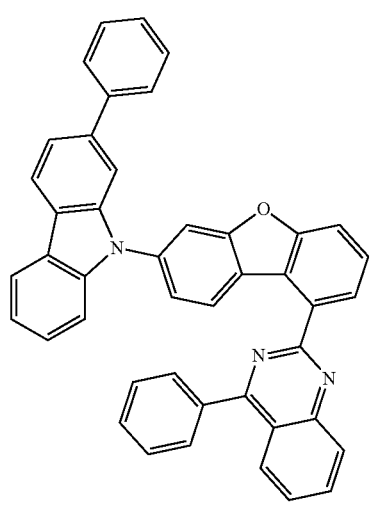
207
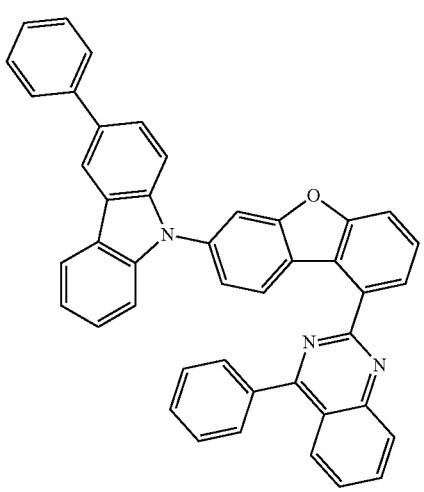
234
-continued
208
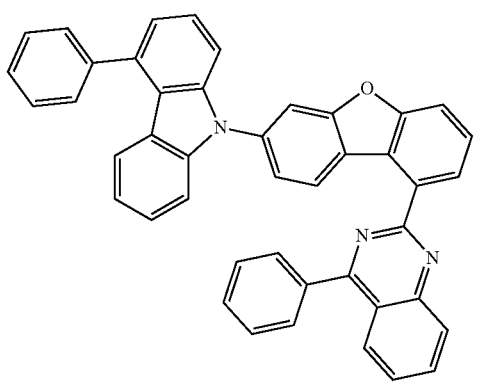
209
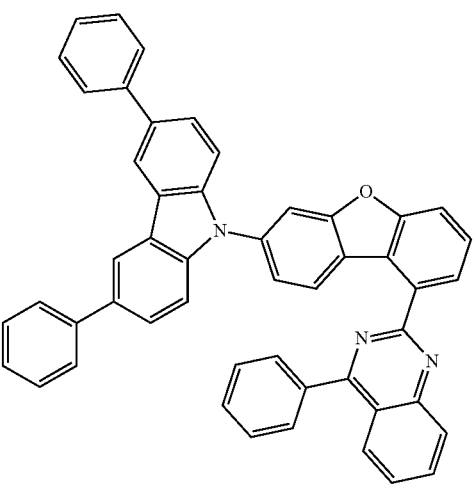
210
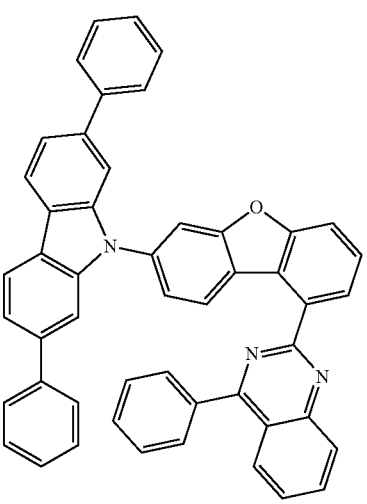

-continued
211
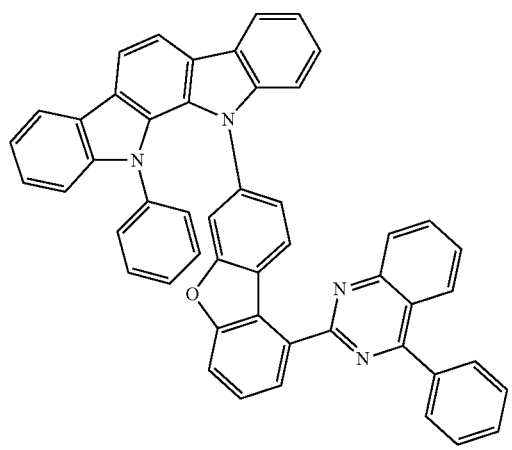
212
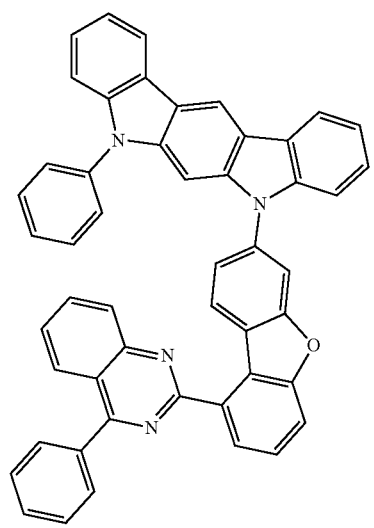
213
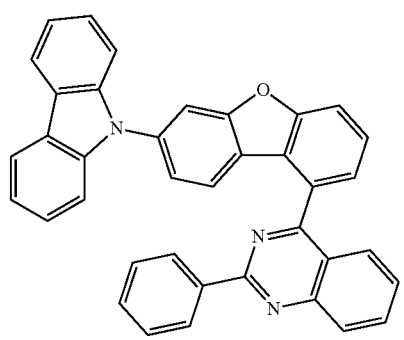
-continued
214
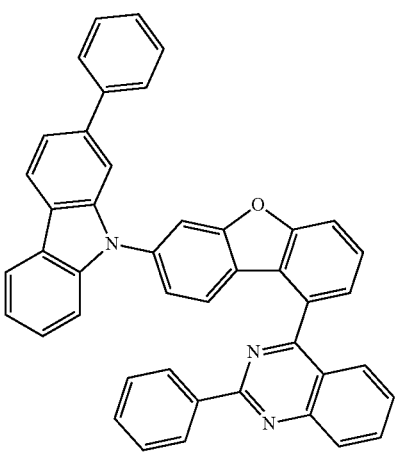
215
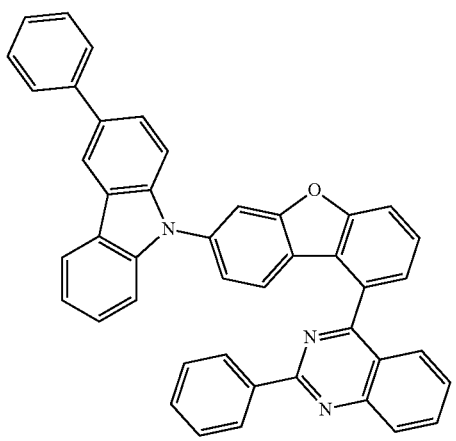
216
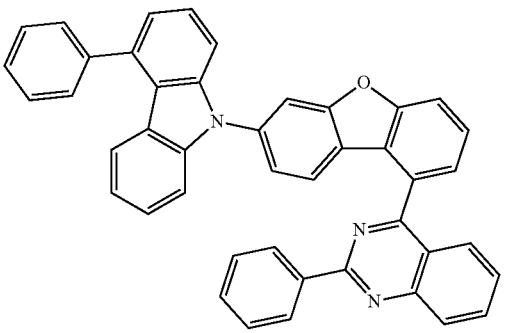

217
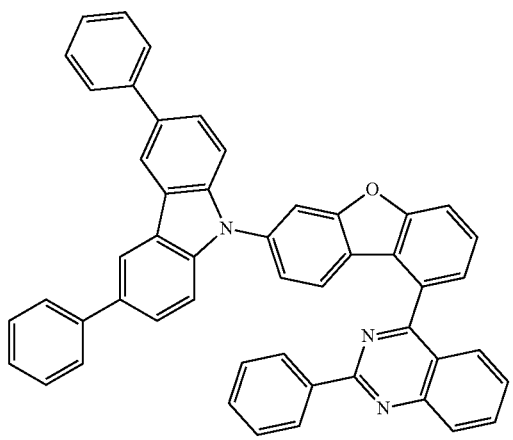
218
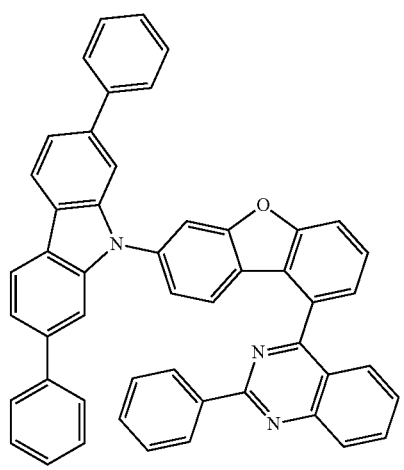
219
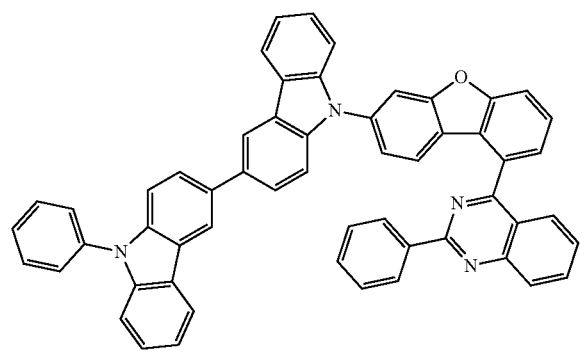
220
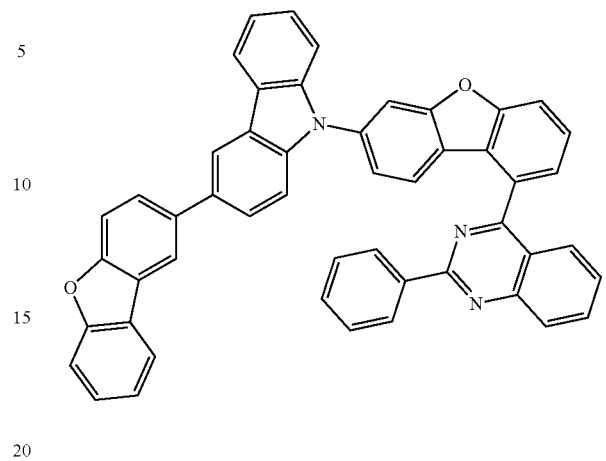
221
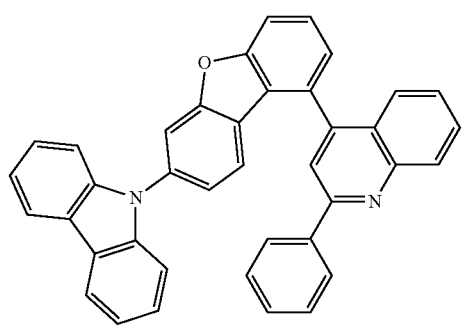
222
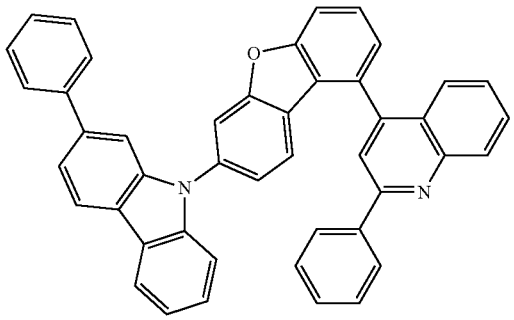
223
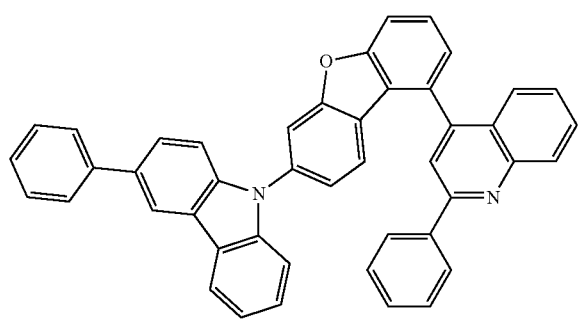

224
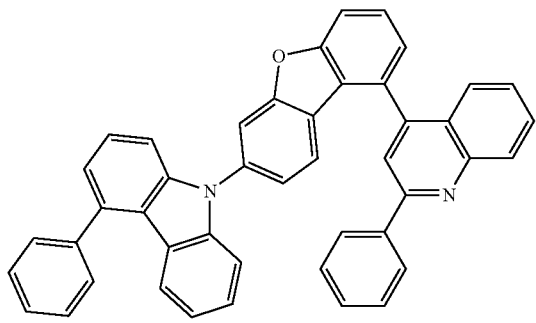
225
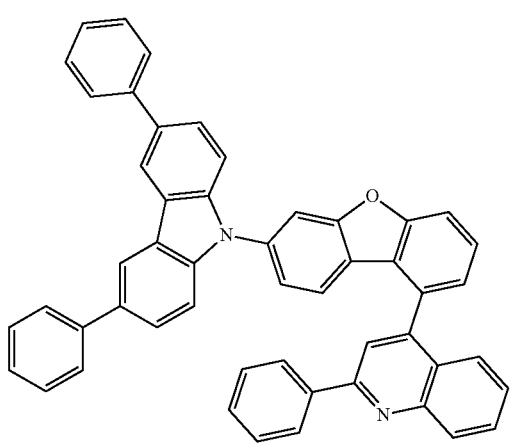
226
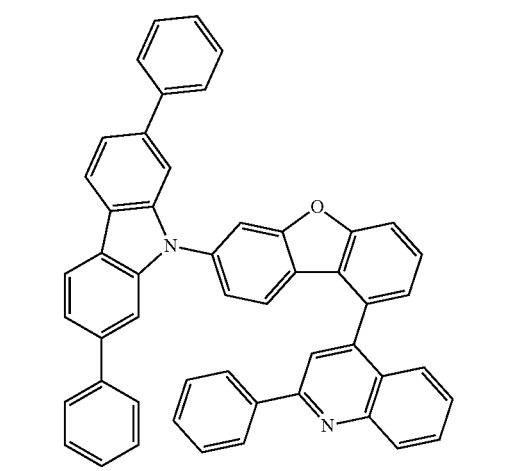
227
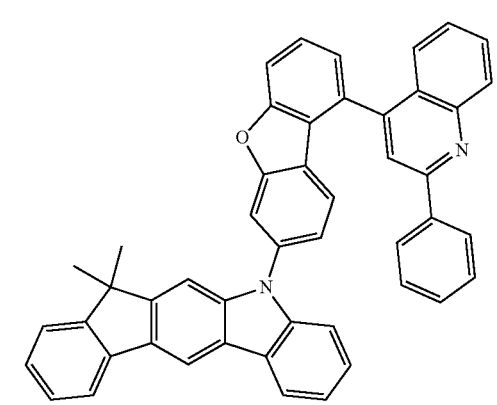
228
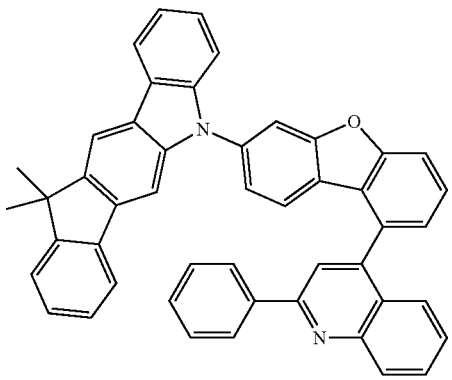
229
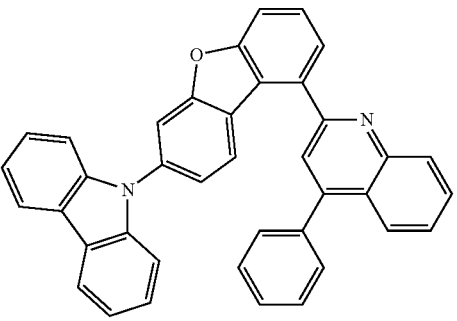
230
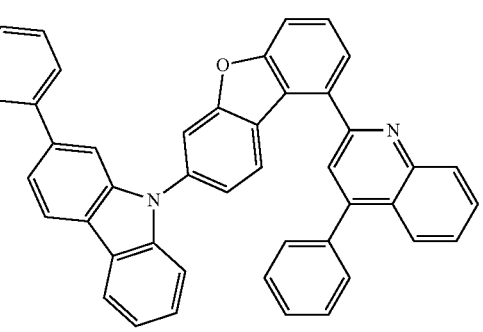
231
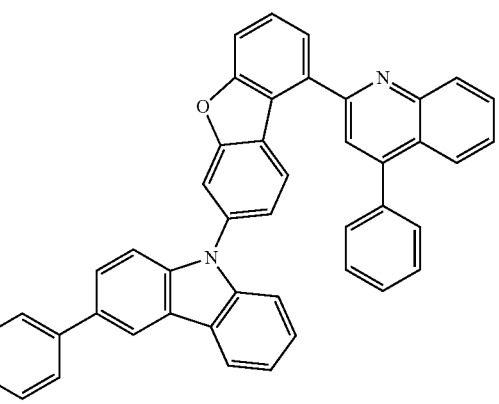

-continued
232
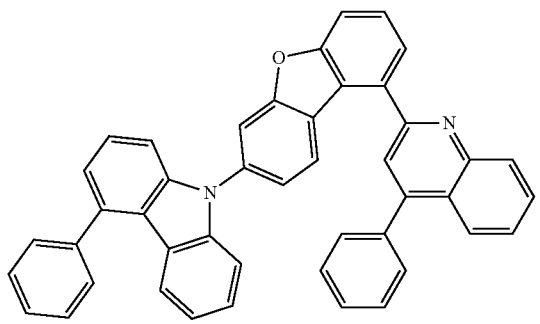
233
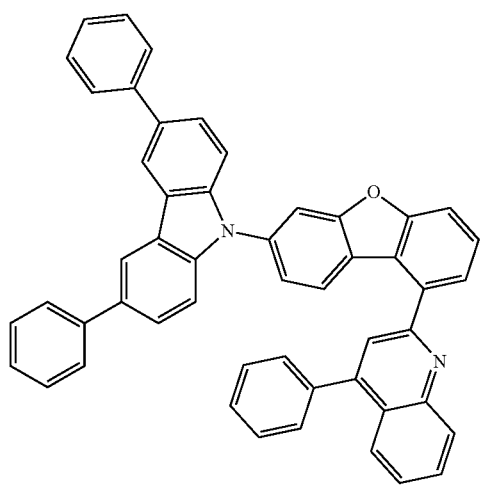
234
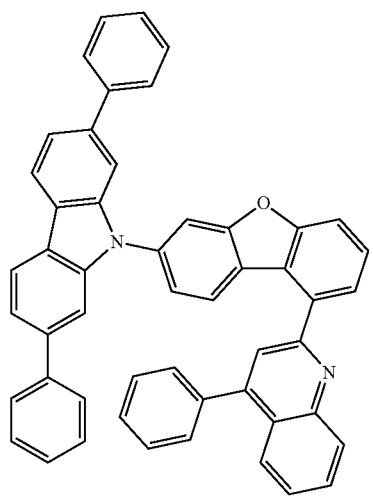
-continued
235
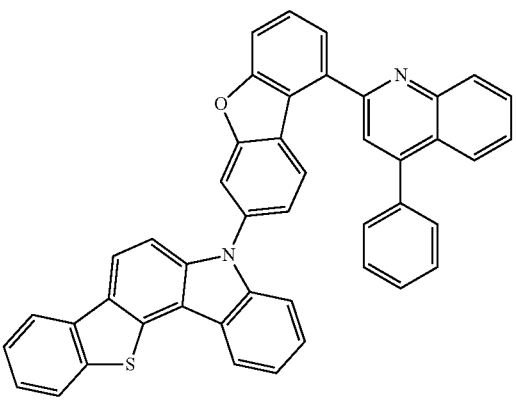
236
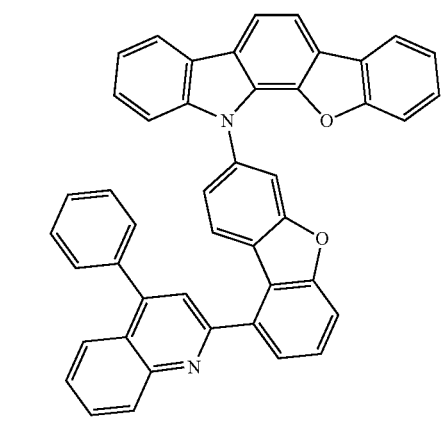
238
239
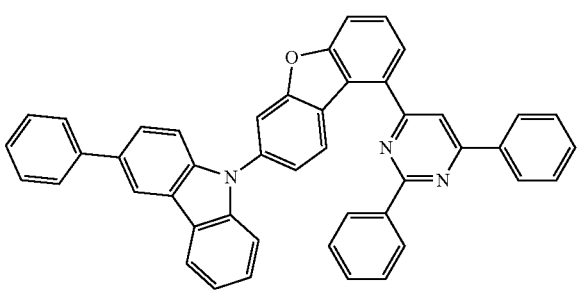

240
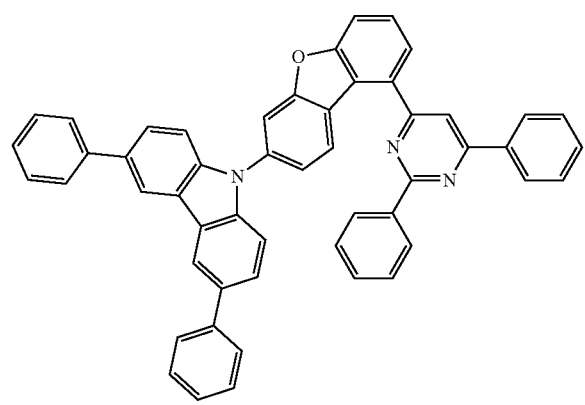
241
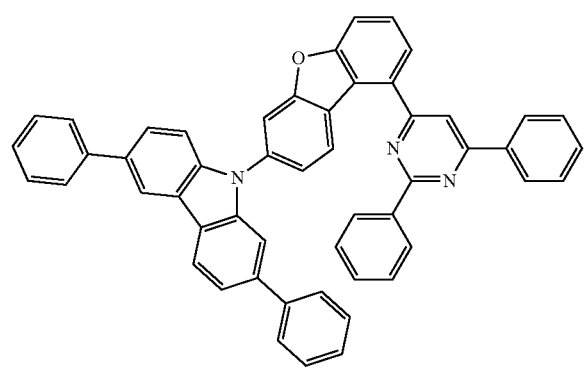
242
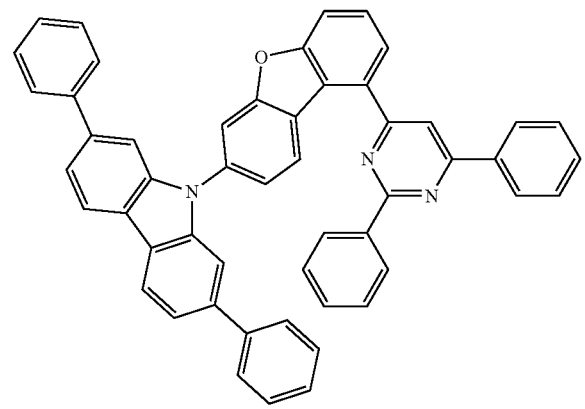
244
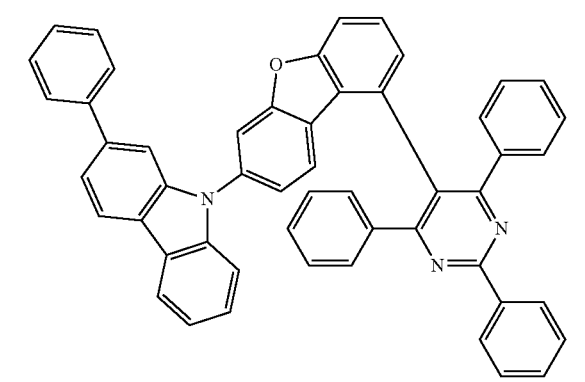
245
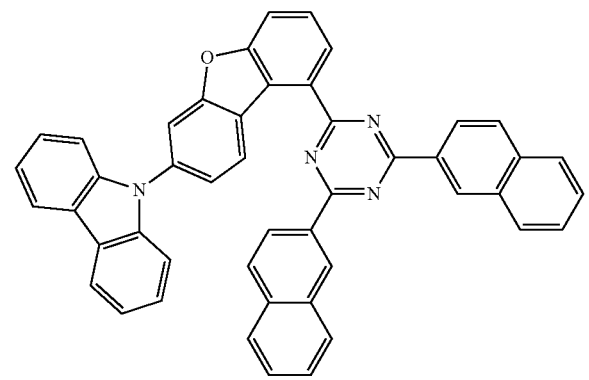
246
247
248
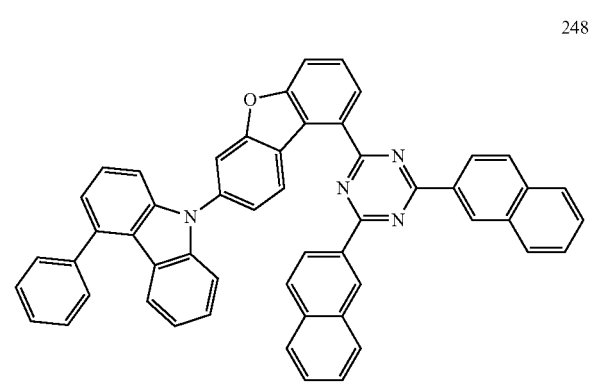

249
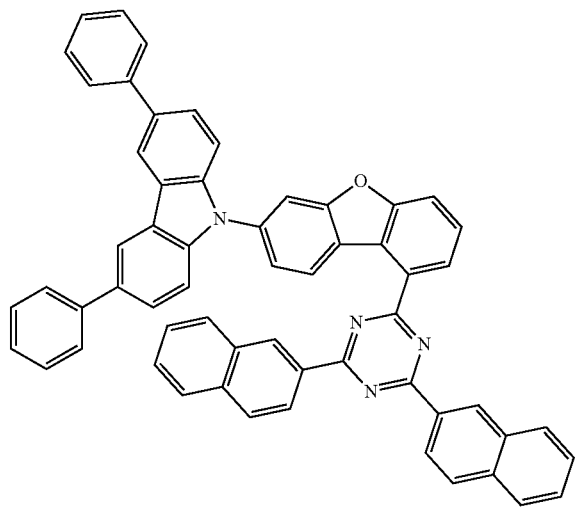
253
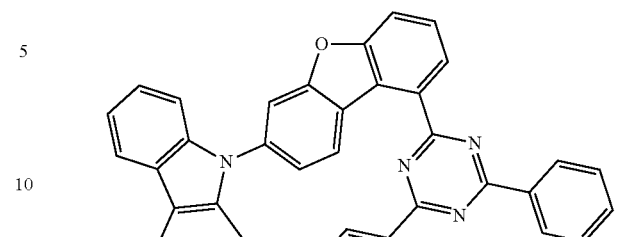
250
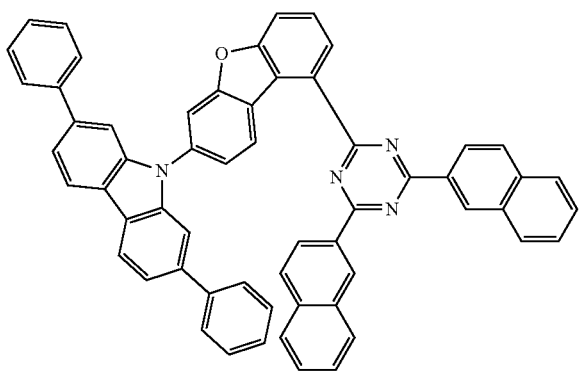
251
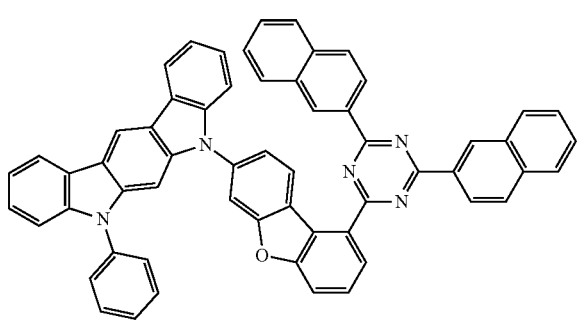
254
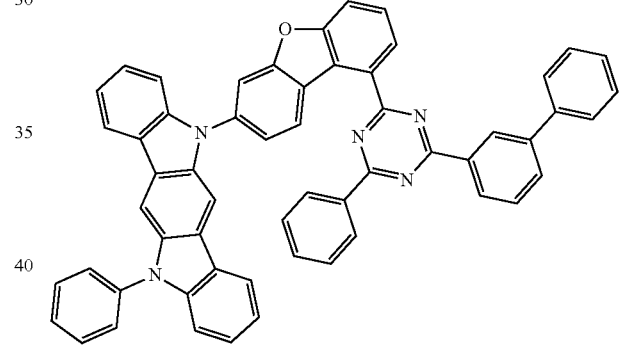
252
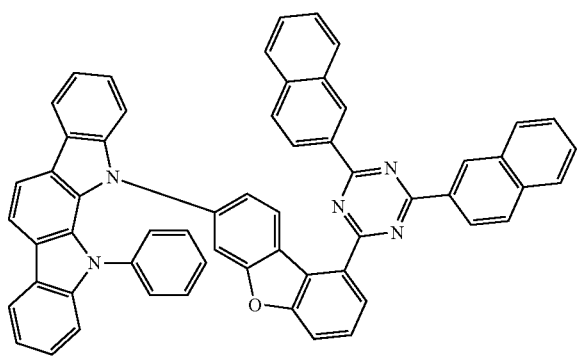
255
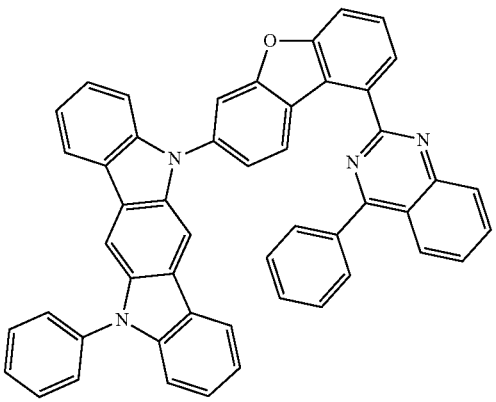

256
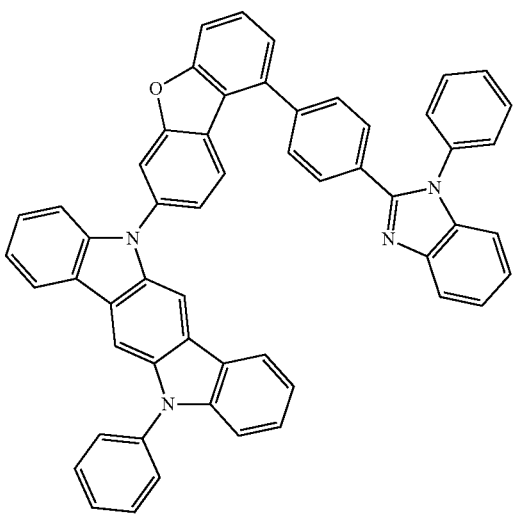
257
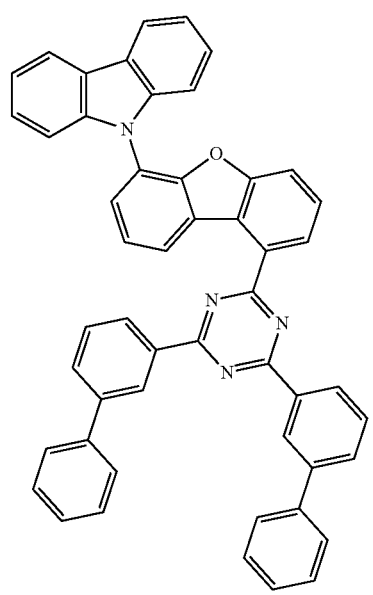
258
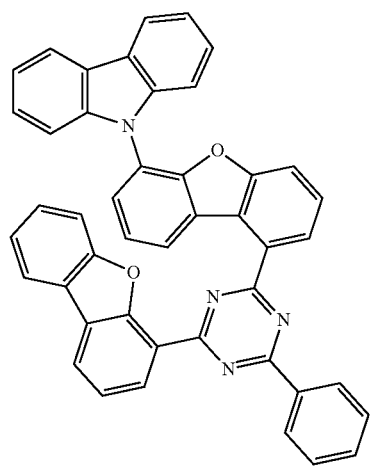
259
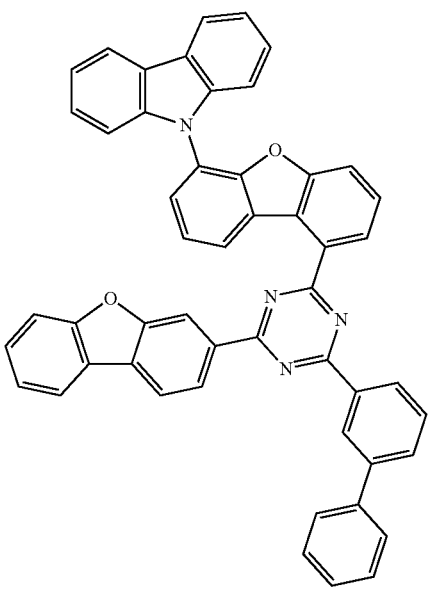
260
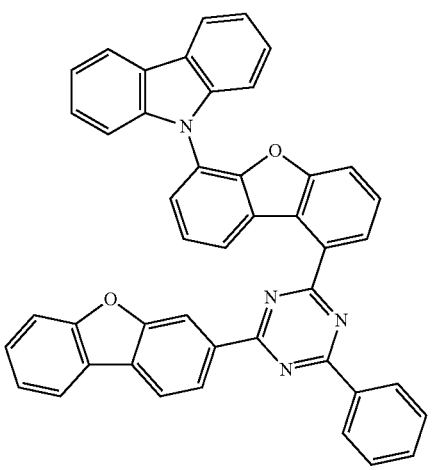
261
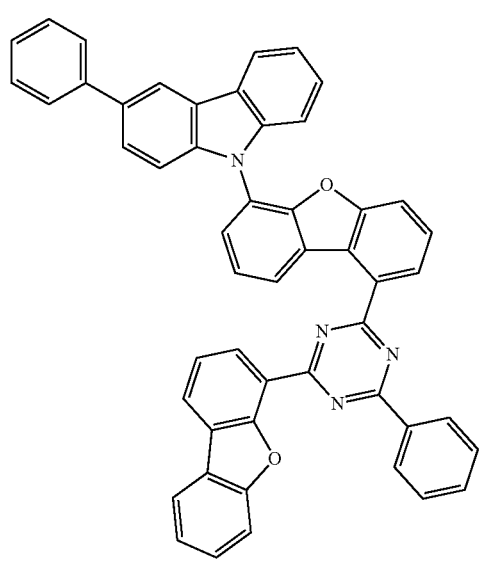

262
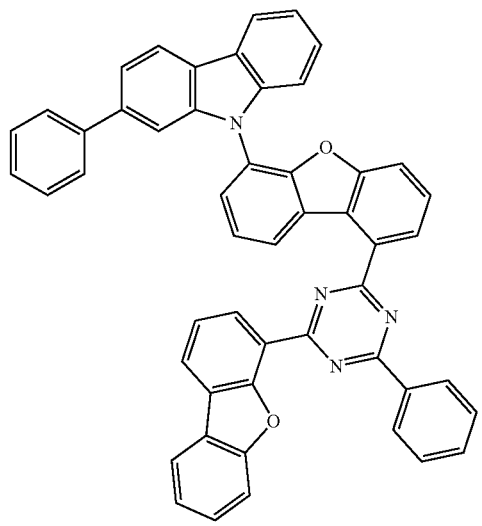
263
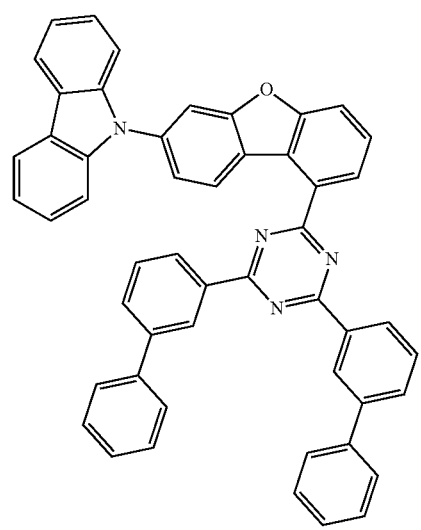 [SMILES: c1ccc(-c2cccc(-c3nc(-c4cccc(-c5ccccc5)c4)nc(-c4cccc5oc6cc(-n7c8ccccc8c8ccccc87)ccc6c45)n3)c2)cc1]
264
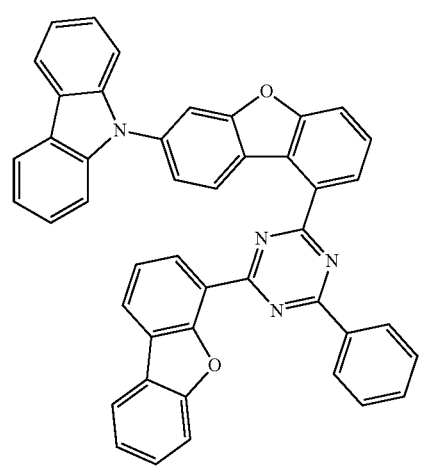
265
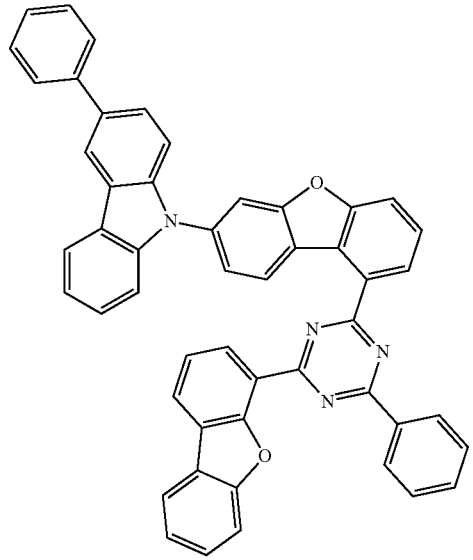
266
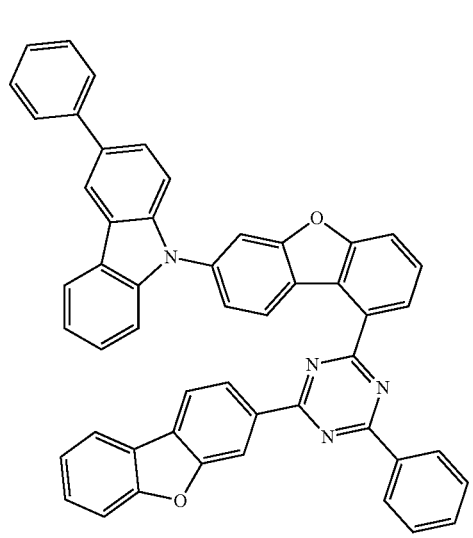
267
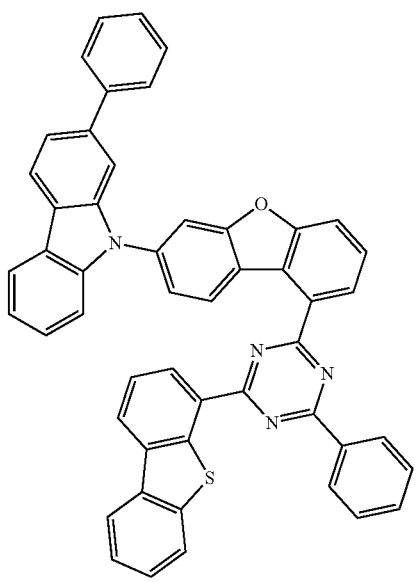

251
-continued
268
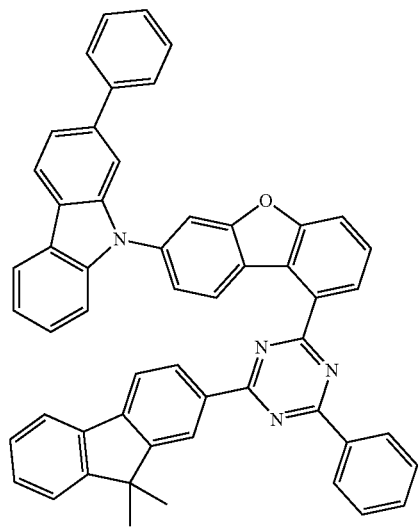
269
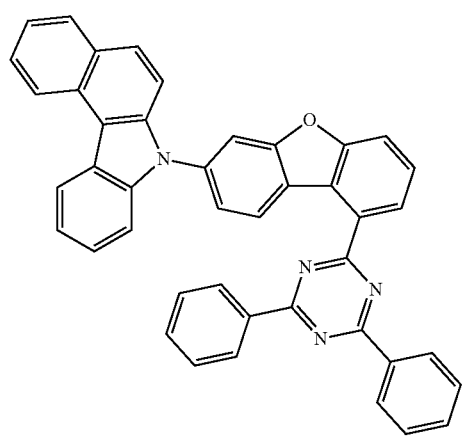
270
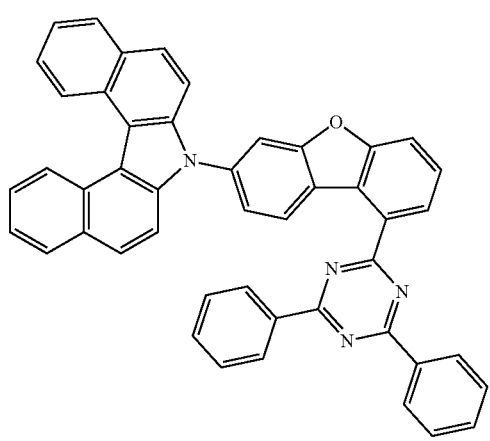
252
-continued
271
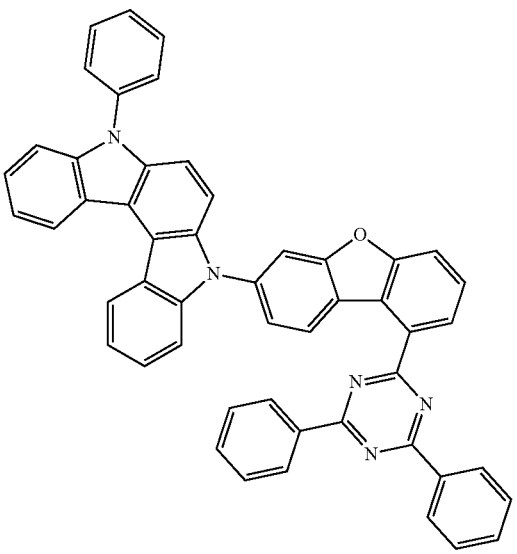 [SMILES: c1ccc(-c2nc(-c3ccccc3)nc(-c3cccc4oc5cc(-n6c7ccccc7c7c8c9ccccc9n(-c9ccccc9)c8ccc76)ccc5c34)n2)cc1]
272
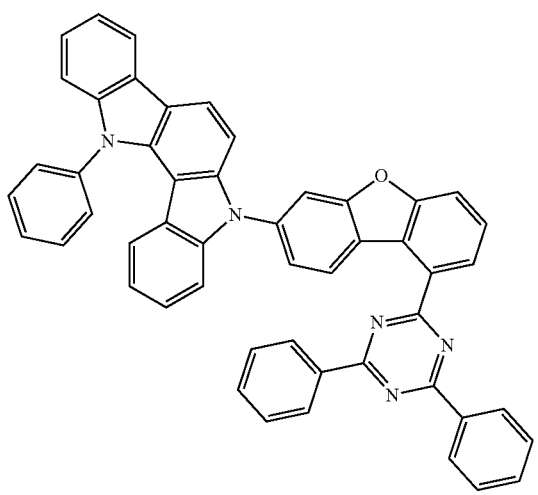 [SMILES: c1ccc(-c2nc(-c3ccccc3)nc(-c3cccc4oc5cc(-n6c7ccccc7c7c6ccc6c8ccccc8n(-c8ccccc8)c67)ccc5c34)n2)cc1]
273
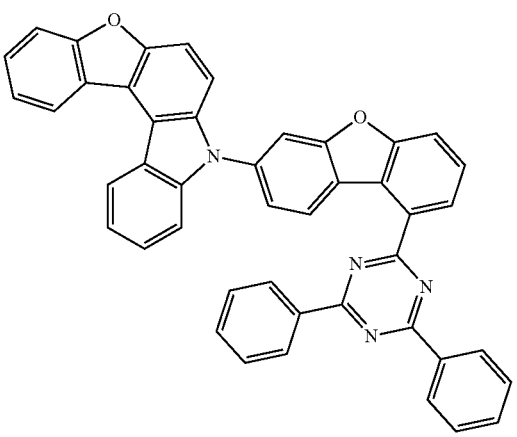

253
-continued
274
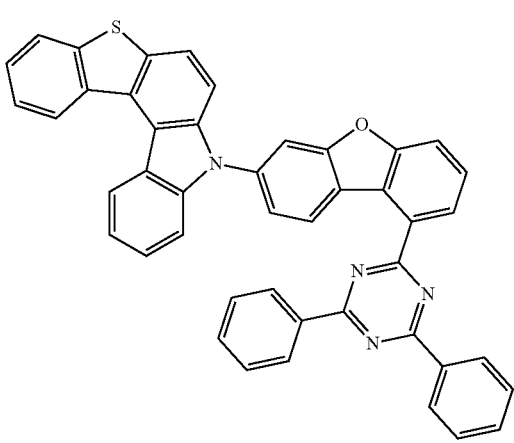
275
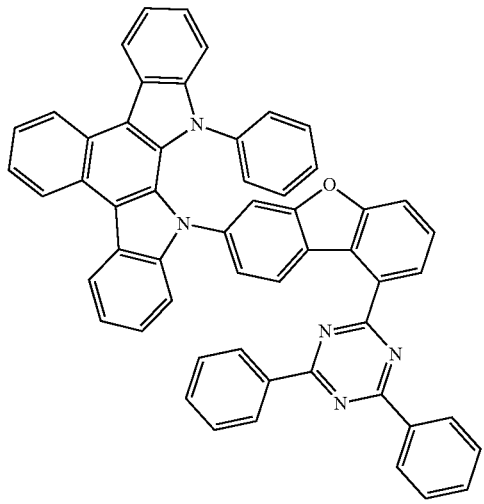
276
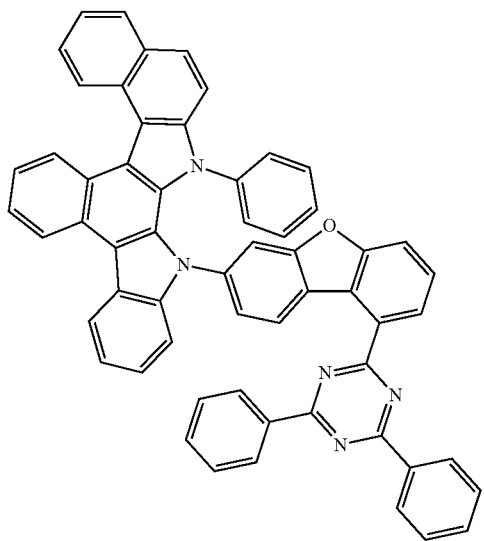
254
-continued
277
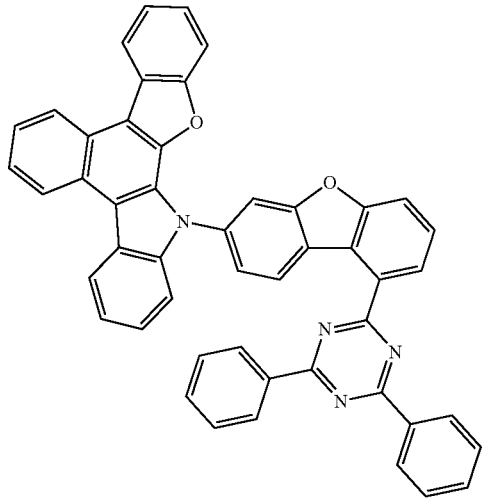
278
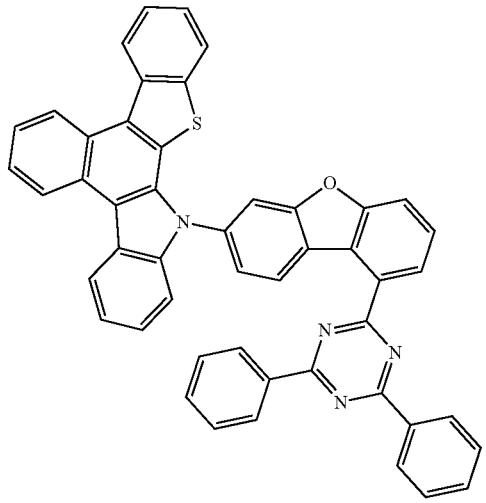
279

280

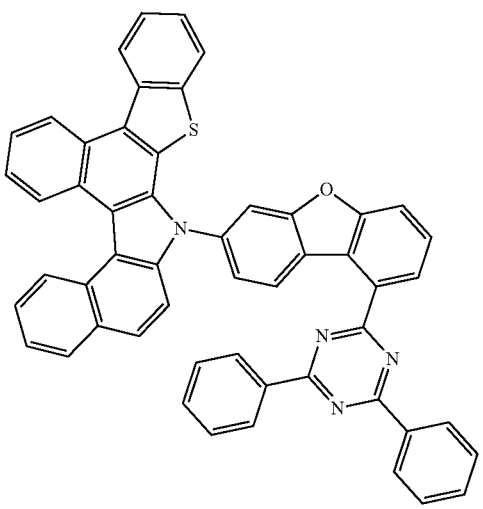

281

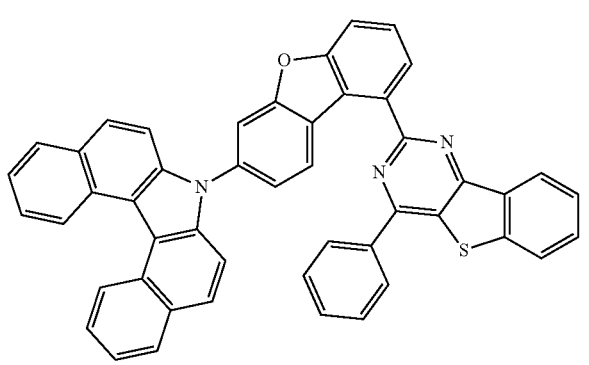

282

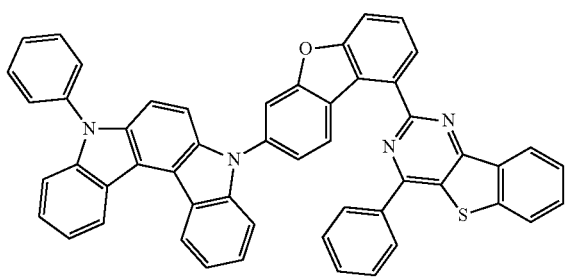

283

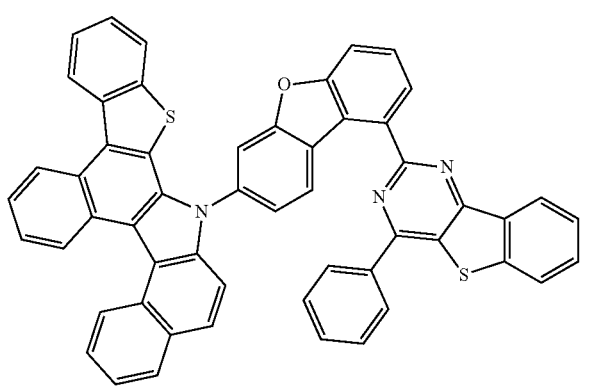

284

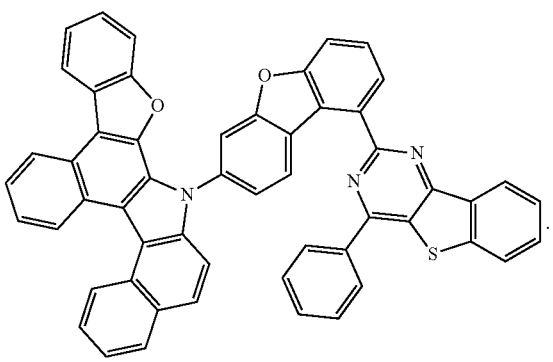

4. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

5. The organic light emitting device of claim 4, wherein the organic material layer comprises a light emitting layer, and the light emitting layer comprises the heterocyclic compound.

6. The organic light emitting device of claim 4, wherein the organic material layer comprises a light emitting layer, the light emitting layer comprises a host material, and the host material comprises the heterocyclic compound.

7. The organic light emitting device of claim 4, wherein the organic material layer comprises an electron injection layer or an electron transfer layer, and the electron transfer layer or the electron injection layer comprises the heterocyclic compound.

8. The organic light emitting device of claim 4, wherein the organic material layer comprises an electron blocking layer or a hole blocking layer, and the electron blocking layer or the hole blocking layer comprises the heterocyclic compound.

9. The organic light emitting device of claim 4, further comprising one, two or more layers selected from the group consisting of a light emitting layer, a hole injection layer, a hole transfer layer, an electron injection layer, an electron transfer layer, an electron blocking layer and a hole blocking layer.

* * * * *